US010648045B2

United States Patent
Kwan et al.

(10) Patent No.: US 10,648,045 B2
(45) Date of Patent: May 12, 2020

(54) CHIMERIC POLYPEPTIDES

(71) Applicant: IPSEN BIOPHARM LIMITED, Wrexham (GB)

(72) Inventors: Daniel Kwan, Abingdon (GB); David Burgin, Abingdon (GB); Stephen Gavin Hackett, Abingdon (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 0 days.

(21) Appl. No.: 15/562,085

(22) PCT Filed: Mar. 22, 2016

(86) PCT No.: PCT/EP2016/056275
§ 371 (c)(1),
(2) Date: Sep. 27, 2017

(87) PCT Pub. No.: WO2016/156113
PCT Pub. Date: Oct. 6, 2016

(65) Prior Publication Data
US 2018/0073089 A1    Mar. 15, 2018

(30) Foreign Application Priority Data

Mar. 27, 2015 (GB) .................... 1505306.9

(51) Int. Cl.
*A61K 39/08*    (2006.01)
*C07K 14/33*    (2006.01)
*C12N 9/52*    (2006.01)

(52) U.S. Cl.
CPC ...... *C12Y 304/24069* (2013.01); *A61K 39/08* (2013.01); *C07K 14/33* (2013.01); *C12N 9/52* (2013.01); *C07K 2319/00* (2013.01); *C07K 2319/01* (2013.01); *C07K 2319/21* (2013.01); *C07K 2319/50* (2013.01)

(58) Field of Classification Search
None
See application file for complete search history.

(56) References Cited

U.S. PATENT DOCUMENTS

2013/0288336 A1* 10/2013 Verhagen ............... C07K 14/33
                                                            435/220

OTHER PUBLICATIONS

Greenspan et al. 1999 (Defining epitopes: It's not as easy as it seems; Nature Biotechnology, 17:936-937) (Year: 1999).*
Raphael et al. 2010 (Sequence Diversity of Genes Encoding Botulinum Neurotoxin Type ; Applied and Environmental Microbiology 76(14): 4805-4812) (Year: 2010).*
Raphael, et al., "Sequence Diversity of Genes Encoding Botulinum Neurotoxin Type F", Applied and Environmental Microbiology, 2010, vol. 76, No. 14, pp. 4805-4812.
Guo, et al., "Expression and Biochemical Characterization of Light Chains of Botulinum Neurotoxin Subtypes F5 and F7", Protein Expression and Purification, 2015, vol. 111, pp. 87-90.

* cited by examiner

Primary Examiner — Mary Maille Lyons
(74) Attorney, Agent, or Firm — Gene J. Yao; Barnes & Thornburg LLP

(57) ABSTRACT

Chimeric clostridial neurotoxins in which the activation loop has been replaced by an activation loop from a different subtype within the same serotype. Methods of producing, activating, and using such neurotoxins. Compositions comprising such neurotoxins. Polynucleotides, vectors and cells for expressing such neurotoxins.

12 Claims, 23 Drawing Sheets
Specification includes a Sequence Listing.

Chimeric protein combines $F_7$ function with $F_1$ activation $F_7$ – poor activation $F_1$ – good activation $F_{7\text{-}1}$ – good activation

FIG. 1A

BoNT/A subtypes

| | | | | |
|---|---|---|---|---|
| UPI0000001386 | 420 | TGLFEFYKLLCVRGIITSKTKS----LDKGYNKALNDLCIKVNNWDLFFSPSEDNFTNDL | 475 | A1 |
| UPI0000ED909E | 420 | TGLFEFYKLLCVRGIITSKTKS----LDKGYNKALNDLCIKVNNWDLFFSPSEDNFTNDL | 475 | A1 |
| UPI0000EF85BD | 420 | TGLFEFYKLLCVRGIITSKTKS----LDKGYNKALNDLCIKVNNWDLFFSPSEDNFTNDL | 475 | A1 |
| UPI00016529B7 | 420 | TGLFEFYKLLCVRGIITSKTKS----LDKGYNKALNDLCIKVNNWDLFFSPSEDNFTNDL | 475 | A1 |
| UPI00027EE164 | 420 | TGLFEFYKLLCVRGIITSKTKS----LDKGYNKALNDLCIKVNNWDLFFSPSEDNFTNDL | 475 | A1 |
| UPI000003409D | 420 | TGLFEFYKLLCVRGIITSKTKS----LDKGYNKALNDLCIKVNNWDLFFSPSEDNFTNDL | 475 | A1 |
| UPI0002AA7E5E | 420 | TGLFEFYKLLCVRGIITSKTKS----LDKGYNKALNDLCIKVNNWDLFFSPSEDNFTNDL | 475 | A1 |
| UPI0001A954C8 | 420 | TGLFEFYKLLCVRGIITSKTKS----LDKGYNKALNDLCIKVNNWDLFFSPSEDNFTNDL | 475 | A1 |
| | | | | |
| UPI000016EA88 | 420 | TGLFEFYKLLCVRGIIPFKTKS----LDEGYNKALNDLCIKVNNWDLFFSPSEDNFTNDL | 475 | A2 |
| UPI0000EF84BD | 420 | TGLFEFYKLLCVRGIIPFKTKS----LDEGYNKALNDLCIKVNNWDLFFSPSEDNFTNDL | 475 | A2 |
| UPI000067C53E | 420 | TGLFEFYKLLCVRGIIPFKTKS----LDEGYNKALNDLCIKVNNWDLFFSPSEDNFTNDL | 475 | A2 |
| UPI000290BDD5 | 420 | TGLFEFYKLLCVRGIIPFKTKS----LDEGYNKALNDLCIKVNNWDLFFSPSEDNFTNDL | 475 | A2 |
| UPI0001C0B376 | 420 | TGLFEFYKLLCVRGIIPFKTKS----LDEGYNKALNDLCIKVNNWDLFFSPSEDNFTNDL | 475 | A2 |
| UPI000290BEB1 | 420 | TGLFEFYKLLCVRGIIPFKTKS----LDEGYNKALNDLCIKVNNWDLFFSPSEDNFTNDL | 475 | A2 |
| UPI0001F3B30D | 420 | TGLFEFYKLLCVRGIIPFKTKS----LDEGYNKALNDLCIKVNNWDLFFSPSEDNFTNDL | 475 | A2 |
| | | | | |
| UPI0001C32E84 | 420 | TGLFEFYKLLCVRGIIPFKTKS----LDEGYNKALNDLCIKVNNWDLFFSPSEDNFTNDL | 475 | A2v2 |
| UPI0003C9D2A1 | 420 | TGLFEFYKLLCVRGIIPFKTKS----LDEGYNKALNDLCIKVNNWDLFFSPSEDNFTNDL | 475 | (A2or3) |
| UPI000290B995 | 420 | TGLFEFYKLLCVRGIITSKTKS----LDEGYNKALNDLCIKVNNWDLFFSPSEDNFTNDL | 475 | (A5,3or2) |
| | | | | |
| UPI00005B712C | 416 | TGLFEFYKLLCVRGIIPFKTKS----LDEGYNKALNYLCIKVNNWDLFFSPSEDNFTNDL | 471 | A3 |
| UPI00016DBC11 | 416 | TGLFEFYKLLCVRGIIPFKTKS----LDEGYNKALNDLCIKVNNWDLFFSPSEDNFTNDL | 471 | A3 |

FIG. 1B

```
UPI000290C320  416  TGLEEFYKLLCVRGIIPFKTKS-----LDEGVRKALNDLCIKVNNWDLFFSPSEDNFTNDL  471  B3
UPI0003058712D  420  TGIEEFYKLLCVRGIITSKTKS-----LDEGVRKALNELCIKVNNWDLFFSPSEDNFTNDL  475  A4
UPI00018DB885   420  TGIEEFYKLLCVRGIITSNTRS-----LDEGVKKALNELCIKVNNWDLFFSPSEDNFTNDL  475  A4
UPI0001AE7D6A   420  TGIEEFYKLLCVRGIITSKTKS-----LDEGVRKALNDLCIKVNNWDLFFSPSEDNFTNDL  475  A5
UPI000198BDAE   420  TGIEEFYKLLCVRGIITSKTKS-----LDEGVRKALNDLCIKVNNWDLFFSPSEDNFTNDL  475  A5
UPI0001B7D251   420  TGIEEFYKLLCVRGIITSNTRS-----LDKGVKKALNDLCIKVNNWDLFFSPSEDNFTNDL  475  A6
```

BoNT/F subtypes

```
UPI000300B66D1  419  KGIVEKIVKFCKSVIPRKGTKA--------------PPRLCIRVNNELFFVASESSYNESD  466  F1
UPI000316BB5D7  419  KGIVEKIIKFCKSI

FIG. 1C

```
UPI0000126B8A  419  KGIVEKIVKFCKSVIPRKGTKA----------------EPRLCIRVANSELFVASESSYHEMD  466 F6
UPI0001C0B1D0  419  KGIVEKIVKFCKSVIPRKGTKA----------------EPRLCIRVANSELFVASESSYHEMD  466 F6
UPI0012E3DAC   411  MGIVERPVGLCKGIVSKKGTK-----------------MSLCIKVMNRDLFVASESSYHEMG  456 F7
UPI0000AF8C    411  MGIVERPVGLCKSIVSKKGTK-----------------MSLCIKVMNRDLFVASESSYHEMG  456 F7
UPI0001C0B221  411  MGIVERFVGLCKSIVSKKGTK-----------------MSLCIKVMNRDLFVASESSYHEMG  456 F7
UPI0001C0B220  411  MGIVERFVGLCKSIVSKKGTK-----------------MSLCIKVMNRDLFVASESSYHEMG  456 F7
```

Figure 3

| | | 1 | 2 | 3 | 4 | 5 | 6 | 7 | 8 | 9 | 10 | 11 | 12 | 13 | 14 | 15 | | |
|---|---|---|---|---|---|---|---|---|---|---|---|---|---|---|---|---|---|---|
| 1 | UPI00000B66D1 | ■ | 83.7 | 83.7 | 84.2 | 92.5 | 92.3 | 70.5 | 88.1 | 87.7 | 88.1 | 88.0 | 74.3 | 74.3 | 73.9 | 74.4 | 1 | F1 |
| 2 | UPI00016BB5D7 | 18.4 | ■ | 99.8 | 97.2 | 83.9 | 83.7 | 74.4 | 90.3 | 89.9 | 90.2 | 90.1 | 69.5 | 69.5 | 69.3 | 69.5 | 2 | F2 |
| 3 | UPI00000B50F1 | 18.4 | 0.2 | ■ | 97.0 | 83.9 | 83.7 | 74.4 | 90.3 | 89.9 | 90.2 | 90.1 | 69.3 | 69.3 | 69.1 | 69.4 | 3 | |
| 4 | UPI0001C0B12F | 17.7 | 2.9 | 3.1 | ■ | 84.3 | 84.1 | 74.4 | 90.1 | 89.7 | 90.0 | 90.0 | 69.8 | 69.8 | 69.7 | 69.9 | 4 | F3 |
| 5 | UPI0001A92658 | 7.9 | 18.1 | 18.1 | 17.6 | ■ | 99.5 | 70.4 | 87.7 | 87.3 | 87.6 | 87.5 | 72.8 | 72.8 | 72.5 | 72.8 | 5 | F4 |
| 6 | UPI0001C0B12D | 8.1 | 18.4 | 18.4 | 17.9 | 0.6 | ■ | 70.0 | 87.5 | 87.1 | 87.4 | 87.3 | 72.8 | 72.8 | 72.5 | 72.8 | 6 | |
| 7 | UPI0001C0B12E | 37.5 | 31.4 | 31.4 | 31.4 | 37.6 | 38.3 | ■ | 74.3 | 73.9 | 74.3 | 74.2 | 64.4 | 64.5 | 64.4 | 64.5 | 7 | F5 |
| 8 | UPI0001C0B1D1 | 13.0 | 10.4 | 10.4 | 10.6 | 13.5 | 13.7 | 31.5 | ■ | 99.6 | 99.9 | 99.8 | 70.8 | 70.8 | 70.5 | 70.8 | 8 | |
| 9 | UPI00000126B8A | 13.4 | 10.9 | 10.9 | 11.1 | 14.0 | 14.2 | 32.2 | 0.4 | ■ | 99.5 | 99.5 | 70.4 | 70.4 | 70.2 | 70.5 | 9 | F6 |
| 10 | UPI0001C0B1D0 | 13.1 | 10.5 | 10.5 | 10.7 | 13.6 | 13.8 | 31.5 | 0.1 | 0.5 | ■ | 99.9 | 70.8 | 70.8 | 70.5 | 70.8 | 10 | |
| 11 | UPI0004E7C8CE | 13.1 | 10.6 | 10.6 | 10.8 | 13.7 | 13.9 | 31.7 | 0.2 | 0.6 | 0.1 | ■ | 70.8 | 70.8 | 70.6 | 70.9 | 11 | |
| 12 | UPI0001DE3DAC | 31.4 | 39.2 | 39.4 | 38.6 | 33.8 | 33.8 | 48.1 | 37.0 | 37.6 | 37.0 | 36.9 | ■ | 99.9 | 99.1 | 99.2 | 12 | F7 |
| 13 | UPI0001C0B220 | 31.4 | 39.2 | 39.4 | 38.6 | 33.8 | 33.8 | 47.9 | 37.0 | 37.6 | 37.0 | 36.9 | 0.1 | ■ | 99.2 | 99.3 | 13 | |
| 14 | UPI00000BAF8C | 32.1 | 39.4 | 39.7 | 38.8 | 34.2 | 34.2 | 48.1 | 37.4 | 38.0 | 37.4 | 37.3 | 0.9 | 0.8 | ■ | 98.5 | 14 | |
| 15 | UPI0001C0B221 | 31.3 | 39.0 | 39.3 | 38.4 | 33.7 | 33.7 | 47.9 | 36.9 | 37.5 | 36.9 | 36.8 | 0.8 | 0.7 | 1.5 | ■ | 15 | |
| | | 1 | 2 | 3 | 4 | 5 | 6 | 7 | 8 | 9 | 10 | 11 | 12 | 13 | 14 | 15 | | |

Divergence (lower left) / Percent Identity (upper right)

FIG. 4A

```
Majority       MPVVINSFNYNDPVNDDTILYMQIPYEERSKKYYKAFEIMRNVWIIPERN
                         +         +         +         +         +
                        10        20        30        40        50
                         +         +         +         +         +
UPI000003366D1 MPVVINSFNYNDPVNDDTILYMQIPYEERSKKYYKAFEIMRNVWIIPERN   50
UPI00016BB5D7  MPVVINSFNYNDPVNDETILYMQKPYEERSRKYYKAFEIMPNVWIMPERD   50
UPI00000B50F1  MPVVINSFNYNDPVNDETILYMQKPYEERSRKYYKAFEIMPNVWIMPERD   50
UPI0001C0B12F  MPVVINSFNYNDPVNDETILYMQKPYEERSRKYYKAFEIMPNVWIMPERD   50
UPI0001A92658  MPVVINSFNYDDPVNDDTILYMQIPYEERSKKYYKAFEIMRNVWIMPERN   50
UPI0001C0B12D  MPVVINSFNYDDPVNDDTILYMQIPYEERSKKYYKAFEIMRNVWIMPERN   50
UPI0001C0B12E  MPVEINSFNYDDLVNDNTILYIRPFYERSNTYFKAFNIMENVWIIPERY    50
UPI0001C0B1D1  MPVAINSFNYNDPVNDDTILYMQIPYEERSKKYYKAFEIMRNVWIIPERN   50
UPI000012688A  MPVAINSFNYNDPVNDDTILYMQIPYEERSKKYYKAFEIMRNVWIIPERN   50
UPI0001C0B1D0  MPVAINSFNYNDPVNDDTILYMQIPYKERSKKYYKAFEIMRNVWIIPERN   50
UPI0004E7C8CE  MPVAINSFNYNDPVNDDTILYMQIPYKEKSKKYYKAFEIMRNVWIIPERN   50
UPI0001DE3DAC  MPVNINNFNYNDPINNTTILYMRMPYYEDSNKYYKAFEIMDNVWIIPERN   50
UPI0001C0B22D  MPVNINNFNYNDPINNTTILYMKMPYYEDSNKYYKAFEIMDNVWIIPERN   50
UPI00000BAF8C  MPVNINNFNYNDPINNTTILYMKMPYYEDSNKYYKAFEIMDNVWIIPERN   50
UPI0001C0B221  MPVNINNFNYNDPINNTTILYMRMPYYEDSNKYYKAFEIMDNVWIIPERN   50

Majority       TIGTKPSDFDPPASLKNGSSAYYDPNYLTTDAEKDRYLKTTIKLFKRINS
                         +         +         +         +         +
                        60        70        80        90       100
                         +         +         +         +         +
UPI000003366D1 TIGTDPSDFDPPASLENGSSAYYDPNYLTTDAEKDRYLKTTIKLFKRINS  100
UPI00016BB5D7  TIGTKPDEFQVPDSLKNGSSAYYDPNYLTTDAEKDRYLKTMIKLFNRINS  100
UPI00000B50F1  TIGTKPDEFQVPDSLKNGSSAYYDPNYLTTDAEKDRYLKTMIKLFNRINS  100
UPI0001C0B12F  TIGTKPDDFQVPDSLKNGSSAYYDPNYLTTDAEKDRYLKTMIKLFNRINS  100
UPI0001A92658  TIGTNPSDFDPPASLKNGSSAYYDPNYLTTDAEKDRYLKTTIKLFKRINS  100
UPI0001C0B12D  TIGTNPSDFDPPASLKNGSSAYYDPNYLTTDAEKDRYLKTTIKLFKRINS  100
UPI0001C0B12E  RLGIEASKFDPPDSLKAGSDGYFDPNYLSTNTEKNRYIQIMIKLFKRINS  100
UPI0001C0B1D1  TIGTNPSDFDPPASLKNGSSAYYDPNYLTTDAEKDRYLKTTIKLFKRINS  100
UPI000012688A  TIGTNPSDFDPPASLKNGSSAYYDPNYLTTDAEKDRYLKTTIKLFKRINS  100
UPI0001C0B1D0  TIGTNPSDFDPPASLKNGSSAYYDPNYLTTDAEKDRYLKTTIKLFKRINS  100
UPI0004E7C8CE  TIGTNPSDFDPPASLKNGSSAYYDPNYLTTDAEKDRYLKTTIKLFKRINS  100
UPI0001DE3DAC  IIGKKPSDFYPPISLDSGSSAYYDPNYLTTDAEKDRFLKTVIKLFNRINS  100
UPI0001C0B22D  IIGKKPSDFYPPISLDSGSSAYYDPNYLTTDAEKDRFLKTVIKLFNRINS  100
UPI00000BAF8C  IIGKKPSDFYPPISLDSGSSAYYDPNYLTTDAEKDRFLKTVIKLFNRINS  100
UPI0001C0B221  IIGKKPSDFYPPISLDSGSSAYYDPNYLTTDAEKDRFLKTVIKLFNRINS  100

Majority       NPAGKVLLXEISXAKPYLGNDHTPINEFXPVNRTTSVNIKLSTNVESSML
                         +         +         +         +         +
                       110       120       130       140       150
                         +         +         +         +         +
UPI000003366D1 NPAGEVLLQEISYAKPYLGNEHTPINEFHPVTRTTSVNIKSSTNVKSSII  150
UPI00016BB5D7  NPTGKVLLEEVSNAPPYLGDDDTLINEFFPVNVTTSVNIKFSTDVESSII  150
UPI00000B50F1  NPTGKVLLEEVSNAPPYLGDDDTLINEFFPVNVTTSVNIKFSTDVESSII  150
UPI0001C0B12F  NPTGKVLLEEVSNARPYLGDDDTLINEFFPVNVTTSVNIKFSTDVESSII  150
UPI0001A92658  NPAGEVLLQEISYAKPYLGNDHTPINEFHPVTRTTSVNIKSSTNVESSII  150
UPI0001C0B12D  NPAGEVLLQEISYAKPYLGNDHTPINEFHPVTRTTSVNIKSSTNVESSII  150
UPI0001C0B12E  NEAGKILLNQIKDAIPYLGNSYTAEDQPTTNNRTISFNVRLANGTIEQEM  150
UPI0001C0B1D1  NPAGKVLLQEISYAKPYLGNDHTPIDEFSPVTRTTSVNIKLSTNVESSML  150
UPI000012688A  NPAGKVLLQEISYAKPYLGNDHTPIDEFSPVTRTTSVNIKLSTNVESSML  150
UPI0001C0B1D0  NPAGKVLLQEISYAKPYLGNDHTPIDEFSPVTRTTSVNIKLSTNVESSML  150
UPI0004E7C8CE  NPAGKVLLQEISYAKPYLGNDHTPIDEFSPVTRTTSVNIKLSTNVESSML  150
UPI0001DE3DAC  NPAGQVLLEEIKNGKPYLGNDHTAVNEFCANNRSTSVEIKESKGTTDSML  150
UPI0001C0B22D  NPAGQVLLEEIKNGKPYLGNDHTAVNEFCANNRSTSVEIKESNGTTDSML  150
UPI00000BAF8C  NPAGQVLLEEIKNGKPYLGNDHTAVNEFCANNRSTSVEIKESNGTTDSML  150
UPI0001C0B221  NPAGQVLLEEIKNGKPYLGNDHTAVNEFCANNRSTSVEIKESNGTTDSML  150

Majority       LNLLVLGAGPDIFEXSCYPVRRXPNSDXVYDPSKXGFGSINIVTFSPEYE
                         +         +         +         +         +
                       160       170       180       190       200
                         +         +         +         +         +
UPI000003366D1 LNLLVLGAGPDIFENSSYPVRRLMDSGGVYDPSNDGFGSINIVTFSPEYE  200
```

FIG. 4B

```
UPI00016BB5D7  SNLLVLGAGPDIFKAYCTPLVRFNKSDKLIEPSNHGFGSINILTFSPEYE  200
UPI00000B50F1  SNLLVLGAGPDIFKAYCTPLVRFNKSDKLIEPSNHGFGSINILTFSPEYE  200
UPI0001C0B12F  SNLLVLGAGPDIFKAYCTPLVRFNKSDKLIEPSNHGFGSINILTFSPEYE  200
UPI0001A92658  LNLLVLGAGPNIFENSSYPVRKLMNSGEVYDPSNDGFGSINIVTFSPEYE  200
UPI0001C0B12D  LNLLVLGAGPNIFENSSYPVRKLMNSGEVYDPSNDGFGSINIVTFSPEYE  200
UPI0001C0B12E  ANLIIWGPGPDLTTNRTGGTTYTPAQSLEAIPYKEGFGSIMTIEFSPEYA  200
UPI0001C0B1D1  LNLLVLGAGPDIFESCCYPVRKLIDPDVVYDPSNYGFGSINIVTFSPEYE  200
UPI0000126B8A  LNLLVLGAGPDIFESCCYPVRKLIDPDVVYDPSNYGFGSINIVTFSPEYE  200
UPI0001C0B1D0  LNLLVLGAGPDIFESCCYPVRKLIDPDVVYDPSNYGFGSINIVTFSPEYE  200
UPI0004E7C8CE  LNLLVLGAGPDIFESCCYPVRKLIDPDVVYDPSNYGFGSINIVTFSPEYE  200
UPI0001DE3DAC  LNLVILGPGPNILECSTFPVRIFPN-NIAYDPSEKGFGSIQLMSFSTEYE  199
UPI0001C0B220  LNLVILGPGPNILECSTFPVRIFPN-NIAYDPSEKGFGSIQLMSFSTEYE  199
UPI00000BAF8C  LNLVILGPGPNILECSTFPVRIFPN-NIAYDPSEKGFGSIQLMSFSTEYE  199
UPI0001C0B221  LNLVILGPGPNILECSTFPVRIFPN-NIAYDPSEKGFGSIQLMSFSTEYE  199

Majority        YTFNDISGGHNSSTESFIADPAISLAHELIHALHGLYGAXGVTYKETIEV
                ----------+---------+---------+---------+---------+
                         210       220       230       240       250
                ----------+---------+---------+---------+---------+

UPI00000B66D1  YTFNDISGGYNSSTESFIADPAISLAHELIHALHGLYGARGVTYKETIKV  250
UPI00016BB5D7  HIFNDISGGNHNSTESFIADPAISLAHELIHALHGLYGAKAVTHKESLVA  250
UPI00000B50F1  HIFNDISGGNHNSTESFIADPAISLAHELIHALHGLYGAKAVTHKESLVA  250
UPI0001C0B12F  HIFNDISGGDHNSTESFIADPAISLAHELIHALHGLYGAKAVTHKETIEV  250
UPI0001A92658  YTFNDISGGHNSSTESFIADPAISLAHELIHALHGLYGARGVTYKETIKV  250
UPI0001C0B12D  YTFNDISGGHNSSTESFIADPAISLAHELIHALHGLYGARGVTYKETIKV  250
UPI0001C0B12E  TAFNDIS-LTSHAPSLFIKDPALILMHELIHVLHGLYGTYTTGFKIKPNI  249
UPI0001C0B1D1  YTFNDISGGHNSSTESFIADPAISLAHELIHALHGLYGARGVTYEETIEV  250
UPI0000126B8A  YTFNDISGGHNSSTESFIADPAISLAHELIHALHGLYGARGVTYEETIEV  250
UPI0001C0B1D0  YTFNDISGGHNSSTESFIADPAISLAHELIHALHGLYGARGVTYEETIEV  250
UPI0004E7C8CE  YTFNDISGGHNSSTESFIADPAISLAHELIHALHGLYGARGVTYEETIEV  250
UPI0001DE3DAC  YAFNDNT-------DLFIADPAISLAHELIHVLHGLYGAKGVTNKKVIEV  242
UPI0001C0B220  YAFNDNT-------DLFIADPAISLAHELIHVLHGLYGAKGVTNKKVIEV  242
UPI00000BAF8C  YAFNDNT-------DLFIADPAISLAHELIHVLHGLYGAKGVTNKKVIEV  242
UPI0001C0B221  YAFNDNT-------DLFIADPAISLAHELIHVLHGLYGAKGVTNKKVIEV  242

Majority        KQXPLMIAEKPIRLEEFLTFGGQDLNIITSAMKEKIYNNLLANYEKIATR
                ----------+---------+---------+---------+---------+
                         260       270       280       290       300
                ----------+---------+---------+---------+---------+

UPI00000B66D1  KQAPLMIAEKPIRLEEFLTFGGQDLNIITSAMKEKIYNNLLANYEKIATR  300
UPI00016BB5D7  ERGPLMIAEKPIRLEEFLTFGGEDLNIIPSAMKEKIYNDLLANYEKIATR  300
UPI00000B50F1  ERGPLMIAEKPIRLEEFLTFGGEDLNIIPSAMKEKIYNDLLANYEKIATR  300
UPI0001C0B12F  KRGPLMIAEKPIRLEEFLTFGGEDLNIIPSAMKEKIYNDLLANYEKIATR  300
UPI0001A92658  KQAPLMIAEKPIRLEEFLTFGGQDLNIITSAMKEKIYNDLLANYEKIATR  300
UPI0001C0B12D  KQAPLMIAEKPIRLEEFLTFGGQDLNIITSAMKEKIYNDLLANYEKIATR  300
UPI0001C0B12E  T-EPYMEVTKPITSGEFLTFGGNDVNKIPQLIQSQLRSKVLDDYEKIASR  298
UPI0001C0B1D1  KQAPLMIAEKPIRLEEFLTFGGQDLNIITSAMKEKIYNNLLANYEKIATR  300
UPI0000126B8A  KQAPLMIAEKPIRLEEFLTFGGQDLNIITSAMKEKIYNNLLANYEKIATR  300
UPI0001C0B1D0  KQAPLMIAEKPIRLEEFLTFGGQDLNIITSAMKEKIYNNLLANYEKIATR  300
UPI0004E7C8CE  KQAPLMIAEKPIRLEEFLTFGGQDLNIITSAMKEKIYNNLLANYEKIATR  300
UPI0001DE3DAC  DQGALMAAEKDIKIEEFITFGGQDLNIITNSTNQKIYDNLLSNYTAIASR  292
UPI0001C0B220  DQGALMAAEKDIKIEEFITFGGQDLNIITNSTNQKIYDNLLSNYTAIASR  292
UPI00000BAF8C  DQGALMAAEKDIKIEEFITFGGQDLNIITNSTNQKIYVILLSNYTAIASR  292
UPI0001C0B221  DQGALMAAEKDIKIEEFITFGGQDLNIVTNSTNQKIYDNLLSNYTAIASR  292

Majority        LSEVNSAPPEYDINEYKDYFQWKYGLDKNADGSYTVNENKFNEIYKKLYS
                ----------+---------+---------+---------+---------+
                         310       320       330       340       350
                ----------+---------+---------+---------+---------+

UPI00000B66D1  LSRVNSAPPEYDINEYKDYFQWKYGLDKNADGSYTVNENKFNEIYKKLYS  350
UPI00016BB5D7  LREVNTAPPGYDINEYKDYFQWKYGLDKNADGSYTVNRNKFNEIYKKLYS  350
UPI00000B50F1  LREVNTAPPGYDINEYKDYFQWKYGLDKNADGSYTVNRNKFNEIYKKLYS  350
UPI0001C0B12F  LREVNTAPPEYDINEYKDYFQWKYGLDKNADGSYTVNRNKFNGIYKKLYS  350
UPI0001A92658  LSEVNSAPPEYDINEYKNYFQWKYGLDKNADGSYTVNENKFNEIYKKLYS  350
UPI0001C0B12D  LSEVNSAPPEYDINEYKDYFQWKYGLDKNADGSYTVNENKFNEIYKKLYS  350
UPI0001C0B12E  LNKVNRATAEININDKFKYSYQLKYQFVKDSNGVYSVDLDKFNKLYDKIYS  348
UPI0001C0B1D1  LSEVNSAPPEYDINEYKDYFQWKYGLDKNADGSYTVNENKFNEIYKKLYS  350
UPI0000126B8A  LSEVNSAPPEYDINEYKDYFQWKYGLDKNADGSYTVNENKFNEIYKKLYS  350
```

FIG. 4C

```
UPI0001C0B1D0  LSEVNSAPPEYDINEYKDYFQWKYGLDKNADGSYTVNENKFNEIYKKLYS    350
UPI0004E7C8CE  LSEVNSAPPEYDINEYKDYFQWKYGLDKNADGSYTVNENKFNEIYKKLYS    350
UPI0001DE3DAC  LSQVNINNSALNTTYYKNFFQWKYGLDQDSNGNYTVNISKFNAIYKKLFS    342
UPI0001C0B220  LSQVNINNSALNTTYYKNFFQWKYGLDQDSNGNYTVNISKFNAIYKKLFS    342
UPI00000BAF8C  LSQVNRNNSALNTTYYKNFFQWKYGLDQDSNGNYTVNISKFNAIYKKLFS    342
UPI0001C0B221  LSQVNINNSALNTTYYKNFFQWKYGLDQDSNGNYTVNISKFNAIYKKLFS    342

Majority       FTEIDLANKFKVKCRNTYFIK-YGFLKVPNLLDDDIYTVSEGFNIGNLAV
               ---------+---------+---------+---------+---------+
                       360       370       380       390       400
               ---------+---------+---------+---------+---------+
UPI00000B66D1  FTEIDLANKFKVKCRNTYFIK-YGFLKVPNLLDDDIYTVSEGFNIGNLAV    399
UPI00016BB5D7  FTEIDLANKFKVKCRNTYFIK-YGFVKVPDLLDDDIYTVSEGFNIGNLAV    399
UPI00000B50F1  FTEIDLANKFKVKCRNTYFIK-YGFVKVPNLLDDDIYTVSEGFNIGNLAV    399
UPI0001C0B12F  FTEIDLANKFKVKCRNTYFIK-YGFVKVPDLLDDDIYTVSEGFNIGNLAV    399
UPI0001A92658  FTEIDLANKFKVKCRNTYFIK-YGFLKVPNLLDDDIYTVSEGFNIGNLAV    399
UPI0001C0B12D  FTEIDLANKFKVKCRNTYFIK-YGFLKVPNLLDDDIYTVSEGFNIGNLAV    399
UPI0001C0B12E  FTEFNLAHEFKIKTRNSYLAKNFGPFYLPNLLDNSIYNEADGFNIGDLSV    398
UPI0001C0B1D1  FTESDLANKFKVKCRNTYFIK-YGFLKVPNLLDDDIYTVSEGFNIGNLAV    399
UPI0000126B8A  FTESDLANKFKVKCRNTYFIK-YEFLKVPNLLDDDIYTVSEGFNIGNLAV    399
UPI0001C0B1D0  FTESDLANKFKVKCRNTYFIK-YGFLKVPNLLDDDIYTVSEGFNIGNLAV    399
UPI0004E7C8CE  FTESDLANKFKVKCRNTYFIK-YGFLKVPNLLDDDIYTVSEGFNIGNLAV    399
UPI0001DE3DAC  FTECDLAQKFQVKNRSNYLFH-FKPFRLLDLLDDNIYSISEGFNIGSLRV    391
UPI0001C0B220  FTECDLAQKFQVKNRSNYLFH-FKPFRLLDLLDDNIYSISEGFNIGSLRV    391
UPI00000BAF8C  FTECDLAQKFQVKNRSNYLFH-FKPFRLLDLLDDNIYSISEGFNIGSLRV    391
UPI0001C0B221  FTECDLAQKFQVKNRSNYLFH-FKPFKLLDLLDDNIYSISEGFNIGSLRV    391

Majority       NNRGQNINLNPKIIDSIPDKGLVEKIVKFCKSIIPRKGTKAPPRLCIRVN
               ---------+---------+---------+---------+---------+
                       410       420       430       440       450
               ---------+---------+---------+---------+---------+
UPI00000B66D1  NNRGQNIKLNPKIIDSIPDKGLVEKIVKFCKSVIPRKGTKAPPRLCIRVN    449
UPI00016BB5D7  NNRGQNINLNPKIIDSIPDKGLVEKIIKFCKSIIPRKGTKQSPSLCIRVN    449
UPI00000B50F1  NNRGQNINLNPKIIDSIPDKGLVEKIIKFCKSIIPRKGTKQSPSLCIRVN    449
UPI0001C0B12F  NNRGQNINLNPKIIDSIPDKGLVEKIIKFCKSIIPRKGTKQSPSLCIRVN    449
UPI0001A92658  NNRGQNINLNPKIIDSIPDKGLVEKIVKLCKSIIPRKGTKAPPRLCIRVN    449
UPI0001C0B12D  NNRGQNINLNPKIIDSIPDKGLVEKIVKLCKSIIPRKGTKAPPRLCIRVN    449
UPI0001C0B12E  NYKGQVIGSDIDSIKKLEGQGVVSRVVRLCLNSSFKKNTKKP--LCITVN    446
UPI0001C0B1D1  NNRGQSIKLNPKIIDSIPDKGLVEKIVKFCKSVIPRKGTKAPPRLCIRVN    449
UPI0000126B8A  NNRGQSIKLNPKIIDSIPDKGLVEKIVKFCKSVIPRKGTKAPPRLCIRVN    449
UPI0001C0B1D0  NNRGQSIKLNPKIIDSIPDKGLVEKIVKFCKSVIPRKGTKAPPRLCIRVN    449
UPI0004E7C8CE  NNRGQSIKLNPKIIDSIPDKGLVEKIVKFCKSVIPRKGTKAPPRLCIRVN    449
UPI0001DE3DAC  NNNGQNINLNSRIVGPIPDNGLVERFVGLCKSIVSKKGTKNS--LCIKVN    439
UPI0001C0B220  NNNGQNINLNSRIVGPIPDNGLVERFVGLCKSIVSKKGTKNS--LCIKVN    439
UPI00000BAF8C  NNNGQNINLNSRIVGPIPDNGLVERFVGLCKSIVSKKGTKNS--LCIKVN    439
UPI0001C0B221  NNNGQNINLNSRIVGPIPDNGLVERFVGLCKSIVSKKGTKNS--LCIKVN    439

Majority       NRELFFVASESSYNENDINTPKEIDDTTNLNNNYRNNLDEVILDYNSETI
               ---------+---------+---------+---------+---------+
                       460       470       480       490       500
               ---------+---------+---------+---------+---------+
UPI00000B66D1  NRELFFVASESSYNENDINTPKEIDDTTNLNNNYRNNLDEVILDYNSETI    499
UPI00016BB5D7  NRELFFVASESSYNESDINTPKEIDDTTNLNNNYRNNLDEVILDYNSETI    499
UPI00000B50F1  NRELFFVASESSYNESDINTPKEIDDTTNLNNNYRNNLDEVILDYNSETI    499
UPI0001C0B12F  NRELFFVASESSYNESDINTPKEIDDTTNLNNNYRNNLDEVILDYNSETI    499
UPI0001A92658  NRELFFVASESSYNENDINTPKEIDDTTNLNNNYRNNLDEVILDYNSETI    499
UPI0001C0B12D  NRELFFVASESSYNENDINTPKEIDDTTNLNNNYRNNLDEVILDYNSETI    499
UPI0001C0B12E  NGDLFFIASEDSYGEDTINTPKEIDDTTLVPSFKNILDKVILDFNKQVT    496
UPI0001C0B1D1  NSELFFVASESSYNENDINTPKEIDDTTNLNNNYRNNLDEVILDYNSQTI    499
UPI0000126B8A  NSELFFVASESSYNENDINTPKEIDDTTNLNNNYRNNLDEVILDYNSQTI    499
UPI0001C0B1D0  NSELFFVASESSYNENDINTPKEIDDTTNLNNNYRNNLDEVILDYNSQTI    499
UPI0004E7C8CE  NSELFFVASESSYNENDINTPKEIDDTTNLNNNYRNNLDEVILDYNSQTI    499
UPI0001DE3DAC  NRDLFFVASESSYNENGINSPKEIDDTTITNNNYKKNLDEVILDYNSDAI    489
UPI0001C0B220  NRDLFFVASESSYNENGINSPKEIDDTTITNNNYKKNLDEVILDYNSDAI    489
UPI00000BAF8C  NRDLFFVASESSYNENGINSPKEIDDTTITNNNYKKNLDEVILDYNSDAI    489
UPI0001C0B221  NRDLFFVASESSYNENGINSPKEIDDTTITNNNYKKNLDEVILDYNSDAI    489
```

FIG. 4D

| | | |
|---|---|---|
| Majority | PQISNRTLNTLVQDDSYVPRYDSNGTSEIEEYDVVDLNVFFYLHAQKVPE | |
| | 510        520        530        540        550 | |
| UPI000003G6D1 | PQISNQTLNTLVQDDSYVPRYDSNGTSEIEEHNVVDLMVFFYLHAQKVPE | 549 |
| UPI000163B5D7 | PQISNPTLNTLVQDNSYVPRYDSNGTSEIEEYDVVDFNVFFYLHAQKVPE | 549 |
| UPI000000B50F1 | PQISNRTLNTLVQDNSYVPRYDSNGTSEIEEYDVVDFNVFFYLHAQKVPE | 549 |
| UPI0001C0B12F | PQISNRTLNTLVQDNSYVPRYDSNGTSEIEEYDVVDFNVFFYLHAQKVPE | 549 |
| UPI0001A92658 | PQISSQTLNTLVQDDSYVPRYDSNGTSEIEEHNVVDLNAFFYLHAQKVPE | 549 |
| UPI0001C0B12D | PQISSQTLNTLVQDDSYVPRYDSNGTSEIEEHNVVTLNAFFYLHAQKVPE | 549 |
| UPI0001C0B12E | PQIPNRRIRTDIQEDNYIPEYDSNGTSEIEEYNVVDLNAFFYLHAQKVPE | 546 |
| UPI0001C0B1D1 | PQISNRTLNTLVQDNSYVPRYDSNGTSEIEEYDVVDFNVFFYLHAQKVPE | 549 |
| UPI0000126B8A | PQISNRTLNTLVQDNSYVPRYDSNGTSEIEEYDVVDFNVFFYLHAQKVPE | 549 |
| UPI0001C0B1D0 | PQISNPTLNTLVQDNSYVPRYDSNGTSEIEEYDVVDFNVFFYLHAQKVPE | 549 |
| UPI0004E7C8CE | PQISNRTLNTLVQDNSYVPRYDSNGTSEIEEYDVVDFNVFFYLHAQKVPE | 549 |
| UPI0001DE3DAC | PNLSSRLLNTTAQNDSYVPRYDSNGTSEIKEYTVDKLNVFFYLYAQKAPE | 539 |
| UPI0001C0B220 | PNLSSRLLNTTAQNDSYVPKYDSNGTSEIKEYTVDKLNVFFYLYAQKAPE | 539 |
| UPI000000BAF8C | PNLSSRLLNTTAQNDSYVPKYDSMGTSEIKEYTVDKLNVFFYLYAQKAPE | 539 |
| UPI0001C0B221 | PNLSSRLLNATAQNDSYVPKYDSNGTSEINEYTVDKLNVFFYLYAQKAPE | 539 |

| | | |
|---|---|---|
| Majority | GETNISLTSSIDTALLEESKVYTPFSSEFIDTINKPVMAALFIDWISKVI | |
| | 560        570        580        590        600 | |
| UPI000003G6D1 | GETNISLTSSIDTALSEESQVYTPFSSEFINTINKPVHAALFISWINQVI | 599 |
| UPI000163B5D7 | GETNISLTSSIDTALLEESKVYTPFSSEFIDTINKPVNAALFIDWISKVI | 599 |
| UPI000000B50F1 | GETNISLTSSIDTALLEESKVYTPFSSEFIDTINKPVNAALFIDWISKVI | 599 |
| UPI0001C0B12F | GETNISLTSSIDTALLEKSKVYTPFSSEFIDTINESVNAALFIDWINKVI | 599 |
| UPI0001A92658 | GETNISLTSSIDTALSEESKVYTPFSSEFINNINKPVHAALFIGWISQVI | 599 |
| UPI0001C0B12D | GETNISLTSSIDTALGEESKVYTPFSSEFINNINKPVHAALFIGWISQVI | 599 |
| UPI0001C0B12E | GETNISLTSSIDTALLEESKVYTPFSSEFIDTINEPVNAALFIDWISKVI | 596 |
| UPI0001C0B1D1 | GETNISLTSSIDTALLEESKVYTPFSSEFIDTINKPVNAALFIDWISKVI | 599 |
| UPI0000126B8A | GETNISLTSSIDTALLEESKD--IFPSSEFIDTINKPVNAALFIDWISKVI | 598 |
| UPI0001C0B1D0 | GETNISLTSSIDTALLEESKVYTPFSSEFIDTINKPVNAALFIDWISKVI | 599 |
| UPI0004E7C8CE | GETNISLTSSIDTALLEESKVYTPFSSEFIDTINKPVNAALFIDWISKVI | 599 |
| UPI0001DE3DAC | GESAISLTSSVNTALLDASKVYTFFSSDFINTVNKPVQAALFISWIQQVI | 589 |
| UPI0001C0B220 | GESAISLTSSVNTALLDASKVYTFFSSDFINTVNKPVQAALFISWIQQVI | 589 |
| UPI000000BAF8C | GESAISLTSSVNTALLDASKVYTFFSSDFINTVNKPVQAALFISWIQQVI | 589 |
| UPI0001C0B221 | GESAISLTSSVDTALLDASKVYTFFSSDFINTVNKPVQAALFISWIQQVI | 589 |

| | | |
|---|---|---|
| Majority | RDFTTEATQKSTVDKIADISLIVPYVGLALNIGNEAEKGNFKEAFELLGA | |
| | 610        620        630        640        650 | |
| UPI000003G6D1 | RDFTTEATQKSTFDKIADISLVVPYVGLALNIVIEAEKGNFEEAFELLGA | 649 |
| UPI000163B5D7 | RDFTTEATQKSTVDKIADISLIVPYVGLALNIVIEAEKGNFEEAFELLGA | 649 |
| UPI000000B50F1 | RDFTTEATQKSTVDKIADISLIVPYVGLALNIVIEAEKGNFEEAFELLGA | 649 |
| UPI0001C0B12F | RDFTTEATQKSTVDKIADISLIVPYVGLALNIVIDAEKGNFQEAFELLGA | 649 |
| UPI0001A92658 | RDFTTESTQKSTVDKIADISLIVPYVGLALNIGNDARKGNFKEAFELLGA | 649 |
| UPI0001C0B12D | RDFTTESTQKSTVDKIADISLIVPYVGLALNIGNDARKGNFKEAFELLGA | 649 |
| UPI0001C0B12E | RDFTTEATQKSTVDKIADISLIVPYVGLALNIVNEYEKGNFKEAFELLGA | 646 |
| UPI0001C0B1D1 | RDFTTEATQKSTVDKIADISLIVPYVGLALNIIIEAEKQNFEEAFELLGV | 649 |
| UPI0000126B8A | RDFTTEATQKSTVDKIADISLIVPYVGLALNIIIEAERGNFEEAFELLGV | 648 |
| UPI0001C0B1D0 | RDFTTEATQKSTVDKIADISLIVPYVGLALNIIIEAERGNFEEAFELLGV | 649 |
| UPI0004E7C8CE | RDFTTEATQKSTVDKIADISLIVPYVGLALNIIIEAERGNFEEAFELLGV | 649 |
| UPI0001DE3DAC | NDFTTEATQKSTIDKIADISLVVPYVGLALNIGNEVQKGNFKEAIELLGA | 639 |
| UPI0001C0B220 | NDFTTEATQKSTIDKIADISLVVPYVGLALNIGNEVQKGNFKEAIELLGA | 639 |
| UPI000000BAF8C | NDFTTEATQKSTIDKIADISLIVPYVGLALNIGNEVQKGNFKEAIELLGA | 639 |
| UPI0001C0B221 | NDFTTEATQKSTIDKIADISLVVPYVGLALNIGNEVQKGNFKEAIELLGA | 639 |

| | | |
|---|---|---|
| Majority | GILLEFVPELXIPVILVFTIKSYIDSYENKNKIIKAINNSLIEREAKWKE | |
| | 660        670        680        690        700 | |
| UPI000003G6D1 | GILLEFVPELLIPTILVFTIKSFIGSSENKNKIIKAINNSLMEREIKWKE | 699 |
| UPI000163B5D7 | GILLEFVPELTIPVILVFTIKSYIDSYENKNKAIKAINNSLIEREAKWKE | 699 |

FID. 4E

```
UPI000003B66D1  GILLEFVPELTIPVILVFTIKSYIDSYENKNKAIKAINNSLIEREAKWKE  699
UPI0001C0B12F   GILLEFVPELTIPVILVFTIKSYIDSYENKNKAIKAINNSLIEREAKWKE  699
UPI0001A92658   AILLEVVPELLIPVILVFTIKSFIDSSKNEDKIIKAINNSLIEREARWKE  699
UPI0001C0B12D   AILLEVVPELLIPVILVFTIKSFIDSSKNEDKIIKAINNSLIEREAKWKE  699
UPI0001C0B12E   GILLEFVPELAIPVILVFTIKSYIDSYENKNKIIKAINNSLIEREAKWKE  696
UPI0001C0B1D1   GILLEFVPELTIPVILVFTIKSYIDSYENKNKAIKAINNSLIEREAKWKE  699
UPI00001268BA   GILLEFVPELTIPVILVFTIKSYIDSYENKNKAIKAINNSLIEREAKWKE  698
UPI0001C0B1D0   GILLEFVPELTIPVILVFTIKSYIDSYENKNKAIKAINNSLIEREAKWKE  699
UPI0004E7C8CE   GILLEFVPELTIPVILVFTIKSYIDSYENKNKAIKAINNSLIEREAKWKE  699
UPI0001DE3DAC   GILLEFVPELLIPTILVFTIKSFINSDDSKNKIIKAINNALRERELKWKE  689
UPI0001C0B220   GILLEFVPELLIPTILVFTIKSFINSDDSKNKIIKAINNALRERELKWKE  689
UPI00000BAF8C   GILLEFVPELLIPTILVFTIKSFINSDDSKNKIIKAINNALRERELKWKE  689
UPI0001C0B221   GILLEFVPELLIPTILVFTIKSFINSDDSKNKIIKAINNALRERELKWKE  689

Majority        IYSNIVSNWLTRINTQFNKRKEQMYQALQNQVDAIKTAIEYKYNNYTSDE
                    +         +         +         +         +
                   710       720       730       740       750
                    +         +         +         +         +
UPI000003B66D1  IYSNIVSNWLTRINTQFNKRKEQMYQALQNQVDAIKTVIEYKYNNYTSDE  749
UPI000163B5D7   IYSNIVSNWLTRINTQFNKRKEQMYQALQNQVDAIKTAIEYKYNNYTSDE  749
UPI000003B50F1  IYSNIVSNWLTRINTQFNKRKEQMYQALQNQVDAIKTAIEYKYNNYTSDE  749
UPI0001C0B12F   IYSNIVSNWLTKINTQFNKRKEQMYQALQNQVDAIKTAIEYKYNNYTSDE  749
UPI0001A92658   VYSNIVSNWLTRINTQFNKRKEQMYQALQNQVDAIKTVIEYKYNSYTSDE  749
UPI0001C0B12D   VYSNIVSNWLTRINTQFNKRKEQMYQALQNQVDAIKTVIEYKYNSYTSDE  749
UPI0001C0B12E   IYSNIVSNWLTRINTQFNKRKEQMYQALQNQVDAIKTAIEYKYNNYTSDE  746
UPI0001C0B1D1   IYSNIVSNWLTRINTQFNKRKEQMYQALQNQVDAIKTAIEYKYNNYTSDE  749
UPI00001268BA   IYSNIVSNWLTRINTQFNKRKEQMYQALQNQVDAIKTAIEYKYNNYTSDE  748
UPI0001C0B1D0   IYSNIVSNWLTPINTQFNKRKEQMYQALQNQVDAIKTAIEYKYNNYTSDE  749
UPI0004E7C8CE   IYSNIVSNWLTRINTQFNKRKEQMYQALQNQVDAIKTAIEYKYNNYTSDE  749
UPI0001DE3DAC   VYSNIVSNWLTRINTQFNKRKEQMYQALQNQVDGIKKIIEYKYNNYTLDE  739
UPI0001C0B220   VYSNIVSNWLTRINTQFNKRKEQMYQALQNQVDGIKKIIEYKYNNYTLDE  739
UPI00000BAF8C   VTSNIVSNWLTRINTQFNKRKEQMYQALQNQVDGIKKIIEYKYNNYTLDE  739
UPI0001C0B221   VYSNIVSNWLTRINTQFNKRKEQMYQALQNQVDGIKKIIEYKYNNYTLDE  739

Majority        KNRLESEYNINNIEEELNKKVSLAMKNIERFMTESSISYLMKLINEAKVG
                    +         +         +         +         +
                   760       770       780       790       800
                    +         +         +         +         +
UPI000003B66D1  KNRLESEYNINNIEEELNKKVSLAMENIERFITESSIFYLMKLINEAEVG  799
UPI000163B5D7   KNRLESKYNINNIEEELNKKVSLAMENIERFITESSISYLMKLINEAEVG  799
UPI000003B50F1  KNRLESKYNINNIEEELNKKVSLAMKNIERFMTESSISYLMKLINEAEVG  799
UPI0001C0B12F   KNRLESEYNINNIEEELNKKVSLAMKNIERFMTESSISYLMKLINEAEVG  799
UPI0001A92658   KNRLESEYNINNIEEELNKKVSLAMKNIERFIAESSISYLMKLINEAKVG  799
UPI0001C0B12D   KNRLESEYNINNIEEELNKKVSLAMKNIERFIAESSISYLMKLINEAKVG  799
UPI0001C0B12E   KNRLESEYNINNIEEELNKKVSLAMKNIERFITESSISYLMKLINEAEVG  796
UPI0001C0B1D1   KNRLESEYNINNIEEELNKKVSLAMKNIERFMTESSISYLMKLINEAKVG  799
UPI00001268BA   KNRLESEYNINNIEEELNKKVSLAMKNIERFMTESSISYLMKLINEAKVG  798
UPI0001C0B1D0   KNRLESEYNINNIEEELNKKVSLAMKNIERFMTESSISYLMKLINEAKVG  799
UPI0004E7C8CE   KNRLESEYNINNIEEELNKKVSLAMKNIEPFMTESSISYLMKLINEAKVG  799
UPI0001DE3DAC   KNRLKAETNIYSIKEELNKKVSLAMQNIDRFLTESSISYLMKLINEAKIN  789
UPI0001C0B220   KNRLKAETNIYSIKEELNKKVSLAMQNIDRFLTESSISYLMKLINEAKIN  789
UPI00000BAF8C   KNRLRAETNIYSIKEELNKKVSLAMQNIDRFLTESSISYLMKLINEAKIN  789
UPI0001C0B221   KNRLKAETNIYNIKEELNKKVSLAMQNIDRFLTESSISYLMKLINEAKIN  789

Majority        KLKEYDKHVKSXLLNYILXHRSILGEQ XQELNDLVTSTLNSSIPFELSS
                    +         +         +         +         +
                   810       820       830       840       850
                    +         +         +         -         +
UPI000003B66D1  KLKEYDEGVKEYLLDYISEHPSILGNS  VQELNDLVTSTLNSSIPFELSS  848
UPI000163B5D7   KLKEYDKHVKSDLLDYILYKKLGEQ    TKELIDLVTSTLNSSIPFELSS  848
UPI000003B50F1  KLKEYDKHVKSDLLDYILYHKLILGEQ  TKELIDLVTSTLNSSIPFELSS  848
UPI0001C0B12F   KLKKYDKHVKSDLLDYILYHKLIGDQ   TKELIDLVTSTLNSSIPFELSS  848
UPI0001A92658   ELREYDEGVKEYLLDYILKNGSILGDH  VQELNDLVTSTLNSSIPFELSS  848
UPI0001C0B12D   ELREYDEGVKEYLLDYILKNGSILGDH  VQELNDLVTSTLNSSIPFELSS  848
UPI0001C0B12E   KLKEYDKRVNPHLLEYIFDYRLILGEQ  GGELIDLVTSTLNTSIPFELSS  845
UPI0001C0B1D1   KLKKYDNHVKSDLLNYILDHRSILGEQ  TNELSDLVTSTLNSSIPFELSS  848
UPI00001268BA   KLKKYDNHVKSDLLNYILDHRSILGEQ  TNELSDLVTSTLNSSIPFELSS  847
```

FIG. 4F

```
UPI00001C0B1D0  KLKSYDNBVKSDLLNYILDHRSILGEQ-TNELSDLVTSTLNSSIPFELSS  848
UPI0004E7C8CE  KLKKYDNBVKSDLLNYILDHRSILGEQ-TNELSDLVTSTLNSSIPFELSS  848
UPI0001DE3DAC  KLSEYDKRVNQYLLNYILENSSTLGTSSVQELNNLVSNTLNNSIPFELSE  839
UPI0001C0B220  KLSEYDKRVNQYLLNYILENSSTLGTSSVQELNNLVSNTLNNSIPFELSE  839
UPI00000AF8C   KLSEYDKRVNQYLLNYILENSSTLGTSSVQELNNLVSNTLNNSIPFELSE  839
UPI0001C0B221  KLSEYDKRVNQYLLNYILENSSTLGTSSVQELNNLVSNTLNNSIPFELSE  839

Majority       YTNDKILIYFNRLYKKIKDSSILDMRYENNKFIDISGYGSNISINGNVY
                    +         +         +         +         +
                   860       870       880       890       900
                    +         +         +         +         +
UPI00000B66D1  YTNDKILILYFNKLYKKIKDNSILDMRYENNKFIDISGYGSNISINGDVY  898
UPI00016BB5D7  YTNDKILIYFNRLYKKIKDSSILDMRYENNKFIDISGYGSNISINGNVY  898
UPI00000B50F1  YTNDKILIYFNRLYKKIKDSSILDMRYENNKFIDISGYGSNISINGNVY  898
UPI0001C0B12F  YTNDKILIYFNRLYKKIKDSSILDMRYENNKFIDISGYGSNISINGNVY  898
UPI0001A92658  YTNDKILIYFNKLYKKIKDNCILDMRYENNKFIDISGYGSNISINGELY  898
UPI0001C0B12D  YTNDKILIYFNKLYKKIKDNCILDMRYENNKFIDISGYGSNISINGELY  898
UPI0001C0B12E  YTNDKILIYFNRLYKKIKDSSILDMRYENNKFIDISGYGSNISINGNVY  895
UPI0001C0B1D1  YTNDKILIYFNRLYKKIKDSSILDMRYENNKFIDISGYGSNISINGNVY  898
UPI000126BBA   YTNDKILIYFNRLYKKIKDSSILDMRYENNKFIDISGYGSNISINGNVY  897
UPI0001C0B1D0  YTNDKILIYFNRLYKKIKDSSILDMRYENNKFIDISGYGSNISINGNVY  898
UPI0004E7C8CE  YTNDKILIYFNRLYKKIKDSGILDMRYENNKFIDISGYGSNISINGNVY  898
UPI0001DE3DAC  YTNDKILISFNRFYKKILDSSILDMRYENNRFIDSSGYGSNISINGDIY  889
UPI0001C0B220  YTNDKILISYFNRFYKRIILSSILDMRYENNRFIDSSGYGSNISINGDIY 889
UPI00000AF8C   YTNDKILIHILIRFYKRIIDSSILDMRYENNRFIDSSGYGSNISINGDIY 889
UPI0001C0B221  YTNDKILISYFNRFYKRIILSSILDMRYENNRFIDSSGYGSNISINGDIY 889

Majority       IYSTNRNQFGIYSSRLSEVNIAQNNDIIYNGRYQNFSISFWVRIPKHYNP
                    +         +         +         +         +
                   910       920       930       940       950
                    +         +         +         +         +
UPI00000B66D1  IYSTNRNQFGIYSSRPSEVNIAQNNDIIYNGRYQNFSISFWVRIPKYPNK  948
UPI00016BB5D7  IYSTNRNQFGIYSGRLSEVNIAQNNDIIYNSRYQNFSISFWVRIPKHYRP  948
UPI00000B50F1  IYSTNPNQFGIYSGRLSEVNIAQNNDIIYNSRYQNFSISFWVTIPKHYGP  948
UPI0001C0B12F  IYSTNPNQFGIYSDRLSEVNIAQNNDIIYNGRYQNFSISFWVRIPKHYGP  948
UPI0001A92658  IYTTNRNQFTIYSGKLSEVNIAQNNDIIYNSRYQNFSISFWVRIPRYSNI  948
UPI0001C0B12D  IYTTNRNQFTIYSGKLSEVNIAQNNDIIYNSRYQNFSISFWVRIPRYGNI  948
UPI0001C0B12E  IYSTNRNQFGIYDDRLSEVNIAQNNDIIYNSRYQNFSISFWVRIPKHYRP  945
UPI0001C0B1D1  IYSTNPNQFGIYNGRLSEVNIAQNNDIIYNSRYQNFSISFWVPIPKHYKP  948
UPI000126BBA   IYSTNRNQFGIYNGRLSEVNIAQNNDIIYNSRYQNFSISFWVRIPKHYKP  947
UPI0001C0B1D0  IYSTNRNQFGIYNGRLSEVNIAQNNDIIYNSRYQNFSISFWVRIPKHYKP  948
UPI0004E7C8CE  IYSTNRNQFGIYNGRLSEVNIAQNNDIIYNSRYQNFSISFWVRIPRHYKP  948
UPI0001DE3DAC  IYSTNRNQFGIYSGRLSEVNITQNNTIIYNSRYQNFSVSFWVRIPKYNNL  939
UPI0001C0B220  IYSTNRNQFGIYSGRLSEVNITQNNTIIYNSRYQNFSVSFWVRIPKYNNL  939
UPI00000AF8C   IYSTNRNQFGIYSGRLSEVNITQNNTIIYNSRYQNFSVSFWVRIPKYNNL  939
UPI0001C0B221  IVSTNPNQFGIYSGRLSEVNITQNNTIIYNSRYQNFSVSFWVRIPKYNNL  939

Majority       MNLNREYTIINCMGNNNSGWKISLRXNKDCEIIWTLQDTGGNKEKLIPPY
                    +         +         +         +         +
                   960       970       980       990      1000
                    +         +         +         +         +
UPI00000B66D1  VNLNREYTIIDCIRNNNSGWKISLNYN   KIIWTLQDTAGNNQKLVFNY  995
UPI00016BB5D7  MRPNREYTIINCMGNNNSGWKISLRTIRDCEIIWTLQDTSGNKEKLIFRY  998
UPI00000B50F1  MNPNREYTIINCMGNNNSGWKISLRTIRDCEIIWTLQDTSGNKEKLIFRY  998
UPI0001C0B12F  MNRNPEYTIINCMGNNNSGWKISLRNIRDCEIIWTLQETSGNKEKLIFPY  998
UPI0001A92658  VNLNNEYTIINCMGNNNSGWKISLNYN   KIIWTLQETAGNNEKLVFNY  995
UPI0001C0B12D  VNLNNEYTIINCMGNNNSGWKISLNYN   KIIWTLQDTAGNNEKLVFNY  995
UPI0001C0B12E  MNHNREYTIINCMGNNNSGWKISLRTTGDCEIIWTLQDTSGNKEKLIFRY  995
UPI0001C0B1D1  MNHNREYTIINCMGNNNSGWKISLRTVRDCEIIWTLQDTSGNKEKLIFPY  998
UPI000126BBA   MNHNREYTIINCMGNNNSGWKISLRTVRDCEIIWTLQDTSGNKEKLIFRY  997
UPI0001C0B1D0  MRHNREYTIINCMGNNNSGWKISLRTVRDCEIIWTLQDTSGNKEKLIFRY  998
UPI0004E7C8CE  MNHNREYTIINCMGNNNSGWKISLRTVRDCEIIWTLQDTSGNKENLIFRY  998
UPI0001DE3DAC  KNLNNEYTIINCMRNNNSGWKISLNYN   NIIWTLQDTTGNNQKLVFNY  986
UPI0001C0B220  KNLNNEYTIINCMRNNNSGWKISLNYN   NIIWTLQDTTGNNQKLVFNY  986
UPI00000AF8C   KNLNNEYTIINCMRNNNSGWKISLNYN   NIIWTLQDTTGNNQKLVFNY  986
UPI0001C0B221  KNLNNEYTIINCMRNNNSGWKISLNYN   NIIWTLQDTTGNNQKLVFNY  986
```

FIG. 4G

```
Majority         XQLISISDYINKWIFVTITNNRLGNSRIYINGNLIVEKSISNLGDIHVSD
                 +         +         +         +         +
                 1010      1020      1030      1040      1050
                 +         +         +         +         +
UPI000008660D1   TQMISISDYINKWIFVTITNNRLGNSRIYINGNLIDEKSISNLGDIHVSD   1045
UPI00016BB5D7    EELASISDYINKWIFVTITNNRLGNSRIYINGNLIVEKSISNLGDIHVSD   1048
UPI000008B50F1   EELAGISDYINKWIFVTITNNRLGNSRIYINGNLIVEKSISNLGDIHVSD   1048
UPI0001C0B12F    EELANISDYINKWIFVTITNNRLGNSRIYINGNLIVEKSISNLGDIHVSD   1048
UPI0001A92658    TQMISISDYINKWIFVTITNNRLGNSRIYINGNLIDQKSISNLGDIHVSD   1045
UPI0001C0B12D    TQMISISDYINKWIFVTITNNRLGNSRIYINGNLIDQKSISNLGDIHVSD   1045
UPI0001C0B12E    SQLKGISDYINKWIFVTITNNRLGNSRIYINGNLIVEKSISNLGDIHVSD   1045
UPI0001C0B1D1    EELNRISNYINKWIFVTITNNRLGNSRIYINGNLIVEKSISNLGDIHVSD   1048
UPI000012688A    EELNRISNYINKWIFVTITNNRLGNSRIYINGNLIVEKSISNLGDIHVSD   1047
UPI0001C0B1D0    EELNRISNYINKWIFVTITNNRLGNSRIYINGNLIVEKSISNLGDIHVSD   1048
UPI0004E7C8CE    EELNRISNYINKWIFVTITNNRLGNSKIYINGNLIVEKSISNLGDIHVSD   1048
UPI0001DE3DAC    TQMIDISDYINKWTFVTITNNRLGNSKLYINGNLTDQKSILNLGNIHVDD   1036
UPI0001C0B220    TQMIDISDYINKWTFVTITNNRLGNSKLYINGNLTDQKSILNLGNIHVDD   1036
UPI000008AF8C    TQMIDISDYINKWTFVTITNNRLGNSKLYINGNLTDQKSILNLGNIHVDD   1036
UPI0001C0B221    TQMIDISDYINKWTFVTITNNRLGNSKLYINGNLTDQKSISNLGNIHVDD   1036

Majority         NILPKIVGCDDTXYVGIRYPKVFNTELDKTEIETLYSNEPDPSILKDYWG
                 +         +         +         +         +
                 1060      1070      1080      1090      1100
                 +         +         +         +         +
UPI000008660D1   NILPKIVGCNDTRYVGIRYPKVFDTELGKTEIETLYSDEPDPSILKDFWG   1095
UPI00016BB5D7    NILPKIVGCDDETYVGIRYPKVFNTELDKTEIETLYSNEPDPSILKDYWG   1098
UPI000008B50F1   NILPKIVGCDDETYVGIRYPKVFNTELDKTEIETLYSNEPDPSILKDYWG   1098
UPI0001C0B12F    NILPKIVGCDDKTYVGIRYPKVFNTELDKTEIETLYSNEPDPSILKDYWG   1098
UPI0001A92658    NILPKIVGCNDTRYVGIRYPKVFDTELDKTEIETLYSDEPDPSILKDFWG   1095
UPI0001C0B12D    NILPKIVGCNDTRYVGIPYPKVFDTELDKTEIETLYSDEPDPSILKDFWG   1095
UPI0001C0B12E    NILPKIVGCDDKMYVGIRYPKVFNTELDKTEIETLYSNEPDPSILKDYWG   1095
UPI0001C0B1D1    NILPKIVGCDDETYVGIRYPKVFNTELDKTEIETLYSNEPDPSILKDYWG   1098
UPI000012688A    NILPKIVGCDDETYVGIRYPKVFNTELDKTEIETLYSNEPDPSILKNYWG   1097
UPI0001C0B1D0    NILPKIVGCDDETYVGIRYPKVFNTELDKTEIETLYSNEPDPSILKDYWG   1098
UPI0004E7C8CE    NILPKIVGCDDETYVGIRYPKVFNTELDKTEIETLYSNEPDPSILKDYWG   1098
UPI0001DE3DAC    NILPKIVGCNDTRYVGIRYPKIFNMELDKTEIETLYHSEPDSTILKDFWG   1086
UPI0001C0B220    NILPKIVGCNDTRYVGIRYPKIFNMELDKTEIETLYHSEPDSTILKDFWG   1086
UPI000008AF8C    NILPKIVGCNDTRYVGIRYPKIFNMELDKTEIETLYHSEPDSTILKDFWG   1086
UPI0001C0B221    NILPKIVGCNDTRYVGIPYPKIFNMELDKTEIETLYHSEPDSTILKDFWG   1086

Majority         NYLLYNKKYYLLRLLRKDKYITXNSGILNINQQRGVTEX-XIFSNYKLYE
                 +         +         +         +         +
                 1110      1120      1130      1140      1150
                 +         +         +         +         +
UPI000008660D1   NYLLYNKRYYLLNLLRTDKSITQNSNFLNINQQRGVTQKPNIFSNTPLYT   1145
UPI00016BB5D7    NYLLYNKKYYLFNLLRKDKYITRNSGILNINQQRGVTGGISVFLNYKLYE   1148
UPI000008B50F1   NYLLYNKKYYLFNLLRKDKYITRNSGILNINQQRGVTGGISVFLNYKLYE   1148
UPI0001C0B12F    NYLLYNKKYYLFNLLRKDKYITRNSGILNINQQRGVTEG-SVFLNYKLYE   1147
UPI0001A92658    NYLLYNKRYYLLNLLRKDKSITQSSTFLSISRPRGVDRKANIFSNKRLYR   1145
UPI0001C0B12D    NYLLYNPRYYLLNLLRKDNAITQSSTFLSISRARGVDRKANIFSNKRLYK   1145
UPI0001C0B12E    NYLLYNKKYYLNLLRNDKYITRNSDILNISHQRGVTKDLFIFSNYKLYE   1145
UPI0001C0B1D1    NYLLYNKKYYLFNLLRKDKYITLNSGILNINQQRGVTEG-SVFLNYKLYE   1147
UPI000012688A    NYLLYNKKYYLFNLLRKDKYITLNSGILNINQQRGVTEG-SVFLNYKLYE   1146
UPI0001C0B1D0    NYLLYNKKYYLFNLLRKDKYITLNSGILNINQQRGVTEG-SVFLNYKLYE   1147
UPI0004E7C8CE    NYLLYNKKYYLFNLLRKDKYITLNSGILNINQQRGVTEG-SVFLNYKLYE   1147
UPI0001DE3DAC    NYLLYNKKYYLLNLLKPNMSVTKNSDILNINRQRGIYSKTNIFSNARLYT   1136
UPI0001C0B220    NYLLYNKKYYLLNLLKPNMSVTKNSDILNINRQRGIYSKTNIFSNARLYT   1136
UPI000008AF8C    NYLLYNKKYYLLNLLKPNMSVTKNSDILNINRQRGIYSKTNIFSNARLYT   1136
UPI0001C0B221    NYLLYNKKYYLLNLLKPNMSVTKNSDILNINRQRGIYSKTWIFSNARLYT   1136

Majority         GVEVIIRKNGPIDISNTDNFVRKNDLAYINVVDRGVEYRLYADTSIXKPE
                 +         +         +         +         +
                 1160      1170      1180      1190      1200
                 +         +         +         +         +
UPI000008660D1   GVEVIIRKNGSTDISNTDNFVRKNDLAYINVVDRDVEYRLYADISIAKPE   1195
UPI00016BB5D7    GVEVIIRKNAPIDISNTDNFVRKNDLAYINVVDHGVEYRLYADISITKSE   1198
UPI000008B50F1   GVEVIIRKNAPIDISNTDNFVRKNDLAYINVVDHGVEYRLYADISITKSE   1198
```

FIG. 4H

```
UPI0001C0B12F  GVEVIIRKNGPIDISNTDNFVRKNDLAYINVVYDVEYRLYADISITKPE     1197
UPI0001A92658  GVEVIIRKNEPIDISNTDNFVRKGDLAYINVVDRDVEYRLYADTSNAQPE     1195
UPI0001C0B12D  GVEVIIPKMEPIDISNTDNFVPKGDLAYINVVDRDVEYRLYANTSNAQPE     1195
UPI0001C0B12E  GVEVIIRKNGPIDISNTDNFVRKNDLAYINVVDNGVEYRLYADISITKPE     1195
UPI0001C0B1D1  GVEVIIRKNGPIDIKSNTDNFVPKNDLAYINVVDKGVEYRLYADTKSEKE     1196
UPI000126B8A   GVEVIIRKNGPIDISNTDNFVRKNDLAYINVVDRGVEYRLYADTKSEKE      1195
UPI0001C0B1D0  GVEVIIRKNGPIDISNTDNFVPKNDLAYINVVDPGVEYRLYADTKSEKE      1196
UPI0004B7C8CE  GVEVIIPKNGPIDISNTDNFVPKNDLAYINVVDPGVEYRLYADTKSEKE      1196
UPI0001DE3DAC  GVEVIIRKVGSTDTSNTDNFVRKNDTVYINVVDGNSEYQLYADVSTSAVE     1186
UPI0001C0B22D  GVEVIIRKVGSTDTSNTDNFVPKNDTVYIRVVDGNSEYQLYADVSTSAVE     1186
UPI00000BAF8C  GVEVIIRKVGSTDTSNTDDFVRKNDTVYIDVVDGRSEYQLYADVSTSAVE     1186
UPI0001C0B221  GVEVIIRKFGSTDTSNTDNFVRKNDTVYISVVDGNSEYQLYADVSTSAVE     1186

Majority       KTIKLIRTSNSNDSLGQIIVMDSIGNNCTMNFQNRNGSNIGLLGFRSNNL
                    +         +         +         +         +
                   1210      1220      1230      1240      1250
                    +         +         +         +         +

UPI00000366D1           KIIKLIPTSNSNNSLGQIIVMDGIGNNCTMNFQNRNGGNIGLLGFRSNNL   1245
UPI00016BB5D7           KIIKLIPTSNPNDSLGQIIVMDSIGNNCTMNFQNNDGSNIGLLGFESDDL   1248
UPI00000350F1           KIIKLIRTSNPNDSLGQIIVMDSIGNNCTMNFQNNRGGSNIGLLGFESDDL  1248
UPI0001C0B12F           KIIKLIRTSNPNDSLGQIIVMDSIGNNCTMNFQNRNGGNIGLLGFRSDNL   1247
UPI0001A92658           KTIKLIPTSNPDDSLGQIIVMDSIGNNCTMNFQRNNGGNIGLLGFRSNTL   1245
UPI0001C0B12D           KTIKLIPTSNSNDSLGQIIVMDSIGNNCTMNFQNRNGGNIGLLGFRSNTL   1245
UPI0001C0B12E           KIIKLIRPSNPDDSLGQIIVMDSIGNNCTMNFQNRNGGNIGLLGFRSDNL   1245
UPI0001C0B1D1                KIIRTSNLNDSLGQIIVMDSIGNNCTMNFQNRNGSNIGLLGFRSNNL     1243
UPI000126B8A                 KIIRTSNLNDSLGQIIVMDSIGNNCTMNFQNRNGSNIGLLGFRSNNL     1242
UPI0001C0B1D0                KIIRTSNLNDSLGQIIVMDSIGNNCTMNFQNRNGSNIGLLGFRSNNL     1243
UPI0004B7C8CE                KIIRTSNLNDSLGQIIVMDSIGNNCTMNFQNRNGSNIGLLGFRSNNL     1243
UPI0001DE3DAC           RTIKLPRISNSNYNGNQMIIMDSIGDNCTMNFKTNNGNDIGLLGFRLNNL   1236
UPI0001C0B22D           KTIKLRPISNSNYNSNQMIIMDSIGDNCTMNFKTNNGNDIGLLGFRLNNL   1236
UPI00000BAF8C           KTIKLRPISNSNYNSNQMIIMDSIGDNCTMNFKTNNGNDIGLLGFRLNNL   1236
UPI0001C0B221           KTIKLRRISNSNYNSNQMIIMDSIGDNCTMNFKTNNGNDIGLLGFRLNNL   1236

Majority               VASSWYYNNIRRNTSSNGCFWSFISKEHGWQE
                            +         +         +
                           1260      1270      1280
                            +         +         +

UPI00000366D1           VASSWYYNNIRKNTSSNGCFWSFISKEHGWQEN    1278
UPI00016BB5D7           VASSWYYNHIRRNTSSNGCFWSFISKEHGWKE     1280
UPI00000350F1           VASSWYYNHIRRNTSSNGCFWSFISKEHGWKE     1280
UPI0001C0B12F           VASSWYYNNIRRNTSSNGCFWSFISKEHGWQE     1279
UPI0001A92658           VASSWYYNNIRRNTSSNGCFWSFISKERGWQEN    1278
UPI0001C0B12D           VASSWYYNNIRRNTSSNGCFWSFISKEHGWQE     1277
UPI0001C0B12E           VASSWYYNNIRRNTSSNGCFWSFISKEHGWQE     1277
UPI0001C0B1D1           VASSWYYNHIRRNTSSNGCFWSFISKENGWKE     1275
UPI000126B8A            VASSWYYNHIRRNTSSNGCFWSSISKENGWKE     1274
UPI0001C0B1D0           VASSWYYNNIRRNTSSNGCFWSFISKENGWKE     1275
UPI0004B7C8CE           VASSWYYNHIRPNTSSNGCFWSFISKEHGWKE     1275
UPI0001DE3DAC           VASSWYYKNIRNNTRNNGCFWSFISKEHGWQE     1268
UPI0001C0B22D           VASSWYYKNIRNNTRNNGCFWSFISKEHGWQE     1268
UPI00000BAF8C           VASSWYYKNIRNNTRNNGCFWSFISKEHGWQE     1268
UPI0001C0B221           VASSWYYKNIRNNTRNNGCFWSFISKEHGWQE     1268
```

FIG. 6A

```
SXN102875_rBoNT_F7   1   MPVNINNFNYNDPINNTTILYMKMPYYEDSNKYYKAFEIM    40
SXN102697_rBoNT_F7       MPVNINNFNYNDPINNTTILYMKMPYYEDSNKYYKAFEIM    40
SXN102691_rBoNT_F1       MPVVINSFNYNDPVNDDTILYMQIPYEEKSRKYYKAFEIM    40

SXN102875_rBoNT_F7   1   DNVWIIPERNIIGKKPSDFYPPISLDSGSSAYYDPNYLTT    80
SXN102697_rBoNT_F7       DNVWIIPERNIIGKKPSDFYPPISLDSGSSAYYDPNYLTT    80
SXN102691_rBoNT_F1       RNVWIIPERNTIGTDPSDFDPPASLENGSSAYYDPNYLTT    80

SXN102875_rBoNT_F7   1   DAEKDRFLKTVIKLFNRINSNPAGQVLLEEIKNGKPYLGN   120
SXN102697_rBoNT_F7       DAEKDRFLKTVIKLFNRINSNPAGQVLLEEIKNGKPYLGN   120
SXN102691_rBoNT_F1       DAEKDRYLKTTIKLFKRINSNPAGEVLLQEISYAKPYLGN   120

SXN102875_rBoNT_F7   1   DHTAVNEFCANNRSTSVEIKESKGTTDSMLINLVILGPGP   160
SXN102697_rBoNT_F7       DHTAVNEFCANNRSTSVEIKESKGTTDSMLINLVILGPGP   160
SXN102691_rBoNT_F1       EHTPINEFHPVTRTTSVNIKSSTNVKSSIILNLLVLGAGP   160

SXN102875_rBoNT_F7   1   NILECSTFPVR-IFPNNIAYDPSEKGFGSIQLMSFSTEYE   199
SXN102697_rBoNT_F7       NILECSTFPVR-IFPNNIAYDPSEKGFGSIQLMSFSTEYE   199
SXN102691_rBoNT_F1       DIFENSSYFVRKLMDSGGVYDPSNDGFGSINIVTFSPEYE   200

SXN102875_rBoNT_F7   1   YAFNDN---------TDLFIADPAISLAHELIHVLHGLYGAK   232
SXN102697_rBoNT_F7       YAFNDN---------TDLFIADPAISLAHELIHVLHGLYGAK   232
SXN102691_rBoNT_F1       YTFNDISGGYNSSTESFIADPAISLAHELIHALHGLYGAR   240

SXN102875_rBoNT_F7   1   GVTNKKVIEVDQGALMAAEKDIKIEEFITFGGQDLNIITN   272
SXN102697_rBoNT_F7       GVTNKRVIEVDQGALMAAEKDIKIEEFITFGGQDLNIITN   272
SXN102691_rBoNT_F1       GVTYKETIKVKQAPLMIAEKPIRLEEFLTFGGQDLNIITS   280

SXN102875_rBoNT_F7   1   STNQKIYDNLLSNYTAIASRLSQVNINNSALNTTYYKNFF   312
SXN102697_rBoNT_F7       STNQKIYDNLLSNYTAIASRLSQVNINNSALNTTYYKNFF   312
SXN102691_rBoNT_F1       AMREKIYNNILANYEKIATRLSRVNSAFFEYDINEYKDYF   320

SXN102875_rBoNT_F7   1   QWKYGLDQDSNGNYTVNISKFNAIYKKLFSFTECDLAQKF   352
SXN102697_rBoNT_F7       QWKYGLDQDSNGNYTVNISKFNAIYKKLFSFTECDLAQKF   352
SXN102691_rBoNT_F1       QWKYGLDKNADGSYTVNENKFNEIYKKLYSFTEIDLANKF   360

SXN102875_rBoNT_F7   1   QVKNRSNYLFHFKPFRLIDLLDDNIYSISEGFNIGSLRVN   392
SXN102697_rBoNT_F7       QVKNRSNYLFHFKPFRLIDLLDDNIYSISEGFNIGSLRVN   392
SXN102691_rBoNT_F1       KVRCRNTYFIKYGFLKVPNILDDDIYTVSEGFNIGNLAVN   400

SXN102875_rBoNT_F7   1   NNGQNINLNSRIVGPIPDNGLVERFVGLCKSVIPRKGTKA   432
SXN102697_rBoNT_F7       NNGQNINLNSRIVGPIPDNGLVERFVGLCKSIVSKKGTEN   432
SXN102691_rBoNT_F1       NRGQNIKLNPKIIDSIPDKGLVEKIVKFCKSVIPRKGTKA   440

SXN102875_rBoNT_F7   1   PPRLCIKVNNRDLFFVASESSYNENGINSPKEIDDTTITN   472
SXN102697_rBoNT_F7       --SLCIKVNNRDLFFVASESSYNENGINSPKEIDDTTITN   470
SXN102691_rBoNT_F1       PPRLCIPVNNRELFFVASESSYRENDINTPFEIDDTTNLN   480

SXN102875_rBoNT_F7   1   NNYKENLDEVILDYNSDAIPNLSSRLLNTTAQNDSYVPKY   512
SXN102697_rBoNT_F7       NNYKENLDEVILDYNSDAIPNLSSRLLNTTAQNDSYVPKY   510
SXN102691_rBoNT_F1       NNYENMLDEVILDYNSETIPQISNQTLNTLVQDDSYVPRY   520

SXN102875_rBoNT_F7   1   DSNGTSEIKEYTVDKLNVFFYLYAQKAPEGESAISLTSSV   552
SXN102697_rBoNT_F7       DSNGTSEIKEYTVDKLNVFFYLYAQKAPEGESAISLTSSV   550
SXN102691_rBoNT_F1       DSNGTSEIEENVVDLNVFPYLHAQKVPEGETNISLTSSI   560

SXN102875_rBoNT_F7   1   NTALLDASKVYTFFSSDFINTVNKFVQAALFISWIQQVIN   592
SXN102697_rBoNT_F7       NTALLDASKVYTFFSSDFINTVNKFVQAALFISWIQQVIN   590
SXN102691_rBoNT_F1       DTALSEESQVYTFFSSEFINTMNKPVEAALFISWINQVIR   600

SXN102875_rBoNT_F7   1   DFTTEATQKSTIDKIADISLVVPYVGLALNIGNEVQKGNF   632
SXN102697_rBoNT_F7       DFTTEATQKSTIDKIADISLVVPYVGLALNIGNEVQKGNF   630
SXN102691_rBoNT_F1       DFTTEATQKSTFDKIADISLVVPYVGLALNIGNEVQKENF   640

SXN102875_rBoNT_F7   1   KERIELLGAGILLEFVPELLIPTILVFTIKSFIGSDGSKN   672
```

FIG. 6B

| | | |
|---|---|---|
| SXN102697_rBoNT F7 | KEAIELLGAGILLEFVPELLIPTILVFTIKSFINGDDSKN | 670 |
| SXN102691_rBoNT F1 | KEAFELLGAGILLEFVPELLIPTILVFTIKSFIGSSENKN | 680 |
| | | |
| SXN102875_rBoNT F7 1 | KIIKAINNALRERELRWKEVYSWIVSNWLTRINTQFNKRK | 712 |
| SXN102697_rBoNT F7 | KIIKAINNALRERELRWKEVYSWIVSNWLTRINTQFNKRK | 710 |
| SXN102691_rBoNT F1 | KIIKAIMNSLMERETKWKEIYSWIVSNWLTRINTQFNKRK | 720 |
| | | |
| SXN102875_rBoNT F7 1 | EQMYQALQNQVDGIKKIIEYKYNNYTLDEKNRLKAEYNIY | 752 |
| SXN102697_rBoNT F7 | EQMYQALQNQVDGIKKIIEYKYNNYTLDEKNRLKAEYNIY | 750 |
| SXN102691_rBoNT F1 | EQMYQALQNQVDAIKTVIEYKYNNYTSDERNRLESEYNIN | 760 |
| | | |
| SXN102875_rBoNT F7 1 | SIKEELNKKVSLAMQNIDRFLTESSISYLMKLINEAKINK | 792 |
| SXN102697_rBoNT F7 | SIKEELNKKVSLAMQNIDRFLTESSISYLMKLINEAKINK | 790 |
| SXN102691_rBoNT F1 | NIREELNKKVSLAMENIERFITESSIFYLMKLINEAKVSK | 800 |
| | | |
| SXN102875_rBoNT F7 1 | LSEYDKRVNQYLLNYILENSSTLGTSSVQELNWLVSNTLN | 832 |
| SXN102697_rBoNT F7 | LSEYDKRVNQYLLNYILEMSSTLGTSSVQELNWLVSNTLN | 830 |
| SXN102691_rBoNT F1 | LREYDEGVKEYLLDYISEHRSILGN-SVQELNDLVTSTLN | 839 |
| | | |
| SXN102875_rBoNT F7 1 | NSIPFELSEYTNDKILISYFNRFYKRIIDSSILNMKYENN | 872 |
| SXN102697_rBoNT F7 | NSIPFELSEYTNDKILISYFNRFYKRIIDSSILNMKYENN | 870 |
| SXN102691_rBoNT F1 | NSIPFELSSYTNDKILILYFNRLYRRIKDNCILNMKTENN | 879 |
| | | |
| SXN102875_rBoNT F7 1 | RFIDSSGYGSNISINGDIYIYSTNRNQFGIYSSRLSEVNI | 912 |
| SXN102697_rBoNT F7 | RFIDSSGYGSNISINGDIYIYSTNRNQFGIYSSRLSEVNI | 910 |
| SXN102691_rBoNT F1 | RFIDIGGYGSNISINGDVYIYSTURNQFGIYSSKPSEVNI | 919 |
| | | |
| SXN102875_rBoNT F7 1 | TQNNTIIYNSRYQNFSVSFWVRIPKYNNLNNLNNEYTIIN | 952 |
| SXN102697_rBoNT F7 | TQNNTIIYNSRYQNFSVSFWVRIPKYNNLKNLNNEYTIIN | 950 |
| SXN102691_rBoNT F1 | AQNNDIIYNGRYQNFSISFWVRIPKYFNKVNLNNEYTIID | 959 |
| | | |
| SXN102875_rBoNT F7 1 | CMRNNRSGWKISLNYNNIIWTLQDTTGNNQKLVFNYTQMI | 992 |
| SXN102697_rBoNT F7 | CMRRNNSGWKISLNYNNIIWTLQDPTGNNQKLVFNYTQMI | 990 |
| SXN102691_rBoNT F1 | CIRNNNSGWKISLNYNKIIWTLQDTAGNNQKLVFNYTQMI | 999 |
| | | |
| SXN102875_rBoNT F7 1 | DISDYINKWTFVTITNMRLGNSKLYINGNLTDQKSILNLG | 1032 |
| SXN102697_rBoNT F7 | DISDYINKWTFVTITNMRLGNSKLYINGNLTDQKSILNLG | 1030 |
| SXN102691_rBoNT F1 | SISDYINKWIFVTITNNRLGNSRIYINGNLIDEKSISNLG | 1039 |
| | | |
| SXN102875_rBoNT F7 1 | NIRVDDNILFKIVGCNDTRYVGIRYFKIFNMELDKTEIET | 1072 |
| SXN102697_rBoNT F7 | NIRVDRNILFKIVGCNDTRYVGIRYFKIFNMELDKTEIET | 1070 |
| SXN102691_rBoNT F1 | DIRVSDNILFKIVGCNDTRYVGIRYFKVFDTELGKTEIET | 1079 |
| | | |
| SXN102875_rBoNT F7 1 | LYHSEPDSTILKDFWGNYLLYNKKYYLLNLLKPNNSVTPN | 1112 |
| SXN102697_rBoNT F7 | LYHSEPDSTILKDFWGNYLLYNKKYYLLNLLKPNNSVTKN | 1110 |
| SXN102691_rBoNT F1 | LYSDEPDPSILKDFWGNYLLYNKRYYLLNLLRTDKSITQN | 1119 |
| | | |
| SXN102875_rBoNT F7 1 | SDILNINRQRGIYSKTNIFSNARLYTGVEVIIRKVGSTDT | 1152 |
| SXN102697_rBoNT F7 | SDILNINRQRGIYGKTNIFSNARLYTGVEVIIRKVGSTDT | 1150 |
| SXN102691_rBoNT F1 | SNELNINQQRGVYQKPNIFSNTRLYTGVEVIIRKNGSTDI | 1159 |
| | | |
| SXN102875_rBoNT F7 1 | SNTDNFVRKNDTVYINVVDGNSEYQLYADVSTGAVEKTIK | 1192 |
| SXN102697_rBoNT F7 | SNTDNFVRKNDTVYINVVDGNSEYQLYADVSTGAVEKTIK | 1190 |
| SXN102691_rBoNT F1 | SNTDRFVRKNDLAYINVVDRDVEYRLYADISIAKPERIIK | 1199 |
| | | |
| SXN102875_rBoNT F7 1 | LRRISNSNYNSNQMIIMDSIGDNCTMNFKTINNGNDIGLLG | 1232 |
| SXN102697_rBoNT F7 | LRRISNSNYNGNQMIIMDSIGDNCTMNFKTNNGNDIGLLG | 1230 |
| SXN102691_rBoNT F1 | LIRTSNSNNSLGQIIVMDSIGNNCTMNFQNNGGNIGLLG | 1239 |
| | | |
| SXN102875_rBoNT F7 1 | FHLNNLVASSWYYNNIRNNTNNGCFWSFISKEHGWQE | 1271 |
| SXN102697_rBoNT F7 | FHLNNLVASSWYYKNIRNNTRNNGCFWSFISKEHGWQE | 1268 |
| SXN102691_rBoNT F1 | FHSNNLVASSWYYNNIPKNTSSNGCFWSFISKEKGWQEN | 1278 |

```
Majority        GLVEKIVKFCKSIIPRKGTKAPPRLCIRVNNRELFFVASES
                          →
SXN102691  F1   GLVEKIVKFCKSVIPRKGTKAPPRLCIRVNNRELFFVASES   460
SXN102692  F2   GLVEKIIKFCKSIIPRKGTKQSPSLCIRVNNRELFFVASES   460
SXN102693  F3   GLVEKIIKFCKSIIPRKGTKQSPSLCIRVNNRELFFVASES   460
SXN102694  F4   GLVEKIVKLCINSSFKKNTKKP--LCITVNNGDLFFIASED   457
SXN102695  F5   GVVSRVVRLCLNSSFKKNTKKP--LCITVNNGDLFFIASED   457
SXN102696  F6   GLVEKIVKFCKSVIPRKGTKAPPRLCIRVNNSELFFVASES   460
SXN102697  F7   GLVERFVGLCKSI SKKGTKNS--LC KVNNRDLFFVASES   450
                                       ↑
                                    Cut here
```

Figure 12

□ F/053112-01/MET
◉ rBoNT/F1 SXN102691
▲ rBoNT/F7-1 SXN102931

| protein | ED50 (pg/mouse) | DAS 4 dose (pg/mouse) |
|---|---|---|
| F/053112-01/MET | 12.1 [9.75-14.44] | 90 |
| rBoNT/F1 (SXN1029691) | 11.7 [9.68-13.69] | 90 |
| rBoNT/F7-1 (SXN102931) | 1.6 [1.41-1.83] | 22.5 | mean DAS max value vs Doses (pg/mouse)

CHIMERIC POLYPEPTIDES

This application is a national stage of International Patent Application No. PCT/EP2016/056275, filed Mar. 22, 2016, which claims the priority of United Kingdom Application No. 1505306.9, filed Mar. 27, 2015, the contents of each are hereby incorporated by reference in their entireties.

FIELD OF THE INVENTION

The invention relates to recombinant clostridial neurotoxins which have been modified to improve their activation. In particular, the present invention relates to chimeric clostridial neurotoxins in which the activation loop has been replaced by the activation loop from a different subtype within the same serotype. The present invention also relates to methods of producing such chimeric clostridial neurotoxins and methods of activating such modified clostridial neurotoxins, as well as polynucleotides, vectors and cells expressing such chimeric clostridial neurotoxins, compositions comprising such chimeric clostridial neurotoxins and uses thereof.

BACKGROUND OF THE INVENTION

Bacteria in the genus *Clostridia* produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

BoNT is produced by *C. botulinum* in the form of a large protein complex, consisting of BoNT itself complexed to a number of accessory proteins. There are at present at least seven different classes of botulinum neurotoxin, namely: botulinum neurotoxin serotypes A, B, $C_1$, D, E, F and G, all of which share similar structures and modes of action. A possible eighth serotype, H, has recently been reported. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are the most potent toxins known, with median lethal dose ($LD_{50}$) values for mice ranging from 0.5 to 5 ng/kg depending on the serotype. BoNTs can enter the body via the gastrointestinal tract and, after entering the general circulation, bind to the presynaptic membrane of cholinergic nerve terminals and prevent the release of the neurotransmitter acetylcholine. BoNT/B, BoNT/D, BoNT/F and BoNT/G cleave synaptobrevin/vesicle-associated membrane protein (VAMP); BoNT/$C_1$, BoNT/A, and BoNT/E cleave the synaptosomal-associated protein of 25 kDa (SNAP-25); and BoNT/$C_1$ cleaves syntaxin. While BoNTs act at the neuromuscular junction and inhibit cholinergic transmission in the peripheral nervous system, TeNT acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, which is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises a C-terminal targeting component ($H_C$ domain) and an N-terminal translocation component ($H_N$ domain). The cleavage site is located between the L-chain and the translocation components, in an exposed loop region called the activation loop (see FIG. 1 and Table 1). Following binding of the $H_C$ domain to its target neuron and internalisation of the bound toxin into the cell by endocytosis, the $H_N$ domain translocates the L-chain across the endocytosed membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial toxins are non-cytotoxic proteases that cleave SNARE proteins.

Under physiological conditions the BoNT heavy chain binds to neuronal gangliosides (via the $H_C$ domain), is received inside the cell by receptor-mediated endocytosis. In the acid medium of the endocytosed compartment, the $H_N$ domain penetrates into the vesicle membrane and forms a pore. The light chain (which is linked to the heavy chain via a disulphide bridge), will be cleaved off the heavy chain, by intracellular redox systems which gain access to the disulphide bridge and reduce it, such that the light chain will ultimately be released into the cytosol.

Botulinum neurotoxins are well known for their ability to cause a flaccid muscle paralysis. In view of the ubiquitous nature of SNARE proteins, clostridial toxins such as BoNTs have been successfully employed in a wide range of therapies. By way of example, we refer to William J. Lipham, Cosmetic and Clinical Applications of Botulinum Toxin (Slack, Inc., 2004), which describes the use of clostridial toxins, such as botulinum neurotoxins (BoNTs), BoNT/A, BoNT/B, BoNT/C1, BoNT/D, BoNT/E, BoNT/F and BoNT/G, and tetanus neurotoxin (TeNT), to inhibit neuronal transmission in a number of therapeutic and cosmetic or aesthetic applications—for example, marketed botulinum toxin products are currently approved as a therapeutic for indications such as focal spasticity, upper limb spasticity, lower limb spasticity, cervical dystonia, blepharospasm, hemifacial spasm, hyperhidrosis of the axillae, chronic migraine, neurogenic detrusor overactivity, glabellar lines, sever lateral canthal lines. In addition, clostridial toxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. Nos. 6,869,610, 6,641,820, 6,464,986, and 6,113,915); for treating fibromyalgia (see U.S. Pat. No. 6,623,742, US 2004/

0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. Nos. 6,620,415, 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. Nos. 6,337,075, 6,416,765); for treating a pancreatic disorder (see U.S. Pat. Nos. 6,261,572, 6,143,306); for treating cancers such as bone tumors (see U.S. Pat. Nos. 6,565,870, 6,368,605, 6,139,845, US 2005/0031648); for treating otic disorders (see U.S. Pat. Nos. 6,358,926, 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US 2004/40253274); for dental therapies and procedures (see US 2004/0115139); for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

Currently all approved drugs/cosmetic preparations comprising BoNTs contain either BoNT/A (e.g. DYSPORT®, BOTOX®, XEOMIN®) or BoNT/B neurotoxins (eg MYOBLOC®). Other BoNT serotypes and subserotypes have potentially desirable properties. However, it can be difficult to exploit those properties/BoNTs due to difficulties in converting the single-chain form of these BoNTs into the activated di-chain form.

Previous attempts to improve BoNT activation have included the use of a heterologous (exogenous) protease that cleaves the single-chain BoNT polypeptide into the active di-chain form, either by using a naturally occurring cleavage site found in the appropriate location within the BoNT polypeptide or by genetically engineering a protease cleavage site of a common, commercially available exogenous protease into the BoNT polypeptide.

A drawback to the use of exogenous proteases is a lack of protease specificity that results in inactive toxin because of proteolytic cleavage in inappropriate locations. For example, the protease most widely used for activation of clostridial neurotoxins, Trypsin, while being useful for activating clostridial neurotoxins of serotypes B (BoNT/B) and E (BoNT/E) appears to produce secondary products for other serotypes, presumably by proteolytic action near the C-terminus of the heavy subunit and, thus, can destroy BoNT binding to its cellular receptor. Thus, such methods of converting the single-chain form of some BoNTs into the active di-chain form are inefficient, cumbersome and/or lead to higher overall production costs.

The BoNT/A activation loop is highly conserved between subtypes (see FIG. 1). It is also the most studied, well understood and known to be an efficient BoNT activator. As a result and based on conventional knowledge, other previous attempts to improve BoNT activation have involved replacing the wild-type cleavage site within a given BoNT with the cleavage site from a BoNT serotype A, for example replacing the BoNT/B activation loop comprising the BoNT/B cleavage site with the BoNT/A activation loop comprising the BoNT/A cleavage site.

SUMMARY OF THE INVENTION

The present inventors have solved the problem that potentially desirable properties of natural BoNTs can be difficult to exploit and/or assess due to poor activation of some recombinant subtypes. In particular, the inventors have generated a recombinant botulinum toxin $F_7$ (rBoNT/$F_{7-1}$) in which the native BoNT/$F_7$ activation loop has been replaced with the BoNT/$F_1$ activation loop. BoNT/$F_7$ has a different mode of substrate binding compared to BoNT/$F_1$ (Kalb S. R. et al., Applied and environmental microbiology 77.4 (2011): 1301-1308). The inventors were therefore willing to test whether BoNT/$F_7$ had differentiated functional properties (such as potency), compared to BoNT/$F_1$, but found it is not easily activated. The inventors surprisingly solved this problem by combining the functional domains from $F_7$ with the activation loop from $F_1$. The inventors also surprisingly found that the chimeric BoNT/$F_{7-1}$ thus obtained had improved properties, in particular improved potency compared to BoNT/$F_1$.

Thus, the present inventors have developed a new way to make fully activated purified, recombinant botulinum neurotoxin (BoNT) proteins that contain desirable functional domains, which evolved within naturally occurring BoNT proteins, but which are not themselves amenable to production as recombinant proteins. The inventors have achieved this by making chimeric BoNTs, containing activation loops from subtypes of a particular BoNT serotype (exemplified by BoNT/F) that show good activation combined into subtypes from the same serotype that activate poorly but are otherwise attractive as possible new drugs.

The present inventors have also provided a new chimeric BoNT/$F_{7-1}$ which has differentiating properties over BoNT/F, in particular a higher potency which is a desirable feature for use in therapy.

Accordingly, the present invention provides a chimeric polypeptide comprising an $LH_N$ backbone from a first botulinum neurotoxin serotype F (BoNT/F) subtype and an activation loop region from a different BoNT/F subtype. The $LH_N$ backbone of the polypeptide may have at least 60% sequence identity with at least one of SEQ ID NO: 17 to 32. Typically, the $LH_N$ backbone of the polypeptide comprises: (a) a polypeptide sequence having at least 40% sequence identity at least one of SEQ ID NOs: 33 to 48; and/or (b) a polypeptide sequence having at least 70% sequence identity at least one of SEQ ID NOs: 49 to 64. Preferably the $LH_N$ backbone of the polypeptide is from a BoNT/$F_5$ subtype or a BoNT/$F_7$ subtype.

The activation loop of the polypeptide of the invention typically comprises an amino acid sequence fitting the consensus sequence KSIIPRKGTKAPPRL (SEQ ID NO: 65), or an amino acid sequence in which no more than five amino acids are added to, deleted from or substituted in the consensus sequence. The activation loop may be from a BoNT/F$_1$ subtype, a BoNT/F$_2$ subtype, a BoNT/F$_3$ subtype, a BoNT/F$_4$ or a BoNT/F$_6$ subtype. In one embodiment, the activation loop comprises an amino acid sequence selected from: KSVIPRKGTKAPPRL (SEQ ID NO: 66); KSIIPRKGTKQSPSL (SEQ ID NO: 67); or KSIIPRKGTKAPPRL (SEQ ID NO: 65).

Typically, the LH$_N$ backbone of the invention is from a BoNT/F$_7$ subtype and the BoNT/F activation loop comprises the amino acid sequence of KSVIPRKGTKAPPRL (SEQ ID NO: 66).

According to the present invention, the polypeptide typically comprises a cleavage site within the BoNT/F activation loop that is specifically recognised and cleaved (or cut) by an endopeptidase. Cleavage by the endopeptidase typically results in the formation of an active holotoxin.

The invention further provides a chimeric di-chain BoNT/F polypeptide comprising: (a) a light chain polypeptide comprising an amino acid sequence having at least 40% sequence identity at least one of SEQ ID NOs: 33 to 48; and (b) an H$_N$ polypeptide comprising an amino acid sequence having at least 70% sequence identity at least one of SEQ ID NOs: 49 to 64; wherein the N-terminus of the H$_N$ polypeptide comprises amino acid residues from a different BoNT/F subtype than the remainder of the H$_N$ polypeptide. Typically the N-terminal amino acid residue of the H$_N$ polypeptide sequence is A or Q. The N-terminus of the H$_N$ polypeptide sequence may begin with an amino acid motif selected from the group consisting of APPRLCIK (SEQ ID NO: 70), APPRLCIT (SEQ ID NO: 71), QSPSLCIK (SEQ ID NO: 72) and QSPSLCIT (SEQ ID NO: 73). The light chain polypeptide sequence and/or the H$_N$ polypeptide sequence of the di-chain polypeptide may be from a BoNT/F$_5$ subtype or a BoNT/F$_7$ subtype.

The di-chain polypeptide of the invention is typically obtainable from the single chain polypeptide of the invention as described herein.

The polypeptide or di-chain polypeptide of the invention may further comprise a targeting moiety which is adapted for binding of the polypeptide to a cell by binding of the targeting moiety directly to a cell or by binding of the targeting moiety to a ligand or ligands that bind to a cell. The targeting moiety may be a targeting moiety from a clostridial neurotoxin. Alternatively, the targeting moiety may be a non-clostridial targeting moiety.

The invention further provides a polynucleotide molecule encoding a polypeptide of the invention.

The invention further provides an expression vector comprising a polynucleotide of the invention, which is operably linked to a promoter.

The invention also provides a method of producing a polypeptide of the invention, comprising the step of expressing a polynucleotide of the invention in a cell, and recovering the expressed polypeptide. Said method may further comprise a step of introducing said polynucleotide into the cell.

The invention also provides a method of activating a polypeptide of the invention, comprising incubating said polypeptide with an endopeptidase, wherein cleavage of the polypeptide in the BoNT/F activation loop converts the polypeptide from a single-chain polypeptide into a di-chain polypeptide, thereby activating the polypeptide. Typically said endopeptidase is Lys-C.

The invention further provides a cell expressing a polypeptide of the invention. Said cell may comprise a polynucleotide or an expression vector of the invention.

The invention further provides a pharmaceutical composition comprising a polypeptide or di-chain polypeptide of the invention. Said pharmaceutical composition may further comprise a pharmaceutically acceptable excipient or diluent.

The invention also provides a pharmaceutical composition of the invention for use in a method of preventing or treating a disease or disorder for which a therapy with a botulinum neurotoxin is indicated.

The invention also provides a use of a pharmaceutical composition of the invention in the manufacture of a medicament for preventing or treating a disease or disorder for which a therapy with a botulinum neurotoxin is indicated.

The invention also provides a cosmetic composition containing a polypeptide or di-chain polypeptide of the invention. Said cosmetic composition may further comprise a cosmetically acceptable excipient or diluent.

The invention further provides a use of a cosmetic composition of the invention for preventing or alleviating a cosmetic indication for which the application of a botulinum neurotoxin is indicated.

The invention further provides a chimeric BoNT/F$_{7-1}$ comprising a backbone from a BoNT/F1 subtype and an activation loop region from a BoNT/F$_7$ subtype.

According to a preferred embodiment the chimeric BoNT/F$_{7-1}$ according to the invention is for use in therapy.

The invention further provides a use of a chimeric BoNT/F$_{7-1}$ according to the invention for preventing or alleviating a cosmetic indication for which the application of a botulinum neurotoxin is indicated.

DESCRIPTION OF FIGURES

FIG. 1: Alignment of the activation loop sequences of all BoNT/A subtypes and all BoNT/F subtypes. The activation sequence for each subtype is underlined. The dotted lines within the activation loops correspond to gaps introduced as part of the alignment process to facilitate alignment between the different BoNT/A and BoNT/F subtypes.

FIG. 3: Table showing the percentage sequence identity and percentage sequence divergence between individual BoNT/F sequences.

FIG. 4: Alignment of all non-redundant BoNT/F amino acid sequences identified in a UniParc BLAST. The light chain is shown in bold, the activation loop is double-underlined, the belt sequence is dotted underlined, the H$_N$ domain is italicised, the H$_{CN}$ domain is single underlined and the H$_{CC}$ domain is dashed underlined. Dotted lines within individual BoNT/F sequences correspond to gaps introduced as part of the alignment process to facilitate alignment between the different BoNT/F subtypes.

FIG. 6: Alignment of the full-length sequences of rBoNT/F$_1$ (UPI00000B66D1), rBoNTF$_7$ (UPI0001DE3DAC) and rBoNTF$_{7-1}$. The light chain is shown in bold, the activation loop is double-underlined, the belt sequence is dotted underlined, the H$_N$ domain is italicised, the H$_{CN}$ domain is single underlined and the H$_{CC}$ domain is dashed underlined.

FIG. 7: SDS PAGE Gel of purified chimeric rBoNTF$_{7-1}$ SXN102875 Batch DB131202 (lane 1: molecular weight markers; lane 2: oxidised rBoNTF$_{7-1}$ sample; lane 3: reduced rBoNTF$_{7-1}$ sample), 1 µg protein loaded per lane FIG. 8: N-terminal processing of rBoNTF$_{7-1}$. FIG. 8A is a schematic identifying the cleavage site within the activation loop. FIG. 8B is an SDS-PAGE gel confirming the presence of the activated di-chain rBoNTF$_{7-1}$. FIG. 8C shows the results of the N-terminal sequencing. FIG. 8D is an alignment of a section comprising the C-terminal end of the light chain, the activation loop and the N-terminal end of the $H_N$ domain of the different BoNT/F subtypes. The cysteine residues forming the neck of the activation loop are bold and underlined. The $BoNTF_1$ residues found at the N-terminus of the $rBoNTF_{7-1}$ $H_N$ domain are bold, italicised, and shaded.

FIG. 9A is a diagram showing the cleavage reaction in which the substrate (VAMP-$2_{2-94}$-GFP) is converted to products (VAMP$2_{2-58}$ and VAMP-$2_{59-94}$-GFP). Panel FIG. 9B shows an example chromatogram to quantify the uncleaved substrate and the cleaved VAMP-$2_{59-94}$-GFP product present in the stopped reaction mix. FIG. 9C shows an example of the proportion of substrate converted to product and the calculated specific activity (nmol substrate converted to product, per hour, per pmol BoNT) for recombinant and native BoNT/F proteins.

FIG. 12: mouse Digit Abduction Scoring assay. Mice received injection, into the gastrocnemius-soleus complex muscles of one hind limb, under short general anesthesia; muscle weakening was measured on a 0-4 scale using the digit abduction score (DAS). DAS max values were determined for each dose and plotted against dose and the data were fitted to a 4-parameter logistic equation, ED50 and dose leading to DAS 4 (DAS 4 dose) values were determined (see table).

DETAILED DESCRIPTION OF THE INVENTION

Botulinum Toxins (BoNTs)

Figure 2:
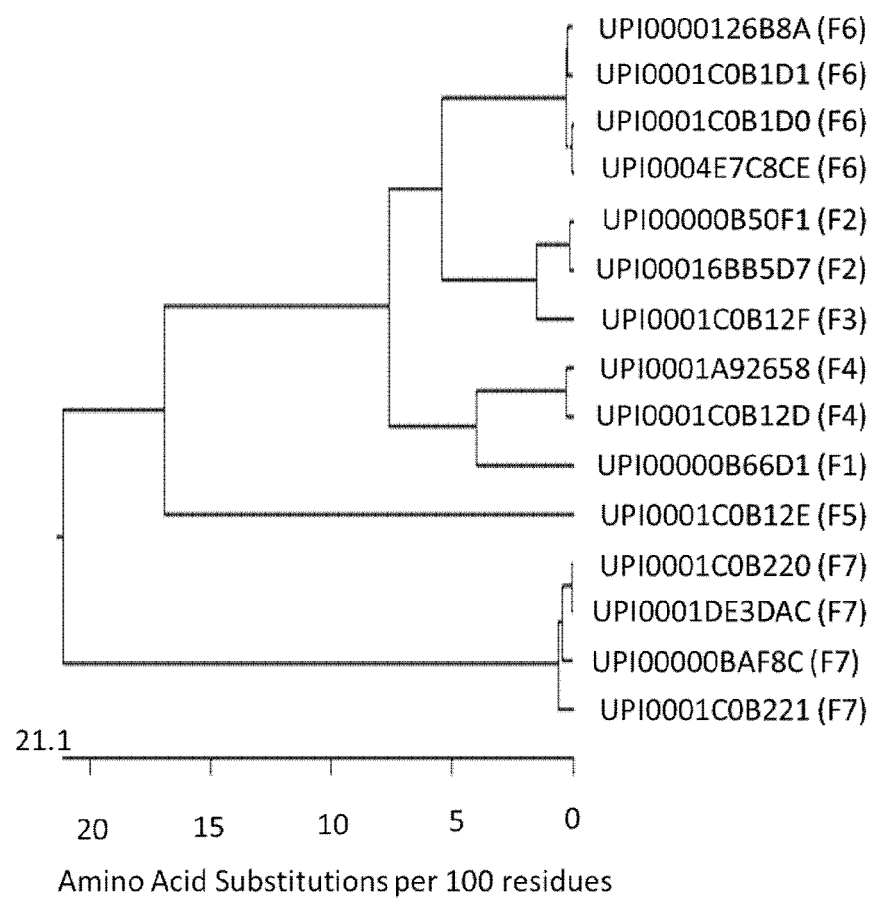
FIG. 2: Phylogenetic analysis of BoNT/F protein sequences based on sequence alignment.

Botulinum neurotoxin (BoNT) is produced by *C. botulinum* in the form of a large protein complex, consisting of BoNT itself complexed to a number of accessory proteins. There are at present eight different classes of botulinum neurotoxin, namely: botulinum neurotoxin serotypes A, B, $C_1$, D, E, F, G, and H, all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/$C_1$, BoNT/A and BoNT/E cleave the synaptosomal-associated protein of 25 kDa (SNAP-25); and BoNT/$C_1$ cleaves syntaxin.

TeNT is produced in a single serotype by *C. tetani*. *C. butyricum* produces BoNT/E, while *C. baratii* produces BoNT/F.

The present invention provides polypeptides comprising chimeric BoNT $LH_N$ domains, and so also encompasses chimeric clostridial toxins. The term "clostridial toxin" is also intended to embrace modified clostridial toxins and derivatives thereof, including but not limited to those described below. A modified clostridial toxin or derivative may contain one or more amino acids that has been modified as compared to the native (unmodified) form of the clostridial toxin, or may contain one or more inserted amino acids that are not present in the native (unmodified) form of the clostridial toxin. By way of example, a modified clostridial toxin may have modified amino acid sequences in one or more domains relative to the native (unmodified) clostridial toxin sequence. Such modifications may modify functional aspects of the toxin, for example biological activity or persistence. Thus, in one embodiment, the engineered clostridial toxin of the invention is an engineered modified clostridial toxin, or an engineered modified clostridial toxin derivative, or an engineered clostridial toxin derivative.

A reference herein to a particular BoNT serotype typically refers to all subtypes within that serotype unless explicitly stated to the contrary.

The present inventors have analysed the exposed loop region within the BoNT light and heavy chains, also known as the activation loop or the di-chain loop, for all subtypes of BoNT serotypes for which amino acid sequences are known. In more detail, the inventors have aligned and annotated the activation loop sequences of all full-length BoNT proteins identified in the UniParc database (which removes redundant sequences). The annotated alignments from all BoNT/A and BoNT/F subtypes are shown in FIG. 1. The inventors have surprisingly found that the BoNT/F subtypes have the most divergent activation loops of all subtypes aligned.

Naturally occurring BoNT proteins are produced within *C. botulinum* bacteria as single chain, precursor proteins. The single chain forms become post-translationally modified, by cleavage (also referred to herein as proteolysis) within the activation loop, to produce fully active, mature, di-chain BoNT proteins. The inventors have previously produced recombinant BoNT proteins, as single chain precursor proteins, in *Escherichia coli* then performed the post-translational proteolytic step on the purified single chain BoNT. Unfortunately, not all purified recombinant BoNT proteins show good activation, where good activation is defined as specific proteolysis at the same site as the naturally occurring protein and not at other sites within the recombinant BoNT. For example, a naturally occurring BoNT protein, subtype BoNT/$F_7$, becomes proteolysed at multiple sites, by all proteases so far tested. The inventors have solved the problem (of activating subtype BoNT/$F_7$) by constructing a chimeric protein in which the region containing the site of desired proteolytic cleavage (called the activation loop) was removed from subtype $F_7$ and replaced it with the equivalent region from another, highly related, BoNT (called subtype BoNT/F$_1$). The inventors have previously identified conditions under which subtype BoNT/F$_1$ does become site-specifically activated. Thus, by substituting the activation loop of BoNT/F$_7$ with the activation loop of BoNT/F$_1$, the inventors have demonstrated that it is possible to generate recombinant BoNT with good activation properties by substituting the activation loop of one BoNT subtype with the activation loop from another BoNT subtype from the same serotype. Without being bound by theory, it is believed that this intra-serotype activation loop swapping is particularly relevant to BoNT/F subtypes due to the divergence in sequence between the activation loops of the different BoNT/F subtypes. The present invention also provides (activated) chimeric di-chain polypeptides. These di-chain polypeptides are themselves chimeric, because they contain both an amino acid sequence from the BoNT/F subtype from which the LH$_N$ backbone is derived and an amino acid sequence from the BoNT/F subtype from which the activation loop is derived. Thus, the resulting chimeric di-chain has a unique amino acid sequence found neither in the BoNT/F subtype from which the LH$_N$ backbone is derived nor in the BoNT/F subtype from which the activation loop is derived. The chimeric di-chain polypeptides of the invention are typically produced by cleavage of the chimeric single chain polypeptides of the invention.

Thus, the present invention provides a means of making fully active, purified, recombinant chimeric BoNTs, containing functional domains with desirable properties, even when those domains have evolved within proteins which are not easily expressed, purified and activated in recombinant form.

Accordingly, the invention provides a chimeric single-chain polypeptide comprising an LH$_N$ backbone from a first botulinum neurotoxin serotype F (BoNT/F) subtype and an activation loop region from a different BoNT/F subtype.

In the context of the present invention, the term "chimeric polypeptide" is one which comprises component parts from two different BoNT/F subtypes. In particular, the chimeric single-chain polypeptide of the invention comprises an LH$_N$ backbone from a first BoNT/F subtype and an activation loop region from a different BoNT/F subtype. A chimeric di-chain polypeptide contains an amino acid sequence from the LH$_N$ backbone of a first BoNT/F subtype and an amino acid sequence from the activation loop of a second BoNT/F subtype, as described herein.

Naturally occurring BoNT/F serotype proteins are classified into seven subtypes (FIG. 2). The light chain of BoNT/F provides a protease function (also known as a non-cytotoxic protease). In particular, the BoNT/F light chain demonstrates a metalloprotease activity and is capable of proteolytically cleaving a vesicle and/or plasma membrane associated protein involved in cellular exocytosis. Typically the substrates for all BoNT/F subtype light chains are vesicle-associated membrane proteins 1, 2 and 3 (VAMP1, VAMP2, and VAMP3). The protease activity of a BoNT light chain or a BoNT/F LH$_N$ backbone may be determined by any appropriate techniques. Standard techniques for determining the cleavage activity of the light chain or fragment or variant thereof are known in the art, for example a mouse hemidiaphragm assay (HDA), or SNARE cleavage assays (see, for example, WO95/33850 and Masuyer G, Beard M, Cadd V A, Chaddock J A, Acharya K R; Structure and activity of a functional derivative of *Clostridium botulinum* neurotoxin B; J Struct Biol. 2011 April; 174(1):52-7), both of which are herein incorporated by reference).

Designation of different BoNTs into serotypes is determined by serological means, rather than being defined by amino acid sequence. Indeed, classification of BoNTs into serotypes A, B, C, D, E, and F, is based solely on, and defined by, their sensitivity to neutralisation by a set of monovalent antitoxins, distributed by the US government Centers for Disease Control and Prevention (CDC), in a standardised mouse bioassay [Botulism in the United States, 1899-1996, Handbook for epidemiologists, clinicians, and laboratory workers; Centers for Disease Control and Prevention, National Center for Infectious Diseases, Division of Bacterial and Mycotic Diseases, 1998, herein incorporated by reference in its entirety]. In this regard, see also: Dezfulian and Bartlett J. Clin. Microbiol. 21(2): 231-233, or Lindstrom and Korkeala Clin. Microbiol. Rev. 19(2): 298-314, 2006, which disclose that serological means are used to define and distinguish between BoNT serotypes, both of which are incorporated by reference.

Accordingly, a reference herein to BoNT/F is a reference to a BoNT that is neutralised by a reference anti-F-serotype monovalent antitoxin as described above. Thus, typically the LH$_N$ backbone of the present invention comprises: (a) a light chain polypeptide sequence which is from a BoNT neutralised by a reference anti-F-serotype monovalent antitoxin; and (b) a H$_N$ polypeptide sequence which is from a BoNT neutralised by a reference anti-F-serotype monovalent antitoxin. The chimeric di-chain polypeptide of the present invention may be neutralised by a reference anti-F-serotype monovalent antitoxin as described herein. In one embodiment of the invention, the term "BoNT/F" embraces BoNT/F hybrid molecules, such as the recently identified BoNT/H, which is believed to be a hybrid of BoNT/F and BoNT/A.

The light chain polypeptide sequence and/or H$_N$ polypeptide sequence of the LH$_N$ backbone of the present invention and/or the di-chain polypeptide of the present invention may also be defined in terms of their sequence identity to known BoNT/F subtypes, as described herein.

According to the present invention, a BoNT/F LH$_N$ backbone may be defined as the region of a BoNT/F neurotoxin which comprises the BoNT/F light chain and the H$_N$ domain. The term LH$_N$ backbone as used herein also embraces LH$_N$ backbones comprising functional fragments or variants of the BoNT/F light chain and/or functional fragments or variants of the BoNT/F H$_N$ domain. Functional fragments or variants of the BoNT/F H$_N$ domain retain the translocation activity of the full-length BoNT/F H$_N$ domain. Functional fragments or variants of the BoNT/F light chain retain the cleavage activity of the full-length light chain as defined herein. In other words, functional BoNT/F light chain fragments or variants can specifically target the core components of the neurotransmitter release apparatus and thus participate in executing the overall cellular mechanism whereby a BoNT/F toxin proteolytically cleaves a substrate. A variant of the BoNT/F light chain as comprised in the BoNT/F LH$_N$ backbone may have at least 70%, at least 75%, at least 80%, at least 85%, least 90%, at least 95%, at least 96%, at least 97%, at least 98%, at least 99% or more, up to 100% sequence identity with the BoNT/F light chain, provided it retains the cleavage activity of the native (unmodified) light chain.

Functional fragments of the BoNT/F light chain include the shortest possible BoNT/F light chain sequence which retains the activity of the full-length light chain, i.e. the minimal BoNT/F light chain fragment, as defined herein. Similarly, functional fragments of the BoNT/F H$_N$ domain include the shortest possible BoNT/F H$_N$ domain sequence which retains the activity of the full-length $H_N$ domain, i.e. the minimal BoNT/F $H_N$ domain fragment, as defined herein.

A BoNT/F $LH_N$ backbone of the invention may have one or more modifications in the amino acid sequence of the BoNT/F light chain sequence, for example modifications in the substrate binding or catalytic domain which may alter or modify the substrate specificity of the modified light chain, and/or which alter or modify the activity of the modified light chain, such as modifying the potency and/or duration of the modified light chain activity. Such modified light chains may have higher or lower activity (potency) and/or longer or shorter duration than a reference light chain. Said reference light chain is typically a native (unmodified) version of the corresponding light chain.

For example, amino acid differences within the light chain sequence of one of the naturally occurring BoNT/F subtypes (subtype $F_5$), compared to other BoNT/F sequences, underlie a difference in which peptide bond of VAMP2 BoNT/$F_5$ cleaves (L54-E55 compared to other BoNT/F subtypes (which cleave between Q58-K59) [Kalb S R, Baudys J, Webb R P, Wright P, Smith T J, Smith L A, Fernández R, Raphael B H, Maslanka S E, Pirkle J L, Barr J R.; FEBS Lett. 2012 Jan. 20; 586(2):109-15; Discovery of a novel enzymatic cleavage site for botulinum neurotoxin $F_5$, which is herein incorporated by reference]. As another example, the light chain sequence may be PEGylated, which increases the duration of the modified light chain activity (see, for example, WO2007/104567, which is herein incorporated by reference) The light chain sequence may contain a degradation sequence, or be ubiquitinated, which decreases the duration of activity of the modified light chain (see, for example, WO 2011/000929, WO 2013/017522, WO 2013/068476, WO 2014/029497 and R. V. Kukreja, et al., Biochim Biophys Acta. (2007) 1774(2):213-22, each of which is incorporated by reference). The light chain sequence may be modified to increase potency, for example by optimisation of the substrate recognition pockets (see, for example, Guo et al. 2013, Toxicon 74: 158-166, which is herein incorporated by reference).

The light chains of clostridial toxins are approximately 420-460 amino acids in length and comprise an enzymatic domain. Typically a full-length BoNT/F light chain is 430 amino acids in length (such as amino acid positions corresponding to residues 1 to 430 of any one of SEQ ID NOs: 1 to 16, including the full-length BoNT/F consensus sequence SEQ ID NO: 1). Thus, a reference herein to a BoNT/F light chain may relate to an amino acid sequence comprising or consisting of amino acids corresponding to residues 1 to 430 of SEQ ID NO: 1, such as amino acid residues from any one of SEQ ID NOs: 2 to 16, preferably from SEQ ID NO: 13, which correspond to amino acid residues 1 to 430 of SEQ ID NO: 1 (as shown in FIG. 4 or Table 1), or a variant thereof.

Research has shown that the entire length of a clostridial toxin light chain is not necessary for the enzymatic activity of the enzymatic domain. Thus, a fragment of the BoNT/F light chain as comprised in $LH_N$ backbone may comprise at least 100, at least 200, at least 250, at least 300, at least 350, at least 400, at least 450, or more continuous or discontinuous amino acids from the BoNT/F light chain, provided it retains the cleavage activity of the native (unmodified) light chain. Typically the fragment of the BoNT/F light chain comprises at least 350, at least 400, at least 450 or more continuous amino acids from the BoNT/F light chain. The light chain portion of the $LH_N$ backbone of the invention may comprise or consist of a minimal BoNT/F light chain fragment, which itself may comprise or consist of amino acid residues corresponding to residues 15 to 412 of any one of SEQ ID NOs: 1 to 16, or amino acids positions from any one of SEQ ID NOs: 2 to 16, preferably SEQ ID NO: 13, which correspond to amino acid residues 15 to 412 of the consensus sequence SEQ ID NO: 1 (for example, see Table 1), or a variant thereof. Suitable light chain fragments according to the invention are shown in bold in FIGS. 4 and 6 herein. A light chain fragment according to the invention may comprise or consist of an amino acid sequence of any one of SEQ ID NOs: 33 to 48, preferably SEQ ID NO: 45 (which define the minimal light chain fragments for non-redundant BoNT/F sequences), or a variant thereof.

A variant of the BoNT/F light chain may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with the reference BoNT/F light chain, provided it retains the cleavage activity of the reference BoNT/F light chain. Typically the reference light chain domain or fragment is a native (unmodified) BoNT/F light chain.

The term fragment also relates to the BoNT/F light chain variants described herein. Thus, by way of example, a BoNT/F light chain fragment of the invention may have at least 350, at least 400, at least 450 or more continuous amino acids, wherein the BoNT/F light chain amino acid sequence has at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity over a corresponding peptide sequence from the reference BoNT/F light chain. Thus, a variant BoNT/F light chain fragment may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity to any BoNT/F light chain fragment disclosed herein.

In a preferred embodiment, the BoNT/F light chain or light chain fragment, or variant thereof, is from BoNT/$F_7$ or BoNT/$F_5$. Thus, a BoNT/F light chain of the invention may comprise or consist of an amino acid sequence from any one of SEQ ID NOs: 8 or 13 to 16 which corresponds to amino acids 1 to 430 of SEQ ID NO: 1. For example, a BoNT/F light chain of the invention may comprise or consist of amino acid residues 1 to 421 of any one of SEQ ID NOs: 13 to 16, preferably SEQ ID NO: 13, or amino acid residues 1 to 428 of SEQ ID NO: 8, or a fragment or variant thereof.

Preferably the $LH_N$ backbone of the invention comprises a light chain fragment which comprises or consists of a minimal light chain fragment from BoNT/$F_7$ or BoNT/$F_5$. Thus, a BoNT/F light chain of the invention may comprise or consist of an amino acid sequence from any one of SEQ ID NOs: 8 or 13 to 16, preferably SEQ ID NO: 13, which corresponds to amino acids 15 to 412 of SEQ ID NO: 1. For example, a BoNT/F light chain of the invention may comprise or consist of amino acid residues 15 to 403 of any one of SEQ ID NOs: 13 to 16 (preferably from SEQ ID NO: 13), or amino acid residues 15 to 410 of SEQ ID NO: 8, or a fragment or variant thereof. The minimal light chain fragment from BoNT/$F_7$ or BoNT/$F_5$ may comprise or consist of the amino acid sequence of any one of SEQ ID NOs: 40 or 45 to 48, preferably SEQ ID NO: 45, or a variant thereof.

The LH$_N$ backbone of the invention typically comprises a (BoNT/F) light chain polypeptide sequence having at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with at least one of SEQ ID NOs: 33 to 48, preferably at least one of SEQ ID NOs: 40 or 45 to 48, more preferably with SEQ ID NO: 45.

There is evidence that BoNT/F subtypes 1, 2, 6 and 7 all cleave VAMP2 at the same peptide bond, namely between Q58-K59 in the human protein (see Kalb et al. (2011) App. Enviro. Microbiol. 77(4):1301-8, which is herein incorporated by reference) but that BoNT/F$_5$ cleaves a different peptide bond, between L54-E55 (see Kalb et al. (2012) FEBS Lett. 586(2): 109-115, which is herein incorporated by reference).

The LH$_N$ backbone of the invention may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of amino acid residues corresponding to residues 1 to 873 of any one of SEQ ID NOs: 1 to 16, or amino acids positions from any one of SEQ ID NOs: 2 to 16, preferably SEQ ID NO: 13, which correspond to amino acid residues 1 to 873 of the consensus sequence of SEQ ID NO: 1 (for example, see Table 1), or a variant thereof, wherein the activation loop sequence within the sequence of any one of SEQ ID NOs: 1 to 16 is replaced by the activation loop sequence from a different BoNT/F subtype (exemplary activation loop sequences are disclosed herein).

The LH$_N$ backbone of the invention may be a minimal LH$_N$ backbone, comprising minimal light chain and H$_N$ domain fragments as disclosed herein. Thus, a minimal LH$_N$ backbone of the invention may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of amino acid residues corresponding to residues 15 to 850 of any one of SEQ ID NOs: 1 to 16, or amino acids positions from any one of SEQ ID NOs: 2 to 16, preferably from SEQ ID NO: 13, which correspond to amino acid residues 15 to 850 of the consensus sequence of SEQ ID NO: 1 (as shown in FIG. 4), or a variant thereof, wherein the activation loop sequence within the sequence of any one of SEQ ID NOs: 1 to 16 is replaced by the activation loop sequence from a different BoNT/F subtype.

For example, the LH$_N$ backbone of the invention may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity or more sequence identity with any one of SEQ ID NOs: 17 to 32 (where SEQ ID NO: 17 is the BoNT/F LH$_N$ domain consensus sequence), preferably SEQ ID NO: 29.

Preferably the LH$_N$ backbone of the invention comprises a light chain fragment and an H$_N$ domain from BoNT/F$_7$ or BoNT/F$_5$. Thus, a LH$_N$ backbone of the invention may comprise or consist of an amino acid sequence from any one of SEQ ID NOs: 8 or 13 to 16, preferably from SEQ ID NO: 13, which corresponds to amino acids 1 to 873, more preferably amino acids 15 to 850, of SEQ ID NO: 1. For example, a BoNT/F LH$_N$ backbone of the invention may comprise or consist of amino acid residues 1 to 862, more preferably amino acid residues 15 to 839, of any one of SEQ ID NOs: 13 to 16 (preferably SEQ ID NO: 13), or amino acid residues 1 to 868, more preferably 15 to 845 of SEQ ID NO: 8, or a fragment or variant thereof, provided the activation loop sequence within the sequence of any one of SEQ ID NOs: 8 or 13 to 16 (preferably SEQ ID NO: 13) is replaced by the activation loop sequence from a different BoNT/F subtype as disclosed herein.

In a preferred embodiment, the LH$_N$ backbone of the invention has at least 60% or more sequence identity with at least one of SEQ ID NOs: 24 or 29 to 32, preferably SEQ ID NO: 29, provided the activation loop sequence within the sequence of any one of SEQ ID NOs: 1 to 16 is replaced by the activation loop sequence from a different BoNT/F subtype.

Typically, a variant LH$_N$ backbone of the invention has at least 60%, at least 65%, at least 70%, at least 75%, at least 80%, at least 85%, at least 90%, at least 95%, at least 96%, at least 97%, at least 98%, at least 99% or more, up to 100% amino acid sequence identity with of the LH$_N$ backbone sequences defined herein. As a non-limiting example, a variant LH$_N$ backbone of the invention may have at least 60%, at least 65%, at least 70%, at least 75%, at least 80%, at least 85%, at least 90%, at least 95%, at least 96%, at least 97%, at least 98%, at least 99% or more, up to 100% amino acid sequence identity with at least one of SEQ ID NOs: 24 or 29 to 32, preferably SEQ ID NO: 29.

The LH$_N$ backbone of the invention typically comprises a BoNT/F light chain fragment and an H$_N$ domain as disclosed herein, preferably a minimal BoNT/F light chain polypeptide sequence and a minimal H$_N$ domain fragment as disclosed herein.

The H$_N$ domain of clostridial toxins are approximately 300-400 amino acids in length and comprise a translocation domain. Typically a full-length BoNT/F H$_N$ domain is approximately 350 amino acids in length (for example, amino acid positions corresponding to residues 520 to 873 of any one of SEQ ID NOs: 1 to 16, including the full-length BoNT/F consensus sequence SEQ ID NO: 1). Thus, a reference herein to a BoNT/F H$_N$ domain may relate to an amino acid sequence comprising or consisting of amino acids corresponding to residues 520 to 873 of SEQ ID NO: 1, such as amino acid residues from any one of SEQ ID NOs: 2 to 16 which correspond to amino acid residues 520 to 873 of SEQ ID NO: 1 (as shown in FIG. 4 and Table 1), or a variant thereof.

According to the present invention, the BoNT/F LH$_N$ backbone comprises a BoNT/F H$_N$ domain. The term LH$_N$ backbone as used herein also embraces LH$_N$ backbones comprising functional fragments or variants of the BoNT/F H$_N$ domain. Functional fragments or variants of the BoNT/F H$_N$ domain retain the translocation activity of the full-length H$_N$ domain as defined herein. In other words, functional BoNT/F H$_N$ domain fragments or variants are capable of forming ion-permeable pores in lipid membranes (e.g. endosomal membranes) under conditions of low pH, enabling the BoNT/F light chain to escape the endosome.

Thus, a fragment of the BoNT/F H$_N$ domain as comprised in LH$_N$ backbone may comprise at least 100, at least 200, at least 250, at least 300, at least 350, at least 400 or more continuous or discontinuous amino acids from the BoNT/F H$_N$ domain, provided it retains the translocation activity of a reference H$_N$ domain. The reference H$_N$ domain may be a native (unmodified) H$_N$ domain. Typically the fragment of the BoNT/F H$_N$ domain comprises at least 300, at least 350, at least 400 or more continuous amino acids from the BoNT/F H$_N$ domain.

The H$_N$ domain portion of the LH$_N$ backbone of the invention may comprise or consist of a minimal BoNT/F H$_N$ domain fragment, which itself may comprise or consist of amino acid residues corresponding to residues 520 to 873 of any one of SEQ ID NOs: 1 to 16, or amino acids positions from any one of SEQ ID NOs: 2 to 16, preferably from SEQ ID NO: 13 which correspond to amino acid residues 520 to 873 of the consensus sequence SEQ ID NO: 1 (for example, see Table 1), or a variant thereof. Suitable H$_N$ domain fragments according to the invention are italicised in FIGS. 4 and 6 herein.

An H$_N$ domain fragment according to the invention may comprise or consist of an amino acid sequence of any one of SEQ ID NOs: 49 to 64, preferably SEQ ID NO: 61 (which define the minimal H$_N$ domain fragments for non-redundant BoNT/F sequences), or a variant thereof. A variant of the BoNT/F H$_N$ domain may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with the reference BoNT/F H$_N$ domain, provided it retains the translocation activity of the reference BoNT/F H$_N$ domain. Typically the reference H$_N$ domain domain or fragment is a native (unmodified) BoNT/F H$_N$ domain as disclosed herein.

The term fragment also relates to the BoNT/F H$_N$ domain variants described herein. Thus, by way of example, a BoNT/F H$_N$ domain fragment of the invention may have at least 300, at least 350, at least 400 or more continuous amino acids, wherein the BoNT/F H$_N$ domain amino acid sequence has at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity over a corresponding peptide sequence from the reference BoNT/F H$_N$ domain. Thus, a variant BoNT/F H$_N$ domain fragment may have at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity to any BoNT/F H$_N$ domain fragment disclosed herein.

In a preferred embodiment, a variant of the BoNT/F H$_N$ domain, or fragment or variant thereof may have at least 70%, at least 75%, at least 80%, at least 85%, least 90%, at least 95%, at least 96%, at least 97%, at least 98%, at least 99% or more, up to 100% amino acid sequence identity with the reference BoNT/F H$_N$ domain, provided it retains the translocation activity of the reference BoNT/F H$_N$ domain. Typically the reference H$_N$ domain is a native (unmodified) BoNT/H$_N$ domain.

In a preferred embodiment, the BoNT/F H$_N$ domain or H$_N$ domain fragment, or variant thereof, is from BoNT/F$_7$ or BoNT/F$_5$. Thus, a BoNT/F H$_N$ domain of the invention may comprise or consist of an amino acid sequence from any one of SEQ ID NOs: 8 or 13 to 16, preferably from SEQ ID NO: 13, which corresponds to amino acids 520 to 873 of SEQ ID NO: 1 (for example, see Table 1). For example, a BoNT/F H$_N$ domain of the invention may comprise or consist of amino acid residues 509 to 862 of any one of SEQ ID NOs: 13 to 16, preferably from SEQ ID NO: 13, or amino acid residues 516 to 868 of SEQ ID NO: 8, or a fragment or variant thereof.

Preferably the LH$_N$ backbone of the invention comprises a H$_N$ domain fragment which comprises or consists of a minimal H$_N$ domain fragment from BoNT/F$_7$ or BoNT/F$_5$. Thus, a BoNT/F H$_N$ domain of the invention may comprise or consist of an amino acid sequence from any one of SEQ ID NOs: 8 or 13 to 16, preferably from SEQ ID NO: 13, which corresponds to amino acids 538 to 850 of SEQ ID NO: 1 (for example, see Table 1). For example, a BoNT/F H$_N$ domain of the invention may comprise or consist of amino acid residues 527 to 839 of any one of SEQ ID NOs: 13 to 16, preferably SEQ ID NO: 13, or amino acid residues 534 to 845 of SEQ ID NO: 8, or a fragment or variant thereof. The minimal H$_N$ domain fragment from BoNT/F$_7$ or BoNT/F$_5$ may comprise or consist of the amino acid sequence of any one of SEQ ID NOs: 56 or 61 to 64, preferably SEQ ID NO: 61, or a variant thereof.

The LH$_N$ backbone of the invention typically comprises a (BoNT/F) H$_N$ domain polypeptide sequence having at least 70%, at least 75%, at least 80%, at least 85%, least 90%, at least 95%, at least 96%, at least 97%, at least 98%, at least 99% or more, up to 100% amino acid sequence identity with at least one of SEQ ID NOs: 49 to 64, preferably at least one of SEQ ID NOs: 56 or 61 to 64, more preferably SEQ ID NO: 61. In some embodiments, the H$_N$ domain of the invention (or fragment or variant thereof) may additionally comprise one or more amino acids from a belt region polypeptide sequence. For example, the H$_N$ domain of the invention (or fragment or variant thereof) may additionally comprise a full-length belt region polypeptide sequence or a fragment or variant thereof. A BoNT belt region is the polypeptide sequence that is located between the activation loop and the start of the H$_N$ domain; it is so named because that region of the heavy chain sequence wraps around the BoNT light chain sub-unit, in the three dimensional structure of the protein, in a way that is reminiscent of a belt wrapping around a person's waist. The position of the belt region in known BoNT/F sequences is shown in Table 1 below (the recited amino acid positions correspond to the positions in the full length BoNT sequence). Thus, a reference herein to a H$_N$ domain of the invention may refer to a H$_N$ domain polypeptide sequence including or excluding one or more amino acids from a belt region polypeptide.

In some embodiments, the present invention relates to a BoNT/F polypeptide sequence which comprises a light chain (or fragment or variant thereof as defined herein), a H$_N$ domain (or fragment or variant thereof as defined herein) and a belt region polypeptide (or fragment or variant thereof) from one BoNT/F subtype, preferably BoNT/F$_7$ or BoNT/F$_5$, and an activation loop from a different BoNT/F subtype, such as BoNT/F$_1$, BoNT/F$_2$, BoNT/F$_3$, BoNT/F$_4$, or BoNT/F$_6$. The BoNT/F light chain fragment and/or H$_N$ domain fragment may be minimal fragments as disclosed herein, or variants thereof. Alternatively, chimeric BoNT/F of the invention may be derived from or essentially identical to a native full-length BoNT/F polypeptide (including a light chain, H$_N$ domain and belt region) from one BoNT/F subtype, preferably BoNT/F$_7$ or BoNT/F$_5$, except that the activation loop from the native BoNT/F has been replaced with the activation loop from a different BoNT/F subtype, such as BoNT/F$_1$, BoNT/F$_2$, BoNT/F$_3$, BoNT/F$_4$, or BoNT/F$_6$.

Typically, the LH$_N$ backbone of the invention comprises: (a) a (BoNT/F) polypeptide sequence having at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of amino acids corresponding to residues 1 to 430 of SEQ ID NO: 1 (such as amino acid residues from any one of SEQ ID NOs: 2 to 16, preferably from SEQ ID NO: 13, which correspond to amino acid residues 1 to 430 of SEQ ID NO: 1); and/or amino acid residues corresponding to residues 15 to 412 of any one of SEQ ID NOs: 1 to 16, or an amino acid sequence comprising or consisting of amino acids positions from any one of SEQ ID NOs: 2 to 16, preferably from SEQ ID NO: 13, which correspond to amino acid residues 15 to 412 of SEQ ID NO: 1; and/or an amino acid sequence which comprises or consists of any one of SEQ ID NOs: 33 to 48, preferably SEQ ID NO: 45; and (b) a (BoNT/F) polypeptide sequence having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% or more, up to 100% amino acid sequence identity with an amino acid sequence comprising or consisting of amino acids corresponding to residues 520 to 873 of any one of SEQ ID NOs: 1 (such as amino acid residues from any one of SEQ ID NOs: 2 to 16, preferably from SEQ ID NO: 13, which correspond to amino acid residues 520 to 873 of SEQ ID NO: 1); and/or an amino acid sequence comprising or consisting of amino acid positions from any one of SEQ ID NOs: 2 to 16, preferably from SEQ ID NO: 13, which correspond to amino acid residues 520 to 873 of SEQ ID NO: 1; and/or an amino acid sequence which comprises or consists of any one of SEQ ID NOs: 49 to 64, preferably SEQ ID NO: 61.

In a preferred embodiment, the $LH_N$ backbone of the invention comprises a BoNT/$F_7$ or BoNT/$F_5$ light chain or light chain fragment and a BoNT/$F_7$ or BoNT/$F_5$ $H_N$ domain or $H_N$ domain fragment. Thus, in a preferred embodiment, the $LH_N$ backbone of the invention comprises: (a) a (BoNT/F) polypeptide sequence having at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of an amino acid sequence from any one of SEQ ID NOs: 8 or 13 to 16, preferably from SEQ ID NO: 13 which corresponds to amino acids 1 to 430 of SEQ ID NO: 1, such as amino acid residues 1 to 421 of any one of SEQ ID NOs: 13 to 16, preferably from SEQ ID NO: 13, or amino acid residues 1 to 428 of SEQ ID NO: 8; and/or an amino acid sequence from any one of SEQ ID NOs: 8 or 13 to 16, preferably from SEQ ID NO: 13, which corresponds to amino acids 15 to 412 of SEQ ID NO: 1, such as amino acid residues 15 to 403 of any one of SEQ ID NOs: 13 to 16, preferably from SEQ ID NO: 13, or amino acid residues 15 to 410 of SEQ ID NO: 8; and/or any one of SEQ ID NOs: 40 or 45 to 48, preferably SEQ ID NO: 45; and (b) at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% or more, up to 100% amino acid sequence identity with an amino acid sequence comprising or consisting of an amino acid sequence from any one of SEQ ID NOs: 8 or 13 to 16 which corresponds to amino acids 520 to 873 of SEQ ID NO: 1, such as amino acid residues 509 to 862 of any one of SEQ ID NOs: 13 to 16, preferably from SEQ ID NO: 13, or amino acid residues 516 to 868 of SEQ ID NO: 8; and/or an amino acid sequence from any one of SEQ ID NOs: 8 or 13 to 16, preferably SEQ ID NO: 13 which corresponds to amino acids 538 to 850 of SEQ ID NO: 1, such as amino acid residues 527 to 839 of any one of SEQ ID NOs: 13 to 16, preferably SEQ ID NO: 13, or amino acid residues 534 to 845 of SEQ ID NO: 8, and/or any one of SEQ ID NOs: 56 or 61 to 64, preferably SEQ ID NO: 61.

The polypeptide of the invention comprises a site for cleavage by a proteolytic enzyme, which cleavage site is an activation loop from a different botulinum type F (BoNT/F) subtype than the BoNT/F $LH_N$ backbone. The BoNT/F activation loop enables the cleavage of the single-chain polypeptide into a di-chain form. Cleavage into the di-chain form typically activates the polypeptide, which is necessary to free the light chain or fragment or variant thereof to carry out its proteolytic cleavage activity in the cell cytoplasm.

As used herein, the term "BoNT/F activation loop" embraces fragments and variants thereof, provided said fragments or variants retain the ability to be cleaved, producing the di-chain form of the polypeptide, activating said polypeptide and freeing the light chain or fragment or variant thereof to carry out its proteolytic cleavage activity. The BoNT/F activation loop may be cleaved by any appropriate protease (Lys-C). The ability of any given protease to cleave at the activation loop may be determined by any appropriate technique known in the art, see for example, WO 1995/033850, Dekleva et al., Biochem. Biophys. Res. Commun. (1989) 162(2):767-72, Giminez, Biochimie. (1990) 72(4):213-7 and Giminez, J. Protein Chem. (1993) 12(3): 351-63, each of which is herein incorporated by reference.

The activation loop of the polypeptide of the invention typically comprises an amino acid sequence fitting the consensus sequence KSIIPRKGTKAPPRL (SEQ ID NO: 65), or an amino acid sequence in which no more than five, no more than four, no more than three, no more than two or no more than one amino acids are added to, deleted from, or substituted in the consensus sequence.

The activation loop may comprise an amino acid sequence selected from (a) KSVIPRKGTKAPPRL (SEQ ID NO: 66); (b) KSIIPRKGTKQSPSL (SEQ ID NO: 67); or (c) KSIIPRKGTKAPPRL (SEQ ID NO: 65), or an amino acid sequence in which no more than five, no more than four, no more than three, no more than two or no more than one amino acids are added to, deleted from, or substituted in the sequence. Preferably the activation loop comprises the amino acid sequence KSVIPRKGTKAPPRL (SEQ ID NO: 66, or an amino acid sequence in which no more than five, no more than four, no more than three, no more than two or no more than one amino acids are added to, deleted from, or substituted in the sequence.

Table 1 (below) shows the precursor, the native di-chain neurotoxin of BoNT/F subtypes and identifies the light chain, the exposed loop (activation loop), the belt region, the $H_N$ domain and the $H_C$ domain (including the $H_{CN}$ and $H_{CC}$ domains).

The reference sequence should be considered a guide as slight variations may occur according to subtypes.

Referring to Table 1, the amino acid positions (residues) indicated for the light chains, $H_N$, $H_{CN}$ and $H_{CC}$ domains correspond to the amino acid positions for said regions in a full length BoNT/F protein sequence. The UniParc Accession Numbers given in Table 1 are examples of the different BoNT/F sub-serotypes. Thus, in one embodiment, the amino acid positions of the light chains, $H_N$, $H_{CN}$ and $H_{CC}$ domains indicated in Table 1 correspond to the amino acid positions in the full length BoNT/F protein sequences identified by Accession Number. The Accession Numbers given in Table 1 above reference the corresponding amino acid sequences as entered in the UniParc database as of the [INSERT FILING DATE OF APPLICATION].

TABLE 1

| BoNT | UniParc Database no. of the protein sequence | Total length | Position of Light Chain | Position of Activation Loop | Belt region | $H_N$ | Heavy Chain $H_C$ $H_{CN}$ | $H_{CC}$ |
|---|---|---|---|---|---|---|---|---|
| BoNT/F | consensus sequence | 1283 | 1-430 | 431-445 | 446-519 | 520-873 | 874-1090 | 1091-1282 |
| BoNT/F$_1$ | UPI00000B66D1 | 1278 | 1-429 | 430-444 | 445-518 | 519-871 | 872-1085 | 1086-1278 |
| BoNT/F$_2$ | UPI00016BB5D7 | 1280 | 1-429 | 430-444 | 445-518 | 519-871 | 872-1088 | 1089-1280 |
| BoNT/F$_2$ | UPI00000B50F1 | 1280 | 1-429 | 430-444 | 445-518 | 519-871 | 872-1088 | 1089-1280 |
| BoNT/F$_3$ | UPI0001C0B12F | 1279 | 1-429 | 430-444 | 445-518 | 519-871 | 872-1088 | 1089-1279 |
| BoNT/F$_4$ | UPI0001A92658 | 1278 | 1-429 | 430-444 | 445-518 | 519-871 | 872-1085 | 1086-1278 |
| BoNT/F$_4$ | UPI0001C0B12D | 1277 | 1-429 | 430-444 | 445-518 | 519-871 | 872-1085 | 1086-1277 |
| BoNT/F$_5$ | UPI0001C0B12E | 1277 | 1-428 | 429-441 | 442-515 | 516-868 | 869-1085 | 1086-1277 |
| BoNT/F$_6$ | UPI0001C0B1D1 | 1275 | 1-429 | 430-444 | 445-518 | 519-871 | 872-1088 | 1089-1275 |
| BoNT/F$_6$ | UPI0000126B8A | 1274 | 1-429 | 430-444 | 445-518 | 519-870 | 871-1087 | 1088-1274 |
| BoNT/F$_6$ | UPI0001C0B1D0 | 1275 | 1-429 | 430-444 | 445-518 | 519-871 | 872-1088 | 1089-1275 |
| BoNT/F$_6$ | UPI0004E7C8CE | 1275 | 1-429 | 430-444 | 445-518 | 519-871 | 872-1088 | 1089-1275 |
| BoNT/F$_7$ | UPI0001DE3DAC | 1268 | 1-421 | 422-434 | 435-508 | 509-862 | 863-1076 | 1077-1268 |
| BoNT/F$_7$ | UPI0001C0B220 | 1268 | 1-421 | 422-434 | 435-508 | 509-862 | 863-1076 | 1077-1268 |
| BoNT/F$_7$ | UPI00000BAF8C | 1268 | 1-421 | 422-434 | 435-508 | 509-862 | 863-1076 | 1077-1268 |
| BoNT/F$_7$ | UPI0001C0B221 | 1268 | 1-421 | 422-434 | 435-508 | 509-862 | 863-1076 | 1077-1268 |

A polypeptide of the invention may comprise an $LH_N$ backbone comprising a sequence from a light chain of any one of the BoNT/F subtypes identified in Table 1, or a fragment (such as a minimal light chain fragment as disclosed herein) or variant thereof. The domain structure of BoNTs is well known in the art and so it is sufficient to refer to the light chain of any particular BoNT, or a fragment or variant thereof. Alternatively, the BoNT/F light chain or fragment or variant thereof may be defined in terms of its sequence or in terms of the amino acid positions corresponding to the amino acid positions in the full-length sequence any one of the BoNT/F subtypes in Table 1 (as described herein). For example, the $LH_N$ backbone may comprise the light chain of the BoNT/F$_7$ of UPI0001DE3DAC. This light chain may further be defined in terms of its sequence (e.g. the minimal light chain fragment of UPI0001DE3DAC has the amino acid sequence of SEQ ID NO: 45), or in terms of the amino acid corresponding to the amino acid positions in the full-length amino acid sequence of the BoNT/F$_7$ of UPI0001DE3DAC (e.g. amino acids corresponding to amino acid positions 1 to 421 (for the full-length light chain sequence) or amino acid positions 15 to 403 (for the minimal light chain sequence) of UPI0001DE3DAC (full length UPI0001DE3DAC has the amino acid sequence of SEQ ID NO: 13). Such definitions (in terms of sequence and/or amino acid position) apply equally to any other BoNT/F $LH_N$ backbones or light chains, including those listed in Table 1.

An $LH_N$ backbone of the invention may comprise a $H_N$ domain of any one of the BoNT/F subtypes identified in Table 1, or a fragment (such as a minimal $H_N$ domain fragment as disclosed herein) or variant thereof. The domain structure of BoNTs is well known in the art and so it is sufficient to refer to the $H_N$ domain of any particular BoNT, or a fragment or variant thereof. Alternatively, the BoNT/F $H_N$ domain or fragment or variant thereof may be defined in terms of its sequence or in terms of the amino acid positions corresponding to the amino acid positions in the full-length sequence any one of the BoNT/F subtypes in Table 1 (as described herein). For example, the $LH_N$ backbone may comprise the $H_N$ domain of the BoNT/F$_7$ of UPI0001DE3DAC. This $H_N$ domain may further be defined in terms of its sequence (e.g. the minimal $H_N$ domain fragment of UPI0001DE3DAC has the amino acid sequence of SEQ ID NO: 61), or in terms of the amino acid corresponding to the amino acid positions in the full-length amino acid sequence of the BoNT/F$_7$ of UPI0001DE3DAC (e.g. amino acids corresponding to amino acid positions 509 to 862 (for the full-length $H_N$ domain sequence) or amino acid positions 527 to 839 (for the minimal $H_N$ domain sequence) of UPI0001DE3DAC (full length UPI0001DE3DAC has the amino acid sequence of SEQ ID NO: 13). Such definitions (in terms of sequence and/or amino acid position) apply equally to any other BoNT/F $LH_N$ backbones or $H_N$ domains, including those listed in Table 1.

A polypeptide of the invention may comprise an activation loop of any one of the BoNT/F subtypes identified in Table 1, or a fragment or variant thereof. The domain structure of BoNTs is well known in the art and so it is sufficient to refer to the activation loop of any particular BoNT, or a fragment or variant thereof. Alternatively, the BoNT/F activation loop or fragment or variant thereof may be defined in terms of its sequence or in terms of the amino acid positions corresponding to the amino acid positions in the full-length sequence any one of the BoNT/F subtypes in Table 1 (as described herein). For example, the polypeptide may comprise the activation loop of the BoNT/F$_1$ of UPI00000B66D1. This activation loop may further be defined in terms of its sequence (SEQ ID NO: 66), or in terms of the amino acid corresponding to the amino acid positions in the full-length amino acid sequence of the BoNT/F$_1$ of UPI00000B66D1 (amino acids corresponding to amino acid positions 430 to 444 of UPI00000B66D1). Such definitions (in terms of sequence and/or amino acid position) apply equally to any other BoNT/F activation loops, including those listed in Table 1.

According to the present invention, the polypeptide comprises an activation loop that is from a different BoNT/F subtype to the BoNT/F $LH_N$ backbone.

Thus, the polypeptide of the invention may comprise a BoNT/F $LH_N$ backbone from any one of BoNT/F$_1$, BoNT/F$_2$, BoNT/F$_3$, BoNT/F$_4$, BoNT/F$_5$, BoNT/F$_6$, or BoNT/F$_7$. Typically the BoNT/F $LH_N$ backbone is from a BoNT/F$_5$, or BoNT/F$_7$ subtype. In a preferred embodiment, the BoNT/F $LH_N$ backbone is from a BoNT/F$_7$ subtype.

The polypeptide of the invention may comprise a BoNT/F activation loop from any one of BoNT/F$_1$, BoNT/F$_2$, BoNT/F$_3$, BoNT/F$_4$, BoNT/F$_5$, BoNT/F$_6$, or BoNT/F$_7$, provided that the activation loop is from a different BoNT/F subtype than the BoNT/F $LH_N$ backbone. Typically the BoNT/F activation loop is from any one of BoNT/F$_1$, BoNT/F$_2$, BoNT/F$_3$, BoNT/F$_4$, or BoNT/F$_6$. In a preferred embodiment, the BoNT/F activation loop is from BoNT/F$_1$ or BoNT/F$_6$.

The polypeptide of the invention typically comprises a BoNT/F LH$_N$ backbone from a BoNT/F$_5$ or BONT/F$_7$ subtype and a BoNT/F activation loop from a BoNT/F$_1$, BoNT/F$_2$, BoNT/F$_3$, BoNT/F$_4$ or BoNT/F$_6$ subtype. In a preferred embodiment the polypeptide of the invention typically comprises a BoNT/F LH$_N$ backbone from a BoNT/F$_5$ or BONT/F$_7$ subtype and a BoNT/F activation loop from a BoNT/F$_1$ or BoNT/F$_6$ subtype.

Chimeric LH$_N$ backbones, in which the light chain (or fragment or variant thereof) and H$_N$ domain (or fragment or variant thereof) are derived from different BoNT/F subtypes are encompassed by the present invention. For example, a chimeric LH$_N$ backbone according to the present invention may comprise a light chain (or fragment or variant thereof) from a BONT/F$_7$ subtype and an H$_N$ domain (or fragment or variant thereof) from a BoNT/F$_5$ subtype or vice versa. When the polypeptide of the invention comprises such a chimeric LH$_N$ backbone, typically the activation loop is derived from a different BoNT/F subtype than either the light chain (or fragment or variant thereof) or the H$_N$ domain (or fragment or variant thereof). As described herein, preferably the BoNT/F activation loop is from a BoNT/F$_1$ or BoNT/F$_6$ subtype. Thus, a chimeric single-chain polypeptide of the present invention may comprise a light chain (or fragment or variant thereof) from a first BoNT/F subtype (for example BoNT/F$_7$), an activation loop from a second BoNT/F subtype (for example BoNT/F$_1$) and an H$_N$ domain (or fragment or variant thereof) from a third BoNT/F subtype (for example BoNT/F$_5$).

The polypeptides of the present invention, especially the light chain component thereof, may be PEGylated—this may help to increase stability, for example duration of action of the protease component. PEGylation preferably includes the addition of PEG to the N-terminus of the protease component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, herein incorporated by reference.

A polypeptide of the invention may comprise one or more modifications that increases or decreases the biological activity and/or the biological persistence of the polypeptide. For example, a polypeptide may comprise a leucine- or tyrosine-based motif, wherein said motif increases or decreases the biological activity and/or the biological persistence of the polypeptide. Suitable leucine-based motifs include xDxxxLL, xExxxLL, xExxxIL, and xExxxLM (wherein x is any amino acid). Suitable tyrosine-based motifs include Y-x-x-Hy (wherein Hy is a hydrophobic amino acid). Examples of modified clostridial toxins comprising leucine- and tyrosine-based motifs are described in WO 2002/08268, which is hereby incorporated by reference in its entirety.

A polypeptide of the invention may comprise one or more cationic modifications. Such polypeptides have properties of increased tissue retention at the site of administration, and which accordingly exhibit a reduction in diffusion away from the administration site. Examples of such cationic clostridial toxins are described in PCT/GB2014/052097, which is hereby incorporated by reference in its entirety.

As described herein, the various elements of the polypeptide of the invention (LH$_N$ backbone, activation loop and/or targeting moiety) may be modified, in that each element may independently comprise at least one amino acid modification, selected from: an amino acid substitution, an amino acid insertion, and an amino acid deletion.

In an amino acid substitution, an amino acid residue that forms part of the clostridial toxin amino acid sequence is replaced with a different amino acid residue. The replacement amino acid residue may be one of the 20 standard amino acids in the Table below.

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

The following amino acids are considered uncharged, polar (meaning they can participate in hydrogen bonding) amino acids: asparagine, glutamine, histidine, serine, threonine, tyrosine, cysteine, methionine, tryptophan.

The following amino acids are considered uncharged, hydrophobic amino acids: alanine, valine, leucine, isoleucine, phenylalanine, proline, and glycine.

Alternatively, the replacement amino acid in an amino acid substitution may be a non-standard amino acid (an amino acid that is not part of the standard set of 20 described above). By way of example, the replacement amino acid may be a basic non-standard amino acid, e.g. L-Ornithine, L-2-amino-3-guanidinopropionic acid, or D-isomers of Lysine, Arginine and Ornithine). Methods for introducing non-standard amino acids into proteins are known in the art, and include recombinant protein synthesis using *E. coli* auxotrophic expression hosts.

In an amino acid insertion, an additional amino acid residue (one that is not normally present) is incorporated into the polypeptide amino acid sequence, thus increasing the total number of amino acid residues in said sequence. In an amino acid deletion, an amino acid residue is removed from the polypeptide amino acid sequence, thus reducing the total number of amino acid residues in said sequence.

Methods for modifying proteins by substitution, insertion or deletion of amino acid residues are known in the art. By way of example, amino acid modifications may be introduced by modification of a DNA sequence encoding the polypeptide. This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively a modified gene sequence can be chemically synthesised.

The at least one amino acid modification may be selected from: substitution of an acidic amino acid residue with a basic amino acid residue; substitution of an acidic amino acid residue with an uncharged amino acid residue; substitution of an uncharged amino acid residue with a basic amino acid residue; insertion of a basic amino acid residue; and deletion of an acidic amino acid residue.

In a preferred embodiment, the at least one amino acid modification is a substitution, which advantageously maintains the same number of amino acid residues in the polypeptide.

A polypeptide of the invention may comprise more than one amino acid modification. Thus, in one embodiment, the polypeptide (as described above) comprises between 1 and 80 amino acid modifications (for example, between 1 and 70, between 1 and 60, between 1 and 50, between 1 and 40, between 1 and 30, between 1 and 20, between 1 and 10, or 9, 8, 7, 6, 5, 4, 3 or 2 amino acid modifications.

Preferred target amino acids for modification may possess certain qualities. By way of example, a preferred target amino acid may be: (i) a surface exposed amino acid; (ii) located outside of the polypeptide secondary structure; (iii) located in region of the polypeptide that is non-essential for protein function; (iv) an amino acid whose identity is not conserved between clostridial toxin types, subtypes, or serotypes; (iv) an amino acid whose modification does not create a predicted ubiquitination site; or (v) any combination of the foregoing.

The polypeptides of the present invention may be free from the complexing proteins that are present in a naturally occurring clostridial toxin complex.

A polypeptide of the present invention may also comprise a limited number of non-standard amino acids. Thus, in addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues. Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomocysteine, nitro-glutamine, homoglutamine, pipecolic acid, tert-leucine, norvaline, 2-azaphenylalanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994.

The polypeptides of the present invention can be produced using recombinant nucleic acid technologies. Thus, in one embodiment, a polypeptide (as described above) is a recombinant polypeptide.

Cleavage of BoNTs into the Active Di-Chain Form

The Clostridium bacteria release the neurotoxins as single-chain polypeptides each having 1251 to 1315 amino acids. Thereafter naturally occurring proteases cleave each of these proteins at a defined location into 2 chains each ('nicking'), the two chains however remaining interlinked by a disulphide-bridge. These di-chain (dual-chain) proteins are referred to as holotoxins (see Shone et al. (1985), Eur J Biochem 151, 75-82). The two chains have different functions, as described herein. According to the invention, Lys-C is used to cleave the single-chain polypeptide into the di-chain form. Cleavage can be determined by any appropriate technique, examples of which are known in the art. See, for example WO 1995/033850, which is herein incorporated by reference. For example, SDS-PAGE gels, stained for total protein, run under reducing and non-reducing conditions may be used to identify the presence of the single- and/or di-chain forms of the polypeptide of the invention.

Targeting Moieties

A polypeptide of the invention may comprise a targeting moiety (TM) which is adapted for binding of the polypeptide to a cell by binding of the TM directly to a target cell or by binding of the TM to a ligand or ligands that bind to a target cell. Typically a TM that binds directly to a cell does so by functionally interacting with a binding site on the cell surface to cause a physical association between the polypeptide of the invention and the surface of the target cell.

Thereafter, the translocation component ($H_N$ domain or fragment or variant thereof) effects transport of the protease component (light chain or fragment or variant thereof) into the cytosol of the target cell. Finally, once inside, the light chain inhibits the exocytic fusion process of the target cell by cleaving SNARE protein present in the cytosol of the target cell. Thus, by inactivating the exocytic fusion apparatus of the target cell, the polypeptide of the invention inhibits secretion by the target cell (for example, inhibits secretion of neurotransmitters such as acetylcholine from a target cholinergic motor neuron).

Targeting Moiety (TM) means any chemical structure that functionally interacts with a binding site to cause a physical association between the polypeptide of the invention and the surface of a target cell. The term TM embraces any molecule (i.e. a naturally occurring molecule, or a chemically/physically modified variant thereof) that is capable of binding to a binding site on the target cell, which binding site is capable of internalisation (e.g. endosome formation)—also referred to as receptor-mediated endocytosis. The TM may possess an endosomal membrane translocation function, in which case separate TM and $H_N$ domain components need not be present in an agent of the present invention. Any appropriate TM may be used in a polypeptide of the present invention.

In a preferred embodiment the TM is selected from the TM of a BoNT, i.e. the TM comprises or consists of a BoNT $H_{CC}$ domain. The term BoNT $H_{CC}$ domain as used herein embraces functional fragments and variants of BoNT $H_{CC}$ domains, i.e. $H_{CC}$ domain fragments and variants which retain the targeting activity of the full-length $H_{CC}$ domain. Alternatively, the TM may comprise or consist of a $H_{CC}$ domain from a non-botulinum clostridial toxin. All relevant disclosure herein in relation to BoNT $H_{CC}$ domain or $H_C$ domain TMs applies equally to non-botulinum $H_{CC}$ domain or $H_C$ domain TMs, including TeNT $H_{CC}$ domain or $H_C$ domain TMs.

As the BoNT $H_{CC}$ domain is comprised within the larger BoNT $H_C$ domain, the TM of the polypeptide of the invention may comprise or consist of a BoNT $H_C$ domain. All description herein of a BoNT $H_{CC}$ domain therefore applies equally to the larger BoNT $H_C$ domain.

The TM of the polypeptide of the invention may comprise or consist of a $H_{CC}$ domain or $H_C$ domain from any one of BoNT/A, BoNT/B, BoNT/$C_1$, BoNT/D, BoNT/E, BoNT/F or BoNT/G. The $H_{CC}$ and $H_C$ domains of different BoNT serotypes and subtypes (sub-serotypes) are known in the art. See, for example, Table 1 of WO 2006/027207, or WO 2006/099590 herein incorporated by reference.

Examples of clostridial toxin $H_{CC}$ domain reference sequences include:
BoNT/A—amino acid residues 1092-1296, for example R1092 to L1296
BoNT/B—amino acid residues 1079-1291, for example S1079 to E1291
BoNT/$C_1$—amino acid residues 1093-1291, for example Q1093 to E1291
BoNT/D—amino acid residues 1080-1276, for example I1080 to E1276
BoNT/E—amino acid residues 1067-1252, for example P1067-K1252
BoNT/F—amino acid residues 1087-1274, for example P1087-E1274
BoNT/G—amino acid residues 1087-1297, for example S1087-E1297
TeNT—amino acid residues 1109-1315, for example L1109-D1315

The above sequence positions may vary slightly according to serotype/subtype.

Examples of clostridial toxin $H_C$ domain reference sequences include:
BoNT/A—amino acid residues 872-1296, for example N872-L1296
BoNT/B—amino acid residues 859-1291, for example E859-E1291
BoNT/$C_1$—amino acid residues 867-1291, for example N867-E1291
BoNT/D—amino acid residues 863-1276, for example S863-E1276
BoNT/E—amino acid residues 846-1252, for example R846-K1252
BoNT/F—amino acid residues 865-1274, for example K865-E1274
BoNT/G—amino acid residues 864-1297, for example N864-E1297
TeNT—amino acid residues 880-1315, for example I880-D1315

The above sequence positions may vary slightly according to serotype/subtype.

In one embodiment, the polypeptide of the present invention comprising a TM that comprises or consists of a $H_{CC}$ domain or $H_C$ domain from a BoNT/F subtype. The BoNT/F $H_{CC}$ domain or $H_C$ domain may be from BoNT/$F_1$, BoNT/$F_2$, BoNT/$F_3$, BoNT/$F_4$, BoNT/$F_5$, BoNT/$F_6$, or BoNT/$F_7$. For example, the $H_{CC}$ domain or $H_C$ domain may be from BoNT/$F_5$, or BoNT/$F_7$.

The $H_{CC}$ domain or $H_C$ domain may be derived from the same BoNT/F subtype as the BoNT/F $LH_N$ backbone of the polypeptide of the invention. For example, if the BoNT/F $LH_N$ backbone is from a BoNT/$F_7$ subtype, the TM may be a BoNT/$F_7$ $H_{CC}$ domain or $H_C$ domain. Thus, in one embodiment, the polypeptide of the invention is identical to a single chain naturally occurring BoNT/F, except that the activation loop has been replaced by the activation loop from a different BoNT/F subtype (and hence, for the avoidance of doubt, the polypeptide of the invention is not a naturally-occurring BoNT).

The BoNT/F $H_{CC}$ domain or $H_C$ domain TM of the invention may be a BoNT/F $H_{CC}$ domain or $H_C$ domain as identified in Table 1 herein. For example, as indicated above, in a preferred embodiment the $H_{CC}$ domain or $H_C$ domain is from BoNT/$F_7$. In this instance, the $H_{CC}$ domain or $H_C$ domain may comprise or consist of the $H_{CC}$ domain or $H_C$ domain of a BoNT/$F_7$ subtype, such as the BoNT/$F_7$ of UPI0001DE3DAC or a fragment or variant thereof. As described herein, it is sufficient to refer to the $H_{CC}$ domain or $H_C$ domain of a BoNT/$F_7$ such as UPI0001DE3DAC, or a fragment or variant thereof. Alternatively, the $H_{CC}$ domain or $H_C$ domain or fragment or variant thereof of BoNT/$F_7$ (e.g. UPI0001DE3DAC) may be defined in terms of its sequence, or in terms of the amino acid corresponding to the amino acid positions in the full-length amino acid sequence of the BoNT/$F_7$ (as described above). Using the non-limiting example of UPI0001DE3DAC, the full-length $H_{CC}$ domain may be referred to as amino acids corresponding to amino acid positions 1077 to 1268 (for the full-length $H_{CC}$ domain) or amino acid positions 1095 to 1260 (for the minimal $H_{CC}$ domain) of UPI0001DE3DAC (full-length UPI0001DE3DAC has the amino acid sequence of SEQ ID NO: 13)). Such definitions (in terms of sequence and/or amino acid position) apply equally to any other BoNT/F $H_{CC}$ domains or $H_C$ domains, including those listed in Table 1.

Thus, in a preferred embodiment, the polypeptide of the invention comprises an amino acid sequence derived from a full-length BoNT/$F_5$ or BoNT/$F_7$ amino acid sequence, except that the BoNT/$F_5$ or BoNT/$F_7$ activation loop sequence has been replaced by an activation loop sequence from a BoNT/F subtype other than BoNT/$F_5$ or BoNT/$F_7$. In a particularly preferred embodiment, the BoNT/$F_5$ or BoNT/$F_7$ activation loop region is replaced by a BoNT/$F_1$ activation loop region. For example, the polypeptide of the invention may comprise or consist of the amino acid sequence of SEQ ID NO: 75, or a variant thereof (as defined herein).

The TM of the invention may be a modified clostridial $H_{CC}$ or $H_C$ domain, see, for example, WO 2006/027207, WO 2006/114308 and WO 2013/180799, each of which is incorporated by reference in its entirety.

The term "binding" as used herein may mean that one molecule (in this instance the $H_{CC}$ or $H_C$ domain) is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. Thus, "binding affinity" means the strength of a molecule (in this instance the $H_{CC}$ or $H_C$ domain) for a particular receptor.

Alternatively, the polypeptide of the invention may be a re-targeted clostridial toxin, i.e. the polypeptide may comprise a BoNT/F $LH_N$ backbone and an BoNT/F activation loop as disclosed herein, but may comprise a non-clostridial TM.

Examples of non-clostridial TMs are described, for example, in EP-B-0689459; WO 1994/021300; EP-B-0939818; U.S. Pat. Nos. 6,461,617; 7,192,596; WO 1998/007864; EP-B-0826051; U.S. Pat. Nos. 5,989,545; 6,395,513; 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; WO 2005/023309; WO 2006/059113; WO 2006/059105; WO 2007/138339; WO 2009/150469; WO 2010/055358; WO 2009/150470; WO 2010/020811; WO 2010/094905; WO 2014/128497 and WO 1999/58571; all of which are hereby incorporated by reference in their entirety. References herein to TSIs and/or to non-clostridial TMs include structural equivalents such as those described in WO 2011/018665, which is herein incorporated by reference.

Polynucleotides of the Invention

The present invention also provides a polynucleotide that encodes the polypeptide of the invention. The term polynucleotide encompasses both DNA and RNA sequences, although typically the polynucleotide comprises a DNA sequence.

The invention further provides an expression vector comprising a polynucleotide of the invention. Typically in the expression vector the polynucleotide of the invention is operably linked to a suitable promoter. The polynucleotide may also be linked to a suitable terminator sequence. Suitable promoter and terminator sequences are well known in the art.

The choice of promoter depends in this case on the expression systems used for expression. In general, constitutive promoters are preferred, but inducible promoters may likewise be used. The construct produced in this manner includes at least one part of a vector, in particular regulatory elements, the vector, for example, being selected from A-derivates, adenoviruses, baculoviruses, vaccinia viruses, SV40-viruses and retroviruses. The vector is preferably capable of expressing the nucleic acid in a given host cell.

The expression vector may a promoter selected from:

| Promoter | Induction Agent | Typical Induction Condition |
|---|---|---|
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

In another preferred embodiment, the vector has a promoter selected from:

| Promoter | Induction Agent | Typical Induction Condition |
|---|---|---|
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |
| T5-lac operator | IPTG | 0.2 mM (0.05-2.0 mM) |

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The expression vector of the present invention is preferably designed in silico, and then synthesised by conventional polynucleotide synthesis techniques.

The polynucleotide sequence information is optionally modified for codon-biasing according to the ultimate host cell (e.g. E. coli) expression system that is to be employed.

The polynucleotide backbone is preferably screened for any inherent nucleic acid sequence, which when transcribed and translated would produce an amino acid sequence corresponding to the protease cleavage site encoded by the light-chain-coding sequence. This screening may be performed manually or with the assistance of computer software (e.g. the MapDraw program by DNASTAR, Inc.).

The present invention also provides polypeptides encoded by polynucleotide sequences as described above.

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

Methods of Production

The invention further provides a method of producing a polypeptide of the invention, said method comprising the step of expressing a polynucleotide of the invention in a cell and recovering the expressed polypeptide. The method typically further comprises a step of introducing the polypeptide of the invention into the cell. For example, the polynucleotide of the invention may be introduced into the cell in the form of an expression vector as described herein.

For example, said method for producing a polypeptide of the invention may the comprise expressing a polynucleotide (as described above) in a suitable host cell, lysing the host cell to provide a host cell homogenate containing the polypeptide, and isolating the polypeptide.

The polynucleotide provided/introduced to the cell may be DNA, RNA or mixtures thereof. The polynucleotide may furthermore be modified with regard to its nuclease resistance, such as e.g. by inserting phosphorthioate bonds. The nucleic acid may be produced from a starting nucleic acid, the latter being accessible e.g. by cloning from genomic or cDNA-databases. Moreover, the nucleic acid may be produced directly by solid phase synthesis. Suitable methods are known to the person skilled in the art. If one assumes a starting nucleic acid, a specific modification, e.g. by locality-specific mutagenesis, may be brought about, resulting in at least one addition, insertion, deletion and/or substitution on the amino acid level. The nucleic acid is then linked operatively to a suitable promoter as described herein.

Typically the polypeptide of the invention from the cell is purified and/or concentrated after recovery from the cell. Any suitable method(s) may be used for the recovery, purification and/or concentration of the polypeptide of the invention. Standard techniques for recovery, purification and/or concentration are known in the art, for example chromatography methods and/or electrophoresis.

The polypeptide of the invention may comprise one or more N-terminal and/or C-terminal located purification tags to assist in the purification of the polypeptide. Whilst any purification tag may be employed, the following are preferred: His-tag (e.g. 6× histidine) (SEQ ID NO: 126), preferably as a C-terminal and/or N-terminal tag; MBP-tag (maltose binding protein), preferably as an N-terminal tag; GST-tag (glutathione-S-transferase), preferably as an N-terminal tag; His-MBP-tag, preferably as an N-terminal tag; GST-MBP-tag, preferably as an N-terminal tag; Thioredoxin-tag, preferably as an N-terminal tag; and/or CBD-tag (Chitin Binding Domain), preferably as an N-terminal tag.

One or more peptide spacer/linker molecules may be included in the polypeptide. For example, a peptide spacer may be employed between a purification tag and the rest of the polypeptide molecule.

Activation Methods

The polypeptides of the invention are prepared in single-chain form (see, for example, WO98/07864), and a proteolytic activation step is typically required for full activity. Therefore, the invention provides a method of activating a polypeptide of the invention by converting the polypeptide from the single-chain form to the di-chain form of the polypeptide. This technique is based on the in vivo bacterial mechanism by which native clostridial neurotoxin (i.e. holotoxin) is produced, and results in a polypeptide having the following 'simplified' structural arrangement:

NH2-[light chain]-[cleavage site]-[$H_N$ domain]-COOH

Thus, typically the polypeptide is activated by treatment with a protease, which cleaves at the cleavage site (activation loop) between the light chain and the $H_N$ domain of the $LH_N$ backbone. A di-chain protein is thus produced, comprising the light chain as a single polypeptide chain covalently attached (via a disulphide bridge) to another single polypeptide chain containing the $H_N$ domain.

Alternative structures of polypeptides of the invention are described, for example, in WO 2006/059113, WO06/059093, WO98/07864 and WO2012/156743, each of which is herein incorporated by reference in its entirety.

Accordingly, the invention provides a method of activating a polypeptide of the invention, comprising incubating said polypeptide with a BoNT/F activation loop protease, wherein cleavage of the polypeptide at the BoNT/F cleavage site converts the polypeptide from a single-chain polypeptide into a di-chain polypeptide. Typically this conversion from a single-chain polypeptide into a di-chain polypeptide activates the polypeptide.

The BoNT/F cleavage site (activation loop) may be cleaved by any appropriate enzyme (such as Lys-C). Lys-C, which is commercially available and may be isolated from *Lysobacter enzymogenes*), is preferred.

Activated Di-Chain Polypeptides

As described herein, activated BoNT are di-chain polypeptides, produced by enzymatic cleavage within the activation loop. The present inventors have conducted N-terminal sequencing on the activated di-chain form of the chimeric BoNT/$F_{7-1}$ described herein (see the Examples) and have found that the chain comprising the $H_N$ domain has a unique N-terminal amino acid sequence not found in either the wild-type (unmodified) BoNT/$F_1$ or BoNT/$F_7$ subtypes.

In particular, the inventors have found that the chain comprising the $H_N$ domain comprises the N-terminal amino acid sequence APPR (SEQ ID NO: 127), more specifically APPRLCIKV (SEQ ID NO: 74). Thus, the activated di-chain form of chimeric BoNT/$F_{7-1}$ comprising a chain comprising the $H_N$ domain which additionally includes some amino acids from the BoNT/$F_1$ activation loop as well as amino acids from the $H_N$ domain of BoNT/$F_7$ (see FIG. 8).

Accordingly, the present invention provides a chimeric di-chain BoNT/F polypeptide comprising: (a) a light chain polypeptide sequence as disclosed herein and (b) a $H_N$ polypeptide sequence as disclosed herein; wherein the N-terminus of the $H_N$ polypeptide comprises amino acid residues from a different BoNT/F subtype than the remainder of the $H_N$ polypeptide. Typically the N-terminal amino acid residue of the $H_N$ polypeptide is A or Q. For example, the N-terminus of the $H_N$ polypeptide may begin with an amino acid motif selected from APPR (SEQ ID NO: 127) or QSPS (SEQ ID NO: 128). In a preferred embodiment, the N-terminus of the $H_N$ polypeptide begins with an amino acid motif selected from APPRLCIK (SEQ ID NO: 70), APPRLCIT (SEQ ID NO: 71), QSPSLCIK (SEQ ID NO: 72) and QSPSLCIT (SEQ ID NO: 73).

In a preferred embodiment, the present invention provides a chimeric di-chain BoNT/F polypeptide comprising: (a) a (BoNT/F) light chain polypeptide sequence having at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of amino acids corresponding to residues 1 to 430 of SEQ ID NO: 1 (such as amino acid residues from any one of SEQ ID NOs: 2 to 16, preferably from SEQ ID NO: 13, which correspond to amino acid residues 1 to 430 of SEQ ID NO: 1); and/or amino acid residues corresponding to residues 15 to 412 of any one of SEQ ID NOs: 1 to 16, or an amino acid sequence comprising or consisting of amino acids positions from any one of SEQ ID NOs: 2 to 16, preferably from SEQ ID NO: 13, which correspond to amino acid residues 15 to 412 of SEQ ID NO: 1; and/or an amino acid sequence which comprises or consists of any one of SEQ ID NOs: 33 to 48, preferably SEQ ID NO: 45; and (b) a (BoNT/F) $H_N$ domain polypeptide sequence having at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of amino acids corresponding to residues 520 to 873 of any one of SEQ ID NOs: 1 (such as amino acid residues from any one of SEQ ID NOs: 2 to 16, preferably from SEQ ID NO: 13, which correspond to amino acid residues 520 to 873 of SEQ ID NO: 1); and/or an amino acid sequence comprising or consisting of amino acid positions from any one of SEQ ID NOs: 2 to 16, preferably from SEQ ID NO: 13, which correspond to amino acid residues 520 to 873 of SEQ ID NO: 1; and/or an amino acid sequence which comprises or consists of any one of SEQ ID NOs: 49 to 64, preferably SEQ ID NO: 61; wherein the N-terminus of the $H_N$ polypeptide comprises amino acid residues from a different BoNT/F subtype than the remainder of the $H_N$ polypeptide.

In a preferred embodiment, the chimeric di-chain BoNT/F polypeptide of the invention comprises a BoNT/$F_7$ or BoNT/$F_5$ light chain or light chain fragment and a BoNT/$F_7$ or BoNT/$_5$ $H_N$ domain or $H_N$ domain fragment. Thus, in a preferred embodiment, the chimeric di-chain BoNT/F polypeptide of the invention comprises: (a) a (BoNT/F) polypeptide sequence having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% or more, up to 100% amino acid sequence identity with an amino acid sequence comprising or consisting of an amino acid sequence from any one of SEQ ID NOs: 8 or 13 to 16, preferably from SEQ ID NO: 13, which corresponds to amino acids 1 to 430 of SEQ ID NO: 1, such as amino acid residues 1 to 421 of any one of SEQ ID NOs: 13 to 16, preferably SEQ ID NO: 13, or amino acid residues 1 to 428 of SEQ ID NO: 8; and/or an amino acid sequence from any one of SEQ ID NOs: 8 or 13 to 16, preferably from SEQ ID NO: 13, which corresponds to amino acids 15 to 412 of SEQ ID NO: 1, such as amino acid residues 15 to 403 of any one of SEQ ID NOs: 13 to 16, preferably SEQ ID NO: 13, or amino acid residues 15 to 410 of SEQ ID NO: 8; and/or any one of SEQ ID NOs: 40 or 45 to 48, preferably SEQ ID NO: 45; and (b) at least 40%, at least 45%, at least 50%, at least 55%, at least 60%, at least 65%, at least 70%, at least 75%, at least 80%, at least 85%, least 90%, at least 95%, at least 96%, at least 97%, at least 98%, at least 99% or more, up to 100% amino acid sequence identity with an amino acid sequence comprising or consisting of an amino acid sequence from any one of SEQ ID NOs: 8 or 13 to 16, preferably from SEQ ID NO: 13, which corresponds to amino acids 520 to 873 of SEQ ID NO: 1, such as amino acid residues 509 to 862 of any one of SEQ ID NOs: 13 to 16, preferably SEQ ID NO: 13, or amino acid residues 516 to 868 of SEQ ID NO: 8; and/or an amino acid sequence from any one of SEQ ID NOs: 8 or 13 to 16, preferably from SEQ ID NO: 13, which corresponds to amino acids 538 to 850 of SEQ ID NO: 1, such as amino acid residues 527 to 839 of any one of SEQ ID NOs: 13 to 16, preferably SEQ ID NO: 13, or amino acid residues 534 to 845 of SEQ ID NO: 8, and/or any one of SEQ ID NOs: 56 or 61 to 64, preferably SEQ ID NO: 61; wherein the N-terminus of the $H_N$ polypeptide comprises amino acid residues from a different BoNT/F subtype than the remainder of the $H_N$ polypeptide.

In a particularly preferred embodiment, the invention provides a chimeric di-chain BoNT/F polypeptide comprising: (a) a light chain polypeptide comprising an amino acid sequence having at least 40% sequence identity at least one of SEQ ID NOs: 33 to 48, preferably SEQ ID NO: 45; and (b) an $H_N$ polypeptide comprising an amino acid sequence having at least 70% sequence identity at least one of SEQ ID NOs: 49 to 64, preferably SEQ ID NO: 61; wherein the N-terminus of the $H_N$ polypeptide comprises amino acid residues from a different BoNT/F subtype than the remainder of the $H_N$ polypeptide.

Typically the N-terminal amino acid residue of the $H_N$ polypeptide is A or Q. For example, the N-terminus of the $H_N$ polypeptide may begin with an amino acid motif selected from APPR (SEQ ID NO: 127) or QSPS (SEQ ID NO: 128). In a preferred embodiment, the N-terminus of the $H_N$ polypeptide begins with an amino acid motif selected from APPRLCIK (SEQ ID NO: 70), APPRLCIT (SEQ ID NO: 71), QSPSLCIK (SEQ ID NO: 72) and QSPSLCIT (SEQ ID NO: 73).

A chimeric di-chain of the present invention may comprise a light chain polypeptide sequence from any BoNT/F subtype, preferably from BoNT/$F_5$ or BoNT/$F_7$. A chimeric di-chain of the present invention may comprise a $H_N$ polypeptide sequence from any BoNT/F subtype, preferably from BoNT/$F_5$ or BoNT/$F_7$. The light chain polypeptide sequence and the $H_N$ polypeptide sequence may be from the same BoNT/F subtype. For example, both the light chain polypeptide sequence and the $H_N$ polypeptide sequence may be from BoNT/$F_5$ or BoNT/$F_7$. The light chain polypeptide sequence and the $H_N$ polypeptide sequence may be from closely related subtypes. For example, the light chain polypeptide sequence may be from BoNT/$F_5$ and the $H_N$ polypeptide sequence may be from BoNT/$F_7$ or vice versa. In a preferred embodiment, the light chain polypeptide sequence and/or the $H_N$ polypeptide sequence is from a BoNT/$F_5$ subtype or a BoNT/$F_7$ subtype. In an even more preferred embodiment, both the light chain polypeptide sequence and the $H_N$ polypeptide sequence are from a BoNT/$F_5$ subtype or a BoNT/$F_7$ subtype, most preferably from a BoNT/$F_7$ subtype. The light chain polypeptide sequence and the $H_N$ polypeptide sequence may be from different BoNT/F subtypes. Typically the light chain polypeptide sequence and the $H_N$ polypeptide sequence are from the same or closely related BoNT/F subtypes.

A chimeric di-chain of the present invention comprises one or more amino acid residues from the activation loop of a different BoNT/F subtype than the BoNT/F subtype of the light chain polypeptide sequence and/or the $H_N$ polypeptide sequence. The one or more amino acids from a different BoNT/F subtype may be retained at the C-terminus of the light chain polypeptide sequence and/or the N-terminus of the $H_N$ polypeptide sequence. Typically the $H_N$ polypeptide sequence of the chimeric di-chain polypeptide of the invention is a BoNT/$F_5$ or BoNT/$F_7$ sequence and its N-terminus comprises one or more amino acids from a BoNT/$F_1$, BoNT/$F_2$, BoNT/$F_3$, BoNT/$F_4$ or BoNT/$F_6$ activation loop, as described herein. In a preferred embodiment, the one or more amino acids are from a BoNT/$F_1$ activation loop, as described herein.

The chimeric di-chain polypeptide of the invention may comprise all the amino acids of the corresponding chimeric single-chain polypeptide, i.e. the sequence of the di-chain polypeptide may be identical to that of the single-chain polypeptide, except that it is split across two polypeptide chains, rather than being in a single chain. Alternatively, the chimeric di-chain polypeptide of the invention may be missing one or more amino acids compared with the corresponding chimeric single-chain polypeptide. Typically this arises due to cleavage at a second (or subsequent) site within the activation loop, resulting in loss of a short fragment of the activation loop sequence from the activated chimeric di-chain polypeptide. Thus, the chimeric di-chain polypeptide may be missing at least one, at least two, at least three, at least four, at least five, at least six, at least seven, at least eight, at least nine, at least ten, at least eleven or more amino acids compared with the corresponding chimeric single-chain polypeptide.

Any of the disclosure herein regarding the definition of the light chain polypeptide sequences and $H_N$ polypeptide sequences in relation to the single-chain chimeric polypeptide of the invention applies equally to these sequences within the chimeric di-chain polypeptide of the invention. For example, the light chain polypeptide sequence and/or the $H_N$ polypeptide sequence in the di-chain polypeptide of the invention is preferably from a BoNT/$F_5$ subtype or a BoNT/$F_7$ subtype. Any disclosure herein relating to TMs of the invention applies equally to the di-chain polypeptide as to the single-chain chimeric polypeptide.

The di-chain polypeptide of the invention is typically obtainable from the single-chain chimeric polypeptide of the invention as described herein.

Cells

The polypeptide of the present invention may be produced by a suitable cell (also known as host cells), such as e.g. *Escherichia coli, Saccharomyces cerevisiae, Pichia pastoris* or *Bacillus megaterium*, which multiplies a recombinant expression vector, the vector coding for a polypeptide of the invention.

Accordingly, the invention further provides cells, which express a polypeptide of the invention. Typically the cells of the invention contain a polynucleotide or expression vector of the invention and are suitable for expressing the polynucleotide or vector. Numerous prokaryotic and eukaryotic expression systems are known in the state of the art, the cells being selected, for example, from prokaryotic cells such as *E. coli* or *B. megaterium*, from eukaryotic cells such as *S. cerevisiae* and *P. pastoris*. Although higher eukaryotic cells, such as insect cells or mammal cells, may be used as well, cells are nevertheless preferred, which, like *C. botulinum*, do not possess a glycosylation apparatus.

Compositions and Therapeutic/Cosmetic Indications

The invention also provides a pharmaceutical composition comprising a polypeptide or di-chain polypeptide of the invention. The pharmaceutical composition may optionally comprise a pharmaceutically acceptable excipient, diluent, carrier, propellant, salt and/or additive. Typically the pharmaceutical composition of the invention is suitable for treating or preventing diseases or disorders in which a therapy with a botulinum neurotoxin is indicated. The pharmaceutical composition is particularly suitable for subcutaneous, intramuscular, implant and/or topical administration. Intramuscular administration is preferred. Compositions suitable for injection may be in the form of solutions, suspensions or emulsions, or dry powders which are dissolved or suspended in a suitable vehicle prior to use.

The invention also provides a cosmetic composition comprising a polypeptide or di-chain polypeptide of the invention. The cosmetic composition may optionally comprise a cosmetically acceptable excipient, diluent, carrier, propellant, salt and/or additive. Typically the cosmetic composition of the invention is suitable for alleviating a cosmetic indication for which the application of a botulinum neurotoxin is indicated.

The cosmetic composition is particularly suitable for subcutaneous, intramuscular, implant and/or topical administration. Intramuscular or subcutaneous administration are preferred. Compositions suitable for injection may be in the form of solutions, suspensions or emulsions, or dry powders which are dissolved or suspended in a suitable vehicle prior to use.

In the case of polypeptide, di-chain polypeptide or composition that is to be delivered locally, the engineered clostridial toxin may be formulated as a cream (e.g. for topical application), or for sub-dermal injection. Topical delivery means may include transdermal delivery (e.g. via an adhesive patch).

Local delivery of either pharmaceutical or cosmetic compositions of the invention is also envisaged. The term local delivery typically indicates that the site of action is at (or near to the site of application). As a non-limiting example, a BoNT injected into a muscle to be weakened would be local delivery to that muscle by intramuscular injection.

Systemic delivery of either pharmaceutical or cosmetic compositions of the invention is also envisaged. The term systemic delivery typically indicates that the site of action is not at (or near to) the site of action, but rather the BoNT is transported (usually in the blood) from where it is applied to where it acts. As a non-limiting example, BoNT injected into the general circulation with the intention of weakening a particular muscle, for which it has specificity, would be systemic delivery.

Polypeptides, di-chain polypeptides and/or compositions of the invention may be administered to a patient by intrathecal or epidural injection in the spinal column at the level of the spinal segment involved in the innervation of an affected organ.

A preferred route of administration is via laparoscopic and/or localised, particularly intramuscular, injection.

The dosage ranges for administration of the polypeptides, di-chain polypeptides or compositions of the present invention are those to produce the desired therapeutic or cosmetic effect. It will be appreciated that the dosage range required depends on the precise nature of the polypeptide, di-chain polypeptide or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.001-10 ng/kg, preferably 0.001-5 ng/kg, more preferably 0.02-5 ng/kg, and particularly preferably 0.04-5 ng/kg. The unit dosage can vary from less than 10 picogram to 300 ng, but typically will be in the region of 0.1 to 10 ng per dose, which may be administered daily or preferably less frequently, such as weekly or six monthly.

A particularly preferred dosing regimen is based on 0.5 ng of polypeptide/di-chain polypeptide as the 1× dose. In this regard, preferred dosages are in the range 1×-100× (i.e. 0.5-50 ng).

Fluid dosage forms are typically prepared utilising the polypeptide/di-chain polypeptide and a pyrogen-free sterile vehicle. The polypeptide or di-chain polypeptide, depending on the vehicle and concentration used, can be either dissolved or suspended in the vehicle. In preparing solutions the polypeptide or di-chain polypeptide can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

A suspending agent, for example, polyvinylpyrrolidone may be included in the composition(s) to facilitate uniform distribution of the components.

Administration in accordance with the present invention may take advantage of a variety of delivery technologies including microparticle encapsulation, viral delivery systems or high-pressure aerosol impingement.

The invention further provides a polypeptide, di-chain polypeptide and/or pharmaceutical composition as described herein for use in a method of preventing or treating a disease or disorder for which a therapy with a botulinum neurotoxin is indicated. The invention further provides the use of a polypeptide, di-chain polypeptide and/or pharmaceutical composition as described herein in the manufacture of a medicament for preventing or treating a disease or disorder for which a therapy with a botulinum neurotoxin is indicated. The invention further provides a method of treating a disease or disorder for which a therapy with a botulinum neurotoxin is indicated comprising administering a pharmaceutically effective dose of a polypeptide, di-chain polypeptide and/or pharmaceutical composition as described herein to an individual in need thereof. The disease or disorder may be any disease or disorder as described herein.

The invention further provides a BoNT/$F_{7-1}$ polypeptide and/or pharmaceutical composition comprising a BoNT/$F_{7-1}$ polypeptide for use in a method of preventing or treating a disease or disorder for which a therapy with a botulinum neurotoxin is indicated. The invention further provides the use of a BoNT/$F_{7-1}$ polypeptide and/or pharmaceutical composition comprising a BoNT/$F_{7-1}$ polypeptide in the manufacture of a medicament for preventing or treating a disease or disorder for which a therapy with a botulinum neurotoxin is indicated. The invention further provides a method of treating a disease or disorder for which a therapy with a botulinum neurotoxin is indicated comprising administering a pharmaceutically effective dose of a BoNT/$F_{7-1}$ polypeptide and/or pharmaceutical composition comprising a BoNT/$F_{7-1}$ polypeptide to an individual in need thereof. The disease or disorder may be any disease or disorder as described herein. The BoNT/$F_{7-1}$ polypeptide is preferable a di-chain (activated) BoNT/$F_{7-1}$ polypeptide.

The invention further provides the use of a polypeptide, di-chain polypeptide and/or cosmetic composition as described herein for preventing or alleviating a cosmetic indication for which the application of a botulinum neurotoxin is indicated. The cosmetic indication may be any cosmetic indication as described herein.

The invention further provides the use of a BoNT/$F_{7-1}$ polypeptide and/or cosmetic composition comprising a BoNT/$F_{7-1}$ polypeptide for preventing or alleviating a cosmetic indication for which the application of a botulinum neurotoxin is indicated. The cosmetic indication may be any cosmetic indication as described herein. The BoNT/$F_{7-1}$ polypeptide is preferable a di-chain (activated) BoNT/$F_{7-1}$ polypeptide.

Any reference herein to therapeutic and/or cosmetic indications, or to pharmaceutical and/or cosmetic compositions applies equally to the single-chain chimeric polypeptides of the inventions and the di-chain polypeptides described herein.

EXAMPLES

The following Examples serve to illustrate particular embodiments of the invention, and do not limit the scope of the invention defined in the claims in any way.

Example 1—Alignment of the Activation Loop Amino Acid Sequences Across all BoNT Serotypes and Subtypes The UniParc database was searched, by a basic local alignment search tool (BLAST) search for full-length BoNT proteins. The amino acid sequences of all full-length BoNTs identified in the BLAST search were analysed and the activation loop sequences identified. The activation loop sequences of all BoNT/A and BoNT/F subtypes were aligned (FIG. 1) and analysed for any significant similarities and differences.

It was surprisingly found that, although there was a high degree of intraserotype conservation of the activation loops sequences between the BoNT/A sequences, the level of conservation between the BoNT/F subtypes was much lower. In particular, it was found that the activation loops from BoNT/$F_5$ and BoNT/$F_7$ subtypes were particularly divergent compared with other BoNT/F subtypes (FIGS. 1, 3 and 4).

Example 2—Preparation of an Expression Plasmid Encoding Chimeric BoNT/$F_{7-1}$ Phylogenetic analysis of the different BoNT/F subtypes was conducted (FIG. 2) to identify a BoNT/$F_1$ subtype and a BoNT/$F_7$ subtype for the generation of a chimeric protein BoNT/$F_{7-1}$.

The naturally occurring protein, UniParc number UPI00000B66D1, is subtype $F_1$ (BoNT/$F_1$). This BoNT/$F_1$ was prepared as a recombinant protein and named SXN102691, recombinant BoNT/F1 (rBoNT/$F_1$).

The naturally occurring protein, UniParc number UPI0001DE3DAC, aligns together with three other, highly similar proteins, into subtype $F_7$ (BoNT/$F_7$). This BoNT/$F_7$ was prepared as a recombinant protein and named SXN102697, recombinant BoNT/$F_7$ (rBoNT/$F_7$).

rBoNT/$F_1$ and rBoNT/$F_7$ were purified as single chain precursor proteins. Conditions were identified for post-translational modification of purified single chain rBoNT/$F_1$ by selective proteolysis by the protease Lys-C. This created the mature di-chain form of the rBoNT/$F_1$ protein. The post-translational proteolysis step is called activation because the mature (activated) forms of BoNT proteins show higher specific activity in functional assays compared to the single chain forms.

In contrast to rBoNT/$F_1$, no conditions to selectively activate rBoNT/$F_7$ could be identified. Instead, under all conditions tested rBoNT/$F_7$ proteolysis was not selective, but rather occurred at several additional sites in the protein. Proteolysis at unwanted sites is called degradation.

Figure 5:
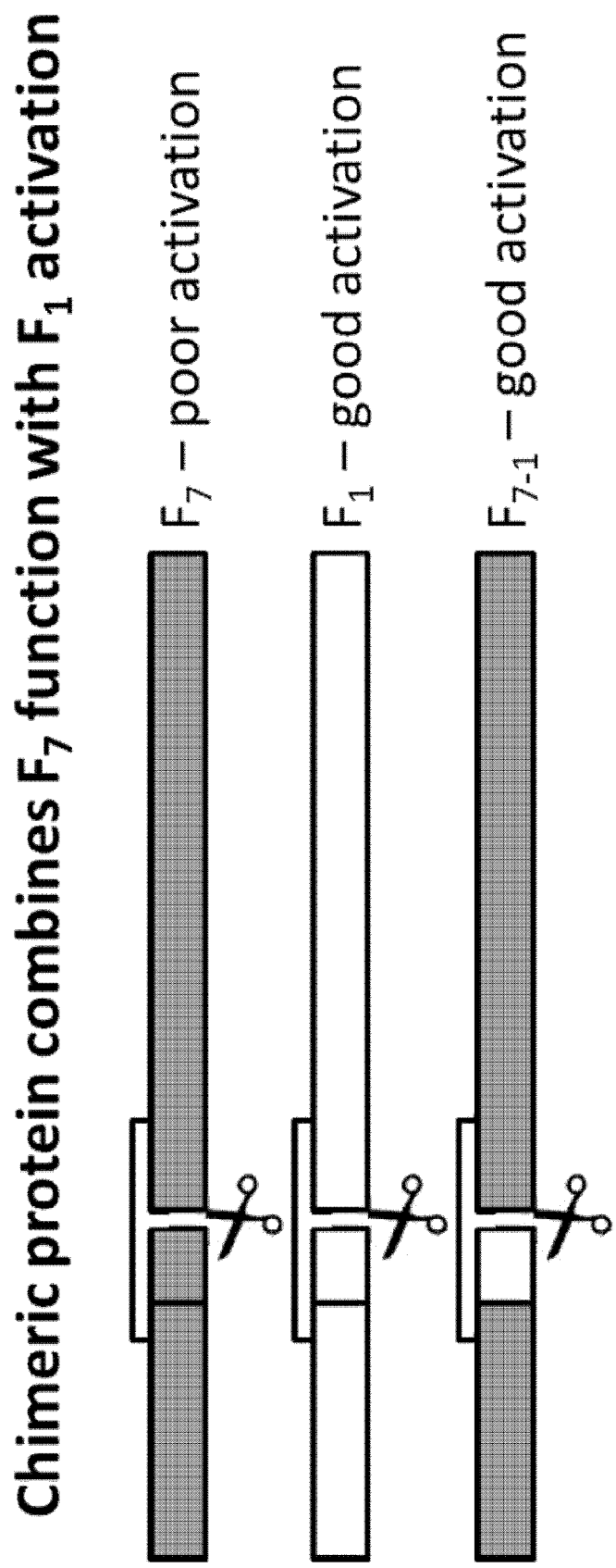
FIG. 5: Schematic of rBoNT/F$_1$, rBoNTF$_7$ and rBoNTF$_{7-1}$

The overall structure of BoNT proteins, including the location of the selectively proteolysed site at which they become activated, is well conserved. Conservation between BoNTs is especially apparent at the levels of secondary and tertiary structures. Therefore it was reasoned that substituting the activation loop from rBoNT/$F_1$ into the structure of rBoNT/$F_7$ would create a chimeric protein that both retained the functional characteristic of rBoNT/$F_7$ and was also amenable to post-translational activation like rBoNT/$F_1$. We called this chimeric protein rBoNT/$F_{71}$ (FIG. 5).

The chimeric protein rBoNT/$F_{1-7}$ is composed of amino acids 1-421 from UPI0001DE3DAC (BoNT/$F_7$), 430-444 from UPI00000B66D1 (BoNT/$F_1$), and 435-1268 from UPI0001DE3DAC (BoNT/$F_7$) (see FIG. 6 for full amino acid sequences). The chimeric protein rBoNT/$F_{7-1}$ is named SXN102875. The percentage identity and divergence of rBoNT/$F_1$, rBoNT/$F_7$ and rBoNT/$F_{7-1}$ is shown in Table 2 below.

TABLE 2

|  |  | Percent Identity | | |
|---|---|---|---|---|
|  |  | rBoNT/F$_{7-1}$ | rBoNT/F$_7$ | rBoNT/F$_1$ |
| Divergence | rBoNT/F$_{7-1}$ |  | 99.5 | 74.9 |
|  | rBoNT/F$_7$ | 0.5 |  | 74.4 |
|  | rBoNT/F$_1$ | 30.6 | 31.3 |  |

An expression plasmid, encoding chimeric BoNT/F$_{7-1}$, was created by two rounds of PCR based site-directed mutagenesis (SDM), to modify the codons for the activation loop region of BoNT/F$_7$ (in our existing expression plasmid for SXN102697) to encode the amino acid sequence of the activation loop region from BoNT/F$_1$. The existing expression plasmid for SXN102697 was made using chemical synthesis techniques and contains an open reading frame which encodes BoNT/F$_7$ (SEQ ID NO: 13—BoNT/F$_7$—UniParc Accession No. UPI0001DE3DAC), and is codon-optimised for efficient protein expression in E. coli bacteria cells.

The amino acid sequence of the BoNT/F$_1$ activation loop is:
(SEQ ID NO: 66)
KSVIPRKGTKAPPRL

The amino acid sequence of the BoNT/F$_7$ activation loop is:
(SEQ ID NO: 69)
KSIVSKKGTKN--SL

Site directed mutagenesis (SDM) primers were:

TABLE 3

| Primer name | Sequence | %GC |
|---|---|---|
| F7_1_For | 5'-CcaagAAGGGTACGAAAGCACCGCC TCGCCTGTGCATTAAAGTCAAC-3' | 53.2 |
| F7_1_Rev | 5'-gtTgactTtaAtgcaCagGcgaGgc ggTgCtTtCgtaccCttcttgg-3' | 53.2 |
| F7_2_For | 5'-CtTcGtgggcctgtgcAaaagcgTT attCcgcgtaagggtAcgaaAgCaC-3' | 54.0 |
| F7_2_Rev | 5'-gtgcTTtcgtaCCcTtacgcGgAat AacgcTTTtgcacaGgCCcacgAag-3' | 54.0 |

First Round of Site Directed Mutagenesis (SDM)

The template plasmid for the first round of SDM was A002697 (and expression plasmid encoding BoNT/F$_7$). Four independent reactions were set up for the first round of SDM:

| Reaction 1 | | Reaction 2 | |
|---|---|---|---|
| Template | 1 µl | Template | 1 µl |
| 10× pFU turbo reaction buffer | 5 µl | 10× pFU turbo reaction buffer | 5 µl |
| F7_1_For primer (10 uM) | 2.5 µl | F7_1_For primer (10 µM) | 2.5 µl |
| F7_1_Rev primer (10 uM) | 2.5 µl | F7_1_Rev primer (10 µM) | 2.5 µl |
| dNTP mix (10 mM each) | 5 µl | dNTP mix (10 mM each) | 5 µl |
| dH$_2$O | 33 µl | dH$_2$O | 30 µl |
| pFU polymerase | 1 µl | MgCl$_2$ (50 mM) | 2.5 µl |
|  |  | pFU polymerase | 1 µl |

| Reaction 3 | | Reaction 4 | |
|---|---|---|---|
| Template | 0.5 µl | Template | 0.5 µl |
| 10× pFU turbo reaction buffer | 5 µl | 10× pFU turbo reaction buffer | 5 µl |
| F7_1_For primer (10 µM) | 2.5 µl | F7_1_For primer (10 µM) | 2.5 µl |
| F7_1_Rev primer (10 µM) | 2.5 µl | F7_1_Rev primer (10 µM) | 2.5 µl |
| dNTP mix (10 mM each) | 5 µl | dNTP mix (10 mM each) | 5 µl |
| dH$_2$O | 33 µl | dH$_2$O | 31 µl |
| pFU polymerase | 1 µl | MgCl$_2$ (50 mM) | 2.5 µl |
|  |  | pFU polymerase | 1 µl |

PCR cycling conditions for all reactions were as follows:

| 95° C. | 30 sec |  |
| 95° C. | 30 sec |  |
| 55° C. | 1 min | 18 cycles |
| 72° C. | 5 min |  |
| 72° C. | 10 min |  |
| 4° C. | hold |  |

The PCR reaction products were digested with DpnI, for 2 hours at 37° C., and then transformed into Top10 cells (Life Technologies, one shot cells Lot 1419720). The DpnI digestion reaction mix was:

| NEB Buffer 4 (10×) | 5 µl |
| PCR reaction mix | 44 µl |
| DpnI | 1 µl |

The transformations into Top10 cells were performed according to the manufacturer's instructions. Briefly, cells were defrosted on ice then 5 µl digestion reaction was added to 50 µl competent cells and incubated on ice for 30 min. Then the cells were heat shocked for 30 sec at 42° C. and returned to ice for a further 2 min. Then 200 µl SOC media (supplied with the competent cells) was added to the transformation reaction and the cells were incubated for 1 hour at 37° C. in a shaking incubator. Transformed cells were plated onto agar-kanamycin plates and incubated overnight at 37° C.

Reaction 1 resulted in 34 colonies
Reaction 2 resulted in 122 colonies
Reaction 3 resulted in 59 colonies
Reaction 4 resulted in 42 colonies A pUC positive control transformation, performed alongside, resulted in 92 colonies.

A single colony was picked from each of the four reaction conditions, grown overnight (10 ml L-Broth, kanamycin), and the plasmid DNA was harvested by Wizard Plus Miniprep (Promega), according to the manufacturer's instructions.

Plasmid DNA from each of the 4 reaction conditions was sent for DNA sequencing, which confirmed that the expected point mutations had been inserted in all four cases.

Second Round of Site Directed Mutagenesis (SDM)

The template plasmid for the second round of SDM was plasmid DNA from the first round (reaction 2). Five different reactions were set up:

| Reaction 1 | | Reaction 2 | |
|---|---|---|---|
| Template | 0.5 µl | Template | 0.5 µl |
| 10× pFU turbo reaction buffer | 5 µl | 10× pFU turbo reaction buffer | 5 µl |
| F7_1_For primer (10 µM) | 2.5 µl | F7_1_For primer (10 µM) | 2.5 µl |

| | | | | |
|---|---|---|---|---|
| F7_1_Rev primer (10 µM) | 2.5 µl | F7_1_Rev primer (10 µM) | 2.5 µl | |
| dNTP mix (10 mM each) | 5 µl | dNTP mix (10 mM each) | 5 µl | |
| dH$_2$O | 33 µl | dH$_2$O | 31 µl | |
| pFU polymerase | 1 µl | MgCl$_2$ (50 mM) | 2.5 µl | |
| | | pFU polymerase | 1 µl | |
| Reaction 3 | | Reaction 4 | | |
| Template | 1 µl | Template | 1 µl | |
| 10× pFU turbo reaction buffer | 5 µl | 10× pFU turbo reaction buffer | 5 µl | |
| F7_1_For primer (10 µM) | 2.5 µl | F7_1_For primer (10 µM) | 2.5 µl | |
| F7_1_Rev primer (10 µM) | 2.5 µl | F7_1_Rev primer (10 µM) | 2.5 µl | |
| dNTP mix (10 mM each) | 5 µl | dNTP mix (10 mM each) | 5 µl | |
| dH$_2$O | 33 µl | dH$_2$O | 30 µl | |
| pFU polymerase | 1 µl | MgCl$_2$ (50 mM) | 2.5 µl | |
| | | pFU polymerase | 1 µl | |
| Reaction 5 (negative control) | | | | |
| Template | | | 0.5 µl | |
| 10× pFU turbo reaction buffer | | | 5 µl | |
| F7_2_For primer (10 µM) | | | 2.5 µl | |
| F7_2_Rev primer (10 µM) | | | 2.5 µl | |
| dNTP mix (10 mM each) | | | 5 µl | |
| dH$_2$O | | | 35 µl | |
| pFU polymerase | | | none | |

PCR Cycling Conditions for all Reactions

| | | |
|---|---|---|
| 95° C. | 30 sec | |
| 95° C. | 30 sec | |
| 55° C. | 1 min | } 18 cycles |
| 72° C. | 5 min | |
| 72° C. | 10 min | |
| 4° C. | hold | |

The PCR reaction products were digested with DpnI then transformed into Top10 cells as described for round 1
Reaction 1 resulted in 13 colonies
Reaction 2 resulted in 16 colonies
Reaction 3 resulted in 15 colonies
Reaction 4 resulted in 0 colonies
Reaction 5 resulted in 0 colonies One colony each from reactions 1 and 2, and 2 from reaction 3, were grown overnight; DNA was extracted and sent for sequencing as described above.

After conformation that the desired sequence encoding protein BoNT/F$_{7-1}$ was present the sequence-verified DNA was transformed into competent BL21 (DE3) cells (Invitrogen), according to the manufacturer's instructions, and cell banks were laid down.

Example 3—Purification of rBoNT/$F_{7-1}$

Lysis by Cell Disruptor/Homogeniser

*E. coli* cells, expressing rBoNT/$F_{7-1}$, were harvested by centrifugation and then resuspended in 3 ml/g of lysis buffer (50 mM Tris pH 8.0, 200 mM NaCl), supplemented with 16 ul Benzonase (90% purity, 25 U/μl). The resuspended cells were held on ice for 5 minutes before lysis.

The cells were lysed by sonication (Misonix 3000 sonicator, 30 sec bursts with 45 sec rests, 8 cycles). The sonicated samples were transferred to a disposable 500 ml centrifuge pots (Corning, #431123), securely capped and the lysate clarified by centrifugation at 4300 g for 1 hour at 4° C.

Butyl Sepharose High Performance Capture Step

The cleared lysate was adjusted to 50 mM Tris pH 8.0, 100 mM NaCl, 1.35 M $(NH_4)_2SO_4$ by the addition of solid (powder) $(NH_4)_2SO_4$. The $(NH_4)_2SO_4$ was added in small increments over 10 minutes with discontinuous mixing. The sample was then decanted into a 500 ml corning tube, balanced and cleared by centrifugation at 4300 g for 1 hour at 20° C. The cleared lysate was then captured on 2× Butyl sepharose high performance HiTrap columns (10 ml resin) equilibrated in equilibration/wash buffer (50 mM Tris pH 8.0, 1.35 M $(NH_4)_2SO_4$). The column was loaded with sample (200 ml), washed for 10 column volumes with equilibration/wash buffer, then eluted over 25 column volumes from 50 mM Tris pH 8.0, 1.35 M $(NH_4)_2SO_4$ to 50 mM Tris pH 8.0. 5 ml fractions were collected throughout the gradient; 25 μl samples from each fraction were added to 25 μl of 4×LDS buffer, made up to 100 μl with $dH_2O$ then run on SDS-PAGE. Fractions containing the target protein were pooled.

Desalting rBoNT/$F_{7-1}$ into Low Salt Q Binding Buffer

The pooled material from the Butyl HP capture step was applied to a pre-equilibrated HiPrep 26/10 desalting column (53 ml column, equilibrated in 50 mM Tris pH 8.5). The sample was then loaded at a flow rate of 8 ml/min in batches of 12 ml before the column was re-equilibrated with buffer. Protein eluting at lower conductivity <2 mSv/cm was collected as one pool.

Intermediate Purification Step HiScreen Q High Performance

The pooled material from the desalting step was loaded onto a pre-equilibrated Q HiScreen HP column (4.7 ml) at a flow rate of 1.2 ml/min. The column was equilibrated in 50 mM Tris pH 8.5. The column was washed with 3 column volumes of 10 mM Tris pH 8.5 at a flow rate of 1.2 ml/min. The protein was then eluted across a linear gradient: 20 column volumes from 50 mM Tris pH 8.5 to 50 mM Tris pH 8.5, 300 mM NaCl; followed by a 5 column volume high salt wash of 10 mM Tris pH 8.5, 1 M NaCl. The elution was completed at a flow rate of 1.2 ml/min and 2.5 ml fractions were collected throughout the elution. 25 μl samples of the load, flow through, fractions were taken for analysis by SDS-PAGE.

SDS-PAGE samples were prepared as follows 25 μl fraction sample, 25 μl LDS-buffer and 50 μl $dH_2O$. The fractions were mixed, spun down, boiled for 5 minutes, mixed and spun down again before loading onto a gel, confirming that purified rBoNT/$F_{7-1}$ had been obtained (FIG. 7).

Protein Concentration and Storage

The protein was concentrated using a 6 ml vivaspin ultrafiltration column (50 kda MWCO). This was achieved by centrifugation at 4300 g until the retentate volume had decreased to give a suitable concentration. The concentration was then determined on a nanodrop lite and final values were derived from this.

Example 4—Activation of rBoNT/$F_{7-1}$ 7 ml of purified, single-chain rBoNT/$F_{7-1}$ (0.201 mg/ml) was removed from the −80° C. freezer and thawed in an MSC1 cabinet. 2.8 μl of Lys-C was added (0.1 mg/ml) to give a final concentration of 0.04 μg/ml (1:5025 ratio). The Lys-C was initially reconstituted in $dH_2O$ to give a 0.1 mg/ml stock.

The sample was incubated at 4° C. overnight (16 hours) alongside a control with no protease added. Samples were taken for SDS-PAGE analysis to make both reduced and none-reduced samples. SDS sample buffer (Invitrogen #

LC2376) was used for oxidising conditions. LDS sample buffer (Invitrogen P0007) and DTT were used for reducing conditions.

Example 5—Phenyl HP Polishing Step of rBoNT/F$_{7-1}$ rBoNT/F$_{7-1}$ was activated for 16 hours overnight after the salt concentration was adjusted to 3 M NaCl by the addition of 1.6 volumes of 50 mM Tris pH 8.0, 5 M NaCl. The sample was then loaded onto a 1 ml HiTrap Phenyl HP column which was pre-equilibrated in 50 mM Tris pH 8.0, 3 M NaCl.

The column was then washed for 10 column volumes with equilibration buffer and the protein was then eluted over a 25 cv linear gradient from 3 M NaCl to 0 M salt. 1 ml fractions were taken across the gradient.

2×10 µl samples were taken for SDS-PAGE analysis. The samples were prepared in either SDS sample buffer (none reduced) or LDS buffer+100 mM DTT (reduced) and run out on SDS-PAGE.

Example 6—N-Terminal Sequencing of Activated rBoNT/F$_{7-1}$

Activated rBoNT/F$_{7-1}$ was subjected to N-terminal sequencing. rBoNT/F$_{7-1}$ was purified, as an activated di-chain protein, as described above. Samples were prepared by adding 200 µl final sample (0.1 mg/ml), to 100 µl SDS loading buffer, 40 µl DTT (1M), and 60 µl H$_2$O. The samples were heated for 5 min at 95° C. then loaded 1 µg per lane (20 µl load volume) onto gels and processed for SDS-PAGE (FIG. 8).

The BoNT/F$_{7-1}$ heavy chain (~100 kDa band) was excised from each of 9-lanes (of a 10 lane gel) and sent to the contract research organization Alta Bioscience for N-terminal sequencing by Edman degradation. The Alta Bioscience service is accredited to ISO 17025:2005 for N-Terminal Protein Sequencing.

The returned N-terminal sequence for the heavy chain of activated BoNT/F$_{7-1}$ chain was:

TABLE 5

| Residue position | Amino acid |
| --- | --- |
| 1 | A? |
| 2 | P |
| 3 | P |
| 4 | — |
| 5 | L? |
| 6 | — |
| 7 | I? |
| Comments: | |
| Very weak signal just above background | |

? = most probable assignment
— = nothing detected at this position
X = unknown component These results show that activated rBoNT/F$_{7-1}$ is a different protein (at the level of primary sequence) compared to activated rBoNT/F$_7$. Activated rBoNT/F$_{7-1}$ contains amino acids APPR, at the extreme N-terminus of the heavy chain moiety. This amino acid sequence does not occur in native sequence rBoNT/F$_7$.

This revealed that the H$_N$ domain containing chain of the activated di-chain polypeptide comprises the N-terminal amino acid sequence APPRLCIKV (FIG. 8). Thus, this N-terminal sequence comprises the amino acid motif APPR from the BoNT/F$_1$ activation loop, the motif LCI (which is common to both the BoNT/F$_1$ and BoNT/F$_7$ subtypes), and the amino acids KV from the N-terminus of the BoNT/F$_7$ H$_N$ domain. The APPR motif (and the extended APPRLCIKV motif) are not found in native BoNT/F$_7$ (as indicated by the circle highlighting the corresponding BoNT/F$_7$ sequence in FIG. 8). Thus, the activated di-chain form of rBoNT/F$_{7-1}$ contains a unique amino acid sequence, which is not found in either the native (unmodified) form of the BoNT/F$_1$ or BoNT/F$_7$ subtypes.

Example 7—Activity of rBoNT/F$_{7-1}$

Figure 9:
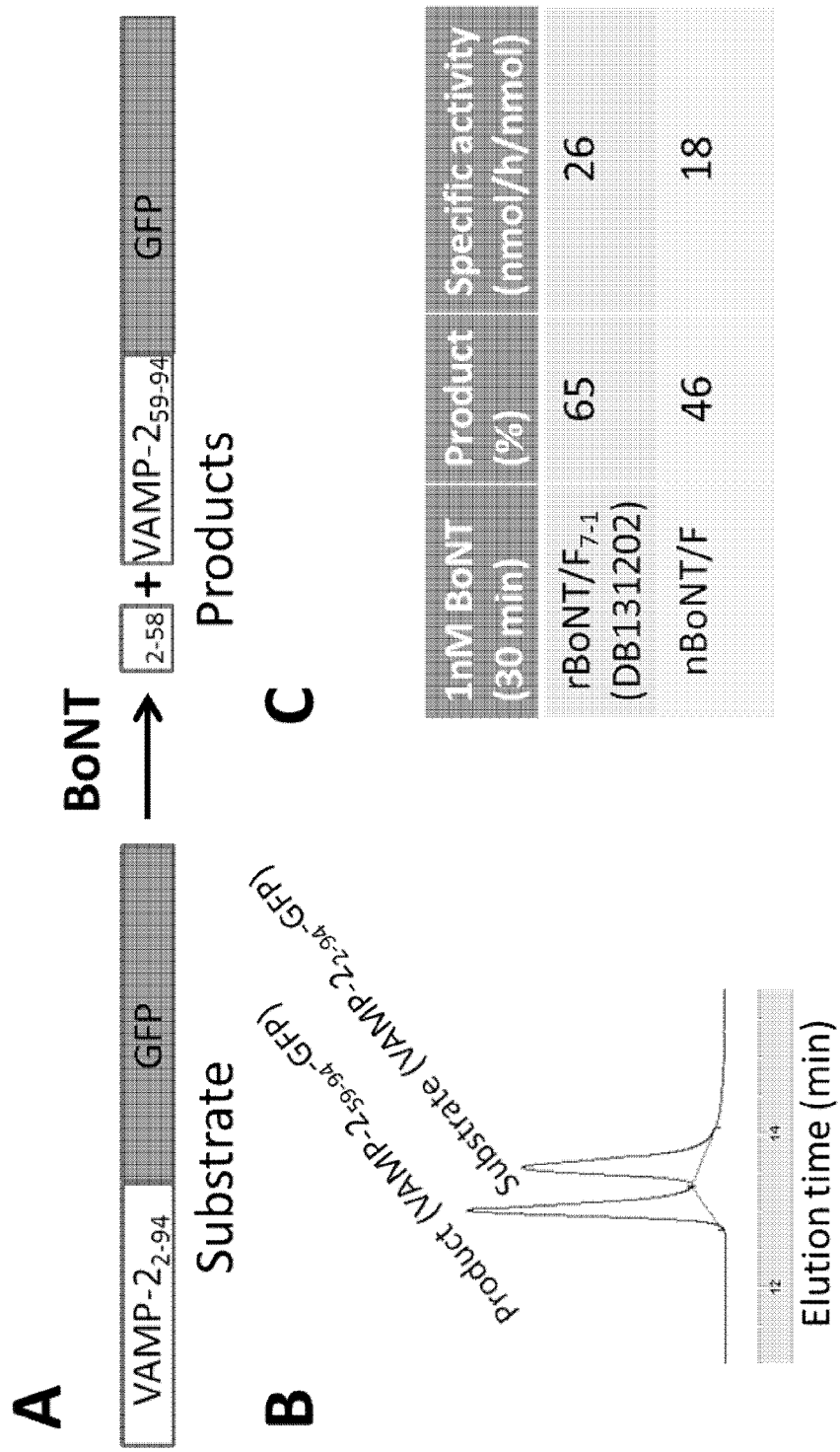
FIG. 9: Cell-free protease activity of purified Chimeric rBoNT/F7-1. A recombinant substrate protein VAMP-$2_{2-94}$-GFP was incubated with either recombinant ($rBoNT/F_{7-1}$) or native (nBoNT/F) BoNT/F, at 37° C., for 30 min, before the reaction was stopped and analysed by reverse phase chromatography.

The activity of rBoNT/F$_{7-1}$ was determined using a number of standard assays, including a cell-free protease activity assay (FIG. 9), a spinal cord neuron (SCN) glycine (Gly) release inhibition assay (FIG. 10), an inhibition of ex-vivo muscle contraction assay (FIG. 11) and an in vivo DAS assay (FIG. 12).

Cell-Free Protease Activity Assay

The method for cell-free protease assay of rBoNT/F$_{7-1}$ was as follows:

A BEH300 C4 reverse phase analytical HPLC column was equilibrated in 0.1% TFA in water (buffer A) for 30 minutes at 0.7 mL/min (starting from 0.1 mL/min and gradually increasing the flow over the First few minutes). The reference and test samples were diluted to 1 nM in 100 µl total volume with 0.2 mg/mL BSA, 2.0 mM DTT, 50 mM Hepes and 20 µM ZnCl2 (assay buffer). The test samples and 100 µl of assay buffer (for negative control) were pre-incubated for 30 minutes at 37° C. The substrate was prepared by diluting a concentrated VAMP2-GFP stock solution to 20 µM with assay buffer. 50 µl of each test sample (or buffer into the negative control) was added to the 50 µl of substrate and mixed by pipetting gently, and then incubated at 37° C. for 30 minutes. The reactions were then stopped by adding 25 µl 0.3M EDTA per tube, mixed by pipetting gently. The samples were diluted by adding 375 µl of buffer A to each reaction mix. Each sample was filtered using luer lock syringe and 0.2 µm PTFE filter. To run the samples, the column temperature was set to 40° C., the detection wavelength to 280 nm, the same injection to 100 µl and the gradient as presented in Table 6 below:

TABLE 6

| Time (min) | % Buffer A | % Buffer B | Event |
| --- | --- | --- | --- |
| 0-2 | 100 | 0 | Flow through |
| 2.1 | 61 | 39 | Gradient |
| 8 | 60.2 | 39.8 | |
| 8.1 | 20 | 80 | Stripping |
| 11 | 20 | 80 | |
| 11.1 | 100 | 0 | Re-equilibration |
| 15 | 100 | 0 | |

Duplicate injections of samples were analysed over an elution period of 15 minutes at 0.7 mL/min.

As shown in FIG. 9B, the rBoNT/F$_{7-1}$ was able to cleave the VAMP2 substrate according to the process identified in the schematic of FIG. 9A. rBoNT/F$_{7-1}$ was shown to yield a higher % of cleaved product compared with the native BoNT/F control (65% versus 46%, as well as greater specific activity (26 nmol/h/pmol vs 18 nmol/h/pmol), as shown in FIG. 9C.

SCN Gly Release Inhibition Assay

The method for SCN gly release inhibition assay of rBoNT/F$_{7-1}$ was as follows:

Primary cultures of rat spinal cord neurons (SCN) were prepared and grown, for 3 weeks, in 96 well tissue culture plates (as described in: Masuyer et al., 2011, J. Struct. Biol. Structure and activity of a functional derivative of *Clostridium botulinum* neurotoxin B; and in: Chaddock et al., 2002, Protein Expr. Purif. Expression and purification of catalytically active, non-toxic endopeptidase derivatives of *Clostridium botulinum* toxin type A). Serial dilutions of BoNT were prepared in SCN feeding medium. The growth medium from the wells to be treated was collected and filtered (0.2 μm filter). 125 μl of the filtered medium was added back to each test well. 125 μl of diluted toxin was then added to the plate (triplicate wells). The treated cells were incubated at 37° C., 10% $CO_2$, for 24±1 hours).

TABLE 7

Example plate layout for two dose-response curves

|   | 1 | 2 | 3 | 4 | 5 | 6 | 7 | 8 | 9 | 10 | 11 | 12 | NOTES |
|---|---|---|---|---|---|---|---|---|---|----|----|----|-------|
| A |   |   |   |   |   |   |   |   |   |    |    |    |       |
| B |   | Basal | 0.0001 | 0.0003 | 0.001 | 0.003 | 0.01 | 0.03 | 0.1 | 0.3 | 1 |    | Native BoNT/F |
| C |   |   |   |   |   |   |   |   |   |    |    |    | standard (nM) |
| D |   |   |   |   |   |   |   |   |   |    |    |    |       |
| E |   | Basal | 0.0001 | 0.0003 | 0.001 | 0.003 | 0.01 | 0.03 | 0.1 | 0.3 | 1 |    | Test sample (nM) |
| F |   |   |   |   |   |   |   |   |   |    |    |    |       |
| G |   |   |   |   |   |   |   |   |   |    |    |    |       |
| H |   |   |   |   |   |   |   |   |   |    |    |    |       |

This example shows example concentration ranges used for native BoNT/F supplied by List Biological laboratories (Cambell, Calif., USA), compared to a recombinant test protein. The concentrations shown are examples of concentrations that might be expected to yield a, well defined, dose-response curve for these two proteins, with data points covering both the upper and lower asymptote regions. In other cases, the actual concentrations tested, which were most optimal for any particular experiment, were first determined empirically.

Figure 10:
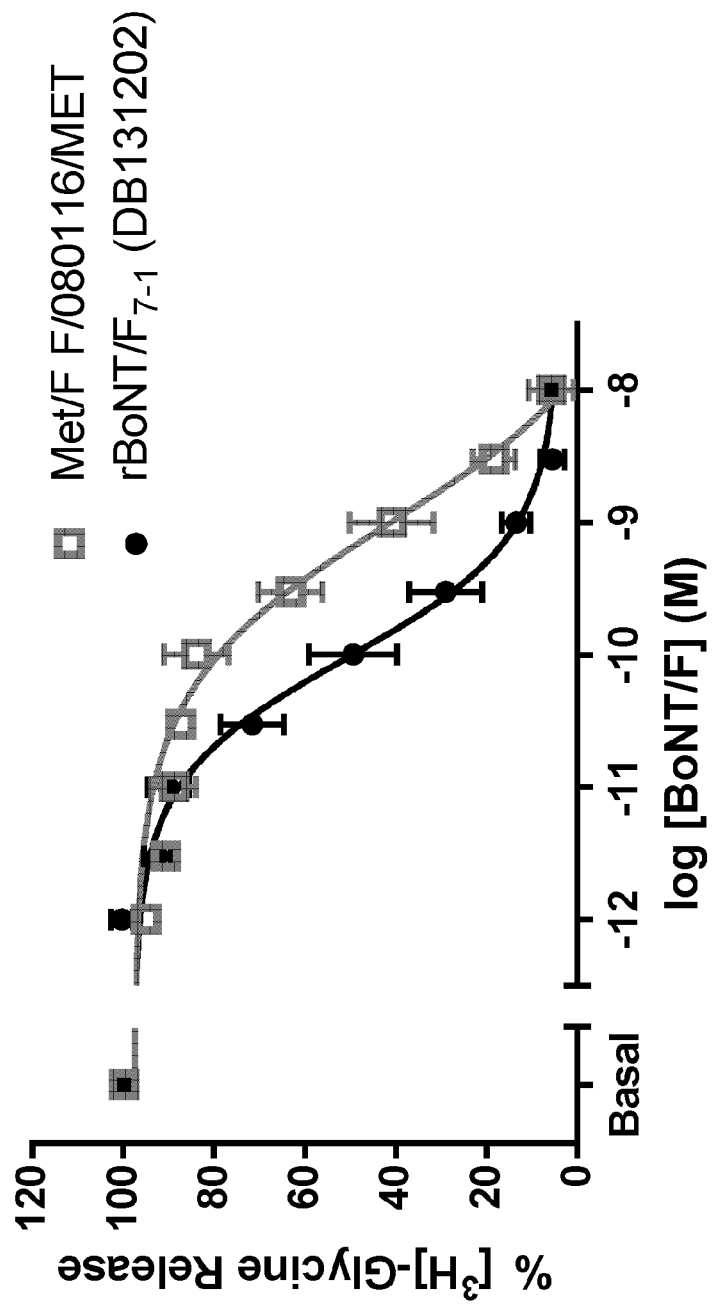
FIG. 10: Inhibition of SCN Gly release by chimeric $rBoNT/F_{7-1}$. Cultured primary spinal cord neurons (SCN) were exposed to various concentrations of recombinant ($rBoNT/F_{7-1}$) or native (Met/F/080116/MET) BoNT/F for 24 hours, then loaded with radiolabelled glycine ([$^3$H]-Glycine), and depolarised (with high potassium buffer) to stimulate neurotransmitter (glycine) release.

As shown in FIG. 10, the % glycine release of rBoNT/$F_{7-1}$ was greater than that of the native BoNT/F control at the same concentration.

[$^3$H] Glycine Release Assay

BoNT Treated SCN Loaded with Radio-Labelled Glycine

BoNT treated SCN were removed from the incubator (24±1 hours after exposure to BoNT) then the medium removed. 280 μl warmed HEPES-buffered MEM (12.5 ml HEPES in 500 ml MEM, 25 mM final concentration) was added to each well (first wash). The plate was then returned to the incubator for 5 min. The 280 μl warmed HEPES-buffered MEM (added in the step above) was removed and replaced with a second 280 μl HEPES-buffered MEM (second wash) and incubate at 35° C. for 5 minutes. The second wash solution was removed and 180 μl [$^3$H]glycine (2 μCi/ml (Perkin Elmer 1 mCi/ml NET00400), in HEPES-buffered MEM) was added to each well. The plate was then incubated for 30 minutes at 35° C. 3×20 μl of the [$^3$H] glycine working stock was retained for counting. After the 30 minute incubation, the [$^3$H]glycine was removed from cells. The cells were washed once for five minutes with HEPES-buffered MEM (250 μl/well), then three times with HEPES-buffered (10 mM) HBSS: 200, 210, 230 μl/well in successive washes (5 minutes per wash).

Collect Basal and Stimulated Secretion Samples

For "basal" reading, 100 μl/well of HBSS was applied gently to all wells. The clock was started at the point of addition to the first well. After 5 min, the contents of the wells were transferred to the pre-chilled tubes, and these samples held at 4° C. until further processing. For "stimulated" reading, 100 μl/well of HBSS containing 56 mM KCl was gently applied to all wells. The clock was started at the point of addition to the first well. After 5 min, the contents of the wells were transferred to the pre-chilled tubes, and these samples held at 4° C. until further processing. The cells were lysed in the plate with 100 μl of 2 M acetic acid/0.1% trifluoroacetic acid (lysis solution) for 10 min, pipetted up and down three times then transfer to final rack of collection tubes. The "basal" and "stimulated" samples were centrifuged in a microfuge at 13000 rpm (16.100×g) for 5 minutes. 50 μl of each supernatant was transferred to a 6 ml scintillation vial and 4 ml Optima Gold MV scintillation fluid added. Counting was carried out using a Perkin Elmer TriCarb 2100 liquid scintillation analyser (LSA) (or equivalent) using a programme written for tritium, using 3 min count times and giving a DPM output.

Data Analysis

The recorded depolarisations per minute (DPM) values were multiplied by two (since only 50 μl of 100 μl collected was counted in the vial). The basal DPM was calculated as % of the (basal+stimulated+lysate) DPM. The stimulated DPM was calculated as % of the (stimulated+lysate) DPM. The Net % release was calculated by subtracting the basal DPM % from the stimulated DPM %. The Net % release for each BoNT treatment was calculated as a % of the average triplicate 'basal' control wells Net % release associated with that treatment (ie, the 'basal' controls will equal 100%, when averaged). The triplicate Net % release values for each BoNT concentration was averaged and the triplicate Net % release as % of average control % release values for each BoNT concentration was averaged.

Table 8 below provides the $EC_{50}$ values determined for rBoNT/$F_{7-1}$ and a control (F/080166/Metv3) in the SCN Gly inhibition assay. The control (F/080166/Metv3) is commercially available, native (not-recombinant) BoNT/F. These results show that recombinant BoNT/$F_{7-1}$ is more potent than purified, naturally occurring BoNT/F, in this assay.

TABLE 8

| Protein | $EC_{50}$ (Log M) |
|---|---|
| SXN102785 | 10.10 ± 0.09 |
| F/080116/METv3 | 9.36 ± 0.11 |

Inhibition of Ex-Vivo Muscle Contraction Assay

The method to measure the activity of BoNT/$F_{7-1}$ in the inhibition of ex-vivo muscle contraction assay was as follows:

Krebs-Henseleit buffer was prepared on the day of the assay: to approximately 1400 ml of $dH_2O$, the following were added: 47 ml*5 M NaCl (Sigma S6546), 2.4 ml*1 M MgSO$_4$ (Sigma M3409), 8.9 ml*45% $_D$-Glucose (Sigma G8769), 100 ml*20× KCl, 100 ml*20× KH$_2$PO$_4$, 20 ml*250 mM CaCl$_2$, 50 ml*1 M NaHCO$_3$, and the pH adjusted to 7.5 as necessary The final volume was then adjusted to 2 litres, with dH$_2$O An EmkaBath4 tissue bath system (or other suitable organ bath equipment) was set up according to the manufacturer's instructions. A left side phrenic nerve/hemi-diaphragm tissue preparation was prepared as described previously (Rasetti-Escarguil et al., 2009, Toxicon, Measurement of botulinum types A, B, and E neurotoxicity using the pherenic nerve-hemidiaphragm: improved precision with in-bred mice; and in Rasetti-Escarguil et al., 2011, Toxicon, Pherenic nerve-hemidiaphragm as a highly sensitive replacement assay for determination of functional botulinum toxin antibodies). The phrenic nerve/hemi-diaphragm was attached to the tissue holder/electrode assembly in the tissue bath. The transducer was then moved up/down to set the tension to approximately 1 g. The tension in the tissue was monitored and small adjustments made as necessary to keep it close to 1 g during an initial baseline stabilisation phase. A tubocurarine control was performed by adding 100 μl of 100× tubocurarine directly to the bath. When full paralysis of the tissue (caused by the tubocurarine) registered on the trace, the tubocurarine was washed out and the baseline contraction allowed to become re-established. The BoNT to be tested was diluted to 10× the desired final concentration, in buffer containing 0.05% gelatine. 1 ml buffer was removed from the bath and 1 ml of 10× BoNT added directly to the bath, which was then mixed by pipetting up/down 5 times. The tension in the tissue was monitored and the post-toxin force calculated as a percentage of the mean pre-toxin force and plotted against time.

The data was then fitted to a modification of the Hill equation (Equation 1)

$$y = \text{bottom} + \frac{(\text{top} - \text{bottom})}{1 + 10^{(t_{50}-x)nH}} \quad \text{Equation (1)}$$

Where x is the time (min), y is the force and $t_{50}$ is the time to reduce the contraction to 50% of the pre-toxin level. Data from this assay are rejected if: the pre-treatment developed force is less than 0.5 g; the response to 3 μM D-tubocurarine is <94% inhibition; and/or a short burst of direct muscle stimulation at the end of the experiment does not result in muscle contraction.

Figure 11:
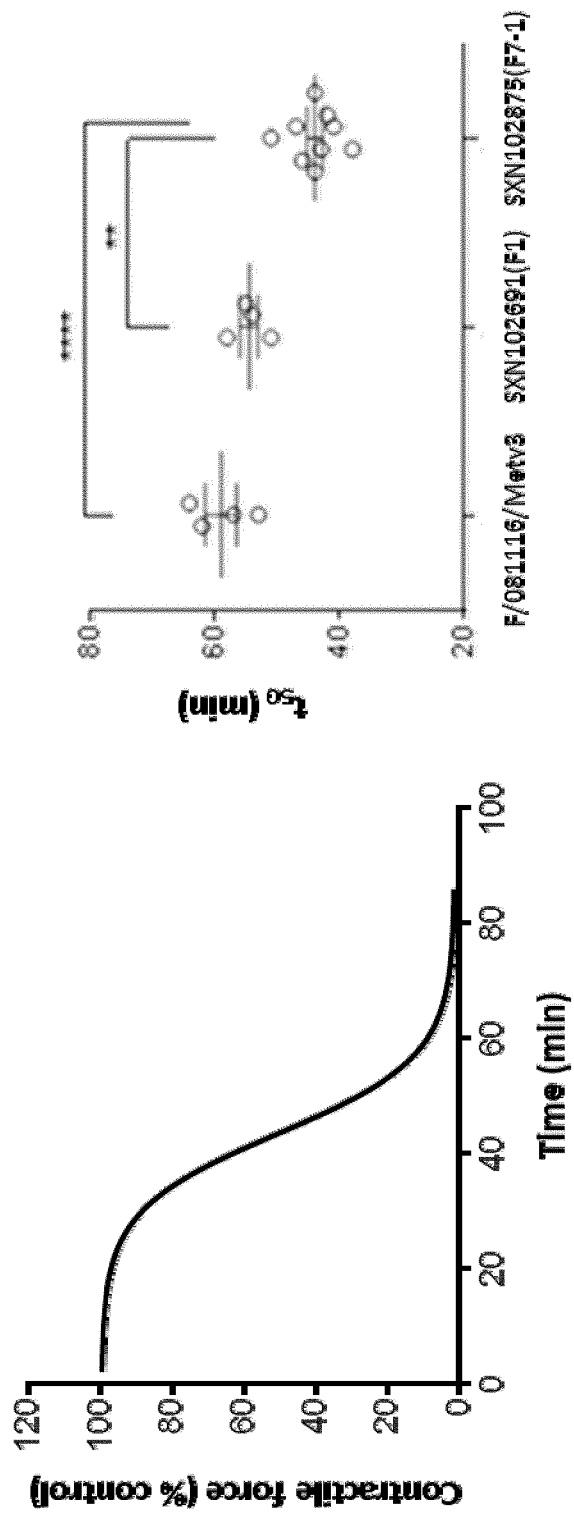
FIG. 11: Inhibition of ex-vivo muscle contraction by chimeric $rBoNT/F_{7-1}$. An isolated phrenic nerve/hemi-diaphragm tissue preparation was set up in a tissue bath. The hemi-diaphragm muscle was attached to a force transducer (to measure contraction) and the pherenic nerve was electro-stimulated, at 1 Hz, (to stimulate muscle contraction). Contractile force was measured continuously for a period up to 100 min after addition of 100 pM BoNT/F. The decrease in force (compared to control) was plotted against time and the time needed, from addition of BoNT, until 50% reduction in the contractile force was recorded as the t50.

As shown in FIG. 11 (left-hand graph), rBoNT/F$_{7-1}$ was able to completely inhibit muscle contraction by 80 minutes post-treatment. FIG. 11 (right-hand graph) shows the $t_{50}$ values for rBoNT/F$_{7-1}$, rBoNT/F$_1$ and a control (F/080166/Metv3), and demonstrates that rBoNT/F$_{7-1}$ has a shorter $t_{50}$ than either rBoNT/F$_1$ or the control. Table 9 below provides the $t_{50}$ values for rBoNT/F$_{7-1}$, rBoNT/F$_1$ and a control (F/080166/Metv3) in the ex vivo muscle contraction assay shown in FIG. 11. The control (F/080166/Metv3) is commercially available, native (not-recombinant) BoNT/F. These results show that recombinant BoNT/F$_{7-1}$ is more potent than (lower $t_{50}$ value=more potent) purified, naturally occurring BoNT/F and recombinant BoNT/F$_1$, in this assay.

TABLE 9

| Protein | Concentration (pM) | $t_{50}$ (min) |
|---|---|---|
| SXN102785 (rBoNT/F$_{7-1}$) | 100 | 44 ± 1 |
| SXN102691 (rBoNT/F$_1$) | 100 | 55 ± 1 |
| F/080116/METv3 | 100 | 59 ± 2 |

Digit Abduction Scoring (DAS) Assay

The method to measure the activity of BoNT/F7-1 in the DAS assay was as follows:

The method is based on the startled response toe spreading reflex of mice, when suspended briefly by the tail. This reflex is scored as Digit Abduction Score (DAS) and is inhibited after administration of BoNT into the gastrocnemius-soleus muscles of the hind paw. Mice are suspended briefly by the tail to elicit a characteristic startled response in which the animal extends its hind limb and abducts its hind digits. (Aoki et al. 1999, Eur. J. Neurol.; 6 (suppl. 4) S3-S10)

On the day of injection, mice are anaesthetized in an induction chamber receiving isoflurane 3% in oxygen. Each mouse receives an intramuscular injection of BoNT or vehicle (phosphate buffer containing 0.2% gelatine) in the gastrocnemius-soleus muscles of the right hind paw.

Following neurotoxin injection, the varying degrees of digit abduction are scored on a scale from zero to four:

Where 0=normal and 4=maximal reduction in digit abduction and leg extension. ED50 is determined by non-linear adjustment analysis using average of maximal effect at each dose. The mathematical model used is the 4 parameters logistic model.

DAS is performed every 2 hours during the first day after dosing; thereafter it is performed 3 times a day for 4 days. FIG. 12 shows the fitted curves for nBoNT/F$_1$ (used as reference), rBoNT/F$_1$ and rBoNT/F$_{7-1}$. While nBoNT/F$_1$ and rBoNT/F$_1$ show very similar dose response, the rBoNT/F$_{7-1}$ curve is shifted to the left, meaning lower doses of rBoNT/F$_{7-1}$ achieved a similar DAS response compared to nBoNT/F$_1$ and rBoNT/F$_1$ and therefore showing that rBoNT/F$_{7-1}$ is more potent than the others in the mouse DAS assay; see also the table below (table 10) that provides the values for the calculated ED50 and the dose leading to DAS 4 (highest score) for each BoNT: to achieve a similar DAS response of 2 or 4, the dose needed is much lower for BoNT/F$_{7-1}$ than rBoNT/F$_1$ and nBoNT/F$_1$.

TABLE 10

| protein | ED50 (pg/mouse) | DAS 4 dose (pg/mouse) |
|---|---|---|
| F/053112-01/MET | 12.1 [9.75-14.44] | 90 |
| rBoNT/F1 (SXN1029691) | 11.7 [9.68-13.69] | 90 |
| rBoNT/F7-1 (SXN102931) | 1.6 [1.41-1.83] | 22.5 |

Sequence Information

BoNT/F consensus sequence

SEQ ID NO: 1

MPVVINSFNYNDPVNDDTILYMQIPYEEKSKKYYKAFEIMRNVWIIPERN   50

TIGTKPSDFDPPASLKNGSSAYYDPNYLTTDAEKDRYLKTTIKLFKRINS   100

-continued

NPAGKVLLXEISXAKPYLGNDHTPINEFXPVNRTTSVNIKLSTNVESSML 150

LNLLVLGAGPDIFEXSCYPVRKXPNSDXVYDPSNXGFGSINIVTFSPEYE 200

YTFNDISGGHNSSTESFIADPAISLAHELIHALHGLYGAXGVTYKETIEV 250

KQXPLMIAEKPIRLEEFLTFGGQDLNIITSAMKEKIYNNLLANYEKIATR 300

LSEVNSAPPEYDINEYKDYFQWKYGLDKNADGSYTVNENKFNEIYKKLYS 350

FTEIDLANKFKVKCRNTYFIK-YGFLKVPNLLDDDIYTVSEGFNIGNLAV 400

NNRGQNINLNPKIIDSIPDKGLVEKIVKFCKSIIPRKGTKAPPRLCIRVN 450

NRELFFVASESSYNENDINTPKEIDDTTNLNNNYRNNLDEVILDYNSETI 500

P0ISNRTLNTLVQDDSYVPRYDSNGTSEIEEYDVVDLNVFFYLHAQKVPE 550

GETNISLTSSIDTALLEESKVYTFFSSEFIDTINKPVNAALFIDWISKVI 600

RDFTTEATQKSTVDKIADISLIVPYVGLALNIGNEAEKGNFKEAFELLGA 650

GILLEFVPELXIPVILVFTIKSYIDSYENKNKIIKAINNSLIEREAKWKE 700

IYSWIVSNWLTRINTQFNKRKEQMYQALQNQVDAIKTAIEYKYNNYTSDE 750

KNRLESEYNINNIEEELNKKVSLAMKNIERFMTESSISYLMKLINEAKVG 800

KLKEYDKHVKSXLLNYILXHRSILGEQ-XQELNDLVTSTLNSSIPFELSS 850

YTNDKILIIYFNRLYKKIKDSSILDMRYENNKFIDISGYGSNISINGNVY 900

IYSTNRNQFGIYSSRLSEVNIAQNNDIIYNSRYQNFSISFWVRIPKHYNP 950

MNLNREYTIINCMGNNNSGWKISLRXNXDCEIIWTLQDTSGNKEKLIFRY 1000

XQLISISDYINKWIFVTITNNRLGNSRIYINGNLIVEKSISNLGDIHVSD 1050

NILFKIVGCDDTXYVGIRYFKVFNTELDKTEIETLYSNEPDPSILKDYWG 1100

NYLLYNKKYYLLNLLRKDKYITXNSGILNINQQRGVTEX-XIFSNYKLYE 1150

GVEVIIRKNGPIDISNTDNFVRKNDLAYINVVDRGVEYRLYADTSIXKPE 1200

KTIKLIRTSNSNDSLGQIIVMDSIGNNCTMNFQNNNGSNIGLLGFHSNNL 1250

VASSWYYNNIRRNTSSNGCFWSFISKEHGWQE- 1283

BoNT/$F_1$ - UniParc Accession No. UPI00000B66D1

SEQ ID NO: 2

MPVVINSFNY NDPVNDDTIL YMQIPYEEKS KKYYKAFEIM RNVWIIPERN 50

TIGTDPSDFD PPASLENGSS AYYDPNYLTT DAEKDRYLKT TIKLFKRINS 100

NPAGEVLLQE ISYAKPYLGN EHTPINEFHP VTRTTSVNIK SSTNVKSSII 150

LNLLVLGAGP DIFENSSYPV RKLMDSGGVY DPSNDGFGSI NIVTFSPEYE 200

YTFNDISGGY NSSTESFIAD PAISLAHELI HALHGLYGAR GVTYKETIKV 250

KQAPLMIAEK PIRLEEFLTF GGQDLNIITS AMKEKIYNNL LANYEKIATR 300

LSRVNSAPPE YDINEYKDYF QWKYGLDKNA DGSYTVNENK FNEIYKKLYS 350

FTEIDLANKF KVKCRNTYFI KYGFLKVPNL LDDDIYTVSE GFNIGNLAVN 400

NRGQNIKLNP KIIDSIPDKG LVEKIVKFCK SVIPRKGTKA PPRLCIRVNN 450

RELFFVASES SYNENDINTP KEIDDTTNLN NNYRNNLDEV ILDYNSETIP 500

QISNQTLNTL VQDDSYVPRY DSNGTSEIEE HNVVDLNVFF YLHAQKVPEG 550

ETNISLTSSI DTALSEESQV YTFFSSEFIN TINKPVHAAL FISWINQVIR 600

DFTTEATQKS TFDKIADISL VVPYVGLALN IGNEVQKENF KEAFELLGAG 650

ILLEFVPELL IPTILVFTIK SFIGSSENKN KIIKAINNSL MERETKWKEI 700

YSWIVSNWLT RINTQFNKRK EQMYQALQNQ VDAIKTVIEY KYNNYTSDER 750

NRLESEYNIN NIREELNKKV SLAMENIERF ITESSIFYLM KLINEAKVSK 800

-continued

```
LREYDEGVKE YLLDYISEHR SILGNSVQEL NDLVTSTLNN SIPFELSSYT      850
NDKILILYFN KLYKKIKDNS ILDMRYENNK FIDISGYGSN ISINGDVYIY      900
STNRNQFGIY SSKPSEVNIA QNNDIIYNGR YQNFSISFWV RIPKYFNKVN      950
LNNEYTIIDC IRNNNSGWKI SLNYNKIIWT LQDTAGNNQK LVFNYTQMIS     1000
ISDYINKWIF VTITNNRLGN SRIYINGNLI DEKSISNLGD IHVSDNILFK     1050
IVGCNDTRYV GIRYFKVFDT ELGKTEIETL YSDEPDPSIL KDFWGNYLLY     1100
NKRYYLLNLL RTDKSITQNS NFLNINQQRG VYQKPNIFSN TRLYTGVEVI     1150
IRKNGSTDIS NTDNFVRKND LAYINVVDRD VEYRLYADIS IAKPEKIIKL     1200
IRTSNSNNSL GQIIVMDSIG NNCTMNFQNN NGGNIGLLGF HSNNLVASSW     1250
YYNNIRKNTS SNGCFWSFIS KEHGWQEN                             1278
```

BoNT/F$_2$ - UniParc Accession No. UPI00016BB5D7
SEQ ID NO: 3
```
MPVVINSFNY NDPVNDETIL YMQKPYEERS RKYYKAFEIM PNVWIMPERD       50
TIGTKPDEFQ VPDSLKNGSS AYYDPNYLTT DAEKDRYLKT MIKLFNRINS      100
NPTGKVLLEE VSNARPYLGD DDTLINEFFP VNVTTSVNIK FSTDVESSII      150
SNLLVLGAGP DIFKAYCTPL VRFNKSDKLI EPSNHGFGSI NILTFSPEYE      200
HIFNDISGGN HNSTESFIAD PAISLAHELI HALHGLYGAK AVTHKESLVA      250
ERGPLMIAEK PIRLEEFLTF GGEDLNIIPS AMKEKIYNDL LANYEKIATR      300
LREVNTAPPG YDINEYKDYF QWKYGLDRNA DGSYTVNRNK FNEIYKKLYS      350
FTEIDLANKF KVKCRNTYFI KYGFVKVPDL LDDDIYTVSE GFNIGNLAVN      400
NRGQNINLNP KIIDSIPDKG LVEKIIKFCK SIIPRKGTKQ SPSLCIRVNN      450
RELFFVASES SYNESDINTP KEIDDTTNLN NNYRNNLDEV ILDYNSETIP      500
QISNRTLNTL VQDNSYVPRY DSNGTSEIEE YDVVDFNVFF YLHAQKVPEG      550
ETNISLTSSI DTALLEESKV YTFFSSEFID TINKPVNAAL FIDWISKVIR      600
DFTTEATQKS TVDKIADISL IVPYVGLALN IVIEAEKGNF EEAFELLGAG      650
ILLEFVPELT IPVILVFTIK SYIDSYENKN KAIKAINNSL IEREAKWKEI      700
YSWIVSNWLT RINTQFNKRK EQMYQALQNQ VDAIKTAIEY KYNNYTSDEK      750
NRLESKYNIN NIEEELNKKV SLAMKNIERF MTESSISYLM KLINEAEVGK      800
LKEYDKHVKS DLLDYILYHK LILGEQTKEL IDLVTSTLNS SIPFELSSYT      850
NDKILIIYFN RLYKKIKDSS ILDMRYENNK FIDISGYGSN ISINGNVYIY      900
STNRNQFGIY SGRLSEVNIA QNNDIIYNSR YQNFSISFWV RIPKHYRPMN      950
RNREYTIINC MGNNNSGWKI SLRTIRDCEI IWTLQDTSGN KEKLIFRYEE     1000
LASISDYINK WIFVTITNNR LGNSRIYING NLIVEKSISN LGDIHVSDNI     1050
LFKIVGCDDE TYVGIRYFKV FNTELDKTEI ETLYSNEPDP SILKDYWGNY     1100
LLYNKKYYLF NLLRKDKYIT RNSGILNINQ QRGVTGGISV FLNYKLYEGV     1150
EVIIRKNAPI DISNTDNFVR KNDLAYINVV DHGVEYRLYA DISITKSEKI     1200
IKLIRTSNPN DSLGQIIVMD SIGNNCTMNF QNNDGSNIGL LGFHSDDLVA     1250
SSWYYNHIRR NTSSNGCFWS FISKEHGWKE                          1280
```

BoNT/F$_2$ - UniParc Accession No. UPI00000B50F1
SEQ ID NO: 4
```
MPVVINSFNY NDPVNDETIL YMQKPYEERS RKYYKAFEIM PNVWIMPERD       50
TIGTKPDEFQ VPDSLKNGSS AYYDPNYLTT DAEKDRYLKT MIKLFNRINS      100
```

```
NPTGKVLLEE VSNARPYLGD DDTLINEFLP VNVTTSVNIK FSTDVESSII        150
SNLLVLGAGP DIFKAYCTPL VRFNKSDKLI EPSNHGFGSI NILTFSPEYE        200
HIFNDISGGN HNSTESFIAD PAISLAHELI HALHGLYGAK AVTHKESLVA        250
ERGPLMIAEK PIRLEEFLTF GGEDLNIIPS AMKEKIYNDL LANYEKIATR        300
LREVNTAPPG YDINEYKDYF QWKYGLDRNA DGSYTVNRNK FNEIYKKLYS        350
FTEIDLANKF KVKCRNTYFI KYGFVKVPNL LDDDIYTVSE GFNIGNLAVN        400
NRGQNINLNP KIIDSIPDKG LVEKIIKFCK SIIPRKGTKQ SPSLCIRVNN        450
RELFFVASES SYNESDINTP KEIDDTTNLN NNYRNNLDEV ILDYNSETIP        500
QISNRTLNTL VQDNSYVPRY DSNGTSEIEE YDVVDFNVFF YLHAQKVPEG        550
ETNISLTSSI DTALLEESKV YTFFSSEFID TINKPVNAAL FIDWISKVIR        600
DFTTEATQKS TVDKIADISL IVPYVGLALN IVIEAEKGNF EEAFELLGAG        650
ILLEFVPELT IPVILVFTIK SYIDSYENKN KAIKAINNSL IEREAKWKEI        700
YSWIVSNWLT RINTQFNKRK EQMYQALQNQ VDAIKTAIEY KYNNYTSDEK        750
NRLESKYNIN NIEEELNKKV SLAMKNIERF MTESSISYLM KLINEAEVGK        800
LKEYDKHVKS DLLDYILYHK LILGEQTKEL IDLVTSTLNS SIPFELSSYT        850
NDKILIIYFN RLYKKIKDSS ILDMRYENNK FIDISGYGSN ISINGNVYIY        900
STNRNQFGIY SGRLSEVNIA QNNDIIYNSR YQNFSISFWV TIPKHYRPMN        950
RNREYTIINC MGNNNSGWKI SLRTIRDCEI IWTLQDTSGN KEKLIFRYEE        1000
LASISDYINK WIFVTITNNR LGNSRIYING NLIVEKSISN LGDIHVSDNI        1050
LFKIVGCDDE TYVGIRYFKV FNTELDKTEI ETLYSNEPDP SILKDYWGNY        1100
LLYNKKYYLF NLLRKDKYIT RNSGILNINQ QRGVTGGISV FLNYKLYEGV        1150
EVIIRKNAPI DISNTDNFVR KNDLAYINVV DHGVEYRLYA DISITKSEKI        1200
IKLIRTSNPN DSLGQIIVMD SIGNNCTMNF QNNDGSNIGL LGFHSDDLVA        1250
SSWYYNHIRR NTSSNGCFWS FISKEHGWKE                             1280
BoNT/F₃ - UniParc Accession No. UPI0001C0B12F
                                                                     SEQ ID NO: 5
MPVVINSFNY NDPVNDETIL YMQKPYEERS RKYYKAFEIM PNVWIMPERD         50
TIGTKPDDFQ VPDSLKNGSS AYYDPNYLTT DAEKDRYLKT MIKLFNRINS        100
NPTGKVLLEE VSNARPYLGD DDTLINEFFP VNVTTSVNIK FSTDVESSII        150
SNLLVLGAGP DIFKAYCTPL VRFNKSDKLI EPSNHGFGSI NILTFSPEYE        200
HIFNDISGGD HNSTESFIAD PAISLAHELI HALHGLYGAK AVTHKETIEV        250
KRGPLMIAEK PIRLEEFLTF GGEDLNIIPS AMKEKIYNDL LANYEKIATR        300
LREVNTAPPE YDINEYKDYF QWKYGLDRNA DGSYTVNRNK FNGIYKKLYS        350
FTEIDLANKF KVKCRNTYFI KYGFVKVPDL LDDDIYTVSE GFNIGNLAVN        400
NRGQNINLNP KIIDSIPDKG LVEKIIKFCK SIIPRKGTKQ SPSLCIRVNN        450
RELFFVASES SYNESDINTP KEIDDTTNLN NNYRNNLDEV ILDYNSETIP        500
QISNRTLNTL VQDNSYVPRY DSNGTSEIEE YDVVDFNVFF YLHAQKVPEG        550
ETNISLTSSI DTALLEKSKV YTFFSSEFID TINESVNAAL FIDWINKVIR        600
DFTTEATQKS TVDKIADISL IVPYVGLALN IVIDAEKGNF QEAFELLGAG        650
ILLEFVPELT IPVILVFTIK SYIDSYENKN KAIKAINNAL IEREAKWKEI        700
YSWIVSNWLT KINTQFNKRK EQMYQALQNQ VDAIKTAIEY KYNNYTSDEK        750
NRLESEYNIN NIEEELNKKV SLAMKNIERF MTESSISYLM KLINEAEVGK        800
```

-continued

```
LKKYDRHVKS DLLDYILYHK LILGDQTKEL IDLVTSTLNS SIPFELSSYT        850

NDKILIIYFN RLYKKIKDSS ILDMRYENNK FIDISGYGSN ISINGNVYIY        900

STNRNQFGIY SDRLSEVNIA QNNDIIYNSR YQNFSISFWV RIPKHYGPMN        950

RNREYTIINC MGNNNSGWKI SLRNIRDCEI IWTLQDTSGN KEKLIFRYEE       1000

LANISDYINK WIFVTITNNR LGNSRIYING NLIVEKSISN LGDIHVSDNI       1050

LFKIVGCDDK TYVGIRYFKV FNTELDKTEI ETLYSNEPDP SILKDYWGNY       1100

LLYNKKYYLF NLLRKDKYIT RNSGILNINQ QRGVTEGSVF LNYKLYEGVE       1150

VIIRKNGPID ISNTDNFVRK NDLAYINVVY HDVEYRLYAD ISITKPEKII       1200

KLIRTSNPND SLGQIIVMDS IGNNCTMNFQ NNNGGNIGLL GFHSDNLVAS       1250

SWYYNNIRRN TSSNGCFWSF ISKEHGWQE                              1279

BoNT/F₄ - UniParc Accession No. UPI0001A92658
                                                            SEQ ID NO: 6
MPVVINSFNY DDPVNDDTIL YMQIPYEEKS KKYYKAFEIM RNVWIMPERN         50

TIGTNPSDFD PPASLKNGSS AYYDPNYLTT DAEKDRYLKT TIKLFKRINS        100

NPAGEVLLQE ISYAKPYLGN DHTPINEFHP VTRTTSVNIK SSTNVESSII        150

LNLLVLGAGP NIFENSSYPV RKLMNSGEVY DPSNDGFGSI NIVTFSPEYE        200

YTFNDISGGH NSSTESFIAD PAISLAHELI HALHGLYGAR GVTYKETIKV        250

KQAPLMIAEK PIRLEEFLTF GGQDLNIITS AMKEKIYNDL LANYEKIATR        300

LSEVNSAPPE YDINEYKNYF QWKYGLDKNA DGSYTVNENK FNEIYKKLYS        350

FTEIDLANKF KVKCRNTYFI KYGFLKVPNL LDDDIYTVSE GFNIGNLAVN        400

NRGQNINLNP KIIDSIPDKG LVEKIVKLCK SIIPRKGTKA PPRLCIRVNN        450

RELFFVASES SYNENDINTP KEIDDTTNLN NNYRNNLDEV ILDYNSETIP        500

QISSQTLNTL VQDDSYVPRY DSNGTSEIEE HNVVDLNAFF YLHAQKVPEG        550

ETNISLTSSI DTALSEESKV YTFFSSEFIN NINKPVHAAL FIGWISQVIR        600

DFTTESTQKS TVDKIADISL IVPYVGLALN IGNDARKGNF KEAFELLGAA        650

ILLEVVPELL IPVILVFTIK SFIDSSKNED KIIKAINNSL IEREAKWKEV        700

YSWIVSNWLT RINTQFNKRK EQMYQALQNQ VDAIKTVIEY KYNSYTSDEK        750

NRLESEYNIN NIEEELNKKV SLAMKNIERF IAESSISYLM KLINEAKVSE        800

LREYDEGVKE YLLDYILKNG SILGDHVQEL NDLVTSTLNS SIPFELSSYT        850

NDKILIIYFN KLYKKIKDNC ILDMRYENNK FIDISGYGSN ISINGELYIY        900

TTNRNQFTIY SGKLSEVNIA QNNDIIYNSR YQNFSISFWV RIPRYSNIVN        950

LNNEYTIINC MGNNNSGWKI SLNYNKIIWT LQDTAGNNEK LVFNYTQMIS       1000

ISDYINKWIF VTITNNRLGN SRIYINGNLI DQKSISNLGD IHVSDNILFK       1050

IVGCNDTRYV GIRYFKVFDT ELDKTEIETL YSDEPDPSIL KDFWGNYLLY       1100

NKRYYLLNLL RKDKSITQSS TFLSISRPRG VDRKANIFSN KRLYKGVEVI       1150

IRKNEPIDIS NTDNFVRKGD LAYINVVDRD VEYRLYADTS NAQPEKTIKL       1200

IRTSNPDDSL GQIIVMDSIG NNCTMNFQNN NGGNIGLLGF HSNTLVASSW       1250

YYNNIRRNTS SNGCFWSFIS KEHGWQEN                               1278

BoNT/F₄ - UniParc Accession No. UPI0001C0812D
                                                            SEQ ID NO: 7
MPVVINSFNY DDPVNDDTIL YMQIPYEEKS KKYYKAFEIM RNVWIMPERN         50

TIGTNPSDFD PPASLKNGSS AYYDPNYLTT DAEKDRYLKT TIKLFKRINS        100
```

```
                              -continued
NPAGEVLLQE ISYAKPYLGN DHTPINEFHP VTRTTSVNIK SSTNVESSII      150

LNLLVLGAGP NIFENSSYPV RKLMNSGEVY DPSNDGFGSI NIVTFSPEYE      200

YTFNDISGGH NSSTESFIAD PAISLAHELI HALHGLYGAR GVTYKETIKV      250

KQAPLMIAEK PIRLEEFLTF GGQDLNIITS AMKEKIYNDL LANYEKIATR      300

LSEVNSAPPE YDINEYKNYF QWKYGLDKNA DGSYTVNENK FNEIYKKLYS      350

FTEIDLANKF KVKCRNTYFI KYGFLKVPNL LDDDIYTVSE GFNIGNLAVN      400

NRGQNINLNP KIIDSIPDKG LVEKIVKLCK SIIPRKGTKA PPRLCIRVNN      450

RELFFVASES SYNENDINTP KEIDDTTNLN NNYRNNLDEV ILDYNSETIP      500

QISSQTLNTL VQDDSYVPRY DSNGTSEIEE HNVVDLNAFF YLHAQKVPEG      550

ETNISLTSSI DTALSEESKV YTFFSSEFIN NINKPVHAAL FIGWISQVIR      600

DFTTESTQKS TVDKIADISL IVPYVGLALN IGNDARKGNF KEAFELLGAA      650

ILLEVVPELL IPVILVFTIK SFIDSSKNED KIIKAINNSL IEREAKWKEV      700

YSWIVSNWLT RINTQFNKRK EQMYQALQNQ VDAIKTVIEY KYNSYTSDEK      750

NRLESEYNIN NIEEELNKKV SLAMKNIERF IAESSISYLM KLINEAKVSE      800

LREYDEGVKE YLLDYILKNG SILGDHVQEL NDLVTSTLNS SIPFELSSYT      850

NDKILIIYFN KLYKKIKDNC ILDMRYENNK FIDISGYGSN ISINGELYIY      900

TTNRNQFTIY SGKLSEVNIA QNNDIIYNSR YQNFSISFWV RIPRYSNIVN      950

LNNEYTIINC MGNNNSGWKI SLNYNKIIWT LQDTAGNNEK LVFNYTQMIS     1000

ISDYINKWIF VTITNNRLGN SRIYINGNLI DQKSISNLGD IHVSDNILFK     1050

IVGCNDTRYV GIRYFKVFDT ELDKTEIETL YSDEPDPSIL KDFWGNYLLY     1100

NKRYYLLNLL RKDNAITQSS TFLSISRARG VDRKANIFSN KRLYKGVEVI     1150

IRKNEPIDIS NTDNFVRKGD LAYINVVDRD VEYRLYANTS NAQPEKTIKL     1200

IRTSNSNDSL DQIIVMDSIG NNCTMNFQNN NGGNIGLLGF HSNTLVASSW     1250

YYNNIRRNTS SNGCFWSFIS KEHGWQE                              1277
BoNT/F5 - UniParc Accession No. UPI0001C0B12E
                                                              SEQ ID NO: 8
MPVEINSFNY DDLVNDNTIL YIRPPYYERS NTYFKAFNIM ENVWIIPERY       50

RLGIEASKFD PPDSLKAGSD GYFDPNYLST NTEKNRYLQI MIKLFKRINS      100

MEAGKILLMQ IKDAIPYLGN SYTAEDQFTT NNRTISFMVR LANGTIEQEM      150

ANLIIWGPGP DLTTNRTGGT TYTPAQSLEA IPYKEGFGSI MTIEFSPEYA      200

TAFNDISLTS HAPSLFIKDP ALILMHELIH VLHGLYGTYT TGFKIKPNIT      250

EPYMEVTKPI TSGEFLTFGG NDVNKIPQLI QSQLRSKVLD DYEKIASRLN      300

KVNRATAEIN IDKFKYSYQL KYQFVKDSNG VYSVDLDKFN KLYDKIYSFT      350

EFNLAHEFKI KTRNSYLAKN FGPFYLPNLL DNSIYNEADG FNIGDLSVNY     400

KGQVIGSDID SIKKLEGQGV VSRVVRLCLN SSFKKNTKKP LCITVNNGDL      450

FFIASEDSYG EDTINTPKEI DDTTTLVPSF KNILDKVILD FNKQVTPQIP      500

NRRIRTDIQE DNYIPEYDSN GTSEIEEYNV VDLNAFFYLH AQKVPEGETN      550

ISLTSSIDTA LSEESKVYTF FSSEFIDTIN EPVNAALFID WISKVIRDFT      600

TEATQKSTVD KIADISLIVP YVGLALNIVN ETEKGNFKEA FELLGAGILL      650

EFVPELAIPV ILVFTIKSYI DSYENKNKII KAINNSLIER EAKWKEIYSW      700

IVSNWLTRIN TQFNKRKEQM YQALQNQVDA IKTAIEYKYN NYTSDEKNRL      750

ESEYNINNIE EELNKKVSLA MKNIERFITE SSISYLMKLI NEAEVGKLKE      800
```

```
YDKRVKRHLL EYIFDYRLIL GEQGGELIDL VTSTLNTSIP FELSSYTNDK        850
ILIIYFNRLY KKIKDSSILD MRYENNKFID ISGYGSNISI NGNVYIYSTN        900
RNQFGIYDDR LSEVNIAQNN DIIYNSRYQN FSISFWVRIP KHYRPMNHNR        950
EYTIINCMGN NNSGWKISLR TTGDCEIIWT LQDTSGNKKK LIFRYSQLGG       1000
ISDYINKWIF VTITNNRLGN SRIYINGNLI VEKSISNLGD IHVSDNILFK       1050
IVGCDDKMYV GIRYFKVFNT ELDKTEIEIL YSNEPDPSIL KDYWGNYLLY       1100
NKKYYLLNLL RNDKYITRNS DILNISHQRG VTKDLFIFSN YKLYEGVEVI       1150
IRKNGPIDIS NTDNFVRKND LAYINVVDHG VEYRLYADIS ITKPEKIIKL       1200
IRRSNPDDSL GQIIVMDSIG NNCTMNFQNN NGGNIGLLGF HSDNLVASSW       1250
YYNNIRRNTS SNGCFWSFIS KEHGWQE                                1277

BoNT/F6 - UniParc Accession No. UPI0001C0B1D1
                                                             SEQ ID NO: 9
MPVAINSFNY NDPVNDDTIL YMQIPYEEKS KKYYKAFEIM RNVWIIPERN         50
TIGTNPSDFD PPASLKNGSS AYYDPNYLTT DAEKDRYLKT TIKLFKRINS        100
NPAGKVLLQE ISYAKPYLGN DHTPIDEFSP VTRTTSVNIK LSTNVESSML        150
LNLLVLGAGP DIFESCCYPV RKLIDPDVVY DPSNYGFGSI NIVTFSPEYE        200
YTFNDISGGH NSSTESFIAD PAISLAHELI HALHGLYGAR GVTYEETIEV        250
KQAPLMIAEK PIRLEEFLTF GGQDLNIITS AMKEKIYNNL LANYEKIATR        300
LSEVNSAPPE YDINEYKDYF QWKYGLDKNA DGSYTVNENK FNEIYKKLYS        350
FTESDLANKF KVKCRNTYFI KYGFLKVPNL LDDDIYTVSE GFNIGNLAVN        400
NRGQSIKLNP KIIDSIPDKG LVEKIVKFCK SVIPRKGTKA PPRLCIRVNN        450
SELFFVASES SYNENDINTP KEIDDTTNLN NNYRNNLDEV ILDYNSQTIP        500
QISNRTLNTL VQDNSYVPRY DSNGTSEIEE YDVVDFNVFF YLHAQKVPEG        550
ETNISLTSSI DTALLEESKV YTFFSSEFID TINKPVNAAL FIDWISKVIR        600
DFTTEATQKS TVDKIADISL IVPYVGLALN IIIEAEKGNF EEAFELLGVG        650
ILLEFVPELT IPVILVFTIK SYIDSYENKN KAIKAINNSL IEREAKWKEI        700
YSWIVSNWLT RINTQFNKRK EQMYQALQNQ VDAIKTAIEY KYNNYTSDEK        750
NRLESEYNIN NIEEELNKKV SLAMKNIERF MTESSISYLM KLINEAKVGK        800
LKKYDNHVKS DLLNYILDHR SILGEQTNEL SDLVTSTLNS SIPFELSSYT        850
NDKILIIYFN RLYKKIKDSS ILDMRYENNK FIDISGYGSN ISINGNVYIY        900
STNRNQFGIY NSRLSEVNIA QNNDIIYNSR YNFFSISFWV RIPKHYKPMN        950
HNREYTIIMC MGNNNSGWKI SLRTVRDCEI IWTLQDTSGN KENLIFRYEE       1000
LNRISNYINK WIFVTITNNR LGNSRIYING NLIVEKSISN LGDIHVSDNI       1050
LFKIVGCDDE TYVGIRYFKV FNTELDKTEI ETLYSNEPDP SILKDYWGNY       1100
LLYNKKYYLF NLLRKDKYIT LNSGILNINQ QRGVTEGSVF LNYKLYEGVE       1150
VIIRKNGPID ISNTDNFVRK NDLAYINVVD RGVEYRLYAD TKSEKEKIIR       1200
TSNLNDSLGQ IIVMDSIGNN CTMNFQNNNG SNIGLLGFHS NNLVASSWYY       1250
NNIRRNTSSN GCFWSFISKE NGWKE                                  1275

BoNT/F6 - UniParc Accession No. UPI0000126B8A
                                                             SEQ ID NO: 10
MPVAINSFNY NDPVNDDTIL YMQIPYEEKS KKYYKAFEIM RNVWIIPERN         50
TIGTNPSDFD PPASLKNGSS AYYDPNYLTT DAEKDRYLKT TIKLFKRINS        100
```

-continued

```
NPAGKVLLQE ISYAKPYLGN DHTPIDEFSP VTRTTSVNIK LSTNVESSML      150

LNLLVLGAGP DIFESCCYPV RKLIDPDVVY DPSNYGFGSI NIVTFSPEYE      200

YTFNDISGGH NSSTESFIAD PAISLAHELI HALHGLYGAR GVTYEETIEV      250

KQAPLMIAEK PIRLEEFLTF GGQDLNIITS AMKEKIYNNL LANYEKIATR      300

LSEVNSAPPE YDINEYKDYF QWKYGLDKNA DGSYTVNENK FNEIYKKLYS      350

FTESDLANKF KVKCRNTYFI KYEFLKVPNL LDDDIYTVSE GFNIGNLAVN      400

NRGQSIKLNP KIIDSIPDKG LVEKIVKFCK SVIPRKGTKA PPRLCIRVNN      450

SELFFVASES SYNENDINTP KEIDDTTNLN NNYRNNLDEV ILDYNSQTIP      500

QISNRTLNTL VQDNSYVPRY DSNGTSEIEE YDVVDFNVFF YLHAQKVPEG      550

ETNISLTSSI DTALLEESKD IFFSSEFIDT INKPVNAALF IDWISKVIRD      600

FTTEATQKST VDKIADISLI VPYVGLALNI IIEAEKGNFE EAFELLGVGI      650

LLEFVPELTI PVILVFTIKS YIDSYENKNK AIKAINNSLI EREAKWKEIY      700

SWIVSNWLTR INTQFNKRKE QMYQALQNQV DAIKTAIEYK YNNYTSDEKN      750

RLESEYNINN IEEELNKKVS LAMKNIERFM TESSISYLMK LINEAKVGKL      800

KKYDNHVKSD LLNYILDHRS ILGEQTNELS DLVTSTLNSS IPFELSSYTN      850

DKILIIYFNR LYKKIKDSSI LDMRYENNKF IDISGYGSNI SINGNVYIYS      900

TNRNQFGIYN SRLSEVNIAQ NNDIIYNSRY QNFSISFWVR IPKHYKPMNH      950

NREYTIINCM GNNNSGWKIS LRTVRDCEII WTLQDTSGNK ENLIFRYEEL     1000

NRISNYINKW IFVTITNNRL GNSRIYINGN LIVEKSISNL GDIHVSDNIL     1050

FKIVGCDDET YVGIRYFKVF NTELDKTEIE TLYSNEPDPS ILKNYWGNYL     1100

LYNKKYYLFN LLRKDKYITL NSGILNINQQ RGVTEGSVFL NYKLYEGVEV     1150

IIRKNGPIDI SNTDNFVRKN DLAYINVVDR GVEYRLYADT KSEKEKIIRT     1200

SNLNDSLGQI IVMDSIGNNC TMNFQNNNGS NIGLLGFHSN NLVASSWYYN     1250

NIRRNTSSNG CFWSSISKEN GWKE                                 1274

BoNT/F₆ - UniParc Accession No. UPI0001C0B1D0
                                                        SEQ ID NO: 11
MPVAINSFNY NDPVNDDTIL YMQIPYKEKS KKYYKAFEIM RNVWIIPERN       50

TIGTNPSDFD PPASLKNGSS AYYDPNYLTT DAEKDRYLKT TIKLFKRINS      100

NPAGKVLLQE ISYAKPYLGN DHTPIDEFSP VTRTTSVNIK LSTNVESSML      150

LNLLVLGAGP DIFESCCYPV RKLIDPDVVY DPSNYGFGSI NIVTFSPEYE      200

YTFNDISGGH NSSTESFIAD PAISLAHELI HALHGLYGAR GVTYEETIEV      250

KQAPLMIAEK PIRLEEFLTF GGQDLNIITS AMKEKIYNNL LANYEKIATR      300

LSEVNSAPPE YDINEYKDYF QWKYGLDKNA DGSYTVNENK FNEIYKKLYS      350

FTESDLANKF KVKCRNTYFI KYGFLKVPNL LDDDIYTVSE GFNIGNLAVN      400

NRGQSIKLNP KIIDSIPDKG LVEKIVKFCK SVIPRKGTKA PPRLCIRVNN      450

SELFFVASES SYNENDINTP KEIDDTTNLN NNYRNNLDEV ILDYNSQTIP      500

QISNRTLNTL VQDNSYVPRY DSNGTSEIEE YDVVDFNVFF YLHAQKVPEG      550

ETNISLTSSI DTALLEESKV YTFFSSEFID TINKPVNAAL FIDWISKVIR      600

DFTTEATQKS TVDKIADISL IVPYVGLALN IIIEAEKGNF EEAFELLGVG      650

ILLEFVPELT IPVILVFTIK SYIDSYENKN KAIKAINNSL IEREAKWKEI      700

YSWIVSNWLT RINTQFNKRK EQMYQALQNQ VDAIKTAIEY KYNNYTSDEK      750

NRLESEYNIN NIEEELNKKV SLAMKNIERF MTESSISYLM KLINEAKVGK      800
```

```
LKKYDNHVKS DLLNYILDHR SILGEQTNEL SDLVTSTLNS SIPFELSSYT      850

NDKILIIYFN RLYKKIKDSS ILDMRYENNK FIDISGYGSN ISINGNVYIY      900

STNRNQFGIY NSRLSEVNIA QNNDIIYNSR YQNFSISFWV RIPKHYKPMN      950

HNREYTIINC MGNNNSGWKI SLRTVRDCEI IWTLQDTSGN KENLIFRYEE     1000

LNRISNYINK WIFVTITNNR LGNSRIYING NLIVEKSISN LGDIHVSDNI     1050

LFKIVGCDDE TYVGIRYFKV FNTELDKTEI ETLYSNEPDP SILKDYWGNY     1100

LLYNKKYYLF NLLRKDKYIT LNSGILNINQ QRGVTEGSVF LNYKLYEGVE     1150

VIIRKNGPID ISNTDNFVRK NDLAYINVVD RGVEYRLYAD TKSEKEKIIR     1200

TSNLNDSLGQ IIVMDSIGNN CTMNFQNNNG SNIGLLGFHS NNLVASSWYY     1250

NNIRRNTSSN GCFWSFISKE NGWKE                               1275
```

BoNT/F$_6$ - UniParc Accession No. UPI0004E7C8CE

SEQ ID NO: 12

```
MPVAINSENY NDPVNDDTIL YMQIPYKEKS KKYYKAFEIM RNVWIIPERN      50

TIGTNPSDFD PPASLKNGSS AYYDPNYLTT DAEKDRYLKT TIKLFKRINS     100

NPAGKVLLQE ISYAKPYLGN DHTPIDEFSP VTRTTSVNIK LSTNVESSML     150

LNLLVLGAGP DIFESCCYPV RKLIDPDVVY DPSNYGFGSI NIVTFSPEYE     200

YTFNDISGGH NSSTESFIAD PAISLAHELI HALHGLYGAR GVTYEETIEV     250

KQAPLMIAEK PIRLEEFLTF GGQDLNIITS AMKEKIYNNL LANYEKIATR     300

LSEVNSAPPE YDINEYKDYF QWKYGLDKNA DGSYTVNENK FNEIYKKLYS     350

FTESDLANKF KVKCRNTYFI KYGFLKVPNL LDDDIYTVSE GFNIGNLAVN     400

NRGQSIKLNP KIIDSIPDKG LVEKIVKFCK SVIPRKGTKA PPRLCIRVNN     450

SELFFVASES SYNENDINTP KEIDDTTNLN NNYRNNLDEV ILDYNSQTIP     500

QISNRTLNTL VQDNSYVPRY DSNGTSEIEE YDVVDFNVFF YLHAQKVPEG     550

ETNISLTSSI DTALLEESKV YTFFSSEFID TINKPVNAAL FIDWISKVIR     600

DFTTEATQKS TVDKIADISL IVPYVGLALN IIIEAEKGNF EEAFELLGVG     650

ILLEFVPELT IPVILVFTIK SYIDSYENKN KAIKAINNSL IEREAKWKEI     700

YSWIVSNWLT RINTQFNKRK EQMYQALQNQ VDAIKTAIEY KYNNYTSDEK     750

NRLESEYNIN NIEEELNKKV SLAMKNIERF MTESSISYLM KLINEAKVGK     800

LKKYDNHVKS DLLNYILDHR SILGEQTNEL SDLVTSTLNS SIPFELSSYT     850

NDKILIIYFN RLYKKIKDSS ILDMRYENNK FIDISGYGSN ISINGNVYIY     900

STNRNQFGIY NSRLSEVNIA QNNDIIYNSR YQNFSISFWV RIPKHYKPMN     950

HNREYTIINC MGNNNSGWKI SLRTVRDCEI IWTLQDTSGN KENLIFRYEE    1000

LNRISNYINK WIFVTITNNR LGNSKIYING NLIVEKSISN LGDIHVSDNI    1050

LFKIVGCDDE TYVGIRYFKV FNTELDKTEI ETLYSNEPDP SILKDYWGNY    1100

LLYNKKYYLF NLLRKDKYIT LNSGILNINQ QRGVTEGSVF LNYKLYEGVE    1150

VIIRKNGPID ISNTDNFVRK NDLAYINVVD RGVEYRLYAD TKSEKEKIIR    1200

TSNLNDSLGQ IIVMDSIGNN CTMNFQNNNG SNIGLLGFHS NNLVASSWYY    1250

NNIRRNTSSN GCFWSFISKE NGWKE                               1275
```

BoNT/$F_7$ - UniParc Accession No. UPI0001DE3DAC

SEQ ID NO: 13

```
MPVNINNFNY NDPINNTTIL YMKMPYYEDS NKYYKAFEIM DNVWIIPERN      50

IIGKKPSDFY PPISLDSGSS AYYDPNYLTT DAEKDRFLKT VIKLFNRINS     100
```

-continued

```
NPAGQVLLEE IKNGKPYLGN DHTAVNEFCA NNRSTSVEIK ESKGTTDSML       150

LNLVILGPGP NILECSTFPV RIFPNNIAYD PSEKGFGSIQ LMSFSTEYEY       200

AFNDNTDLFI ADPAISLAHE LIHVLHGLYG AKGVTNKKVI EVDQGALMAA       250

EKDIKIEEFI TFGGQDLNII TNSTNQKIYD NLLSNYTAIA SRLSQVNINN       300

SALNTTYYKN FFQWKYGLDQ DSNGNYTVNI SKFNAIYKKL FSFTECDLAQ       350

KFQVKNRSNY LFHFKPFRLL DLLDDNIYSI SEGFNIGSLR VNNNGQNINL       400

NSRIVGPIPD NGLVERFVGL CKSIVSKKGT KNSLCIKVNN RDLFFVASES       450

SYNENGINSP KEIDDTTITN NNYKKNLDEV ILDYNSDAIP NLSSRLLNTT       500

AQNDSYVPKY DSNGTSEIKE YTVDKLNVFF YLYAQKAPEG ESAISLTSSV       550

NTALLDASKV YTFFSSDFIN TVNKPVQAAL FISWIQQVIN DFTTEATQKS       600

TIDKIADISL VVPYVGLALN IGNEVQKGNF KEAIELLGAG ILLEFVPELL       650

IPTILVFTIK SFINSDDSKN KIIKAINNAL RERELKWKEV YSWIVSNWLT       700

RINTQFNKRK EQMYQALQNQ VDGIKKIIEY KYNNYTLDEK NRLKAEYNIY       750

SIKEELNKKV SLAMQNIDRF LTESSISYLM KLINEAKINK LSEYDKRVNQ       800

YLLNYILENS STLGTSSVQE LNNLVSNTLN NSIPFELSEY TNDKILISYF       850

NRFYKRIIDS SILNMKYENN RFIDSSGYGS NISINGDIYI YSTNRNQFGI       900

YSSRLSEVNI TQNNTIIYNS RYQNFSVSFW VRIPKYNNLK NLNNEYTIIN       950

CMRNNNSGWK ISLNYNNIIW TLQDTTGNNQ KLVFNYTQMI DISDYINKWT      1000

FVTITNNRLG HSKLYINGNL TDQKSILNLG NIHVDDNILF KIVGCNDTRY      1050

VGIRYFKIFN MELDKTEIET LYHSEPDSTI LKDFWGNYLL YNKKYYLLNL      1100

LKPNMSVTKN SDILNINRQR GIYSKTNIFS NARLYTGVEV IIRKVGSTDT      1150

SNTDNFVRKN DTVYINVVDG NSEYQLYADV STSAVEKTIK LRRISNSNYN      1200

SNQMIIMDSI GDNCTMNFKT NNGNDIGLLG FHLNNLVASS WYYKNIRNNT      1250

RNNGCFWSFI SKEHGWQE                                         1268
```

BoNT/F$_7$ - UniParc Accession No. UPI0001C0E220

SEQ ID NO: 14

```
MPVNINNFNY NDPINNTTIL YMKMPYYEDS NKYYKAFEIM DNVWIIPERN        50

IIGKKPSDFY PPISLDSGSS AYYDPNYLTT DAEKDRFLKT VIKLFNRINS       100

NPAGQVLLEE IKNGKPYLGN DHTAVNEFCA NNRSTSVEIK ESNGTTDSML       150

LNLVILGPGP NILECSTFPV RIFPNNIAYD PSEKGFGSIQ LMSFSTEYEY       200

AFNDNTDLFI ADPAISLAHE LIHVLHGLYG AKGVTNKKVI EVDQGALMAA       250

EKDIKIEEFI TFGGQDLNII TNSTNQKIYD NLLSNYTAIA SRLSQVNINN       300

SALNTTYYKN FFQWKYGLDQ DSNGNYTVNI SKFNAIYKKL FSFTECDLAQ       350

KFQVKNRSNY LFHFKPFRLL DLLDDNIYSI SEGFNIGSLR VNNNGQNINL       400

NSRIVGPIPD NGLVERFVGL CKSIVSKKGT KNSLCIKVNN RDLFFVASES       450

SYNENGINSP KEIDDTTITN NNYKKNLDEV ILDYNSDAIP NLSSRLLNTT       500

AQNDSYVPKY DSNGTSEIKE YTVDKLNVFF YLYAQKAPEG ESAISLTSSV       550

NTALLDASKV YTFFSSDFIN TVNKPVQAAL FISWIQQVIN DFTTEATQKS       600

TIDKIADISL VVPYVGLALN IGNEVQKGNF KEAIELLGAG ILLEFVPELL       650

IPTILVFTIK SFINSDDSKN KIIKAINNAL RERELKWKEV YSWIVSNWLT       700

RINTQFNKRK EQMYQALQNQ VDGIKKIIEY KYNNYTLDEK NRLKAEYNIY       750

SIKEELNKKV SLAMQNIDRF LTESSISYLM KLINEAKINK LSEYDKRVNQ       800
```

-continued

```
YLLNYILENS STLGTSSVQE LNNLVSNTLN NSIPFELSEY TNDKILISYF     850
NRFYKRIIDS SILNMKYENN RFIDSSGYGS NISINGDIYI YSTNRNQFGI     900
YSSRLSEVNI TQNNTIIYNS RYQNFSVSFW VRIPKYNNLK NLNNEYTIIN     950
CMRNNNSGWK ISLNYNNIIW TLQDTTGNNQ KLVFNYTQMI DISDYINKWT    1000
FVTITNNRLG HSKLYINGNL TDQKSILNLG NIHVDDNILF KIVGCNDTRY    1050
VGIRYFKIFN MELDKTEIET LYHSEPDSTI LKDFWGNYLL YNKKYYLLNL    1100
LKPNMSVTKN SDILNINRQR GIYSKTNIFS NARLYTGVEV IIRKVGSTDT    1150
SNTDNFVRKN DTVYINVVDG NSEYQLYADV STSAVEKTIK LRRISNSNYN    1200
SNQMIIMDSI GDNCTMNFKT NNGNDIGLLG FHLNNLVASS WYYKNIRNNT    1250
RNNGCFWSFI SKEHGWQE                                       1268
```

BoNT/$F_7$ - UniParc Accession No. UPI00000BAF8C

SEQ ID NO: 15

```
MPVNINNFNY NDPINNTTIL YMKMPYYEDS NKYYKAFEIM DNVWIIPERN      50
IIGKKPSDFY PPISLDSGSS AYYDPNYLTT DAEKDRFLKT VIKLFNRINS     100
NPAGQVLLEE IKNGKPYLGN DHTAVNEFCA NNRSTSVEIK ESNGTTDSML     150
LNLVILGPGP NILECSTFPV RIFPNNIAYD PSEKGFGSIQ LMSFSTEYEY     200
AFNDNTDLFI ADPAISLAHE LIHVLHGLYG AKGVTNKKVI EVDQGALMAA     250
EKDIKIEEFI TFGGQDLNII TNSTNQKIYV ILLSNYTAIA SRLSQVNRNN     300
SALNTTYYKN FFQWKYGLDQ DSNGNYTVNI SKFNAIYKKL FSFTECDLAQ     350
KFQVKNRSNY LFHFKPFRLL DLLDDNIYSI SEGFNIGSLR VNNNGQNINL     400
NSRIVGPIPD NGLVERFVGL CKSIVSKKGT KNSLCIKVNN RDLFFVASES     450
SYNENGINSP KEIDDTTITN NNYKKNLDEV ILDYNSDAIP NLSSRLLNTT     500
AQNDSYVPKY DSNGTSEIKE YTVDKLNVFF YLYAQKAPEG ESAISLTSSV     550
NTALLDASKV YTFFSSDFIN TVNKPVQAAL FISWIQQVIN DFTTEATQKS     600
TIDKIADISL IVPYVGLALN IGNEVQKGNF KEAIELLGAG ILLEFVPELL     650
IPTILVFTIK SFINSDDSKN KIIKAINNAL RERELKWKEV YSWIVSNWLT     700
RINTQFNKRK EQMYQALQNQ VDGIKKIIEY KYNNYTLDEK NRLRAEYNIY     750
SIKEELNKKV SLAMQNIDRF LTESSISYLM KLINEAKINK LSEYDKRVNQ     800
YLLNYILENS STLGTSSVPE LNNLVSNTLN NSIPFELSEY TNDKILIHIL     850
IRFYKRIIDS SILNMKYENN RFIDSSGYGS NISINGDIYI YSTNRNQFGI     900
YSSRLSEVNI TQNNTIIYNS RYQNFSVSFW VRIPKYNNLK NLNNEYTIIN     950
CMRNNNSGWK ISLNYNNIIW TLQDTTGNNQ KLVFNYTQMI DISDYINKWT    1000
FVTITNNRLG HSKLYINGNL TDQKSILNLG NIHVDDNILF KIVGCNDTRY    1050
VGIRYFKIFN MELDKTEIET LYHSEPDSTI LKDFWGNYLL YNKKYYLLNL    1100
LKPNMSVTKN SDILNINRQR GIYSKTNIFS NARLYTGVEV IIRKVGSTDT    1150
SNTDNFVRKN DTVYINVVDG NSEYQLYADV STSAVEKTIK LRRISNSNYN    1200
SNQMIIMDSI GDNCTMNFKT NNGNDIGLLG FHLNNLVASS WYYKNIRNNT    1250
RNNGCFWSFI SKEHGWQE                                       1268
```

BoNT/$F_7$ - UniParc Accession No. UPI0001C0B221

SEQ ID NO: 16

```
MPVNINNFNY NDPINNTTIL YMKMPYYEDS NKYYKAFEIM DNVWIIPERN      50
IIGKKPSDFY PPISLDSGSS AYYDPNYLTT DAEKDRFLKT VIKLFNRINS     100
```

```
NPAGQVLLEE IKNGKPYLGN DHTAVNEFCA NNRSTSVEIK ESNGTTDSML        150

LNLVILGPGP NILECSTFPV RIFPNNIAYD PSEKGFGSIQ LMSFSTEYEY        200

AFNDNTDLFI ADPAISLAHE LIHVLHGLYG AKGVTNKKVI EVDQGALMAA        250

EKDIKIEEFI TFGGQDLNIV TNSTNQKIYD NLLSNYTAIA SRLSQVNINN        300

SALNTTYYKN FFQWKYGLDQ DSNGNYTVNI SKFNAIYKKL FSFTECDLAQ        350

KFQVKNRSNY LFHFKPFKLL DLLDDNIYSI SEGFNIGSLR VNNNGQNINL        400

NSRIVGPIPD NGLVERFVGL CKSIVSKKGT KNSLCIKVNN RDLFFVASES        450

SYNENGINSP KEIDDTTITN NNYKKNLDEV ILDYNSDAIP NLSSRLLNAT        500

AQNDSYVPKY DSNGTSEINE YTVDKLNVFF YLYAQKAPEG ESAISLTSSV        550

DTALLDASKV YTFFSSDFIN TVNKPVQAAL FISWIQQVIN DFTTEATQKS        600

TIDKIADISL VVPYVGLALN IGNEVQKGNF KEAIELLGAG ILLEFVPELL        650

IPTILVFTIK SFINSDDSKN KIIKAINNAL RERELKWKEV YSWIVSNWLT        700

RINTQFNKRK EQMYQALQNQ VDGIKKIIEY KYNNYTLDEK NRLKAEYNIY        750

NIKEELNKKV SLAMQNIDRF LTESSISYLM KLINEAKINK LSEYDKRVNQ        800

YLLNYILENS STLGTSSVQE LNNLVSNTLN NSIPFELSEY TNDKILISYF        850

NRFYKRIIDS SILNMKYENN RFIDSSGYGS NISINGDIYI YSTNRNQFGI        900

YSSRLSEVNI TQNNTIIYNS RYQNFSVSFW VRIPKYNNLK NLNNEYTIIN        950

CMRNNNSGWK ISLNYNNIIW TLQDTTGNNQ KLVFNYTQMI DISDYINKWT       1000

FVTITNNRLG HSKLYINGNL TDQKSISNLG NIHVDDNILF KIVGCNDTRY       1050

VGIRYFKIFN MELDKTEIET LYHSEPDSTI LKDFWGNYLL YNKKYYLLNL       1100

LKPNMSVTKN SDILNINRQR GIYSKTNIFS NARLYTGVEV IIRKFGSTDT       1150

SNTDNFVRKN DTVYISVVDG NSEYQLYADV STSAVEKTIK LRRISNSNYN       1200

SNQMIIMDSI GDNCTMNFKT NNGNDIGLLG FHLNNLVASS WYYKNIRNNT       1250

RNNGCFWSFI SKEHGWQE                                         1268
```

BoNT/F consensus sequence minimal LH$_N$ backbone (including activation loop)

SEQ ID NO: 17

NDDTILYMQIPYEEKSKKYYKAFEIMRNVWIIPERNTIGTKPSDFDPPASLKNGSSAYYDPNYLTTDAEKDRYLKT

TIKLFKRINSNPAGKVLLXEISXAKPYLGNDHTPINEFXPVNRTTSVNIKLSTNVESSMLLNLLVLGAGPDIFEXS

CYPVRKXPNSDXVYDPSNXGFGSINIVTFSPEYEYTFNDISGGHNSSTESFIADPAISLAHELIHALHGLYGAXGV

TYKETIEVKQXPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTEIDLANKFKVKCRNTYFIK-YGFLKVPNLLDDDIYTVSEGFN

IGNLAVNNRGQNINLNPKIIDSIPDKGLVEKIVKFCKSIIPRKGTKAPPRLCIRVNNRELFFVASESSYNENDINT

PKEIDDTTNLNNNYRNNLDEVILDYNSETIPQISNRTLNTLVQDDSYVPRYDSNGTSEIEEYDVVDLNVFFYLHAQ

KVPEGETNISLTSSIDTALLEESKVYTFFSSEFIDTINKPVNAALFIDWISKVIRDFTTEATQKSTVDKIADISLI

VPYVGLALNIGNEAEKGNFKEAFELLGAGILLEFVPELXIPVILVFTIKSYIDSYENKNKIIKAINNSLIEREAKW

KEIYSWIVSNWLTRINTQFNKRKEQMYQALQNQVDAIKTAIEYKYNNYTSDEKNRLESEYNINNIEEELNKKVSLA

MKNIERFMTESSISYLMKLINEAKVGKLKEYDKHVKSXLLNYILXHRSILGEQ-XQELNDLVTSTLNSSIPFELSS

BoNT/F$_1$ - UniParc Accession No. UPI00000B66D1 minimal LH$_N$ backbone (including activation loop)

SEQ ID NO: 18

NDDTILYMQIPYEEKSKKYYKAFEIMRNVWIIPERNTIGTDPSDFDPPASLENGSSAYYDPNYLTTDAEKDRYLKT

TIKLFKRINSNPAGEVLLQEISTAKPYLGNEHTPINEFHPVTRTTSVNIKSSTNVKSSIILNLLVLGAGPDIFENS

SYPVRKLMDSGGVYDPSNDGFGSINIVTFSPEYEYTFNDISGGYNSSTESFIADPAISLAHELIHALHGLYGARGV

-continued

TYKETIKVKQAPLMIAEKPIRLEEFLTFGGQDLNIITSAMKEKIYNNLLANYEKIATRLSRVNSAPPEYDINEYKD

YFQWKYGLDKNADGSYTVNENKFNEIYKKLYSFTEIDLANKFKVKCRNTYFIKYGFLKVPNLLDDDIYTVSEGFNI

GNLAVNNRGQNIKLNPKIIDSIPDKGLVEKIVKFCKSVIPRKGTKAPPRLCIRVNNRELFFVASESSYNENDINTP

KEIDDTTNLNNNYRNNLDEVILDYNSETIPQISNQTLNTLVQDDSYVPRYDSNGTSEIEEHNVVDLNVFFYLHAQK

VPEGETNISLTSSIDTALSEESQVYTFFSSEFINTINKPVHAALFISWINQVIRDFTTEATQKSTFDKIADISLVV

PYVGLALNIGNEVQKENFKEAFELLGAGILLEFVPELLIPTILVFTIKSFIGSSENKNKIIKAINNSLMERETKWK

EIYSWIVSNWLTRINTQFNKRKEQMYQALQNQVDAIKTVIEYKYNNYTSDERNRLESEYNINNIREELNKKVSLAM

ENIERFITESSIFYLMKLINEAKVSKLREYDEGVKEYLLDYISEHRSILGNSVQELNDLVTSTLNNSIPFELSS

BoNT/F$_2$ - UniParc Accession No. UPI00016BB5D7 minimal LH$_N$ backbone
(including activation loop)

SEQ ID NO: 19

NDETILYMQKPYEERSRKYYKAFEIMPNVWIMPERDTIGTKPDEFQVPDSLKNGSSAYYDPNYLTTDAEKDRYLKT

MIKLFNRINSNPTGKVLLEEVSNARPYLGDDDTLINEFFPVNVTTSVNIKFSTDVESSIISNLLVLGAGPDIFKAY

CTPLVRFNKSDKLIEPSNHGFGSINILTFSPEYEHIFNDISGGNHNSTESFIADPAISLAHELIHALHGLYGAKAV

THKESLVAERGPLMIAEKPIRLEEFLTFGGEDLNIIPSAMKEKIYNDLLANYEKIATRLREVNTAPPGYDINEYKD

YFQWKYGLDRNADGSYTVNRNKFNEIYKKLYSFTEIDLANKFKVKCRNTYFIKYGFVKVPDLLDDDIYTVSEGFNI

GNLAVNNRGQNINLNPKIIDSIPDKGLVEKIIKFCKSIIPRKGTKQSPSLCIRVNNRELFFVASESSYNESDINTP

KEIDDTTNLNNNYRNNLDEVILDYNSETIPQISNRTLNTLVQDNSYVPRYDSNGTSEIEEYDVVDFNVFFYLHAQK

VPEGETNISLTSSIDTALLEESKVYTFFSSEFIDTINKPVNAALFIDWISKVIRDFTTEATQKSTVDKIADISLIV

PYVGLALNIVIEAEKGNFEEAFELLGAGILLEFVPELTIPVILVFTIKSYIDSYENKNKAIKAINNSLIEREAKWK

EIYSWIVSNWLTRINTQFNKRKEQMYQALQNQVDAIKTAIEYKYNNYTSDEKNRLESKYNINNIEEELNKKVSLAM

KNIERFMTESSISYLMKLINEAEVGKLKEYDKHVKSDLLQYILYHKLILGEQTKELIDLVTSTLMSSIPFELSS

BoNT/F$_2$ - UniParc Accession No. UPI00000B50F1 minimal LH$_N$ backbone
(including activation loop)

SEQ ID NO: 20

NDETILYMQKPYEERSRKYYKAFEIMPNVWIMPERDTIGTKPDEFQVPDSLKNGSSAYYDPNYLTTDAEKDRYLKT

MIKLFNRINSNPTGKVLLEEVSNARPYLGDDDTLINEFLPVNVTTSVNIKFSTDVESSIISNLLVLGAGPDIFKAY

CTPLVRFNKSDKLIEPSNHGFGSINILTFSPEYEHIFNDISGGNHNSTESFIADPAISLAHELIHALHGLYGAKAV

THKESLVAERGPLMIAEKPIRLEEFLTFGGEDLNIIPSAMKEKIYNDLLANYEKIATRLREVNTAPPGYDINEYKD

YFQWKYGLDRNADGSYTVNRNKFNEIYKKLYSFTEIDLANKFKVKCRNTYFIKYGFVKVPNLLDDDIYTVSEGFNI

GNLAVNNRGQNINLNPKIIDSIPDKGLVEKIIKFCKSIIPRKGTKQSPSLCIRVNNRELFFVASESSYNESDINTP

KEIDDTTNLNNNYRNNLDEVILDYNSETIPQISNRTLNTLVQDNSYVPRYDSNGTSEIEEYDVVDFNVFFYLHAQK

VPEGETNISLTSSIDTALLEESKVYTFFSSEFIDTINKPVNAALFIDWISKVIRDFTTEATQKSTVDKIADISLIV

PYVGLALNIVIEAEKGNFEEAFELLGAGILLEFVPELTIPVILVFTIKSYIDSYENKNKAIKAINNSLIEREAKWK

EIYSWIVSNWLTRINTQFNKRKEQMYQALQNQVDAIKTAIEYKYNNYTSDEKNRLESKYNINNIEEELNKKVSLAM

KNIERFMTESSISYLMKLINEAEVGKLKEYDKHVKSDLLDYILYHKLILGEQTKELIDLVTSTLNSSIPFELSS

BoNT/F$_3$ - UniParc Accession No. UPI0001C0B12F minimal LH$_N$ backbone
(including activation loop)

SEQ ID NO: 21

NDETILYMQKPYEERSRKYYKAFEIMPNVWIMPERDTIGTKPDDFQVPDSLKNGSSAYYDPNYLTTDAEKDRYLKT

MIKLFNRINSNPTGKVLLEEVSNARPYLGDDDTLINEFFPVNVTTSVNIKFSTDVESSIISNLLVLGAGPDIFKAY

CTPLVRFNKSDKLIEPSNHGFGSINILTFSPEYEHIFNDISGGDHNSTESFIADPAISLAHELIHALHGLYGAKAV

THKETIEVKRGPLMIAEKPIRLEEFLTFGGEDLNIIPSAMKEKIYNDLLANYEKIATRLREVNTAPPEYDINEYKD

YFQWKYGLDRNADGSYTVNRNKFNGIYKKLYSFTEIDLANKFKVKCRNTYFIKYGFVKVPDLLDDDIYTVSEGFNI

GNLAVNNRGQNINLNPKIIDSIPDKGLVEKIIKFCKSIIPRKGTKQSPSLCIRVNNRELFFVASESSYNESDINTP

-continued

KEIDDTTNLNNNYRNNLDEVILDYNSETIPQISNRTLNTLVQDNSYVPRYDSNGTSEIEEYDVVDFNVFFYLHAQK

VPEGETNISLTSSIDTALLEKSKVYTFFSSEFIDTINESVNAALFIDWINKVIRDFTTEATQKSTVDKIADISLIV

PYVGLALNIVIDAEKGNFQEAFELLGAGILLEFVPELTIPVILVFTIKSYIDSYENKNKAIKAINNALIEREAKWK

EIYSWIVSNWLTKINTQFNKRKEQMYQALQNQVDAIKTAIEYKYNNYTSDEKNRLESEYNINNIEEELNKKVSLAM

KNIERFMTESSISYLMKLINEAEVGKLKKYDRHVKSDLLDYILYHKLILGDQTKELIDLVTSTLNSSIPFELSS

BoNT/F$_4$ - UniParc Accession No. UPI0001A92658 minimal LH$_N$ backbone
(including activation loop)

SEQ ID NO: 22

NDDTILYMQIPYEEKSKKYYKAFEIMRNVWIMPERNTIGINPSDFDPPASLKNGSSAYYDPNYLITDAEKDRYLKT

TIKLFKRINSNPAGEVLLQEISTAKPYLGNDHIPINEFHPVIRTTSVNIKSSTNVESSIILNLLVLGAGPNIFENS

SYPVRKLMNSGEVYDPSNQGFGSINIVTFSPEYEYTFNDISGGHNSSTESFIADPAISLAHELIHALHGLYGARGV

TYKETIKVKQAPLMIAEKPIRLEEFLTFGGQDLNIITSAMKEKIYNDLLANYEKIATRLSEVNSAPPEYDINEYKN

YFQWKYGLDKNADGSYTVNENKFNEIYKKLYSFTEIDLANKFKVKCRNTYFIKYGFLKVPNLLDDDIYTVSEGFNI

GNLAVNNRGQNINLNPKIIDSIPDKGLVEKIVKLCKSIIPRKGTKAPPRLCIRVNNRELFFVASESSYNENDINTP

KEIDDTTNLNNNYRNNLDEVILDYNSETIPQISSQTLNTLVQDDSYVPRYDSNGTSEIEEHNVVDLNAFFYLHAQK

VPEGETNISLTSSIDTALSEESKVYTFFSSEFINNINKPVHAALFIGWISQVIRDFTTESTQKSTVDKIADISLIV

PYVGLALNIGNDARKGNFKEAFELLGAAILLEVVPELLIPVILVFTIKSFIDSSKNEDKIIKAINNSLIEREAKWK

EVYSWIVSNWLTRINTQFNKRKEQMYQALQNQVDAIKTVIEYKYNSYTSDEKNRLESEYNINNIEEELNKKVSLAM

KNIERFIAESSISYLMKLINEAKVSELREYDEGVKEYLLDYILKNGSILGDHVQELNDLVTSTLNSSIPFELSS

BoNT/F$_4$ - UniParc Accession No. UPI0001C0B12D minimal LH$_N$ backbone
(including activation loop)

SEQ ID NO: 23

NDDTILYMQIPYEEKSKKYYKAFEIMRNVWIMPERNTIGINPSDFDPPASLKNGSSAYYDPNYLITDAEKDRYLKT

TIKLFKRINSNPAGEVLLQEISTAKPYLGNDHIPINEFHPVIRTTSVNIKSSTNVESSIILNLLVLGAGPNIFENS

SYPVRKLMNSGEVYDPSNDGFGSINIVTFSPEYEYTFNDISGGHNSSTESFIADPAISLAHELIHALHGLYGARGV

TYKETIKVKQAPLMIAEKPIRLEEFLTFGGQDLNIITSAMKEKIYNDLLANYEKIATRLSEVNSAPPEYDINEYKN

YFQWKYGLDKNADGSYTVNENKFNEIYKKLYSFTEIDLANKFKVKCRNTYFIKYGFLKVPNLLDDDIYTVSEGFNI

GNLAVNNRGQNINLNPKIIDSIPDKGLVEKIVKLCKSIIPRKGTKAPPRLCIRVNNRELFFVASESSYNENDINTP

KEIDDTTNLNNNYRNNLDEVILDYNSETIPQISSQTLNTLVQDDSYVPRYDSNGTSEIEEHNVVDLNAFFYLHAQK

VPEGETNISLTSSIDTALSEESKVYTFFSSEFINNINKPVHAALFIGWISQVIRDFTTESTQKSTVDKIADISLIV

PYVGLALNIGNDARKGNFKEAFELLGAAILLEVVPELLIPVILVFTIKSFIDSSKNEDKIIKAINNSLIEREAKWK

EVYSWIVSNWLTRINTQFNKRKEQMYQALQNQVDAIKTVIEYKYNSYTSDEKNRLESEYNINNIEEELNKKVSLAM

KNIERFIAESSISYLMKLINEAKVSELREYDEGVKEYLLDYILKNGSILGDHVQELNDLVTSTLMSSIPFELSS

BoNT/F$_5$ - UniParc Accession No. UPI0001C0B12E minimal LH$_N$ backbone
(including activation loop)

SEQ ID NO: 24

NDNTILYIRPPYYERSNTYFKAFNIMENVWIIPERYRLGIEASKFDPPDSLKAGSDGYFDPNYLSTNTEKNRYLQI

MIKLFKRINSNEAGKILLNQIKDAIPYLGNSYTAEDQFTTNNRTISFNVRLANGTIEQEMANLIIWGPGPDLITNR

TGGTTYTPAQSLEAIPYKEGFGSIMTIEFSPEYATAFNDISLTSHAPSLFIKDPALILMHELIHVLHGLYGTYTTG

FKIKPNITEPYMEVTKPITSGEFLTFGGNDVNKIPQLIQSQLRSKVLDDYEKIASRLNKVNRATAEINIDKFKYSY

QLKYQFVKDSNGVYSVDLDKFNKLYDKIYSFTEFNLAHEFKIKTRNSYLAKNFGPFYLPNLLDNSIYNEADGFNIG

DLSVNYKGQVIGSDIDSIKKLEGQGVVSRVVRLCLNSSFKKNTKKPLCITVNNGDLFFIASEDSYGEDTINTPKEI

DDTTTLVPSFKNILDKVILDFNKQVIPQIPNRRIRTDIQEDNYIPEYDSNGTSEIEEYNVVDLNAFFYLHAQKVPE

GETNISLTSSIDTALSEESKVYTFFSSEFIDTINEPVNAALFIDWISKVIRDFTTEATQKSTVDKIADISLIVPYV

GLALNIVNETEKGNFKEAFELLGAGILLEFVPELAIPVILVFTIKSYIDSYENKNKIIKAINNSLIEREAKWKEIY

-continued

SWIVSNWLTRINTQFNKRKEQMYQALQNQVDAIKTAIEYKYNNYTSDEKNRLESEYNINNIEEELNKKVSLAMKNI

ERFITESSISYLMKLINEAEVGKLKEYDKRVKRHLLEYIFDYRLILGEQGGELIDLVISTLNISIPPFELSS

BoNT/F$_6$ - UniParc Accession No. UPI0001C0B1D1 minimal LH$_N$ backbone
(including activation loop)

SEQ ID NO: 25

NDDTILYMQIPYEEKSKKYYKAFEIMRNVWIIPERNTIGTNPSDFDPPASLKNGSSAYYDPNYLTTDAEKDRYLKT

TIKLFKRINSNPAGKVLLQEISTAKPYLGNDHIPIDEFSPVIRTTSVNIKLSTNVESSMLLNLLVLGAGPDIFESC

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYGFLKVPNLLDDDIYTVSEGFNI

GNLAVNNRGQSIKLNPKIIDSIPDKGLVEKIVKFCKSVIPRKGTKAPPRLCIRVNNSELFFVASESSYNENDINTP

KEIDDTTNLNNNYRNNLDEVILDYNSQTIPQISNRTLNTLVQDNSYVPRYDSNGTSEIEEYDVVDFNVFFYLHAQK

VPEGETNISLTSSIDTALLEESKVYTFFSSEFIDTINKPVNAALFIDWISKVIRDFTTEATQKSTVDKIADISLIV

PYVGLALNIIIEAEKGNFEEAFELLGVGILLEFVPELTIPVILVFTIKSYIDSYENKNKAIKAINNSLIEREAKWK

EIYSWIVSNWLTRINTQFNKRKEQMYQALQNQVDAIKTAIEYKYNNYTSDEKNRLESEYNINNIEEELNKKVSLAM

KNIERFMTESSISYLMKLINEAKVGKLKKYDNHVKSDLLNYILDHRSILGEQTNELSDLVTSTLNSSIPFELSS

BoNT/F$_6$ - UniParc Accession No. UPI0000126B8A minimal LH$_N$ backbone
(including activation loop)

SEQ ID NO: 26

NDDTILYMQIPYEEKSKKYYKAFEIMRNVWIIPERNTIGTNPSDFDPPASLKNGSSAYYDPNYLTTDAEKDRYLKT

TIKLFKRINSNPAGKVLLQEISTAKPYLGNDHTPIDEFSPVTRTTSVNIKLSTNVESSMLLNLLVLGAGPDIFESC

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYEFLKVPNLLDDDIYTVSEGFNI

GNLAVNNRGQSIKLNPKIIDSIPDKGLVEKIVKFCKSVIPRKGTKAPPRLCIRVNNSELFFVASESSYNENDINTP

KEIDDTTNLNNNYRNNLDEVILDYNSQTIPQISNRTLNTLVQDNSYVPRYDSNGTSEIEEYDVVDFNVFFYLHAQK

VPEGETNISLTSSIDTALLEESKDIFFSSEFIDTINKPVNAALFIDWISKVIRDFTTEATQKSTVDKIADISLIVP

YVGLALNIIIEAEKGNFEEAFELLGVGILLEFVPELTIPVILVFTIKSYIDSYENKNKAIKAINNSLIEREAKWKE

IYSWIVSNWLTRINTQFNKRKEQMYQALQNQVDAIKTAIEYKYNNYTSDEKNRLESEYNINNIEEELNKKVSLAMK

NIERFMTESSISYLMKLINEAKVGKLKKYDNHVKSDLLNYILDHRSILGEQTNELSDLVTSTLNSSIPFELSS

BoNT/F$_6$ - UniParc Accession No. UPI0001C0B1D0 minimal LH$_N$ backbone
(including activation loop)

SEQ ID NO: 27

NDDTILYMQIPYKEKSKKYYKAFEIMRNVWIIPERNTIGTNPSDFDPPASLKNGSSAYYDPNYLTTDAEKDRYLKT

TIKLFKRINSNPAGKVLLQEISYAKPYLGNDHTPIDEFSPVTRTTSVNIKLSTNVESSMLLNLLVLGAGPDIFESC

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYGFLKVPNLLDDDIYTVSEGFNI

GNLAVNNRGQSIKLNPKIIDSIPDKGLVEKIVKFCKSVIPRKGTKAPPRLCIRVNNSELFFVASESSYNENDINTP

KEIDDTTNLNNNYRNNLDEVILDYNSQTIPQISNRTLNTLVQDNSYVPRYDSNGTSEIEEYDVVDFNVFFYLHAQK

VPEGETNISLTSSIDTALLEESKVYTFFSSEFIDTINKPVNAALFIDWISKVIRDFTTEATQKSTVDKIADISLIV

PYVGLALNIIIEAEKGNFEEAFELLGVGILLEFVPELTIPVILVFTIKSYIDSYENKNKAIKAINNSLIEREAKWK

EIYSWIVSNWLTRINTQFNKRKEQMYQALQNQVDAIKTAIEYKYNNYTSDEKNRLESEYNINNIEEELNKKVSLAM

KNIERFMTESSISYLMKLINEAKVGKLKKYDNHVKSDLLNYILDHRSILGEQTNELSDLVTSTLNSSIPFELSS

-continued

BoNT/F$_6$ - UniParc Accession No. UPI0004E7C8CE minimal LH$_N$ backbone
(including activation loop)

SEQ ID NO: 28

NDDTILYMQIPYKEKSKKYYKAFEIMRNVWIIPERNTIGTNPSDFDPPASLKNGSSAYYDPNYLTTDAEKDRYLKT

TIKLFKRINSNPAGKVLLQEISTAKPYLGNDHTPIDEFSPVTRTTSVNIKLSTNVESSMLLNLLVLGAGPDIFESC

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYGFLKVPNLLDDDIYTVSEGFNI

GNLAVNNRGQSIKLNPKIIDSIPDKGLVEKIVKFCKSVIPRKGTKAPPRLCIRVNNSELFFVASESSYNENDINTP

KEIDDTTNLNNNYRNNLDEVILDYNSQTIPQISNRTLNTLVQDNSYVPRYDSNGTSEIEEYDVVDFNVFFYLHAQK

VPEGETNISLTSSIDTALLEESKVYTFFSSEFIDTINKPVNAALFIDWISKVIRDFTTEATQKSTVDKIADISLIV

PYVGLALNIIIEAEKGNFEEAFELLGVGILLEFVPELTIPVILVFTIKSYIDSYENKNKAIKAINNSLIEREAKWK

EIYSWIVSNWLTRINTQFNKRKEQMYQALQNQVDAIKTAIEYKYNNYTSDEKNRLESEYNINNIEEELNKKVSLAM

KNIERFMTESSISYLMKLINEAKVGKLKKYDNHVKSDLLNYILDHRSILGEQTNELSDLVTSTLNSSIPFELSS

BoNT/F$_7$ - UniParc Accession No. UPI0001DE3DAC minimal LH$_N$ backbone
(including activation loop)

SEQ ID NO: 29

NNTTILYMKMPYYEDSNKYYKAFEIMDNVWIIPERNIIGKKPSDFYPPISLDSGSSAYYDPNYLTTDAEKDRFLKT

VIKLFNRINSNPAGQVLLEEIKNGKPYLGNDHTAVNEFCANNRSTSVEIKESKGTTDSMLLNLVILGPGPNILECS

TFPVRIFPNNIAYDPSEKGFGSIQLMSFSTEYEYAFNDTDLFIADPAISLAHELIHVLHGLYGAKGVTNKKVIEV

DQGALMAAEKDIKIEEFITFGGQDLNIITNSTNQKIYDNLLSNYTAIASRLSQVNINNSALNTTYYKNFFQWKYGL

DQDSNGNYTVNISKFNAIYKKLFSFTECDLAQKFQVKNRSNYLFHFKPFRLLDLLDDNIYSISEGFNIGSLRVNNN

GQNINLNSRIVGPIPDNGLVERFVGLCKSIVSKKGTKNSLCIKVNNRDLFFVASESSYNENGINSPKEIDDTTITN

NNYKKNLDEVILDYNSDAIPNLSSRLLNTTAQNDSYVPKYDSNGTSEIKEYTVDKLNVFFYLYAQKAPEGESAISL

TSSVNTALLDASKVYTFFSSDFINTVNKPVQAALFISWIQQVINDFTTEATQKSTIDKIADISLVVPYVGLALNIG

NEVQKGNFKEAIELLGAGILLEFVPELLIPTILVFTIKSFINSDDSKNKIIKAINNALRERELKWKEVYSWIVSNW

LTRINTQFNKRKEQMYQALQNQVDGIKKIIEYKYNNYTLDEKNRLKAEYNIYSIKEELNKKVSLAMQNIDRFLTES

SISYLMKLINEAKINKLSEYDKRVNQYLLNYILENSSTLGTSSVQELNNLVSNTLNNSIPFELSE

BoNT/F$_7$ - UniParc Accession No. UPI0001C0B220 minimal LH$_N$ backbone
(including activation loop)

SEQ ID NO: 30

NNTTILYMKMPYYEDSNKYYKAFEIMDNVWIIPERNIIGKKPSDFYPPISLDSGSSAYYDPNYLTTDAEKDRFLKT

VIKLFNRINSNPAGQVLLEEIKNGKPYLGNDHTAVNEFCANNRSTSVEIKESNGTTDSMLLNLVILGPGPNILECS

TFPVRIFPNNIAYDPSEKGFGSIQLMSFSTEYEYAFNDTDLFIADPAISLAHELIHVLHGLYGAKGVTNKKVIEV

DQGALMAAEKDIKIEEFITFGGQDLNIITNSTNQKIYDNLLSNYTAIASRLSQVNINNSALNTTYYKNFFQWKYGL

DQDSNGNYTVNISKFNAIYKKLFSFTECDLAQKFQVKNRSNYLFHFKPFRLLDLLDDNIYSISEGFNIGSLRVNNN

GQNINLNSRIVGPIPDNGLVERFVGLCKSIVSKKGTKNSLCIKVNNRDLFFVASESSYNENGINSPKEIDDTTITN

NNYKKNLDEVILDYNSDAIPNLSSRLLNTTAQNDSYVPKYDSNGTSEIKEYTVDKLNVFFYLYAQKAPEGESAISL

TSSVNTALLDASKVYTFFSSDFINTVNKPVQAALFISWIQQVINDFTTEATQKSTIDKIADISLVVPYVGLALNIG

NEVQKGNFKEAIELLGAGILLEFVPELLIPTILVFTIKSFINSDDSKNKIIKAINNALRERELKWKEVYSWIVSNW

LTRINTQFNKRKEQMYQALQNQVDGIKKIIEYKYNNYTLDEKNRLKAEYNIYSIKEELNKKVSLAMQNIDRFLTES

SISYLMKLINEAKINKLSEYDKRVNQYLLNYILENSSTLGTSSVQELNNLVSNTLNNSIPFELSE

BoNT/F$_7$ - UniParc Accession No. UPI00000BAF8C minimal LH$_N$ backbone
(including activation loop)

SEQ ID NO: 31

NNTTILYMKMPYYEDSNKYYKAFEIMDNVWIIPERNIIGKKPSDFYPPISLDSGSSAYYDPNYLTTDAEKDRFLKT

VIKLFNRINSNPAGQVLLEEIKNGKPYLGNDHTAVNEFCANNRSTSVEIKESNGTIDSMLLNLVILGPGPNILECS

-continued

TFPVRIFPNNIAYDPSEKGFGSIQLMSFSTEYEYAFNDNIDLFIADPAISLAHELIHVLHGLYGAKGVTNKKVIEV

DQGALMAAEKDIKIEEFITFGGQDLNIITNSTMQKIYVILLLSNYTAIASRLSQVNRMNSALNTTYYKNFFQWKYGL

DQDSNGNYTVNISKFNAIYKKLFSFTECDLAQKFQVKNRSNYLFHFKPFRLLDLLDDNIYSISEGFNIGSLRVNNN

GQNINLNSRIVGPIPDNGLVERFVGLCKSIVSKKGTKNSLCIKVNNRDLFFVASESSYNENGINSPKEIDDTTITN

NNYKKNLDEVILDYNSDAIPNLSSRLLNTTAQNDSYVPKYDSNGTSEIKEYTVDKLNVFFYLYAQKAPEGESAISL

TSSVNTALLDASKVYTFFSSDFINTVNKPVQAALFISWIQQVINDFTTEATQKSTIDKIADISLIVPYVGLALNIG

NEVQKGNFKEAIELLGAGILLEFVPELLIPTILVFTIKSFINSDDSKNKIIKAINNALRERELKWKEVYSWIVSNW

LTRINTQFNKRKEQMYQALQNQVDGIKKIIEYKYNNYTLDEKNRLRAEYNIYSIKEELNKKVSLAMQNIDRFLTES

SISYLMKLINEAKINKLSEYDKRVNQYLLNYILENSSTLGTSSVPELNNLVSNTLNNSIPFELSE

BoNT/F₇ - UniParc Accession No. UPI0001C0B221 minimal LH_N backbone
(including activation loop)
SEQ ID NO: 32
NNTTILYMKMPYYEDSNKYYKAFEIMDNVWIIPERNIIGKKPSDFYPPISLDSGSSAYYDPNYLTTDAEKDRFLKT

VIKLETRINSNPAGQVLLEEIKNGKPYLGNDHTAVNEFCANNRSTSVEIKESNGTIDSMLLNLVILGPGPNILECS

TFPVRIFPNNIAYDPSEKGFGSIQLMSFSTEYEYAFNDNIDLFIADPAISLAHELIHVLHGLYGAKGVTNKKVIEV

DQGALMAAEKDIKIEEFITFGGQDLNIVTNSTNQKIYDNLLSNYTAIASRLSQVNINNSALNITYYKNEFQWKYGL

DQDSNGNYTVNISKFNAIYKKLFSFTECDLAQKFQVKNRSNYLFHFKPFKLLDLLDDNIYSISEGFNIGSLRVNNN

GQNINLNSRIVGPIPDNGLVERFVGLCKSIVSKKGTKNSLCIKVNNRDLFFVASESSYNENGINSPKEIDDTTITN

NNYKKNLDEVILDYNSDAIPNLSSRLLNATAQNDSYVPKYDSNGTSEINEYTVDKLNVFFYLYAQKAPEGESAISL

TSSVDTALLDASKVYTFFSSDFINTVNKPVQAALFISWIQQVINDFTTEATQKSTIDKIADISLVVPYVGLALNIG

NEVQKGNFKEAIELLGAGILLEFVPELLIPTILVFTIKSFINSDDSKNKIIKAINNALRERELKWKEVYSWIVSNW

LTRINTQFNKRKEQMYQALQNQVDGIKKIIEYKYNNYTLDEKNRLKAEYNIYNIKEELNKKVSLAMQNIDRFLTES

SISYLMKLINEAKINKLSEYDKRVNQYLLNYILENSSTLGTSSVQELNNLVSNTLNNSIPFELSE

BoNT/F consensus sequence minimal L chain fragment
SEQ ID NO: 33
NDDTILYMQIPYEEKSKKYYKAFEIMRNVWIIPERNTIGTKPSDFDPPASLKNGSSAYYDPNYLTTDAEKDRYLKT

TIKLFKRINSNPAGKVLLXEISXAKPYLGNDHTPINEFXPVNRTTSVNIKLSTNVESSMLLNLLVLGAGPDIFEXS

CYPVRKXPNSDXVYDPSNXGFGSINIVTFSPEYEYTENDISGGHNSSTESFIADPAISLAHELIHALHGLYGAXGV

TYKETIEVKQXPLMIAEKPIRLEEFLTFGGQDLNIITSAMKEKIYNNLLANYEKIATRLSEVNSAPPEYDINEYKD

YFQWKYGIAKNADGSYTVNENKFNEIYKKLYSFTEIDLANKFKVKCRNTYFIK-YGFLKVPNLLDDDIYTVSEGFN

IGNLAVNNRGQNINLNPK

BoNT/F₁ - UniParc Accession No. UPI00000B66D1 minimal L chain fragment
SEQ ID NO: 34
NDDTILYMQIPYEEKSKKYYKAFEIMRNVWIIPERNTIGTDPSDFDPPASLENGSSAYYDPNYLITDAEKDRYLKT

TIKLFKRINSNPAGEVLLQEISYAKPYLGNEHTPINEFHPVIRTTSVNIKSSTNVKSSIILNLLVLGAGPDIFENS

SYPVRKLMDSGGVYDPSNDGEGSINIVTESPEYEYTENDISGGYNSSTESFIADPAISLAHELIHALHGLYGARGV

TYKETIKVKQAPLMIAEKPIRLEEFLTFGGQDLNIITSAMKEKIYNNLLANYEKIATRLSRVNSAPPEYDINEYKD

YFQWKYGLDKNADGSYTVNENKFNEIYKKLYSFTEIDLANKFKVKCRNTYFIKYGFLKVPNLLDDDIYTVSEGFNI

GNLAVNNRGQNIKLNPK

BoNT/F₂ - UniParc Accession No. UPI00016BB5D7 minimal L chain fragment
SEQ ID NO: 35
NDETILYMQKPYEERSRKYYKAFEIMPNVWIMPERDTIGTKPDEFQVPDSLKNGSSAYYDPNYLTIDAEKDRYLKT

MIKLENRINSNPTGKVLLEEVSNARPYLGDDDTLINEFFPVNVTTSVNIKFSTDVESSIISNLLVLGAGPDIFKAY

CIPLVRFNKSDKLIEPSNHGEGSINILTESPEYEHIENDISGGNHNSTESFIADPAISLAHELIHALHGLYGAKAV

THKESLVAERGPLMIAEKPIRLEEFLTFGGEDLNIIPSAMKEKIYNDLLANYEKIATRLREVNTAPPGYDINEYKD

-continued

YFQWKYGLDRNADGSYTVNRNKFNEIYKKLYSFTEIDLANKFKVKCRNTYFIKYGFVKVPDLLDDDIYTVSEGFNI
GNLAVNNRGQNINLNPK

BoNT/$F_2$ - UniParc Accession No. UPI00000B50F1 minimal L chain fragment

SEQ ID NO: 36

NDETILYMQKPYEERSRKYYKAFEIMPNVWIMPERDTIGTKPDEFQVPDSLKNGSSAYYDPNYLTTDAEKDRYLKT

MIKLFNRINSNPTGKVLLEEVSNARPYLGDDDTLINEFLPVNVTTSVNIKFSTDVESSIISNLLVLGAGPDIFKAY

CTPLVRFNKSDKLIEPSNHGFGSINILTFSPEYEHIFNDISGGNHNSTESFIADPAISLAHELIHALHGLYGAKAV

THKESLVAERGPLMIAEKPIRLEEFLTFGGEDLNIIPSAMKEKIYNDLLANYEKIATRLREVNTAPPGYDINEYKD

YFQWKYGLDRNADGSYTVNRNKFNEIYKKLYSFTEIDLANKFKVKCRNTYFIKYGFVKVPNLLDDDIYTVSEGFNI

GNLAVNNRGQNINLNPK

BoNT/$F_3$ - UniParc Accession No. UPI0001C0B12F minimal L chain fragment

SEQ ID NO: 37

MDETILYMQKPYEERSRKYYKAFEIMPNVWIMPERDTIGTKPODFQVPDSLKNGSSAYYDPNYLTTDAEKDRYLKT

MIKLFNRINSNPTGKVLLEEVSNARPYLGDDDTLINEFFPVNVTTSVNIKFSTDVESSIISNLLVLGAGPDIFKAY

CTPLVRFNKSDKLIEPSNHGFGSINILTFSPEYEHIFNDISGGDHNSTESFIADPAISLAHELIHALHGLYGAKAV

THKETIEVKRGPLMIAEKPIRLEEFLTFGGEDLNIIPSAMKEKIYNDLLANYEKIATRLREVNTAPPEYDINEYKD

YFQWKYGLDRNADGSYTVNRNKFNGIYKKLYSFTEIDLANKFKVKCRNTYFIKYGFVKVPDLLDDDIYTVSEGFNI

GNLAVNNRGQNINLNPK

BoNT/$F_4$ - UniParc Accession No. UPI0001A92658 minimal L chain fragment

SEQ ID NO: 38

NDDTILYMQIPYEEKSKKYYKAFEIMRNVWIMPERNTIGTNPSDFDPPASLKNGSSAYYDPNYLTTDAEKDRYLKT

TIKLFKRINSNPAGEVLLQEISYAKPYLGNDHTPINEFHPVTRTTSVNIKSSTNVESSIILNLLVLGAGPNIFENS

SYPVRKLMNSGEVYDPSNDGFGSINIVTFSPEYEYTFNDISGGHNSSTESFIADPAISLAHELIHALHGLYGARGV

TYKETIKVKQAPLMIAEKPIRLEEFLTFGGQDLNIITSAMKEKIYNDLLANYEKIATRLSEVNSAPPEYDINEYKN

YFQWKYGLDKNADGSYTVNENKFNEIYKKLYSFTEIDLANKFKVKCRNTYFIKYGFLKVPNLLDDDIYTVSEGFNI

GNLAVNNRGQNINLNPK

BoNT/$F_4$ - UniParc Accession No. UPI0001C0B12D minimal L chain fragment

SEQ ID NO: 39

NDDTILYMQIPYEEKSKKYYKAFEIMRNVWIMPERNTIGTNPSDFDPPASLKNGSSAYYDPNYLTTDAEKDRYLKT

TIKLFKRINSNPAGEVLLQEISYAKPYLGNDHTPINEFHPVTRTTSVNIKSSTNVESSIILNLLVLGAGPNIFENS

SYPVRKLMNSGEVYDPSNDGFGSINIVTFSPEYEYTFNDISGGHNSSTESFIADPAISLAHELIHALHGLYGARGV

TYKETIKVKQAPLMIAEKPIRLEEFLTFGGQDLNIITSAMKEKIYNDLLANYEKIATRLSEVNSAPPEYDINEYKN

YFQWKYGLDKNADGSYTVNENKFNEIYKKLYSFTEIDLANKFKVKCRNTYFIKYGFLKVPNLLDDDIYTVSEGFNI

GNLAVNNRGQNINLNPK

BoNT/$F_5$ - UniParc Accession No. UPI0001C0B12E minimal L chain fragment

SEQ ID NO: 40

NDNTILYIRPPYYERSNTYFKAFNIMENVWIIPERYRLGIEASKFDPPDSLKAGSDGYFDPNYLSTNTEKNRYLQI

MIKLFKRINSNEAGKILLNQIKDAIPYLGNSYTAEDQFTTNNRTISFNVRLANGTIEQEMANLIIWGPGPDLTTNR

TGGTTYTPAQSLEAIPYKEGFGSIMTIEFSPEYATAFNDISLTSHAPSLFIKDPALILMHELIHVLHGLYGTYTTG

FKIKPNITEPYMEVTKPITSGEFLTFGGNDVNKIPQLIQSQLRSKVLDDYEKIASRLNKVNRATAEINIDKFKYSY

QLKYQFVKDSNGVYSVDLDKFNKLYDKIYSFTEFNLAHEFKIKTRNSYLAKNFGPFYLPNLLDNSIYNEADGFNIG

DLSVNYKGQVIGSDID

BoNT/$F_6$ - UniParc Accession No. UPI0001C0B1D1 minimal L chain fragment

SEQ ID NO: 41

NDDTILYMQIPYEEKSKKYYKAFEIMRNVWIIPERNTIGTNPSDFDPPASLKNGSSAYYDPNYLTTDAEKDRYLKT

TIKLFKRINSNPAGKVLLQEISYAKPYLGNDHTPIDEFSPVTRTTSVNIKLSTNVESSMLLNLLVLGAGPDIFESC

-continued

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYGFLKVPNLLDDDIYTVSEGFNI

GNLAVNNRGQSIKLNPK

BoNT/F$_6$ - UniParc Accession No. UPI0000126B8A minimal L chain fragment
SEQ ID NO: 42
NDDTILYMQIPYEEKSKKYYKAFEIMRNVWIIPERNTIGTNPSDFDPPASLKNGSSAYYDPNYLTTDAEKDRYLKT

TIKLFKRINSNPAGKVLLQEISYAKPYLGNDHTPIDEFSPVTRTTSVNIKLSTNVESSMLLNLLVLGAGPDIFESC

CYPVRKLIDPDVVYDPSNYGFGSINIVTFSPEYEYTFNDISGGHNSSTESFIADPAISLAHELIHALHGLYGARGV

TYEETIEVKQAPLMIAEKPIRLEEFLTFGGQDLNIITSAMKEKIYNNLLANYEKIATRLSEVNSAPPEYDINEYKD

YFQWKYGLDKNADGSYTVNENKFNEIYKKLYSFTESDLANKFKVKCRNTYFIKYEFLKVPNLLDDDIYTVSEGFNI

GNLAVNNRGQSIKLNPK

BoNT/F$_6$ - UniParc Accession No. UPI0001C0B1D0 minimal L chain fragment
SEQ ID NO: 43
NEDTILYMQIPYKEKSKEYYKAFEIMPNVWIIPERNTIGINPSDFDPPASLENGSSAYYDPNYLTTDAEKDRYLKT

TIELFKRINSNPAGEVLLQEISYAKPYLGNEHTPIDEFSPVTPTTSVNIKLSTNVESSMLLNLLVLGAGPDIFESC

CYPVRKLIDPDVVYDPSNYGEGSINIVTESPEYEYTENDISGGENSSTESFIADPAISLAHELIHALEGLYGARGV

TYEETIEVKQAPLMIAEKPIRLEEFLTEGGQDLNIITSAMKEKIYNNLLANYEKIATRLSEVNSAPPEYDINEYKD

YFQWEYGLDKNADGSYTVNENKFNEIYKKLYSFTESDLANKFEVECRNTYFIKYGFLKVPNLLDEDIYTVSEGFNI

GNLAVNNRGQSIKLNPK

BoNT/F$_6$ - UniParc Accession No. UPI0004E7C8CE minimal L chain fragment
SEQ ID NO: 44
NEDTILYMQIPYKEKSKEYYKAFEIMPNVWIIPERNTIGINPSDFDPPASLENGSSAYYDPNYLTTDAEKDRYLKT

TIELFKRINSNPAGEVLLQEISYAKPYLGNEHTPIDEFSPVTRTTSVNIKLETNVESSMLLNLLVLGAGPDIFESC

CYPVRKLIDPDVVYDPSNYGEGSINIVTESPEYEYTENDISGGHNSSTESFIADPAISLAHELIHALHGLYGARGV

TYEETIEVKQAPLMIAEKPIRLEEFLTEGGQDLNIITSAMKEKIYNNLLANYEKIATRLSEVNSAPPEYDINEYKD

YFQWEYGLDKNADGSYTVNENKFNEIYKKLYSFTESDLANKFEVECRNTYFIKYGFLKVPNLLEDDITIVSEGFNI

GNLAVNNRGQSIKLNPK

BoNT/F$_7$ - UniParc Accession No. UPI0001DE3DAC minimal L chain fragment
SEQ ID NO: 45
NNTTILYMKMPYYEDSNKYYKAFEIMENVWIIPERNIIGKEPSDFYPPISLDSGSSAYYDPNYLTTDAEKDRFLET

VIKLENRINSNPAGQVLLEEIENGKPYLGNEHTAVNEFCANNRSTSVEIKESEGTTESMLLNLVILGPGPNILECS

TFPVRIFPNNIAYDPSEKGEGSIQLMSFSTEYEYAFNENTELFIADPAISLAHELIHVLHGLYGAKGVINKKVIEV

DQGALMAAEKDIKIEEFITEGGQDLNIITNSTNQKIYDNLLSNYTAIASRLSQVNINNSALNITYYKNEFQWEYGL

DQDSNGNYTVNISKFNAIYKKLFSFTECELAQKFQVENRSNYLFHFKPFRLLDLLEDNIYSISEGFNIGSLRVNNN

GQNINLNSR

BoNT/F$_7$ - UniParc Accession No. UPI0001C0B220 minimal L chain fragment
SEQ ID NO: 46
NNTTILYMKMPYYEDSNKYYKAFEIMDNVWIIPERNIIGKKPSDFYPPISLDSGSSAYYDPNYLTTDAEKDRFLKT

VIKLENRINSNPAGQVLLEEIENGEPYLGNEHTAVNEFCANNRSTSVEIKESNGTTESMLLNLVILGPGPNILECS

TFPVRIFPNNIAYDPSEKGEGSIQLMSFSTEYEYAFNENTELFIADPAISLAHELIHVLEGLYGAKGVINKKVIEV

DQGALMAAEKDIKIEEFITEGGQDLNIITNSTNQKIYDNLLSNYTAIASRLSQVNINNSALNITYYKNEFQWEYGL

DQDSNGNYTVNISKFNAIYKKLFSFTECELAQKFQVENRSNYLFHFKPFRLLDLLEDNIYSISEGFNIGSLRVNNN

GQNINLNSR

-continued

BoNT/F₇ - UniParc Accession No. UPI00000BAF8C minimal L chain fragment
SEQ ID NO: 47
NNTTILYMEMPYYEDSNKYYKAFEIMENVWIIPERNIIGKEPSDFYPPISLDSGSSAYYDPNYLTTDAEKDRFLET

VIKLENRINSNPAGQVLLEEIENGEPYLGNEHTAVNEFCANNRSTSVEIKESNGTTESMLLNLVILGPGPNILECS

TFPVRIFPNNIAYDPSEKGEGSIQLMSFSTEYEYAFNENTELFIADPAISLAHELIHVLHGLYGAKGVINKKVIEV

DQGALMAAEKDIKIEEFITEGGQDLNIITNSTNQKIYVILLSNYTAIASRLSQVNRNNSALNITYYKNEFQWEYGL

DQESNGNYTVNISKFNAIYKKLFSFTECELAQKFQVKNRSNYLFHFKPFRLLDLLEDNIYSISEGFNIGSLRVNNN

GQNINLNSR

BoNT/F₇ - UniParc Accession No. UPI0001C0B221 minimal L chain fragment
SEQ ID NO: 48
NNTTILYMKMPYYEDSNKYYKAFEIMENVWIIPERNIIGKKPSDFYPPISLDSGSSAYYDPNYLTTDAEKDRFLET

VIKLENRINSNPAGQVLLEEIENGKPYLGNEHTAVNEFCANNRSTSVEIKESNGTTESMLLNLVILGPGPNILECS

TFPVRIFPNNIAYDPSEKGEGSIQLMSFSTEYEYAFNENTELFIADPAISLAHELIHVLHGLYGAKGVINKKVIEV

DQGALMAAEKDIKIEEFITFGGQDLNIVTNSTMQKIYDNLLSNYTAIASRLSQVNINNSALNTTYYKNFFQWKYGL

DQESNGNYTVNISKFNAIYKKLFSFTECELAQKFQVKNRSNYLFHFKPFKLLDLLEDNIYSISEGFNIGSLRVNNN

GQNINLNSR

BoNT/F consensus sequence minimal $H_N$ fragment
SEQ ID NO: 49
NVFFYLHAQKVPEGETNISLTSSIDTALLEESKVYTFFSSEFIDTINKPVNAALFIDWISKVIREFTTEATQKSTV

DKIADISLIVPYVGLALNIGNEAEKGNFKEAFELLGAGILLEFVPELXIPVILVFTIKSYIDSYENKNKIIKAINN

SLIEREAKWKEIYSWIVSNWLTRINTQFNERKEQMYQALQNQVDAIKTAIEYKYNNYTSDEKNRLESEYNINNIEE

ELNKKVSLAMKNIERFMTESSISYLMKLINEAKVGKLKEYEKHVESXLLNYILXHRSILGEQ-XQELNDLVISTLN

SSIPFELSS

BoNT/F₁ - UniParc Accession No. UPI00000B66D1 minimal $H_N$ fragment
SEQ ID NO: 50
NVFFYLHAQKVPEGETNISLTSSIDTALSEESQVYTFFSSEFINTINKPVHAALFISWINQVIRDFTTEATQKSTF

DKIADISLVVPYVGLALNIGNEVQKENFKEAFELLGAGILLEFVPELLIPTILVFTIKSFIGSSENKNKIIKAINN

SLMERETKWKEIYSWIVSNWLTRINTQFNKRKEQMYQALQNQVDAIKTVIEYKYNNYTSDERNRLESEYNINNIRE

ELNKKVSLAMENIERFITESSIFYLMKLINEAKVSKLREYDEGVKEYLLDYISEHRSILGNSVQELNDLVTSTLNN

SIPFELSS

BoNT/F₂ - UniParc Accession No. UPI00016BB5D7 minimal $H_N$ fragment
SEQ ID NO: 51
NVFFYLHAQKVPEGETNISLTSSIDTALLEESKVYTFFSSEFIDTINKPVNAALFIDWISKVIRDFTTEATQKSTV

DKIADISLIVPYVGLALNIVIEAEKGNFEEAFELLGAGILLEFVPELTIPVILVFTIKSYIDSYENKNKAIKAINN

SLIEREAKWKEIYSWIVSNWLTRINTQFNKRKEQMYQALQNQVDAIKTAIEYKYNNYTSDEKNRLESKYNINNIEE

ELNKKVSLAMKNIERFMTESSISYLMKLINEAEVGKLKEYDKHVKSDLLDYILYHKLILGEQTKELIDLVTSTLNS

SIPFELSS

BoNT/F₂ - UniParc Accession No. UPI00000B50F1 minimal $H_N$ fragment
SEQ ID NO: 52
NVFFYLHAQKVPEGETNISLTSSIDTALLEESKVYTFFSSEFIDTINKPVNAALFIDWISKVIRDFTTEATQKSTV

DKIADISLIVPYVGLALNIVIEAEKGNFEEAFELLGAGILLEFVPELTIPVILVFTIKSYIDSYENKNKAIKAINN

SLIEREAKWKEIYSWIVSNWLTRINTQFNKRKEQMYQALQNQVDAIKTAIEYKYNNYTSDEKNRLESKYNINNIEE

ELNKKVSLAMKNIERFMTESSISYLMKLINEAEVGKLKEYDKHVKSDLLDYILYHKLILGEQTKELIDLVTSTLNS

SIPFELSS

BoNT/F₃ - UniParc Accession No. UPI0001C0B12F minimal $H_N$ fragment
SEQ ID NO: 53
NVFFYLHAQKVPEGETNISLTSSIDTALLEKSKVYTFFSSEFIDTINESVNAALFIDWINKVIRDFTTEATQKSTV

DKIADISLIVPYVGLALNIVIDAEKGNFQEAFELLGAGILLEFVPELTIPVILVFTIKSYIDSYENKNKAIKAINN

BoNT/F₄ - UniParc Accession No. UPI0001A92658 minimal H_N fragment

SEQ ID NO: 54

NAFFYLHAQKVPEGETNISLTSSIDTALSEESKVYTFFSSEFINNINKPVHAALFIGWISQVIRDFTTESTQKSTV
DKIADISLIVPYVGLALNIGNDARKGNFKEAFELLGAAILLEVVPELLIPVILVFTIKSFIDSSKNEDKIIKAINN
SLIEREAKWKEVYSWIVSNWLTRINTQFNKRKEQMYQALQNQVDAIKTVIEYKYNSYTSDEKNRLESEYNINNIEE
ELNKKVSLAMKNIERFIAESSISYLMKLINEAKVSELREYDEGVKEYLLDYILKNGSILGDHVQELNDLVTSTLNS
SIPFELSS

BoNT/F₄ - UniParc Accession No. UPI0001C0B12D minimal H_N fragment

SEQ ID NO: 55

NAFFYLHAQKVPEGETNISLTSSIDTALSEESKVYTFFSSEFINNINKPVHAALFIGWISQVIRDFTTESTQKSTV
DKIADISLIVPYVGLALNIGNDARKGNFKEAFELLGAAILLEVVPELLIPVILVFTIKSFIDSSKNEDKIIKAINN
SLIEREAKWKEVYSWIVSNWLTRINTQFNKRKEQMYQALQNQVDAIKTVIEYKYNSYTSDEKNRLESEYNINNIEE
ELNKKVSLAMKNIERFIAESSISYLMKLINEAKVSELREYDEGVKEYLLDYILKNGSILGDHVQELNDLVTSTLNS
SIPFELSS

BoNT/F₅ - UniParc Accession No. UPI0001C0B12E minimal H_N fragment

SEQ ID NO: 56

NAFFYLHAQKVPEGETNISLTSSIDTALSEESKVYTFFSSEFIDTINEPVNAALFIDWISKVIRDFTTEATQKSTV
DKIADISLIVPYVGLALNIVNETEKGNFKEAFELLGAGILLEFVPELAIPVILVFTIKSYIDSYENKNKIIKAINN
SLIEREAKWKEIYSWIVSNWLTRINTQFNKRKEQMYQALQNQVDAIKTAIEYKYNNYTSDEKNRLESEYNINNIEE
ELNKKVSLAMKNIERFITESSISYLMKLINEAEVGKLKEYDKRVKRHLLEYIFDYRLILGEQGGELIDLVTSTLNT
SIPFELSS

BoNT/F₆ - UniParc Accession No. UPI0001C0B1D1 minimal H_N fragment

SEQ ID NO: 57

NVFFYLHAQKVPEGETNISLTSSIDTALLEESKVYTFFSSEFIDTINKPVNAALFIDWISKVIRDFTTEATQKSTV
DKIADISLIVPYVGLALNIIIEAEKGNFEEAFELLGVGILLEFVPELTIPVILVFTIKSYIDSYENKNKAIKAINN
SLIEREAKWKEIYSWIVSNWLTRINTQFNKRKEQMYQALQNQVDAIKTAIEYKYNNYTSDEKNRLESEYNINNIEE
ELNKKVSLAMKNIERFMTESSISYLMKLINEAKVGKLKKYDNHVKSDLLNYILDHRSILGEQTNELSDLVTSTLNS
SIPFELSS

BoNT/F₆ - UniParc Accession No. UPI0000126B8A minimal H_N fragment

SEQ ID NO: 58

NVFFYLHAQKVPEGETNISLTSSIDTALLEESKDIFFSSEFIDTINKPVNAALFIDWISKVIRDFTTEATQKSTVD
KIADISLIVPYVGLALNIIIEAEKGNFEEAFELLGVGILLEFVPELTIPVILVFTIKSYIDSYENKNKAIKAINNS
LIEREAKWKEIYSWIVSNWLTRINTQFNKRKEQMYQALQNQVDAIKTAIEYKYNNYTSDEKNRLESEYNINNIEEE
LNKKVSLAMKNIERFMTESSISYLMKLINEAKVGKLKKYDNHVKSDLLNYILDHRSILGEQTNELSDLVTSTLNSS
IPFELSS

BoNT/F₆ - UniParc Accession No. UPI0001C0B1D0 minimal H_N fragment

SEQ ID NO: 59

NVFFYLHAQKVPEGETNISLTSSIDTALLEESKVYTFFSSEFIDTINKPVNAALFIDWISKVIRDFTTEATQKSTV
DKIADISLIVPYVGLALNIIIEAEKGNFEEAFELLGVGILLEFVPELTIPVILVFTIKSYIDSYENKNKAIKAINN
SLIEREAKWKEIYSWIVSNWLTRINTQFNKRKEQMYQALQNQVDAIKTAIEYKYNNYTSDEKNRLESEYNINNIEE
ELNKKVSLAMKNIERFMTESSISYLMKLINEAKVGKLKKYDNHVKSDLLNYILDHRSILGEQTNELSDLVTSTLNS
SIPFELSS

BoNT/F₆ - UniParc Accession No. UPI0004E7C8CE minimal H_N fragment

SEQ ID NO: 60

NVFFYLHAQKVPEGETNISLTSSIDTALLEESKVYTFFSSEFIDTINKPVNAALFIDWISKVIRDFTTEATQKSTV

DKIADISLIVPYVGLALNIIIEAEKGNFEEAFELLGVGILLEFVPELTIPVILVFTIKSYIDSYENKNKAIKAINN

SLIEREAKWKEIYSWIVSNWLTRINTQFNKRKEQMYQALQNQVDAIKTAIEYKYNNYTSDEKNRLESEYNINNIEE

ELNKKVSLAMKNIERFMTESSISYLMKLINEAKVGKLKKYDNHVKSDLLNYILDHRSILGEQTNELSDLVTSTLNS

SIPFELSS

BoNT/F₇ - UniParc Accession No. UPI0001DE3DAC minimal H_N fragment

SEQ ID NO: 61

NVFFYLYAQKAPEGESAISLTSSVNTALLDASKVYTFFSSDFINTVNKPVQAALFISWIQQVINDFTTEATQKSTI

DKIADISLVVPYVGLALNIGNEVQKGNFKEAIELLGAGILLEFVPELLIPTILVFTIKSFINSDDSKNKIIKAINN

ALRERELKWKEVYSWIVSNWLTRINTQFNKRKEQMYQALQNQVDGIKKIIEYKYNNYTLDEKNRLKAEYNIYSIKE

ELNKKVSLAMUIDRFLTESSISYLMKLINEAKINKLSEYDKRVNQYLLNYILENSSTLGTSSVIDELNNLVSNTLN

NSIPFELSE

BoNT/F₇ - UniParc Accession No. UPI0001C0B220 minimal H_N fragment

SEQ ID NO: 62

NVFFYLYAQKAPEGESAISLTSSVNTALLDASKVYTFFSSDFINTVNKPVQAALFISWIQQVINDFTTEATQKSTI

DKIADISLVVPYVGLALNIGNEVQKGNFKEAIELLGAGILLEFVPELLIPTILVFTIKSFINSDDSKNKIIKAINN

ALRERELKWKEVYSWIVSNWLTRINTQFNKRKEQMYQALQNQVDGIKKIIEYKYNNYTLDEKNRLKAEYNIYSIKE

ELNKKVSLAMQNIDRFLTESSISYLMKLINEAKINKLSEYDKRVNQYLLNYILENSSTLGTSSVQELNNLVSNTLN

NSIPFELSE

BoNT/F₇ - UniParc Accession No. UPI00000BAF8C minimal H_N fragment

SEQ ID NO: 63

NVFFYLYAQKAPEGESAISLTSSVNTALLDASKVYTFFSSDFINTVNKPVQAALFISWIQQVINDFTTEATQKSTI

DKIADISLIVPYVGLALNIGNEVQKGNFKEAIELLGAGILLEFVPELLIPTILVFTIKSFINSDDSKNKIIKAINN

ALRERELKWKEVYSWIVSNWLTRINTQFNKRKEQMYQALQNQVDGIKKIIEYKYNNYTLDEKNRLRAEYNIYSIKE

ELNKKVSLAMQNIDRFLTESSISYLMKLINEAKINKLSEYDKRVNQYLLNYILENSSTLGTSSVPELNNLVSNTLN

NSIPFELSE

BoNT/F₇ - UniParc Accession No. UPI0001C0B221 minimal H_N fragment

SEQ ID NO: 64

NVFFYLYAQKAPEGESAISLTSSVDTALLDASKVYTFFSSDFINTVNKPVQAALFISWIQQVINDFTTEATQKSTI

DKIADISLVVPYVGLALNIGNEVQKGNFKEAIELLGAGILLEFVPELLIPTILVFTIKSFINSDDSKNKIIKAINN

ALRERELKWKEVYSWIVSNWLTRINTQFNKRKEQMYQALQNQVDGIKKIIEYKYNNYTLDEKNRLKAEYNIYNIKE

ELNKKVSLAMQNIDRFLTESSISYLMKLINEAKINKLSEYDKRVNQYLLNYILENSSTLGTSSVQELNNLVSNTLN

NSIPFELSE

BoNT/F consensus sequence minimal activation loop (also activation
loop sequence for UPI0001A92658 (BoNT/F₄) and UPI0001C0B12D (BoNT/F₄))

SEQ ID NO: 65

KSIIPRKGTKAPPRL

BoNT/F₁ - UniParc Accession No. UPI00000B66D1 minimal
activation loop (also activation loop sequence for UPI0001C0B1D1 (BoNT/F₆),
UPI0000126B8A (BoNT/F₆), UPI0001C0B1D0 (BoNT/F₆) and UPI0004E7C8CE (BoNT/F₆))

SEQ ID NO: 66

KSVIPRKGTKAPPRL

BoNT/F₂ - UniParc Accession No. UPI00016BB5D7 minimal
activation loop (also activation loop sequence for UPI00000B50F1 (BoNT/F₂)
and UPI0001C0B12F (BoNT/F₃))

SEQ ID NO: 67

KSIIPRKGTKQSPSL

BoNT/F₅ - UniParc Accession No. UPI0001C0B12E minimal activation loop

SEQ ID NO: 68

LNSSFKKNTKKPL

BoNT/F₇ - UniParc Accession No. UPI0001DE3DAC minimal
activation loop (also activation loop sequence for UPI0001C0B220 (BoNT/F₇),
UPI00000BAF8C (BoNT/F₇) and UPI0001C0B221 (BoNT/F₇))

SEQ ID NO: 69

KSIVSKKGTKNSL

F1/4/6 activation loop sequence (after cleavage site) + start of F7 heavy
chain sequence

SEQ ID NO: 70

APPRLCIK

F1/4/6 activation loop sequence (after cleavage site) + start of F5 heavy
chain sequence

SEQ ID NO: 71

APPRLCIT

F2/3 activation loop sequence (after cleavage site) + start of F7 heavy
chain sequence

SEQ ID NO: 72

QSPSLCIK

F2/3 activation loop sequence (after cleavage site) + start of F5 heavy
chain sequence

SEQ ID NO: 73

QSPSLCIT

F1/4/6 activation loop sequence (after cleavage site) + start of F7 heavy
chain sequence

SEQ ID NO: 74

APPRLCIKV full-length recombinant BoNT/F7-1 (SXN102875_rBoNT-F7-1)

SEQ ID NO: 75

MPVNINNFNYNDPINNTTILYMKMPYYEDSNKYYKAFEIMDNVWIIPERNIIGKKPSDFYPPISLDSGSSAYYDPN

YLTTDAEKDRFLKTVIKLFNRINSNPAGQVLLEEIKNGKPYLGNDHTAVNEFCANNRSTSVEIKESKGTTDSMLLN

LVILGPGPMILECSTFPVRIFPNNIAYDPSEKGFGSIQLMSFSTEYEYAFNDNTDLFIADPAISLAHELIHVLHGL

YGAKGVTNKKVIEVDQGALMAAEKDIKIEEFITFGGQDLNIITNSTNQKIYDNLLSNYTAIASRLSQVNINNSALN

TTYYKNFFQWKYGLDQDSNGNYTVNISKFNAIYKKLFSFTECDLAQKFQVKNRSNYLFHFKPFRLLDLLDDNIYSI

SEGFNIGSLRVNNNGQNINLNSRIVGPIPDNGLVERFVGLCKSVIPRKGTKAPPRLCIKVNNRDLFFVASESSYNE

NGINSPKEIDDTTITNNNYKKNLDEVILDYNSDAIPNLSSRLLNTTAQNDSYVPKYDSNGTSEIKEYTVDKLNVFF

YLYAQKAPEGESAISLTSSVNTALLDASKVYTFFSSDFINTVNKPVQAALFISWIQQVINDFTTEATQKSTIDKIA

DISLVVPYVGLALNIGNEVQKGNFKEAIELLGAGILLEFVPELLIPTILVFTIKSFINSDDSKNKIIKAINNALRE

RELKWKEVYSWIVSNWLTRINTQFNKRKEQMYQALQNQVDGIKKIIEYKYNNYTLDEKNRLKAEYNIYSIKEELNK

KVSLAMQNIDRFLTESSISYLMKLINEAKINKLSEYDKRVNQYLLNYILENSSTLGTSSVQELNNLVSNTLNNSIP

FELSEYTNDKILISYFNRFYKRIIDSSILNMKYENNRFIDSSGYGSNISINGDIYIYSTNRNQFGIYSSRLSEVNI

TQNNTIIYNSRYQNFSVSFWVRIPKYNNLKNLNNEYTIINCMRNNNSGWKISLNYNNIIWTLQDTTGNNQKLVFNY

TQMIDISDYINKWTFVTITNNRLGHSKLYINGNLTDQKSILNLGNIHVDDNILFKIVGCNDTRYVGIRYFKIFNME

LDKTEIETLYHSEPDSTILKDFWGNYLLYNKKYYLLNLLKPNMSVTKNSDILNINRQRGIYSKTNIFSNARLYTGV

EVIIRKVGSTDTSNTDNFVRKNDTVYINVVDGNSEYQLYADVSTSAVEKTIKLRRISNSNYNSNQMIIMDSIGDNC

TMNFKTNNGNDIGLLGFHLNNLVASSWYYKNIRNNTRNNGCFWSFISKEHGWQE

UPI0000001386 (BoNT/A₁) sequence spanning activation loop

SEQ ID NO: 76

TGLFEFYKLLCVRGIITSKTKSLDKGYNKALNDLCIKVNNWDLFFSPSEDNFTNDL

UPI0000ED909E (BoNT/A₁) sequence spanning activation loop

SEQ ID NO: 77

TGLFEFYKLLCVRGIITSKTKSLDKGYNKALNDLCIKVNNWDLFFSPSEDNFTNDL

UPI0000EF85BD (BoNT/A₁) sequence spanning activation loop

SEQ ID NO: 78

TGLFEFYKLLCVRGIITSKTKSLDKGYNKALNDLCIKVNNWDLFFSPSEDNFTNDL

-continued

| | |
|---|---|
| UPI00016529B7 (BoNT/A₁) sequence spanning activ

-continued

UPI0001AE7D6A (BoNT/A₅) sequence spanning activation loop
TGLFEFYKLLCVRGIITSKTKSLDEGYNKALNDLCIKVNNWDLFFSPSEDNFTNDL
SEQ ID NO: 99

UPI000198BDAE (BoNT/A₅) sequence spanning activation loop
TGLFEFYKLLCVRGIITSKTKSLDEGYNKALNDLCIKVNNWDLFFSPSEDNFTNDL
SEQ ID NO: 100

UPI0001B7D251 (BoNT/A₆) sequence spanning activation loop
TGLFEFYKLLCVRGIITSKTKSLDKGYNKALNDLCIKVNNWDLFFSPSEDNFTNDL
SEQ ID NO: 101

UPI00000B66D1 (BoNT/F₁) sequence spanning activation loop
KGLVEKIVKFCKSVIPRKGTKAPPRLCIRVNNRELFFVASESSYNEND
SEQ ID NO: 102

UPI00016BB5D7 (BoNT/F₂) sequence spanning activation loop
KGLVEKIIKFCKSIIPRKGTKQSPSLCIRVNNRELFFVASESSYNESD
SEQ ID NO: 103

UPI00000B50F1 (BoNT/F₂) sequence spanning activation loop
KGLVEKIIKFCKSIIPRKGTKQSPSLCIRVNNRELFFVASESSYNESD
SEQ ID NO: 104

UPI0001C0B12F (BoNT/F₃) sequence spanning activation loop
KGLVEKIIKFCKSIIPRKGTKQSPSLCIRVNNRELFFVASESSYNESD
SEQ ID NO: 105

UPI0001A92658 (BoNT/F₄) sequence spanning activation loop
KGLVEKIVKLCKSIIPRKGTKAPPRLCIRVNNRELFFVASESSYNEND
SEQ ID NO: 106

UPI0001C0B12D (BoNT/F₄) sequence spanning activation loop
KGLVEKIVKLCKSIIPRKGTKAPPRLCIRVNNRELFFVASESSYNEND
SEQ ID NO: 107

UPI0001C0B12E (BoNT/F₅) sequence spanning activation loop
QGVVSRVVRLCLNSSFKKNTKKPLCITVNNGDLFFIASEDSYGEDT
SEQ ID NO: 108

UPI0001C0B1D1 (BoNT/F₆) sequence spanning activation loop
KGLVEKIVKFCKSVIPRKGTKAPPRLCIRVNNSELFFVASESSYNEND
SEQ ID NO: 109

UPI0000126B8A (BoNT/F₆) sequence spanning activation loop
KGLVEKIVKFCKSVIPRKGTKAPPRLCIRVNNSELFFVASESSYNEND
SEQ ID NO: 110

UPI0001C0B1D0 (BoNT/F₆) sequence spanning activation loop
KGLVEKIVKFCKSVIPRKGTKAPPRLCIRVNNSELFFVASESSYNEND
SEQ ID NO: 111

UPI0001DE3DAC (BoNT/F₇) sequence spanning activation loop
NGLVERFVGLCKSIVSKKGTKNSLCIKVNNRDLFFVASESSYNENG
SEQ ID NO: 112

UPI00000BAF8C (BoNT/F₇) sequence spanning activation loop
NGLVERFVGLCKSIVSKKGTKNSLCIKVNNRDLFFVASESSYNENG
SEQ ID NO: 113

UPI0001C0B221 (BoNT/F₇) sequence spanning activation loop
NGLVERFVGLCKSIVSKKGTKNSLCIKVNNRDLFFVASESSYNENG
SEQ ID NO: 114

UPI0001C0B220 (BoNT/F₇) sequence spanning activation loop
NGLVERFVGLCKSIVSKKGTKNSLCIKVNNRDLFFVASESSYNENG
SEQ ID NO: 115

BoNT/F₇/₁ chimeric nucleic acid sequence spanning activation loop
GGCCTGTGCAAAAGCGTTATTCCGCGTAAGGGTACGAAAGCACCGCCTCGCCTGTGCATTAAAGT
SEQ ID NO: 116

BoNT/F₇/₁ chimeric amino acid sequence spanning activation loop
GLCKSVIPRKGTKAPPRLCIKV
SEQ ID NO: 117

BoNT/F consensus amino acid sequence around activation loop
GLVEKIVKFCKSIIPRKGTKAPPRLCIRVNNRELFFVASES
SEQ ID NO: 118

-continued

SXN102691 F$_1$ amino acid sequence around activation loop
SEQ ID NO: 119
GLVEKIVKFCKSVIPRKGTKAPPRLCIRVNNRELFFVASES SXN102692 F$_2$ amino acid sequence around activation loop
SEQ ID NO: 120
GLVEKIIKFCKSIIPRKGTKQSPSLCIRVNNRELFFVASES SXN102693 F$_3$ amino acid sequence around activation loop
SEQ ID NO: 121
GLVEKIIKFCKSIIPRKGTKQSPSLCIRVNNRELFEVASES SXN102694 F$_4$ amino acid sequence around activation loop
SEQ ID NO: 122
GLVEKIVKLCKSIIPRKGTKAPPRLCIRVNNRELFFVASES SXN102695 F$_5$ amino acid sequence around activation loop
SEQ ID NO: 123
GVVSRVVRLCLNSSFKKNTKKPLCITVNNGDLFFIASED SXN102696 F$_6$ amino acid sequence around activation loop
SEQ ID NO: 124
GLVEKIVKFCKSVIPRKGTKAPPRLCIRVNNSELFFVASES SXN102697 F$_7$ amino acid sequence around activation loop
SEQ ID NO: 125
GLVERFVGLCKSIVSKKGTKNSLCIKVNNRDLFFVASES His tag
SEQ ID NO: 126
HHHHHH F$_1$/$_4$/$_5$ activation loop sequence (after cleavage site) + start of F$_7$ heavy chain sequence
SEQ ID NO: 127
APPR F$_2$/$_3$ activation loop sequence (after cleavage site) + start of F$_5$ heavy chain sequence
SEQ ID NO: 128
QSPS F$_7$ 1 forward primer
SEQ ID NO: 129
CcaagAAGGGTACGAAAGCACCGCCTCGCCTGTGCATTAAAGTCAAC F$_7$ 1 reverse primer
SEQ ID NO: 130
gtTgactTtaAtgcaCagGcgaGgcggTgCtTtCgtaccCttcttgg F$_7$ 2 forward primer
SEQ ID NO: 131
CtTcGtgggcctgtgcAaaagcgTTattCcgcgtaagggtAcgaaAgCaC F$_7$ 2 reverse primer
SEQ ID NO: 132
gtgcTTtcgtaCCcTtacgcGgAatAacgcTTTtgcacaGgCCcacgAag

---

SEQUENCE LISTING

<160> NUMBER OF SEQ ID NOS: 132

<210> SEQ ID NO 1
<211> LENGTH: 1279
<212> TYPE: PRT
<213> ORGANISM: Clostridium botulinum
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (129)..(129)

```
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (811)..(811)
<223> OTHER INFORMATION: Xaa can be any naturally occurring amino acid
<220> FEATURE:
<221> NAME/KEY: misc_feature
<222> LOCATION: (818)..(818)
<223> OTHER INFORMATION: Xaa can be any naturally occurring amino acid
<220> FEATURE:
<221> NAME/KEY: misc_feature
<222> LOCATION: (827)..(827)
<223> OTHER INFORMATION: Xaa can be any naturally occurring amino acid
<220> FEATURE:
<221> NAME/KEY: misc_feature
<222> LOCATION: (974)..(974)
<223> OTHER INFORMATION: Xaa can be any naturally occurring amino acid
<220> FEATURE:
<221> NAME/KEY: misc_feature
<222> LOCATION: (976)..(976)
<223> OTHER INFORMATION: Xaa can be any naturally occurring amino acid
<220> FEATURE:
<221> NAME/KEY: misc_feature
<222> LOCATION: (999)..(999)
<223> OTHER INFORMATION: Xaa can be any naturally occurring amino acid
<220> FEATURE:
<221> NAME/KEY: misc_feature
<222> LOCATION: (1061)..(1061)
<223> OTHER INFORMATION: Xaa can be any naturally occurring amino acid
<220> FEATURE:
<221> NAME/KEY: misc_feature
<222> LOCATION: (1121)..(1121)
<223> OTHER INFORMATION: Xaa can be any naturally occurring amino acid
<220> FEATURE:
<221> NAME/KEY: misc_feature
<222> LOCATION: (1137)..(1138)
<223> OTHER INFORMATION: Xaa can be any naturally occurring amino acid
<220> FEATURE:
<221> NAME/KEY: misc_feature
<222> LOCATION: (1194)..(1194)
<223> OTHER INFORMATION: Xaa can be any naturally occurring amino acid

<400> SEQUENCE: 1

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
```

```
            35                  40                  45
Arg Asn Thr Ile Gly Thr Lys Pro Ser Asp Phe Asp Pro Ala Ser
 50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Lys Val Leu Leu Xaa Glu Ile Ser
                100                 105                 110

Xaa Ala Lys Pro Tyr Leu Gly Asn Asp His Thr Pro Ile Asn Glu Phe
            115                 120                 125

Xaa Pro Val Asn Arg Thr Thr Ser Val Asn Ile Lys Leu Ser Thr Asn
130                 135                 140

Val Glu Ser Ser Met Leu Leu Asn Leu Val Leu Gly Ala Gly Pro
145                 150                 155                 160

Asp Ile Phe Glu Xaa Ser Cys Tyr Pro Val Arg Lys Xaa Pro Asn Ser
                165                 170                 175

Asp Xaa Val Tyr Asp Pro Ser Asn Xaa Gly Phe Gly Ser Ile Asn Ile
            180                 185                 190

Val Thr Phe Ser Pro Glu Tyr Glu Tyr Thr Phe Asn Asp Ile Ser Gly
            195                 200                 205

Gly His Asn Ser Ser Thr Glu Ser Phe Ile Ala Asp Pro Ala Ile Ser
210                 215                 220

Leu Ala His Glu Leu Ile His Ala Leu His Gly Leu Tyr Gly Ala Xaa
225                 230                 235                 240

Gly Val Thr Tyr Lys Glu Thr Ile Glu Val Lys Gln Xaa Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys Tyr Gly Phe Leu Lys Val Pro Asn Leu Leu Asp Asp Asp
            370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Val Lys Phe Cys Lys Ser Ile
            420                 425                 430

Ile Pro Arg Lys Gly Thr Lys Ala Pro Pro Arg Leu Cys Ile Arg Val
            435                 440                 445

Asn Asn Arg Glu Leu Phe Phe Val Ala Ser Glu Ser Tyr Asn Glu
450                 455                 460
```

```
Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
                500                 505                 510

Asp Asp Ser Tyr Val Pro Arg Tyr Asp Ser Asn Gly Thr Ser Glu Ile
            515                 520                 525

Glu Glu Tyr Asp Val Val Asp Leu Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
                580                 585                 590

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
610                 615                 620

Val Gly Leu Ala Leu Asn Ile Gly Asn Glu Ala Glu Lys Gly Asn Phe
625                 630                 635                 640

Lys Glu Ala Phe Glu Leu Leu Gly Ala Gly Ile Leu Leu Glu Phe Val
                645                 650                 655

Pro Glu Leu Xaa Ile Pro Val Ile Leu Val Phe Thr Ile Lys Ser Tyr
                660                 665                 670

Ile Asp Ser Tyr Glu Asn Lys Asn Lys Ile Ile Lys Ala Ile Asn Asn
            675                 680                 685

Ser Leu Ile Glu Arg Glu Ala Lys Trp Lys Glu Ile Tyr Ser Trp Ile
            690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
            740                 745                 750

Leu Glu Ser Glu Tyr Asn Ile Asn Asn Ile Glu Glu Glu Leu Asn Lys
            755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Lys Val Gly Lys
785                 790                 795                 800

Leu Lys Glu Tyr Asp Lys His Val Lys Ser Xaa Leu Leu Asn Tyr Ile
                805                 810                 815

Leu Xaa His Arg Ser Ile Leu Gly Glu Gln Xaa Gln Glu Leu Asn Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Arg Leu Tyr Lys
            850                 855                 860

Lys Ile Lys Asp Ser Ser Ile Leu Asp Met Arg Tyr Glu Asn Asn Lys
865                 870                 875                 880
```

-continued

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Ser
            900                 905                 910

Arg Leu Ser Glu Val Asn Ile Ala Gln Asn Asn Asp Ile Ile Tyr Asn
            915                 920                 925

Ser Arg Tyr Gln Asn Phe Ser Ile Ser Phe Trp Val Arg Ile Pro Lys
        930                 935                 940

His Tyr Asn Pro Met Asn Leu Asn Arg Glu Tyr Thr Ile Ile Asn Cys
945                 950                 955                 960

Met Gly Asn Asn Asn Ser Gly Trp Lys Ile Ser Leu Arg Xaa Asn Xaa
                965                 970                 975

Asp Cys Glu Ile Ile Trp Thr Leu Gln Asp Thr Ser Gly Asn Lys Glu
                980                 985                 990

Lys Leu Ile Phe Arg Tyr Xaa Gln Leu Ile Ser Ile Ser Asp Tyr Ile
            995                 1000                1005

Asn Lys Trp Ile Phe Val Thr Ile Thr Asn Asn Arg Leu Gly Asn
        1010                1015                1020

Ser Arg Ile Tyr Ile Asn Gly Asn Leu Ile Val Glu Lys Ser Ile
        1025                1030                1035

Ser Asn Leu Gly Asp Ile His Val Ser Asp Asn Ile Leu Phe Lys
        1040                1045                1050

Ile Val Gly Cys Asp Asp Thr Xaa Tyr Val Gly Ile Arg Tyr Phe
        1055                1060                1065

Lys Val Phe Asn Thr Glu Leu Asp Lys Thr Glu Ile Glu Thr Leu
        1070                1075                1080

Tyr Ser Asn Glu Pro Asp Pro Ser Ile Leu Lys Asp Tyr Trp Gly
        1085                1090                1095

Asn Tyr Leu Leu Tyr Asn Lys Lys Tyr Tyr Leu Leu Asn Leu Leu
        1100                1105                1110

Arg Lys Asp Lys Tyr Ile Thr Xaa Asn Ser Gly Ile Leu Asn Ile
        1115                1120                1125

Asn Gln Gln Arg Gly Val Thr Glu Xaa Xaa Ile Phe Ser Asn Tyr
        1130                1135                1140

Lys Leu Tyr Glu Gly Val Glu Val Ile Ile Arg Lys Asn Gly Pro
        1145                1150                1155

Ile Asp Ile Ser Asn Thr Asp Asn Phe Val Arg Lys Asn Asp Leu
        1160                1165                1170

Ala Tyr Ile Asn Val Val Asp Arg Gly Val Glu Tyr Arg Leu Tyr
        1175                1180                1185

Ala Asp Thr Ser Ile Xaa Lys Pro Glu Lys Thr Ile Lys Leu Ile
        1190                1195                1200

Arg Thr Ser Asn Ser Asn Asp Ser Leu Gly Gln Ile Ile Val Met
        1205                1210                1215

Asp Ser Ile Gly Asn Asn Cys Thr Met Asn Phe Gln Asn Asn Asn
        1220                1225                1230

Gly Ser Asn Ile Gly Leu Leu Gly Phe His Ser Asn Asn Leu Val
        1235                1240                1245

Ala Ser Ser Trp Tyr Tyr Asn Asn Ile Arg Arg Asn Thr Ser Ser
        1250                1255                1260

Asn Gly Cys Phe Trp Ser Phe Ile Ser Lys Glu His Gly Trp Gln
        1265                1270                1275

Glu

<210> SEQ ID NO 2
<211> LENGTH: 1278
<212> TYPE: PRT
<213> ORGANISM: Clostridium botulinum

<400> SEQUENCE: 2

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
```

-continued

```
            370                 375                 380
Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Lys Ala Pro Pro Arg Leu Cys Ile Arg Val
                435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
                500                 505                 510

Asp Asp Ser Tyr Val Pro Arg Tyr Asp Ser Asn Gly Thr Ser Glu Ile
                515                 520                 525

Glu Glu His Asn Val Val Asp Leu Asn Val Phe Phe Tyr Leu His Ala
                530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
                580                 585                 590

Ser Trp Ile Asn Gln Val Ile Arg Asp Phe Thr Thr Glu Ala Thr Gln
                595                 600                 605

Lys Ser Thr Phe Asp Lys Ile Ala Asp Ile Ser Leu Val Val Pro Tyr
                610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
                660                 665                 670

Ile Gly Ser Ser Glu Asn Lys Asn Lys Ile Ile Lys Ala Ile Asn Asn
                675                 680                 685

Ser Leu Met Glu Arg Glu Thr Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
                740                 745                 750

Leu Glu Ser Glu Tyr Asn Ile Asn Asn Ile Arg Glu Glu Leu Asn Lys
                755                 760                 765

Lys Val Ser Leu Ala Met Glu Asn Ile Glu Arg Phe Ile Thr Glu Ser
                770                 775                 780

Ser Ile Phe Tyr Leu Met Lys Leu Ile Asn Glu Ala Lys Val Ser Lys
785                 790                 795                 800
```

-continued

```
Leu Arg Glu Tyr Asp Glu Gly Val Lys Glu Tyr Leu Asp Tyr Ile
            805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
            835                 840                 845

Tyr Thr Asn Asp Lys Ile Leu Ile Leu Tyr Phe Asn Lys Leu Tyr Lys
            850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
            885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
            915                 920                 925

Gly Arg Tyr Gln Asn Phe Ser Ile Ser Phe Trp Val Arg Ile Pro Lys
930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
            980                 985                 990

Phe Asn Tyr Thr Gln Met Ile Ser Ile Ser Asp Tyr Ile Asn Lys Trp
            995                 1000                1005

Ile Phe Val Thr Ile Thr Asn Asn Arg Leu Gly Asn Ser Arg Ile
            1010                1015                1020

Tyr Ile Asn Gly Asn Leu Ile Asp Glu Lys Ser Ile Ser Asn Leu
            1025                1030                1035

Gly Asp Ile His Val Ser Asp Asn Ile Leu Phe Lys Ile Val Gly
            1040                1045                1050

Cys Asn Asp Thr Arg Tyr Val Gly Ile Arg Tyr Phe Lys Val Phe
            1055                1060                1065

Asp Thr Glu Leu Gly Lys Thr Glu Ile Glu Thr Leu Tyr Ser Asp
            1070                1075                1080

Glu Pro Asp Pro Ser Ile Leu Lys Asp Phe Trp Gly Asn Tyr Leu
            1085                1090                1095

Leu Tyr Asn Lys Arg Tyr Tyr Leu Leu Asn Leu Leu Arg Thr Asp
            1100                1105                1110

Lys Ser Ile Thr Gln Asn Ser Asn Phe Leu Asn Ile Asn Gln Gln
            1115                1120                1125

Arg Gly Val Tyr Gln Lys Pro Asn Ile Phe Ser Asn Thr Arg Leu
            1130                1135                1140

Tyr Thr Gly Val Glu Val Ile Ile Arg Lys Asn Gly Ser Thr Asp
            1145                1150                1155

Ile Ser Asn Thr Asp Asn Phe Val Arg Lys Asn Asp Leu Ala Tyr
            1160                1165                1170

Ile Asn Val Val Asp Arg Asp Val Glu Tyr Arg Leu Tyr Ala Asp
            1175                1180                1185

Ile Ser Ile Ala Lys Pro Glu Lys Ile Ile Lys Leu Ile Arg Thr
            1190                1195                1200
```

Ser Asn Ser Asn Asn Ser Leu Gly Gln Ile Ile Val Met Asp Ser
1205              1210                   1215

Ile Gly Asn Asn Cys Thr Met Asn Phe Gln Asn Asn Gly Gly
1220              1225                   1230

Asn Ile Gly Leu Leu Gly Phe His Ser Asn Asn Leu Val Ala Ser
1235              1240                   1245

Ser Trp Tyr Tyr Asn Asn Ile Arg Lys Asn Thr Ser Ser Asn Gly
1250              1255                   1260

Cys Phe Trp Ser Phe Ile Ser Lys Glu His Gly Trp Gln Glu Asn
1265              1270                   1275

<210> SEQ ID NO 3
<211> LENGTH: 1280
<212> TYPE: PRT
<213> ORGANISM: Clostridium botulinum

<400> SEQUENCE: 3

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
                20                  25                  30

Tyr Tyr Lys Ala Phe Glu Ile Met Pro Asn Val Trp Ile Met Pro Glu
            35                  40                  45

Arg Asp Thr Ile Gly Thr Lys Pro Asp Glu Phe Gln Val Pro Asp Ser
50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Phe Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

```
Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
            325                 330                 335

Asn Arg Asn Lys Phe Asn Glu Ile Tyr Lys Lys Leu Tyr Ser Phe Thr
        340                 345                 350

Glu Ile Asp Leu Ala Asn Lys Phe Lys Val Lys Cys Arg Asn Thr Tyr
    355                 360                 365

Phe Ile Lys Tyr Gly Phe Val Lys Val Pro Asp Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
            405                 410                 415

Pro Asp Lys Gly Leu Val Glu Lys Ile Ile Lys Phe Cys Lys Ser Ile
        420                 425                 430

Ile Pro Arg Lys Gly Thr Lys Gln Ser Pro Ser Leu Cys Ile Arg Val
    435                 440                 445

Asn Asn Arg Glu Leu Phe Phe Val Ala Ser Glu Ser Ser Tyr Asn Glu
450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
        500                 505                 510

Asp Asn Ser Tyr Val Pro Arg Tyr Asp Ser Asn Gly Thr Ser Glu Ile
    515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
            565                 570                 575

Glu Phe Ile Asp Thr Ile Asn Lys Pro Val Asn Ala Ala Leu Phe Ile
        580                 585                 590

Asp Trp Ile Ser Lys Val Ile Arg Asp Phe Thr Thr Glu Ala Thr Gln
    595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
            645                 650                 655

Pro Glu Leu Thr Ile Pro Val Ile Leu Val Phe Thr Ile Lys Ser Tyr
        660                 665                 670

Ile Asp Ser Tyr Glu Asn Lys Asn Lys Ala Ile Lys Ala Ile Asn Asn
    675                 680                 685

Ser Leu Ile Glu Arg Glu Ala Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720
```

-continued

```
Glu Gln Met Tyr Gln Ala Leu Gln Asn Gln Val Asp Ala Ile Lys Thr
            725                 730                 735

Ala Ile Glu Tyr Lys Tyr Asn Asn Tyr Thr Ser Asp Glu Lys Asn Arg
        740                 745                 750

Leu Glu Ser Lys Tyr Asn Ile Asn Asn Ile Glu Glu Glu Leu Asn Lys
        755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Arg Leu Tyr Lys
    850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Ile Tyr Asn
            915                 920                 925

Ser Arg Tyr Gln Asn Phe Ser Ile Ser Phe Trp Val Arg Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu Leu Ala Ser Ile Ser Asp Tyr Ile
            995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
    1100                1105                1110

Arg Lys Asp Lys Tyr Ile Thr Arg Asn Ser Gly Ile Leu Asn Ile
    1115                1120                1125

Asn Gln Gln Arg Gly Val Thr Gly Gly Ile Ser Val Phe Leu Asn
```

```
                    1130                1135                1140

Tyr Lys Leu Tyr Glu Gly Val Glu Val Ile Ile Arg Lys Asn Ala
        1145                1150                1155

Pro Ile Asp Ile Ser Asn Thr Asp Asn Phe Val Arg Lys Asn Asp
    1160                1165                1170

Leu Ala Tyr Ile Asn Val Val Asp His Gly Val Glu Tyr Arg Leu
    1175                1180                1185

Tyr Ala Asp Ile Ser Ile Thr Lys Ser Glu Lys Ile Ile Lys Leu
    1190                1195                1200

Ile Arg Thr Ser Asn Pro Asn Asp Ser Leu Gly Gln Ile Ile Val
    1205                1210                1215

Met Asp Ser Ile Gly Asn Asn Cys Thr Met Asn Phe Gln Asn Asn
    1220                1225                1230

Asp Gly Ser Asn Ile Gly Leu Leu Gly Phe His Ser Asp Asp Leu
    1235                1240                1245

Val Ala Ser Ser Trp Tyr Tyr Asn His Ile Arg Arg Asn Thr Ser
    1250                1255                1260

Ser Asn Gly Cys Phe Trp Ser Phe Ile Ser Lys Glu His Gly Trp
    1265                1270                1275

Lys Glu
    1280

<210> SEQ ID NO 4
<211> LENGTH: 1280
<212> TYPE: PRT
<213> ORGANISM: Clostridium botulinum

<400> SEQUENCE: 4

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
                20                  25                  30

Tyr Tyr Lys Ala Phe Glu Ile Met Pro Asn Val Trp Ile Met Pro Glu
            35                  40                  45

Arg Asp Thr Ile Gly Thr Lys Pro Asp Glu Phe Gln Val Pro Asp Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Thr Leu Ile Asn Glu Phe
        115                 120                 125

Leu Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Gly Tyr Glu His Ile Phe Asn Asp Ile Ser Gly
        195                 200                 205
```

```
Gly Asn His Asn Ser Thr Glu Ser Phe Ile Ala Asp Pro Ala Ile Ser
            210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
            275                 280                 285

Asp Leu Leu Ala Asn Tyr Glu Lys Ile Ala Thr Arg Leu Arg Glu Val
290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
            435                 440                 445

Asn Asn Arg Glu Leu Phe Phe Val Ala Ser Glu Ser Tyr Asn Glu
450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Glu Ala Glu Lys Gly Asn Phe
```

-continued

```
    625                 630                 635                 640
Glu Glu Ala Phe Glu Leu Leu Gly Ala Gly Ile Leu Leu Glu Phe Val
                645                 650                 655
Pro Glu Leu Thr Ile Pro Val Ile Leu Val Phe Thr Ile Lys Ser Tyr
                660                 665                 670
Ile Asp Ser Tyr Glu Asn Lys Asn Lys Ala Ile Lys Ala Ile Asn Asn
                675                 680                 685
Ser Leu Ile Glu Arg Glu Ala Lys Trp Lys Glu Ile Tyr Ser Trp Ile
                690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Ala Ile Lys Thr
                725                 730                 735
Ala Ile Glu Tyr Lys Tyr Asn Asn Tyr Thr Ser Asp Glu Lys Asn Arg
                740                 745                 750
Leu Glu Ser Lys Tyr Asn Ile Asn Asn Ile Glu Glu Leu Asn Lys
                755                 760                 765
Lys Val Ser Leu Ala Met Lys Asn Ile Glu Arg Phe Met Thr Glu Ser
770                 775                 780
Ser Ile Ser Tyr Leu Met Lys Leu Ile Asn Glu Ala Glu Val Gly Lys
785                 790                 795                 800
Leu Lys Glu Tyr Asp Lys His Val Lys Ser Asp Leu Leu Asp Tyr Ile
                805                 810                 815
Leu Tyr His Lys Leu Ile Leu Gly Glu Gln Thr Lys Glu Leu Ile Asp
                820                 825                 830
Leu Val Thr Ser Thr Leu Asn Ser Ser Ile Pro Phe Glu Leu Ser Ser
                835                 840                 845
Tyr Thr Asn Asp Lys Ile Leu Ile Ile Tyr Phe Asn Arg Leu Tyr Lys
                850                 855                 860
Lys Ile Lys Asp Ser Ser Ile Leu Asp Met Arg Tyr Glu Asn Asn Lys
865                 870                 875                 880
Phe Ile Asp Ile Ser Gly Tyr Gly Ser Asn Ile Ser Ile Asn Gly Asn
                885                 890                 895
Val Tyr Ile Tyr Ser Thr Asn Arg Asn Gln Phe Gly Ile Tyr Ser Gly
                900                 905                 910
Arg Leu Ser Glu Val Asn Ile Ala Gln Asn Asn Asp Ile Ile Tyr Asn
                915                 920                 925
Ser Arg Tyr Gln Asn Phe Ser Ile Ser Phe Trp Val Thr Ile Pro Lys
                930                 935                 940
His Tyr Arg Pro Met Asn Arg Asn Arg Glu Tyr Thr Ile Ile Asn Cys
945                 950                 955                 960
Met Gly Asn Asn Asn Ser Gly Trp Lys Ile Ser Leu Arg Thr Ile Arg
                965                 970                 975
Asp Cys Glu Ile Ile Trp Thr Leu Gln Asp Thr Ser Gly Asn Lys Glu
                980                 985                 990
Lys Leu Ile Phe Arg Tyr Glu Glu  Leu Ala Ser Ile Ser  Asp Tyr Ile
                995                 1000                 1005
Asn Lys  Trp Ile Phe Val Thr  Ile Thr Asn Asn Arg  Leu Gly Asn
                1010                 1015                 1020
Ser Arg  Ile Tyr Ile Asn Gly  Asn Leu Ile Val Glu  Lys Ser Ile
                1025                 1030                 1035
Ser Asn  Leu Gly Asp Ile His  Val Ser Asp Asn Ile  Leu Phe Lys
                1040                 1045                 1050
```

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Tyr Tyr Leu Phe Asn Leu Leu
    1100                1105                1110

Arg Lys Asp Lys Tyr Ile Thr Arg Asn Ser Gly Ile Leu Asn Ile
    1115                1120                1125

Asn Gln Gln Arg Gly Val Thr Gly Gly Ile Ser Val Phe Leu Asn
    1130                1135                1140

Tyr Lys Leu Tyr Glu Gly Val Glu Val Ile Ile Arg Lys Asn Ala
    1145                1150                1155

Pro Ile Asp Ile Ser Asn Thr Asp Asn Phe Val Arg Lys Asn Asp
    1160                1165                1170

Leu Ala Tyr Ile Asn Val Val Asp His Gly Val Glu Tyr Arg Leu
    1175                1180                1185

Tyr Ala Asp Ile Ser Ile Thr Lys Ser Glu Lys Ile Ile Lys Leu
    1190                1195                1200

Ile Arg Thr Ser Asn Pro Asn Asp Ser Leu Gly Gln Ile Ile Val
    1205                1210                1215

Met Asp Ser Ile Gly Asn Asn Cys Thr Met Asn Phe Gln Asn Asn
    1220                1225                1230

Asp Gly Ser Asn Ile Gly Leu Leu Gly Phe His Ser Asp Asp Leu
    1235                1240                1245

Val Ala Ser Ser Trp Tyr Tyr Asn His Ile Arg Arg Asn Thr Ser
    1250                1255                1260

Ser Asn Gly Cys Phe Trp Ser Phe Ile Ser Lys Glu His Gly Trp
    1265                1270                1275

Lys Glu
    1280

<210> SEQ ID NO 5
<211> LENGTH: 1279
<212> TYPE: PRT
<213> ORGANISM: Clostridium botulinum

<400> SEQUENCE: 5

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
                20                  25                  30

Tyr Tyr Lys Ala Phe Glu Ile Met Pro Asn Val Trp Ile Met Pro Glu
                35                  40                  45

Arg Asp Thr Ile Gly Thr Lys Pro Asp Asp Phe Gln Val Pro Asp Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
                100                 105                 110

Asn Ala Arg Pro Tyr Leu Gly Asp Asp Asp Thr Leu Ile Asn Glu Phe

```
            115                 120                 125
Phe Pro Val Asn Val Thr Thr Ser Val Asn Ile Lys Phe Ser Thr Asp
130                 135                 140
Val Glu Ser Ser Ile Ile Ser Asn Leu Leu Val Leu Gly Ala Gly Pro
145                 150                 155                 160
Asp Ile Phe Lys Ala Tyr Cys Thr Pro Leu Val Arg Phe Asn Lys Ser
                165                 170                 175
Asp Lys Leu Ile Glu Pro Ser Asn His Gly Phe Gly Ser Ile Asn Ile
            180                 185                 190
Leu Thr Phe Ser Pro Glu Tyr Glu His Ile Phe Asn Asp Ile Ser Gly
        195                 200                 205
Gly Asp His Asn Ser Thr Glu Ser Phe Ile Ala Asp Pro Ala Ile Ser
    210                 215                 220
Leu Ala His Glu Leu Ile His Ala Leu His Gly Leu Tyr Gly Ala Lys
225                 230                 235                 240
Ala Val Thr His Lys Glu Thr Ile Glu Val Lys Arg Gly Pro Leu Met
                245                 250                 255
Ile Ala Glu Lys Pro Ile Arg Leu Glu Glu Phe Leu Thr Phe Gly Gly
            260                 265                 270
Glu Asp Leu Asn Ile Ile Pro Ser Ala Met Lys Glu Lys Ile Tyr Asn
        275                 280                 285
Asp Leu Leu Ala Asn Tyr Glu Lys Ile Ala Thr Arg Leu Arg Glu Val
    290                 295                 300
Asn Thr Ala Pro Pro Glu Tyr Asp Ile Asn Glu Tyr Lys Asp Tyr Phe
305                 310                 315                 320
Gln Trp Lys Tyr Gly Leu Asp Arg Asn Ala Asp Gly Ser Tyr Thr Val
                325                 330                 335
Asn Arg Asn Lys Phe Asn Gly Ile Tyr Lys Lys Leu Tyr Ser Phe Thr
            340                 345                 350
Glu Ile Asp Leu Ala Asn Lys Phe Lys Val Lys Cys Arg Asn Thr Tyr
        355                 360                 365
Phe Ile Lys Tyr Gly Phe Val Lys Val Pro Asp Leu Leu Asp Asp Asp
    370                 375                 380
Ile Tyr Thr Val Ser Glu Gly Phe Asn Ile Gly Asn Leu Ala Val Asn
385                 390                 395                 400
Asn Arg Gly Gln Asn Ile Asn Leu Asn Pro Lys Ile Ile Asp Ser Ile
                405                 410                 415
Pro Asp Lys Gly Leu Val Glu Lys Ile Ile Lys Phe Cys Lys Ser Ile
            420                 425                 430
Ile Pro Arg Lys Gly Thr Lys Gln Ser Pro Ser Leu Cys Ile Arg Val
        435                 440                 445
Asn Asn Arg Glu Leu Phe Phe Val Ala Ser Glu Ser Ser Tyr Asn Glu
    450                 455                 460
Ser Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
                485                 490                 495
Glu Thr Ile Pro Gln Ile Ser Asn Arg Thr Leu Asn Thr Leu Val Gln
            500                 505                 510
Asp Asn Ser Tyr Val Pro Arg Tyr Asp Ser Asn Gly Thr Ser Glu Ile
        515                 520                 525
Glu Glu Tyr Asp Val Val Asp Phe Asn Val Phe Phe Tyr Leu His Ala
    530                 535                 540
```

```
Gln Lys Val Pro Glu Gly Glu Thr Asn Ile Ser Leu Thr Ser Ser Ile
545                 550                 555                 560

Asp Thr Ala Leu Leu Glu Lys Ser Lys Val Tyr Thr Phe Phe Ser Ser
                565                 570                 575

Glu Phe Ile Asp Thr Ile Asn Glu Ser Val Asn Ala Ala Leu Phe Ile
            580                 585                 590

Asp Trp Ile Asn Lys Val Ile Arg Asp Phe Thr Thr Glu Ala Thr Gln
                595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Asp Ala Glu Lys Gly Asn Phe
625                 630                 635                 640

Gln Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
                660                 665                 670

Ile Asp Ser Tyr Glu Asn Lys Asn Lys Ala Ile Lys Ala Ile Asn Asn
                675                 680                 685

Ala Leu Ile Glu Arg Glu Ala Lys Trp Lys Glu Ile Tyr Ser Trp Ile
690                 695                 700

Val Ser Asn Trp Leu Thr Lys Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
                740                 745                 750

Leu Glu Ser Glu Tyr Asn Ile Asn Asn Ile Glu Glu Leu Asn Lys
                755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Lys Tyr Asp Arg His Val Lys Ser Asp Leu Leu Asp Tyr Ile
                805                 810                 815

Leu Tyr His Lys Leu Ile Leu Gly Asp Gln Thr Lys Glu Leu Ile Asp
                820                 825                 830

Leu Val Thr Ser Thr Leu Asn Ser Ser Ile Pro Phe Glu Leu Ser Ser
                835                 840                 845

Tyr Thr Asn Asp Lys Ile Leu Ile Ile Tyr Phe Asn Arg Leu Tyr Lys
                850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Asp
                900                 905                 910

Arg Leu Ser Glu Val Asn Ile Ala Gln Asn Asn Asp Ile Ile Tyr Asn
                915                 920                 925

Ser Arg Tyr Gln Asn Phe Ser Ile Ser Phe Trp Val Arg Ile Pro Lys
                930                 935                 940

His Tyr Gly Pro Met Asn Arg Asn Arg Glu Tyr Thr Ile Ile Asn Cys
945                 950                 955                 960
```

Met Gly Asn Asn Asn Ser Gly Trp Lys Ile Ser Leu Arg Asn Ile Arg
                965                 970                 975

Asp Cys Glu Ile Ile Trp Thr Leu Gln Asp Thr Ser Gly Asn Lys Glu
    980                 985                 990

Lys Leu Ile Phe Arg Tyr Glu Glu Leu Ala Asn Ile Ser Asp Tyr Ile
        995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Lys Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
    1100                1105                1110

Arg Lys Asp Lys Tyr Ile Thr Arg Asn Ser Gly Ile Leu Asn Ile
    1115                1120                1125

Asn Gln Gln Arg Gly Val Thr Glu Gly Ser Val Phe Leu Asn Tyr
    1130                1135                1140

Lys Leu Tyr Glu Gly Val Glu Val Ile Ile Arg Lys Asn Gly Pro
    1145                1150                1155

Ile Asp Ile Ser Asn Thr Asp Asn Phe Val Arg Lys Asn Asp Leu
    1160                1165                1170

Ala Tyr Ile Asn Val Val Asp Arg His Asp Val Glu Tyr Arg Leu Tyr
    1175                1180                1185

Ala Asp Ile Ser Ile Thr Lys Pro Glu Lys Ile Ile Lys Leu Ile
    1190                1195                1200

Arg Thr Ser Asn Pro Asn Asp Ser Leu Gly Gln Ile Ile Val Met
    1205                1210                1215

Asp Ser Ile Gly Asn Asn Cys Thr Met Asn Phe Gln Asn Asn Asn
    1220                1225                1230

Gly Gly Asn Ile Gly Leu Leu Gly Phe His Ser Asp Asn Leu Val
    1235                1240                1245

Ala Ser Ser Trp Tyr Tyr Asn Asn Ile Arg Arg Asn Thr Ser Ser
    1250                1255                1260

Asn Gly Cys Phe Trp Ser Phe Ile Ser Lys Glu His Gly Trp Gln
    1265                1270                1275

Glu

<210> SEQ ID NO 6
<211> LENGTH: 1278
<212> TYPE: PRT
<213> ORGANISM: Clostridium botulinum

<400> SEQUENCE: 6

Met Pro Val Val Ile Asn Ser Phe Asn Tyr Asp Asp Pro Val Asn Asp
1               5                   10                  15

Asp Thr Ile Leu Tyr Met Gln Ile Pro Tyr Glu Glu Lys Ser Lys Lys
            20                  25                  30

-continued

```
Tyr Tyr Lys Ala Phe Glu Ile Met Arg Asn Val Trp Ile Met Pro Glu
         35                  40                  45
Arg Asn Thr Ile Gly Thr Asn Pro Ser Asp Phe Asp Pro Pro Ala Ser
 50                  55                  60
Leu Lys Asn Gly Ser Ser Ala Tyr Tyr Asp Pro Asn Tyr Leu Thr Thr
 65                  70                  75                  80
Asp Ala Glu Lys Asp Arg Tyr Leu Lys Thr Thr Ile Lys Leu Phe Lys
                 85                  90                  95
Arg Ile Asn Ser Asn Pro Ala Gly Glu Val Leu Leu Gln Glu Ile Ser
                100                 105                 110
Tyr Ala Lys Pro Tyr Leu Gly Asn Asp His Thr Pro Ile Asn Glu Phe
             115                 120                 125
His Pro Val Thr Arg Thr Thr Ser Val Asn Ile Lys Ser Ser Thr Asn
         130                 135                 140
Val Glu Ser Ser Ile Ile Leu Asn Leu Leu Val Leu Gly Ala Gly Pro
145                 150                 155                 160
Asn Ile Phe Glu Asn Ser Ser Tyr Pro Val Arg Lys Leu Met Asn Ser
                165                 170                 175
Gly Glu Val Tyr Asp Pro Ser Asn Asp Gly Phe Gly Ser Ile Asn Ile
            180                 185                 190
Val Thr Phe Ser Pro Glu Tyr Glu Tyr Thr Phe Asn Asp Ile Ser Gly
        195                 200                 205
Gly His Asn Ser Ser Thr Glu Ser Phe Ile Ala Asp Pro Ala Ile Ser
    210                 215                 220
Leu Ala His Glu Leu Ile His Ala Leu His Gly Leu Tyr Gly Ala Arg
225                 230                 235                 240
Gly Val Thr Tyr Lys Glu Thr Ile Lys Val Lys Gln Ala Pro Leu Met
                245                 250                 255
Ile Ala Glu Lys Pro Ile Arg Leu Glu Glu Phe Leu Thr Phe Gly Gly
            260                 265                 270
Gln Asp Leu Asn Ile Ile Thr Ser Ala Met Lys Glu Lys Ile Tyr Asn
        275                 280                 285
Asp Leu Leu Ala Asn Tyr Glu Lys Ile Ala Thr Arg Leu Ser Glu Val
    290                 295                 300
Asn Ser Ala Pro Pro Glu Tyr Asp Ile Asn Glu Tyr Lys Asn Tyr Phe
305                 310                 315                 320
Gln Trp Lys Tyr Gly Leu Asp Lys Asn Ala Asp Gly Ser Tyr Thr Val
                325                 330                 335
Asn Glu Asn Lys Phe Asn Glu Ile Tyr Lys Lys Leu Tyr Ser Phe Thr
            340                 345                 350
Glu Ile Asp Leu Ala Asn Lys Phe Lys Val Lys Cys Arg Asn Thr Tyr
        355                 360                 365
Phe Ile Lys Tyr Gly Phe Leu Lys Val Pro Asn Leu Leu Asp Asp Asp
    370                 375                 380
Ile Tyr Thr Val Ser Glu Gly Phe Asn Ile Gly Asn Leu Ala Val Asn
385                 390                 395                 400
Asn Arg Gly Gln Asn Ile Asn Leu Asn Pro Lys Ile Ile Asp Ser Ile
                405                 410                 415
Pro Asp Lys Gly Leu Val Glu Lys Ile Val Lys Leu Cys Lys Ser Ile
            420                 425                 430
Ile Pro Arg Lys Gly Thr Lys Ala Pro Pro Arg Leu Cys Ile Arg Val
        435                 440                 445
Asn Asn Arg Glu Leu Phe Phe Val Ala Ser Glu Ser Ser Tyr Asn Glu
```

```
                450             455             460
Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Ser Gln Thr Leu Asn Thr Leu Val Gln
            500                 505                 510

Asp Asp Ser Tyr Val Pro Arg Tyr Asp Ser Asn Gly Thr Ser Glu Ile
            515                 520                 525

Glu Glu His Asn Val Val Asp Leu Asn Ala Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Lys Val Tyr Thr Phe Phe Ser Ser
                565                 570                 575

Glu Phe Ile Asn Asn Ile Asn Lys Pro Val His Ala Ala Leu Phe Ile
                580                 585                 590

Gly Trp Ile Ser Gln Val Ile Arg Asp Phe Thr Thr Glu Ser Thr Gln
                595                 600                 605

Lys Ser Thr Val Asp Lys Ile Ala Asp Ile Ser Leu Ile Val Pro Tyr
            610                 615                 620

Val Gly Leu Ala Leu Asn Ile Gly Asn Asp Ala Arg Lys Gly Asn Phe
625                 630                 635                 640

Lys Glu Ala Phe Glu Leu Leu Gly Ala Ala Ile Leu Leu Glu Val Val
                645                 650                 655

Pro Glu Leu Leu Ile Pro Val Ile Leu Val Phe Thr Ile Lys Ser Phe
            660                 665                 670

Ile Asp Ser Ser Lys Asn Glu Asp Lys Ile Ile Lys Ala Ile Asn Asn
            675                 680                 685

Ser Leu Ile Glu Arg Glu Ala Lys Trp Lys Glu Val Tyr Ser Trp Ile
            690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Ser Tyr Thr Ser Asp Glu Lys Asn Arg
            740                 745                 750

Leu Glu Ser Glu Tyr Asn Ile Asn Asn Ile Glu Glu Glu Leu Asn Lys
            755                 760                 765

Lys Val Ser Leu Ala Met Lys Asn Ile Glu Arg Phe Ile Ala Glu Ser
            770                 775                 780

Ser Ile Ser Tyr Leu Met Lys Leu Ile Asn Glu Ala Lys Val Ser Glu
785                 790                 795                 800

Leu Arg Glu Tyr Asp Glu Gly Val Lys Glu Tyr Leu Leu Asp Tyr Ile
                805                 810                 815

Leu Lys Asn Gly Ser Ile Leu Gly Asp His Val Gln Glu Leu Asn Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Lys Leu Tyr Lys
850                 855                 860

Lys Ile Lys Asp Asn Cys Ile Leu Asp Met Arg Tyr Glu Asn Asn Lys
865                 870                 875                 880
```

```
Phe Ile Asp Ile Ser Gly Tyr Gly Ser Asn Ile Ser Ile Asn Gly Glu
                885                 890                 895

Leu Tyr Ile Tyr Thr Thr Asn Arg Asn Gln Phe Thr Ile Tyr Ser Gly
            900                 905                 910

Lys Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Arg Ile Pro Arg
    930                 935                 940

Tyr Ser Asn Ile Val Asn Leu Asn Glu Tyr Thr Ile Ile Asn Cys
945                 950                 955                 960

Met Gly Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Glu Lys Leu Val
            980                 985                 990

Phe Asn Tyr Thr Gln Met Ile Ser Ile Ser Asp Tyr Ile Asn Lys Trp
        995                 1000                1005

Ile Phe Val Thr Ile Thr Asn Asn Arg Leu Gly Asn Ser Arg Ile
    1010                1015                1020

Tyr Ile Asn Gly Asn Leu Ile Asp Gln Lys Ser Ile Ser Asn Leu
    1025                1030                1035

Gly Asp Ile His Val Ser Asn Ile Leu Phe Lys Ile Val Gly
    1040                1045                1050

Cys Asn Asp Thr Arg Tyr Val Gly Ile Arg Tyr Phe Lys Val Phe
    1055                1060                1065

Asp Thr Glu Leu Asp Lys Thr Glu Ile Glu Thr Leu Tyr Ser Asp
    1070                1075                1080

Glu Pro Asp Pro Ser Ile Leu Lys Asp Phe Trp Gly Asn Tyr Leu
    1085                1090                1095

Leu Tyr Asn Lys Arg Tyr Tyr Leu Leu Asn Leu Leu Arg Lys Asp
    1100                1105                1110

Lys Ser Ile Thr Gln Ser Ser Thr Phe Leu Ser Ile Ser Arg Pro
    1115                1120                1125

Arg Gly Val Asp Arg Lys Ala Asn Ile Phe Ser Asn Lys Arg Leu
    1130                1135                1140

Tyr Lys Gly Val Glu Val Ile Ile Arg Lys Asn Glu Pro Ile Asp
    1145                1150                1155

Ile Ser Asn Thr Asp Asn Phe Val Arg Lys Gly Asp Leu Ala Tyr
    1160                1165                1170

Ile Asn Val Val Asp Arg Asp Val Glu Tyr Arg Leu Tyr Ala Asp
    1175                1180                1185

Thr Ser Asn Ala Gln Pro Glu Lys Thr Ile Lys Leu Ile Arg Thr
    1190                1195                1200

Ser Asn Pro Asp Asp Ser Leu Gly Gln Ile Ile Val Met Asp Ser
    1205                1210                1215

Ile Gly Asn Asn Cys Thr Met Asn Phe Gln Asn Asn Asn Gly Gly
    1220                1225                1230

Asn Ile Gly Leu Leu Gly Phe His Ser Asn Thr Leu Val Ala Ser
    1235                1240                1245

Ser Trp Tyr Tyr Asn Asn Ile Arg Arg Asn Thr Ser Ser Asn Gly
    1250                1255                1260

Cys Phe Trp Ser Phe Ile Ser Lys Glu His Gly Trp Gln Glu Asn
    1265                1270                1275
```

```
<210> SEQ ID NO 7
<211> LENGTH: 1277
<212> TYPE: PRT
<213> ORGANISM: Clostridium botulinum

<400> SEQUENCE: 7

Met Pro Val Val Ile Asn Ser Phe Asn Tyr Asp Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Met Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Asp His Thr Pro Ile Asn Glu Phe
        115                 120                 125

His Pro Val Thr Arg Thr Thr Ser Val Asn Ile Lys Ser Ser Thr Asn
    130                 135                 140

Val Glu Ser Ser Ile Ile Leu Asn Leu Leu Val Leu Gly Ala Gly Pro
145                 150                 155                 160

Asn Ile Phe Glu Asn Ser Ser Tyr Pro Val Arg Lys Leu Met Asn Ser
                165                 170                 175

Gly Glu Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asp Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asn Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380
```

```
Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
            405                 410                 415

Pro Asp Lys Gly Leu Val Glu Lys Ile Val Lys Leu Cys Lys Ser Ile
            420                 425                 430

Ile Pro Arg Lys Gly Thr Lys Ala Pro Pro Arg Leu Cys Ile Arg Val
            435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Ser Gln Thr Leu Asn Thr Leu Val Gln
            500                 505                 510

Asp Asp Ser Tyr Val Pro Arg Tyr Asp Ser Asn Gly Thr Ser Glu Ile
            515                 520                 525

Glu Glu His Asn Val Val Asp Leu Asn Ala Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Lys Val Tyr Thr Phe Phe Ser Ser
            565                 570                 575

Glu Phe Ile Asn Asn Ile Asn Lys Pro Val His Ala Ala Leu Phe Ile
            580                 585                 590

Gly Trp Ile Ser Gln Val Ile Arg Asp Phe Thr Thr Glu Ser Thr Gln
            595                 600                 605

Lys Ser Thr Val Asp Lys Ile Ala Asp Ile Ser Leu Ile Val Pro Tyr
            610                 615                 620

Val Gly Leu Ala Leu Asn Ile Gly Asn Asp Ala Arg Lys Gly Asn Phe
625                 630                 635                 640

Lys Glu Ala Phe Glu Leu Leu Gly Ala Ala Ile Leu Leu Glu Val Val
            645                 650                 655

Pro Glu Leu Leu Ile Pro Val Ile Leu Val Phe Thr Ile Lys Ser Phe
            660                 665                 670

Ile Asp Ser Ser Lys Asn Glu Asp Lys Ile Ile Lys Ala Ile Asn Asn
            675                 680                 685

Ser Leu Ile Glu Arg Glu Ala Lys Trp Lys Glu Val Tyr Ser Trp Ile
            690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Val Ile Glu Tyr Lys Tyr Asn Ser Tyr Thr Ser Asp Glu Lys Asn Arg
            740                 745                 750

Leu Glu Ser Glu Tyr Asn Ile Asn Asn Ile Glu Glu Glu Leu Asn Lys
            755                 760                 765

Lys Val Ser Leu Ala Met Lys Asn Ile Glu Arg Phe Ile Ala Glu Ser
            770                 775                 780

Ser Ile Ser Tyr Leu Met Lys Leu Ile Asn Glu Ala Lys Val Ser Glu
785                 790                 795                 800
```

```
Leu Arg Glu Tyr Asp Glu Gly Val Lys Glu Tyr Leu Leu Asp Tyr Ile
                805                 810                 815

Leu Lys Asn Gly Ser Ile Leu Gly Asp His Val Gln Glu Leu Asn Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Tyr Phe Asn Lys Leu Tyr Lys
        850                 855                 860

Lys Ile Lys Asp Asn Cys Ile Leu Asp Met Arg Tyr Glu Asn Asn Lys
865                 870                 875                 880

Phe Ile Asp Ile Ser Gly Tyr Gly Ser Asn Ile Ser Ile Asn Gly Glu
            885                 890                 895

Leu Tyr Ile Tyr Thr Thr Asn Arg Asn Gln Phe Thr Ile Tyr Ser Gly
            900                 905                 910

Lys Leu Ser Glu Val Asn Ile Ala Gln Asn Asn Asp Ile Ile Tyr Asn
            915                 920                 925

Ser Arg Tyr Gln Asn Phe Ser Ile Ser Phe Trp Val Arg Ile Pro Arg
            930                 935                 940

Tyr Ser Asn Ile Val Asn Leu Asn Asn Glu Tyr Thr Ile Ile Asn Cys
945                 950                 955                 960

Met Gly Asn Asn Asn Ser Gly Trp Lys Ile Ser Leu Asn Tyr Asn Lys
            965                 970                 975

Ile Ile Trp Thr Leu Gln Asp Thr Ala Gly Asn Asn Glu Lys Leu Val
            980                 985                 990

Phe Asn Tyr Thr Gln Met Ile Ser Ile Ser Asp Tyr Ile Asn Lys Trp
            995                 1000                1005

Ile Phe Val Thr Ile Thr Asn Asn Arg Leu Gly Asn Ser Arg Ile
            1010                1015                1020

Tyr Ile Asn Gly Asn Leu Ile Asp Gln Lys Ser Ile Ser Asn Leu
            1025                1030                1035

Gly Asp Ile His Val Ser Asp Asn Ile Leu Phe Lys Ile Val Gly
            1040                1045                1050

Cys Asn Asp Thr Arg Tyr Val Gly Ile Arg Tyr Phe Lys Val Phe
            1055                1060                1065

Asp Thr Glu Leu Asp Lys Thr Glu Ile Glu Thr Leu Tyr Ser Asp
            1070                1075                1080

Glu Pro Asp Pro Ser Ile Leu Lys Asp Phe Trp Gly Asn Tyr Leu
            1085                1090                1095

Leu Tyr Asn Lys Arg Tyr Tyr Leu Leu Asn Leu Leu Arg Lys Asp
            1100                1105                1110

Asn Ala Ile Thr Gln Ser Ser Thr Phe Leu Ser Ile Ser Arg Ala
            1115                1120                1125

Arg Gly Val Asp Arg Lys Ala Asn Ile Phe Ser Asn Lys Arg Leu
            1130                1135                1140

Tyr Lys Gly Val Glu Val Ile Ile Arg Lys Asn Glu Pro Ile Asp
            1145                1150                1155

Ile Ser Asn Thr Asp Asn Phe Val Arg Lys Gly Asp Leu Ala Tyr
            1160                1165                1170

Ile Asn Val Val Asp Arg Asp Val Glu Tyr Arg Leu Tyr Ala Asn
            1175                1180                1185

Thr Ser Asn Ala Gln Pro Glu Lys Thr Ile Lys Leu Ile Arg Thr
            1190                1195                1200

Ser Asn Ser Asn Asp Ser Leu Asp Gln Ile Ile Val Met Asp Ser
```

```
                    1205                1210                1215
Ile Gly Asn Asn Cys Thr Met Asn Phe Gln Asn Asn Asn Gly Gly
                1220                1225                1230

Asn Ile Gly Leu Leu Gly Phe His Ser Asn Thr Leu Val Ala Ser
    1235                1240                1245

Ser Trp Tyr Tyr Asn Asn Ile Arg Arg Asn Thr Ser Ser Asn Gly
        1250                1255                1260

Cys Phe Trp Ser Phe Ile Ser Lys Glu His Gly Trp Gln Glu
    1265                1270                1275

<210> SEQ ID NO 8
<211> LENGTH: 1277
<212> TYPE: PRT
<213> ORGANISM: Clostridium botulinum

<400> SEQUENCE: 8

Met Pro Val Glu Ile Asn Ser Phe Asn Tyr Asp Asp Leu Val Asn Asp
1               5                   10                  15

Asn Thr Ile Leu Tyr Ile Arg Pro Pro Tyr Tyr Glu Arg Ser Asn Thr
            20                  25                  30

Tyr Phe Lys Ala Phe Asn Ile Met Glu Asn Val Trp Ile Ile Pro Glu
        35                  40                  45

Arg Tyr Arg Leu Gly Ile Glu Ala Ser Lys Phe Asp Pro Pro Asp Ser
    50                  55                  60

Leu Lys Ala Gly Ser Asp Gly Tyr Phe Asp Pro Asn Tyr Leu Ser Thr
65                  70                  75                  80

Asn Thr Glu Lys Asn Arg Tyr Leu Gln Ile Met Ile Lys Leu Phe Lys
                85                  90                  95

Arg Ile Asn Ser Asn Glu Ala Gly Lys Ile Leu Leu Asn Gln Ile Lys
            100                 105                 110

Asp Ala Ile Pro Tyr Leu Gly Asn Ser Tyr Thr Ala Glu Asp Gln Phe
        115                 120                 125

Thr Thr Asn Asn Arg Thr Ile Ser Phe Asn Val Arg Leu Ala Asn Gly
    130                 135                 140

Thr Ile Glu Gln Glu Met Ala Asn Leu Ile Ile Trp Gly Pro Gly Pro
145                 150                 155                 160

Asp Leu Thr Thr Asn Arg Thr Gly Gly Thr Thr Tyr Thr Pro Ala Gln
                165                 170                 175

Ser Leu Glu Ala Ile Pro Tyr Lys Glu Gly Phe Gly Ser Ile Met Thr
            180                 185                 190

Ile Glu Phe Ser Pro Glu Tyr Ala Thr Ala Phe Asn Asp Ile Ser Leu
        195                 200                 205

Thr Ser His Ala Pro Ser Leu Phe Ile Lys Asp Pro Ala Leu Ile Leu
    210                 215                 220

Met His Glu Leu Ile His Val Leu His Gly Leu Tyr Gly Thr Tyr Thr
225                 230                 235                 240

Thr Gly Phe Lys Ile Lys Pro Asn Ile Thr Glu Pro Tyr Met Glu Val
                245                 250                 255

Thr Lys Pro Ile Thr Ser Gly Glu Phe Leu Thr Phe Gly Gly Asn Asp
            260                 265                 270

Val Asn Lys Ile Pro Gln Leu Ile Gln Ser Gln Leu Arg Ser Lys Val
        275                 280                 285

Leu Asp Asp Tyr Glu Lys Ile Ala Ser Arg Leu Asn Lys Val Asn Arg
    290                 295                 300
```

```
Ala Thr Ala Glu Ile Asn Ile Asp Lys Phe Lys Tyr Ser Tyr Gln Leu
305                 310                 315                 320

Lys Tyr Gln Phe Val Lys Asp Ser Asn Gly Val Tyr Ser Val Asp Leu
            325                 330                 335

Asp Lys Phe Asn Lys Leu Tyr Asp Lys Ile Tyr Ser Phe Thr Glu Phe
                340                 345                 350

Asn Leu Ala His Glu Phe Lys Ile Lys Thr Arg Asn Ser Tyr Leu Ala
            355                 360                 365

Lys Asn Phe Gly Pro Phe Tyr Leu Pro Asn Leu Leu Asp Asn Ser Ile
370                 375                 380

Tyr Asn Glu Ala Asp Gly Phe Asn Ile Gly Asp Leu Ser Val Asn Tyr
385                 390                 395                 400

Lys Gly Gln Val Ile Gly Ser Asp Ile Asp Ser Ile Lys Lys Leu Glu
                405                 410                 415

Gly Gln Gly Val Val Ser Arg Val Val Arg Leu Cys Leu Asn Ser Ser
                420                 425                 430

Phe Lys Lys Asn Thr Lys Lys Pro Leu Cys Ile Thr Val Asn Asn Gly
            435                 440                 445

Asp Leu Phe Phe Ile Ala Ser Glu Asp Ser Tyr Gly Glu Asp Thr Ile
450                 455                 460

Asn Thr Pro Lys Glu Ile Asp Asp Thr Thr Thr Leu Val Pro Ser Phe
465                 470                 475                 480

Lys Asn Ile Leu Asp Lys Val Ile Leu Asp Phe Asn Lys Gln Val Thr
                485                 490                 495

Pro Gln Ile Pro Asn Arg Arg Ile Arg Thr Asp Ile Gln Glu Asp Asn
                500                 505                 510

Tyr Ile Pro Glu Tyr Asp Ser Asn Gly Thr Ser Glu Ile Glu Glu Tyr
            515                 520                 525

Asn Val Val Asp Leu Asn Ala Phe Phe Tyr Leu His Ala Gln Lys Val
530                 535                 540

Pro Glu Gly Glu Thr Asn Ile Ser Leu Thr Ser Ser Ile Asp Thr Ala
545                 550                 555                 560

Leu Ser Glu Glu Ser Lys Val Tyr Thr Phe Phe Ser Ser Glu Phe Ile
                565                 570                 575

Asp Thr Ile Asn Glu Pro Val Asn Ala Ala Leu Phe Ile Asp Trp Ile
                580                 585                 590

Ser Lys Val Ile Arg Asp Phe Thr Thr Glu Ala Thr Gln Lys Ser Thr
            595                 600                 605

Val Asp Lys Ile Ala Asp Ile Ser Leu Ile Val Pro Tyr Val Gly Leu
610                 615                 620

Ala Leu Asn Ile Val Asn Glu Thr Glu Lys Gly Asn Phe Lys Glu Ala
625                 630                 635                 640

Phe Glu Leu Leu Gly Ala Gly Ile Leu Leu Glu Phe Val Pro Glu Leu
                645                 650                 655

Ala Ile Pro Val Ile Leu Val Phe Thr Ile Lys Ser Tyr Ile Asp Ser
                660                 665                 670

Tyr Glu Asn Lys Asn Lys Ile Ile Lys Ala Ile Asn Asn Ser Leu Ile
            675                 680                 685

Glu Arg Glu Ala Lys Trp Lys Glu Ile Tyr Ser Trp Ile Val Ser Asn
690                 695                 700

Trp Leu Thr Arg Ile Asn Thr Gln Phe Asn Lys Arg Lys Glu Gln Met
705                 710                 715                 720

Tyr Gln Ala Leu Gln Asn Gln Val Asp Ala Ile Lys Thr Ala Ile Glu
```

-continued

```
                725                 730                 735
Tyr Lys Tyr Asn Asn Tyr Thr Ser Asp Glu Lys Asn Arg Leu Glu Ser
            740                 745                 750
Glu Tyr Asn Ile Asn Asn Ile Glu Glu Glu Leu Asn Lys Lys Val Ser
            755                 760                 765
Leu Ala Met Lys Asn Ile Glu Arg Phe Ile Thr Glu Ser Ser Ile Ser
            770                 775                 780
Tyr Leu Met Lys Leu Ile Asn Glu Ala Glu Val Gly Lys Leu Lys Glu
785                 790                 795                 800
Tyr Asp Lys Arg Val Lys Arg His Leu Leu Glu Tyr Ile Phe Asp Tyr
                805                 810                 815
Arg Leu Ile Leu Gly Glu Gln Gly Gly Glu Leu Ile Asp Leu Val Thr
                820                 825                 830
Ser Thr Leu Asn Thr Ser Ile Pro Phe Glu Leu Ser Ser Tyr Thr Asn
                835                 840                 845
Asp Lys Ile Leu Ile Ile Tyr Phe Asn Arg Leu Tyr Lys Lys Ile Lys
850                 855                 860
Asp Ser Ser Ile Leu Asp Met Arg Tyr Glu Asn Asn Lys Phe Ile Asp
865                 870                 875                 880
Ile Ser Gly Tyr Gly Ser Asn Ile Ser Ile Asn Gly Asn Val Tyr Ile
                885                 890                 895
Tyr Ser Thr Asn Arg Asn Gln Phe Gly Ile Tyr Asp Asp Arg Leu Ser
                900                 905                 910
Glu Val Asn Ile Ala Gln Asn Asp Ile Ile Tyr Asn Ser Arg Tyr
                915                 920                 925
Gln Asn Phe Ser Ile Ser Phe Trp Val Arg Ile Pro Lys His Tyr Arg
            930                 935                 940
Pro Met Asn His Asn Arg Glu Tyr Thr Ile Ile Asn Cys Met Gly Asn
945                 950                 955                 960
Asn Asn Ser Gly Trp Lys Ile Ser Leu Arg Thr Thr Gly Asp Cys Glu
                965                 970                 975
Ile Ile Trp Thr Leu Gln Asp Thr Ser Gly Asn Lys Lys Lys Leu Ile
                980                 985                 990
Phe Arg Tyr Ser Gln Leu Gly Gly  Ile Ser Asp Tyr Ile  Asn Lys Trp
            995                 1000                1005
Ile Phe Val Thr Ile Thr Asn  Asn Arg Leu Gly Asn  Ser Arg Ile
        1010                1015                1020
Tyr Ile Asn Gly Asn Leu Ile  Val Glu Lys Ser Ile  Ser Asn Leu
        1025                1030                1035
Gly Asp Ile His Val Ser Asp  Asn Ile Leu Phe Lys  Ile Val Gly
        1040                1045                1050
Cys Asp Asp Lys Met Tyr Val  Gly Ile Arg Tyr Phe  Lys Val Phe
        1055                1060                1065
Asn Thr Glu Leu Asp Lys Thr  Glu Ile Glu Ile Leu  Tyr Ser Asn
        1070                1075                1080
Glu Pro Asp Pro Ser Ile Leu  Lys Asp Tyr Trp Gly  Asn Tyr Leu
        1085                1090                1095
Leu Tyr Asn Lys Lys Tyr Tyr  Leu Leu Asn Leu Leu  Arg Asn Asp
        1100                1105                1110
Lys Tyr  Ile Thr Arg Asn Ser  Asp Ile Leu Asn Ile  Ser His Gln
        1115                1120                1125
Arg Gly Val Thr Lys Asp Leu  Phe Ile Phe Ser Asn  Tyr Lys Leu
        1130                1135                1140
```

-continued

Tyr Glu Gly Val Glu Val Ile Ile Arg Lys Asn Gly Pro Ile Asp
    1145            1150                1155

Ile Ser Asn Thr Asp Asn Phe Val Arg Lys Asn Asp Leu Ala Tyr
    1160            1165                1170

Ile Asn Val Val Asp His Gly Val Glu Tyr Arg Leu Tyr Ala Asp
    1175            1180                1185

Ile Ser Ile Thr Lys Pro Glu Lys Ile Ile Lys Leu Ile Arg Arg
    1190            1195                1200

Ser Asn Pro Asp Asp Ser Leu Gly Gln Ile Ile Val Met Asp Ser
    1205            1210                1215

Ile Gly Asn Asn Cys Thr Met Asn Phe Gln Asn Asn Asn Gly Gly
    1220            1225                1230

Asn Ile Gly Leu Leu Gly Phe His Ser Asp Asn Leu Val Ala Ser
    1235            1240                1245

Ser Trp Tyr Tyr Asn Asn Ile Arg Arg Asn Thr Ser Ser Asn Gly
    1250            1255                1260

Cys Phe Trp Ser Phe Ile Ser Lys Glu His Gly Trp Gln Glu
    1265            1270                1275

<210> SEQ ID NO 9
<211> LENGTH: 1275
<212> TYPE: PRT
<213> ORGANISM: Clostridium botulinum

<400> SEQUENCE: 9

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg

-continued

```
            225                 230                 235                 240
Gly Val Thr Tyr Glu Glu Thr Ile Glu Val Lys Gln Ala Pro Leu Met
                    245                 250                 255
Ile Ala Glu Lys Pro Ile Arg Leu Glu Glu Phe Leu Thr Phe Gly Gly
                    260                 265                 270
Gln Asp Leu Asn Ile Ile Thr Ser Ala Met Lys Glu Lys Ile Tyr Asn
                    275                 280                 285
Asn Leu Leu Ala Asn Tyr Glu Lys Ile Ala Thr Arg Leu Ser Glu Val
    290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                    325                 330                 335
Asn Glu Asn Lys Phe Asn Glu Ile Tyr Lys Lys Leu Tyr Ser Phe Thr
                    340                 345                 350
Glu Ser Asp Leu Ala Asn Lys Phe Lys Val Lys Cys Arg Asn Thr Tyr
                    355                 360                 365
Phe Ile Lys Tyr Gly Phe Leu Lys Val Pro Asn Leu Leu Asp Asp Asp
    370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                    405                 410                 415
Pro Asp Lys Gly Leu Val Glu Lys Ile Val Lys Phe Cys Lys Ser Val
                    420                 425                 430
Ile Pro Arg Lys Gly Thr Lys Ala Pro Pro Arg Leu Cys Ile Arg Val
                    435                 440                 445
Asn Asn Ser Glu Leu Phe Phe Val Ala Ser Glu Ser Ser Tyr Asn Glu
                    450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
                    485                 490                 495
Gln Thr Ile Pro Gln Ile Ser Asn Arg Thr Leu Asn Thr Leu Val Gln
                    500                 505                 510
Asp Asn Ser Tyr Val Pro Arg Tyr Asp Ser Asn Gly Thr Ser Glu Ile
                    515                 520                 525
Glu Glu Tyr Asp Val Val Asp Phe Asn Val Phe Phe Tyr Leu His Ala
                    530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Val Tyr Thr Phe Phe Ser Ser
                    565                 570                 575
Glu Phe Ile Asp Thr Ile Asn Lys Pro Val Asn Ala Ala Leu Phe Ile
                    580                 585                 590
Asp Trp Ile Ser Lys Val Ile Arg Asp Phe Thr Thr Glu Ala Thr Gln
                    595                 600                 605
Lys Ser Thr Val Asp Lys Ile Ala Asp Ile Ser Leu Ile Val Pro Tyr
                    610                 615                 620
Val Gly Leu Ala Leu Asn Ile Ile Ile Glu Ala Glu Lys Gly Asn Phe
625                 630                 635                 640
Glu Glu Ala Phe Glu Leu Leu Gly Val Gly Ile Leu Leu Glu Phe Val
                    645                 650                 655
```

```
Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
            675                 680                 685

Ser Leu Ile Glu Arg Glu Ala Lys Trp Lys Glu Ile Tyr Ser Trp Ile
            690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Ala Ile Glu Tyr Lys Tyr Asn Asn Tyr Thr Ser Asp Glu Lys Asn Arg
            740                 745                 750

Leu Glu Ser Glu Tyr Asn Ile Asn Asn Ile Glu Glu Leu Asn Lys
            755                 760                 765

Lys Val Ser Leu Ala Met Lys Asn Ile Glu Arg Phe Met Thr Glu Ser
            770                 775                 780

Ser Ile Ser Tyr Leu Met Lys Leu Ile Asn Glu Ala Lys Val Gly Lys
785                 790                 795                 800

Leu Lys Lys Tyr Asp Asn His Val Lys Ser Asp Leu Leu Asn Tyr Ile
            805                 810                 815

Leu Asp His Arg Ser Ile Leu Gly Glu Gln Thr Asn Glu Leu Ser Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Arg Leu Tyr Lys
            850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
            885                 890                 895

Val Tyr Ile Tyr Ser Thr Asn Arg Asn Gln Phe Gly Ile Tyr Asn Ser
            900                 905                 910

Arg Leu Ser Glu Val Asn Ile Ala Gln Asn Asn Asp Ile Ile Tyr Asn
            915                 920                 925

Ser Arg Tyr Gln Asn Phe Ser Ile Ser Phe Trp Val Arg Ile Pro Lys
            930                 935                 940

His Tyr Lys Pro Met Asn His Asn Arg Glu Tyr Thr Ile Ile Asn Cys
945                 950                 955                 960

Met Gly Asn Asn Asn Ser Gly Trp Lys Ile Ser Leu Arg Thr Val Arg
            965                 970                 975

Asp Cys Glu Ile Ile Trp Thr Leu Gln Asp Thr Ser Gly Asn Lys Glu
            980                 985                 990

Asn Leu Ile Phe Arg Tyr Glu Glu Leu Asn Arg Ile Ser Asn Tyr Ile
            995                 1000                1005

Asn Lys Trp Ile Phe Val Thr Ile Thr Asn Asn Arg Leu Gly Asn
            1010                1015                1020

Ser Arg Ile Tyr Ile Asn Gly Asn Leu Ile Val Glu Lys Ser Ile
            1025                1030                1035

Ser Asn Leu Gly Asp Ile His Val Ser Asp Asn Ile Leu Phe Lys
            1040                1045                1050

Ile Val Gly Cys Asp Asp Glu Thr Tyr Val Gly Ile Arg Tyr Phe
            1055                1060                1065
```

-continued

```
Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Tyr Tyr Leu Phe Asn Leu Leu
    1100                1105                1110

Arg Lys Asp Lys Tyr Ile Thr Leu Asn Ser Gly Ile Leu Asn Ile
    1115                1120                1125

Asn Gln Gln Arg Gly Val Thr Glu Gly Ser Val Phe Leu Asn Tyr
    1130                1135                1140

Lys Leu Tyr Glu Gly Val Glu Val Ile Ile Arg Lys Asn Gly Pro
    1145                1150                1155

Ile Asp Ile Ser Asn Thr Asp Asn Phe Val Arg Lys Asn Asp Leu
    1160                1165                1170

Ala Tyr Ile Asn Val Val Asp Arg Gly Val Glu Tyr Arg Leu Tyr
    1175                1180                1185

Ala Asp Thr Lys Ser Glu Lys Glu Lys Ile Ile Arg Thr Ser Asn
    1190                1195                1200

Leu Asn Asp Ser Leu Gly Gln Ile Ile Val Met Asp Ser Ile Gly
    1205                1210                1215

Asn Asn Cys Thr Met Asn Phe Gln Asn Asn Gly Ser Asn Ile
    1220                1225                1230

Gly Leu Leu Gly Phe His Ser Asn Asn Leu Val Ala Ser Ser Trp
    1235                1240                1245

Tyr Tyr Asn Asn Ile Arg Arg Asn Thr Ser Ser Asn Gly Cys Phe
    1250                1255                1260

Trp Ser Phe Ile Ser Lys Glu Asn Gly Trp Lys Glu
    1265                1270                1275

<210> SEQ ID NO 10
<211> LENGTH: 1274
<212> TYPE: PRT
<213> ORGANISM: Clostridium botulinum

<400> SEQUENCE: 10

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160
```

```
Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575
```

```
Phe Ile Asp Thr Ile Asn Lys Pro Val Asn Ala Ala Leu Phe Ile Asp
                580                 585                 590
Trp Ile Ser Lys Val Ile Arg Asp Phe Thr Thr Glu Ala Thr Gln Lys
            595                 600                 605
Ser Thr Val Asp Lys Ile Ala Asp Ile Ser Leu Ile Val Pro Tyr Val
        610                 615                 620
Gly Leu Ala Leu Asn Ile Ile Glu Ala Glu Lys Gly Asn Phe Glu
625                 630                 635                 640
Glu Ala Phe Glu Leu Leu Gly Val Gly Ile Leu Leu Glu Phe Val Pro
                645                 650                 655
Glu Leu Thr Ile Pro Val Ile Leu Val Phe Thr Ile Lys Ser Tyr Ile
            660                 665                 670
Asp Ser Tyr Glu Asn Lys Asn Lys Ala Ile Lys Ala Ile Asn Asn Ser
        675                 680                 685
Leu Ile Glu Arg Glu Ala Lys Trp Lys Glu Ile Tyr Ser Trp Ile Val
690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
                725                 730                 735
Ile Glu Tyr Lys Tyr Asn Asn Tyr Thr Ser Asp Glu Lys Asn Arg Leu
            740                 745                 750
Glu Ser Glu Tyr Asn Ile Asn Asn Ile Glu Glu Leu Asn Lys Lys
        755                 760                 765
Val Ser Leu Ala Met Lys Asn Ile Glu Arg Phe Met Thr Glu Ser Ser
770                 775                 780
Ile Ser Tyr Leu Met Lys Leu Ile Asn Glu Ala Lys Val Gly Lys Leu
785                 790                 795                 800
Lys Lys Tyr Asp Asn His Val Lys Ser Asp Leu Leu Asn Tyr Ile Leu
                805                 810                 815
Asp His Arg Ser Ile Leu Gly Glu Gln Thr Asn Glu Leu Ser Asp Leu
            820                 825                 830
Val Thr Ser Thr Leu Asn Ser Ser Ile Pro Phe Glu Leu Ser Ser Tyr
        835                 840                 845
Thr Asn Asp Lys Ile Leu Ile Ile Tyr Phe Asn Arg Leu Tyr Lys Lys
850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
            900                 905                 910
Leu Ser Glu Val Asn Ile Ala Gln Asn Asn Asp Ile Ile Tyr Asn Ser
        915                 920                 925
Arg Tyr Gln Asn Phe Ser Ile Ser Phe Trp Val Arg Ile Pro Lys His
930                 935                 940
Tyr Lys Pro Met Asn His Asn Arg Glu Tyr Thr Ile Ile Asn Cys Met
945                 950                 955                 960
Gly Asn Asn Asn Ser Gly Trp Lys Ile Ser Leu Arg Thr Val Arg Asp
                965                 970                 975
Cys Glu Ile Ile Trp Thr Leu Gln Asp Thr Ser Gly Asn Lys Glu Asn
            980                 985                 990
Leu Ile Phe Arg Tyr Glu Glu Leu  Asn Arg Ile Ser Asn  Tyr Ile Asn
```

```
                  995                1000               1005
        Lys Trp Ile Phe Val Thr Ile Thr Asn Asn Arg Leu Gly Asn Ser
            1010               1015               1020

Arg Ile Tyr Ile Asn Gly Asn Leu Ile Val Glu Lys Ser Ile Ser
            1025               1030               1035

Asn Leu Gly Asp Ile His Val Ser Asp Asn Ile Leu Phe Lys Ile
            1040               1045               1050

Val Gly Cys Asp Asp Glu Thr Tyr Val Gly Ile Arg Tyr Phe Lys
            1055               1060               1065

Val Phe Asn Thr Glu Leu Asp Lys Thr Glu Ile Glu Thr Leu Tyr
            1070               1075               1080

Ser Asn Glu Pro Asp Pro Ser Ile Leu Lys Asn Tyr Trp Gly Asn
            1085               1090               1095

Tyr Leu Leu Tyr Asn Lys Lys Tyr Tyr Leu Phe Asn Leu Leu Arg
            1100               1105               1110

Lys Asp Lys Tyr Ile Thr Leu Asn Ser Gly Ile Leu Asn Ile Asn
            1115               1120               1125

Gln Gln Arg Gly Val Thr Glu Gly Ser Val Phe Leu Asn Tyr Lys
            1130               1135               1140

Leu Tyr Glu Gly Val Glu Val Ile Ile Arg Lys Asn Gly Pro Ile
            1145               1150               1155

Asp Ile Ser Asn Thr Asp Asn Phe Val Arg Lys Asn Asp Leu Ala
            1160               1165               1170

Tyr Ile Asn Val Val Asp Arg Gly Val Glu Tyr Arg Leu Tyr Ala
            1175               1180               1185

Asp Thr Lys Ser Glu Lys Glu Lys Ile Ile Arg Thr Ser Asn Leu
            1190               1195               1200

Asn Asp Ser Leu Gly Gln Ile Ile Val Met Asp Ser Ile Gly Asn
            1205               1210               1215

Asn Cys Thr Met Asn Phe Gln Asn Asn Asn Gly Ser Asn Ile Gly
            1220               1225               1230

Leu Leu Gly Phe His Ser Asn Asn Leu Val Ala Ser Ser Trp Tyr
            1235               1240               1245

Tyr Asn Asn Ile Arg Arg Asn Thr Ser Ser Asn Gly Cys Phe Trp
            1250               1255               1260

Ser Ser Ile Ser Lys Glu Asn Gly Trp Lys Glu
            1265               1270

<210> SEQ ID NO 11
<211> LENGTH: 1275
<212> TYPE: PRT
<213> ORGANISM: Clostridium botulinum

<400> SEQUENCE: 11

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Lys Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
65                  70                  75                  80
```

-continued

Asp Ala Glu Lys Asp Arg Tyr Leu Lys Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
            405                 410                 415

Pro Asp Lys Gly Leu Val Glu Lys Ile Val Lys Phe Cys Lys Ser Val
        420                 425                 430

Ile Pro Arg Lys Gly Thr Lys Ala Pro Pro Arg Leu Cys Ile Arg Val
    435                 440                 445

Asn Asn Ser Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Gln Thr Ile Pro Gln Ile Ser Asn Arg Thr Leu Asn Thr Leu Val Gln

```
                500             505             510
Asp Asn Ser Tyr Val Pro Arg Tyr Asp Ser Asn Gly Thr Ser Glu Ile
            515                 520             525

Glu Glu Tyr Asp Val Val Asp Phe Asn Val Phe Phe Tyr Leu His Ala
            530                 535             540

Gln Lys Val Pro Glu Gly Glu Thr Asn Ile Ser Leu Thr Ser Ser Ile
545             550                 555                 560

Asp Thr Ala Leu Leu Glu Glu Ser Lys Val Tyr Thr Phe Phe Ser Ser
                565                 570             575

Glu Phe Ile Asp Thr Ile Asn Lys Pro Val Asn Ala Ala Leu Phe Ile
            580                 585             590

Asp Trp Ile Ser Lys Val Ile Arg Asp Phe Thr Thr Glu Ala Thr Gln
            595                 600             605

Lys Ser Thr Val Asp Lys Ile Ala Asp Ile Ser Leu Ile Val Pro Tyr
            610                 615             620

Val Gly Leu Ala Leu Asn Ile Ile Ile Glu Ala Glu Lys Gly Asn Phe
625             630                 635                 640

Glu Glu Ala Phe Glu Leu Leu Gly Val Gly Ile Leu Leu Glu Phe Val
                645                 650             655

Pro Glu Leu Thr Ile Pro Val Ile Leu Val Phe Thr Ile Lys Ser Tyr
                660                 665             670

Ile Asp Ser Tyr Glu Asn Lys Asn Lys Ala Ile Lys Ala Ile Asn Asn
            675                 680             685

Ser Leu Ile Glu Arg Glu Ala Lys Trp Lys Glu Ile Tyr Ser Trp Ile
            690                 695             700

Val Ser Asn Trp Leu Thr Arg Ile Asn Thr Gln Phe Asn Lys Arg Lys
705             710                 715                 720

Glu Gln Met Tyr Gln Ala Leu Gln Asn Gln Val Asp Ala Ile Lys Thr
                725                 730             735

Ala Ile Glu Tyr Lys Tyr Asn Asn Tyr Thr Ser Asp Glu Lys Asn Arg
                740                 745             750

Leu Glu Ser Glu Tyr Asn Ile Asn Asn Ile Glu Glu Glu Leu Asn Lys
            755                 760             765

Lys Val Ser Leu Ala Met Lys Asn Ile Glu Arg Phe Met Thr Glu Ser
770             775                 780

Ser Ile Ser Tyr Leu Met Lys Leu Ile Asn Glu Ala Lys Val Gly Lys
785             790                 795                 800

Leu Lys Lys Tyr Asp Asn His Val Lys Ser Asp Leu Leu Asn Tyr Ile
                805             810                 815

Leu Asp His Arg Ser Ile Leu Gly Glu Gln Thr Asn Glu Leu Ser Asp
            820                 825             830

Leu Val Thr Ser Thr Leu Asn Ser Ser Ile Pro Phe Glu Leu Ser Ser
            835                 840             845

Tyr Thr Asn Asp Lys Ile Leu Ile Ile Tyr Phe Asn Arg Leu Tyr Lys
            850                 855             860

Lys Ile Lys Asp Ser Ser Ile Leu Asp Met Arg Tyr Glu Asn Asn Lys
865             870                 875                 880

Phe Ile Asp Ile Ser Gly Tyr Gly Ser Asn Ile Ser Ile Asn Gly Asn
                885                 890             895

Val Tyr Ile Tyr Ser Thr Asn Arg Asn Gln Phe Gly Ile Tyr Asn Ser
                900                 905             910

Arg Leu Ser Glu Val Asn Ile Ala Gln Asn Asn Asp Ile Ile Tyr Asn
            915                 920             925
```

Ser Arg Tyr Gln Asn Phe Ser Ile Ser Phe Trp Val Arg Ile Pro Lys
        930                 935                 940

His Tyr Lys Pro Met Asn His Asn Arg Glu Tyr Thr Ile Ile Asn Cys
945                 950                 955                 960

Met Gly Asn Asn Asn Ser Gly Trp Lys Ile Ser Leu Arg Thr Val Arg
                965                 970                 975

Asp Cys Glu Ile Ile Trp Thr Leu Gln Asp Thr Ser Gly Asn Lys Glu
            980                 985                 990

Asn Leu Ile Phe Arg Tyr Glu Glu Leu Asn Arg Ile Ser Asn Tyr Ile
        995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
    1100                1105                1110

Arg Lys Asp Lys Tyr Ile Thr Leu Asn Ser Gly Ile Leu Asn Ile
    1115                1120                1125

Asn Gln Gln Arg Gly Val Thr Glu Gly Ser Val Phe Leu Asn Tyr
    1130                1135                1140

Lys Leu Tyr Glu Gly Val Glu Val Ile Ile Arg Lys Asn Gly Pro
    1145                1150                1155

Ile Asp Ile Ser Asn Thr Asp Asn Phe Val Arg Lys Asn Asp Leu
    1160                1165                1170

Ala Tyr Ile Asn Val Val Asp Arg Gly Val Glu Tyr Arg Leu Tyr
    1175                1180                1185

Ala Asp Thr Lys Ser Glu Lys Glu Lys Ile Ile Arg Thr Ser Asn
    1190                1195                1200

Leu Asn Asp Ser Leu Gly Gln Ile Ile Val Met Asp Ser Ile Gly
    1205                1210                1215

Asn Asn Cys Thr Met Asn Phe Gln Asn Asn Asn Gly Ser Asn Ile
    1220                1225                1230

Gly Leu Leu Gly Phe His Ser Asn Asn Leu Val Ala Ser Ser Trp
    1235                1240                1245

Tyr Tyr Asn Asn Ile Arg Arg Asn Thr Ser Ser Asn Gly Cys Phe
    1250                1255                1260

Trp Ser Phe Ile Ser Lys Glu Asn Gly Trp Lys Glu
    1265                1270                1275

<210> SEQ ID NO 12
<211> LENGTH: 1275
<212> TYPE: PRT
<213> ORGANISM: Clostridium botulinum

<400> SEQUENCE: 12

Met Pro Val Ala Ile Asn Ser Phe Asn Tyr Asn Asp Pro Val Asn Asp

-continued

```
1               5                   10                  15
Asp Thr Ile Leu Tyr Met Gln Ile Pro Tyr Lys Glu Lys Ser Lys Lys
                20                  25                  30
Tyr Tyr Lys Ala Phe Glu Ile Met Arg Asn Val Trp Ile Ile Pro Glu
                35                  40                  45
Arg Asn Thr Ile Gly Thr Asn Pro Ser Asp Phe Asp Pro Pro Ala Ser
        50                  55                  60
Leu Lys Asn Gly Ser Ser Ala Tyr Tyr Asp Pro Asn Tyr Leu Thr Thr
65                  70                  75                  80
Asp Ala Glu Lys Asp Arg Tyr Leu Lys Thr Thr Ile Lys Leu Phe Lys
                85                  90                  95
Arg Ile Asn Ser Asn Pro Ala Gly Lys Val Leu Leu Gln Glu Ile Ser
                100                 105                 110
Tyr Ala Lys Pro Tyr Leu Gly Asn Asp His Thr Pro Ile Asp Glu Phe
                115                 120                 125
Ser Pro Val Thr Arg Thr Thr Ser Val Asn Ile Lys Leu Ser Thr Asn
        130                 135                 140
Val Glu Ser Ser Met Leu Leu Asn Leu Leu Val Leu Gly Ala Gly Pro
145                 150                 155                 160
Asp Ile Phe Glu Ser Cys Cys Tyr Pro Val Arg Lys Leu Ile Asp Pro
                165                 170                 175
Asp Val Tyr Asp Pro Ser Asn Tyr Gly Phe Gly Ser Ile Asn Ile
                180                 185                 190
Val Thr Phe Ser Pro Glu Tyr Glu Tyr Thr Phe Asn Asp Ile Ser Gly
                195                 200                 205
Gly His Asn Ser Ser Thr Glu Ser Phe Ile Ala Asp Pro Ala Ile Ser
        210                 215                 220
Leu Ala His Glu Leu Ile His Ala Leu His Gly Leu Tyr Gly Ala Arg
225                 230                 235                 240
Gly Val Thr Tyr Glu Glu Thr Ile Glu Val Lys Gln Ala Pro Leu Met
                245                 250                 255
Ile Ala Glu Lys Pro Ile Arg Leu Glu Glu Phe Leu Thr Phe Gly Gly
                260                 265                 270
Gln Asp Leu Asn Ile Ile Thr Ser Ala Met Lys Glu Lys Ile Tyr Asn
        275                 280                 285
Asn Leu Leu Ala Asn Tyr Glu Lys Ile Ala Thr Arg Leu Ser Glu Val
        290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                325                 330                 335
Asn Glu Asn Lys Phe Asn Glu Ile Tyr Lys Lys Leu Tyr Ser Phe Thr
                340                 345                 350
Glu Ser Asp Leu Ala Asn Lys Phe Lys Val Lys Cys Arg Asn Thr Tyr
                355                 360                 365
Phe Ile Lys Tyr Gly Phe Leu Lys Val Pro Asn Leu Leu Asp Asp Asp
370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                405                 410                 415
Pro Asp Lys Gly Leu Val Glu Lys Ile Val Lys Phe Cys Lys Ser Val
                420                 425                 430
```

```
Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
        530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590

Asp Trp Ile Ser Lys Val Ile Arg Asp Phe Thr Thr Glu Ala Thr Gln
        595                 600                 605

Lys Ser Thr Val Asp Lys Ile Ala Asp Ile Ser Leu Ile Val Pro Tyr
        610                 615                 620

Val Gly Leu Ala Leu Asn Ile Ile Ile Glu Ala Glu Lys Gly Asn Phe
625                 630                 635                 640

Glu Glu Ala Phe Glu Leu Leu Gly Val Gly Ile Leu Leu Glu Phe Val
                645                 650                 655

Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
        675                 680                 685

Ser Leu Ile Glu Arg Glu Ala Lys Trp Lys Glu Ile Tyr Ser Trp Ile
        690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
            740                 745                 750

Leu Glu Ser Glu Tyr Asn Ile Asn Asn Ile Glu Glu Leu Asn Lys
            755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Lys Val Gly Lys
785                 790                 795                 800

Leu Lys Lys Tyr Asp Asn His Val Lys Ser Asp Leu Leu Asn Tyr Ile
                805                 810                 815

Leu Asp His Arg Ser Ile Leu Gly Glu Gln Thr Asn Glu Leu Ser Asp
            820                 825                 830

Leu Val Thr Ser Thr Leu Asn Ser Ser Ile Pro Phe Glu Leu Ser Ser
        835                 840                 845
```

-continued

```
Tyr Thr Asn Asp Lys Ile Leu Ile Ile Tyr Phe Asn Arg Leu Tyr Lys
    850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Asn Ser
        900                 905                 910

Arg Leu Ser Glu Val Asn Ile Ala Gln Asn Asn Asp Ile Tyr Asn
            915                 920                 925

Ser Arg Tyr Gln Asn Phe Ser Ile Ser Phe Trp Val Arg Ile Pro Lys
    930                 935                 940

His Tyr Lys Pro Met Asn His Asn Arg Glu Tyr Thr Ile Ile Asn Cys
945                 950                 955                 960

Met Gly Asn Asn Asn Ser Gly Trp Lys Ile Ser Leu Arg Thr Val Arg
                965                 970                 975

Asp Cys Glu Ile Ile Trp Thr Leu Gln Asp Thr Ser Gly Asn Lys Glu
            980                 985                 990

Asn Leu Ile Phe Arg Tyr Glu Glu  Leu Asn Arg Ile Ser  Asn Tyr Ile
            995                 1000                1005

Asn Lys  Trp Ile Phe Val Thr  Ile Thr Asn Asn Arg  Leu Gly Asn
    1010                1015                1020

Ser Lys  Ile Tyr Ile Asn Gly  Asn Leu Ile Val Glu  Lys Ser Ile
    1025                1030                1035

Ser Asn  Leu Gly Asp Ile His  Val Ser Asp Asn Ile  Leu Phe Lys
    1040                1045                1050

Ile Val  Gly Cys Asp Asp Glu  Thr Tyr Val Gly Ile  Arg Tyr Phe
    1055                1060                1065

Lys Val  Phe Asn Thr Glu Leu  Asp Lys Thr Glu Ile  Glu Thr Leu
    1070                1075                1080

Tyr Ser  Asn Glu Pro Asp Pro  Ser Ile Leu Lys Asp  Tyr Trp Gly
    1085                1090                1095

Asn Tyr  Leu Leu Tyr Asn Lys  Lys Tyr Tyr Leu Phe  Asn Leu Leu
    1100                1105                1110

Arg Lys  Asp Lys Tyr Ile Thr  Leu Asn Ser Gly Ile  Leu Asn Ile
    1115                1120                1125

Asn Gln  Gln Arg Gly Val Thr  Glu Gly Ser Val Phe  Leu Asn Tyr
    1130                1135                1140

Lys Leu  Tyr Glu Gly Val Glu  Val Ile Ile Arg Lys  Asn Gly Pro
    1145                1150                1155

Ile Asp  Ile Ser Asn Thr Asp  Asn Phe Val Arg Lys  Asn Asp Leu
    1160                1165                1170

Ala Tyr  Ile Asn Val Val Asp  Arg Gly Val Glu Tyr  Arg Leu Tyr
    1175                1180                1185

Ala Asp  Thr Lys Ser Glu Lys  Glu Lys Ile Ile Arg  Thr Ser Asn
    1190                1195                1200

Leu Asn  Asp Ser Leu Gly Gln  Ile Ile Val Met Asp  Ser Ile Gly
    1205                1210                1215

Asn Asn  Cys Thr Met Asn Phe  Gln Asn Asn Asn Gly  Ser Asn Ile
    1220                1225                1230

Gly Leu  Leu Gly Phe His Ser  Asn Asn Leu Val Ala  Ser Ser Trp
    1235                1240                1245

Tyr Tyr  Asn Asn Ile Arg Arg  Asn Thr Ser Ser Asn  Gly Cys Phe
```

```
                    1250              1255              1260
Trp Ser  Phe Ile Ser Lys Glu  Asn Gly Trp Lys Glu
    1265              1270              1275

<210> SEQ ID NO 13
<211> LENGTH: 1268
<212> TYPE: PRT
<213> ORGANISM: Clostridium botulinum

<400> SEQUENCE: 13

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Ser Lys Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Asp Asn Leu Leu Ser Asn Tyr Thr Ala
        275                 280                 285

Ile Ala Ser Arg Leu Ser Gln Val Asn Ile Asn Ser Ala Leu Asn
    290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350
```

```
Gln Val Lys Asn Arg Ser Asn Tyr Leu Phe His Phe Lys Pro Phe Arg
            355                 360                 365

Leu Leu Asp Leu Leu Asp Asp Asn Ile Tyr Ser Ile Ser Glu Gly Phe
    370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys Val Asn Asn Arg Asp Leu Phe Phe Val Ala Ser
            435                 440                 445

Glu Ser Ser Tyr Asn Glu Asn Gly Ile Asn Ser Pro Lys Glu Ile Asp
    450                 455                 460

Asp Thr Thr Ile Thr Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
            500                 505                 510

Asn Gly Thr Ser Glu Ile Lys Glu Tyr Thr Val Asp Lys Leu Asn Val
            515                 520                 525

Phe Phe Tyr Leu Tyr Ala Gln Lys Ala Pro Glu Gly Glu Ser Ala Ile
            530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Gln Val Ile Asn Asp Phe
            580                 585                 590

Thr Thr Glu Ala Thr Gln Lys Ser Thr Ile Asp Lys Ile Ala Asp Ile
            595                 600                 605

Ser Leu Val Val Pro Tyr Val Gly Leu Ala Leu Asn Ile Gly Asn Glu
610                 615                 620

Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Asp Ser Asn Lys Ile
            660                 665                 670

Ile Lys Ala Ile Asn Asn Ala Leu Arg Glu Arg Glu Leu Lys Trp Lys
            675                 680                 685

Glu Val Tyr Ser Trp Ile Val Ser Asn Trp Leu Thr Arg Ile Asn Thr
            690                 695                 700

Gln Phe Asn Lys Arg Lys Glu Gln Met Tyr Gln Ala Leu Gln Asn Gln
705                 710                 715                 720

Val Asp Gly Ile Lys Lys Ile Glu Tyr Lys Tyr Asn Asn Tyr Thr
                725                 730                 735

Leu Asp Glu Lys Asn Arg Leu Lys Ala Glu Tyr Asn Ile Tyr Ser Ile
                740                 745                 750

Lys Glu Glu Leu Asn Lys Lys Val Ser Leu Ala Met Gln Asn Ile Asp
            755                 760                 765

Arg Phe Leu Thr Glu Ser Ser Ile Ser Tyr Leu Met Lys Leu Ile Asn
```

```
            770                 775                 780
Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Gln Glu Leu Asn Asn Leu Val Ser Asn Thr Leu Asn Asn Ser
                820                 825                 830

Ile Pro Phe Glu Leu Ser Glu Tyr Thr Asn Asp Lys Ile Leu Ile Ser
                835                 840                 845

Tyr Phe Asn Arg Phe Tyr Lys Arg Ile Ile Asp Ser Ser Ile Leu Asn
                850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
                900                 905                 910

Asn Asn Thr Ile Ile Tyr Asn Ser Arg Tyr Gln Asn Phe Ser Val Ser
                915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
                980                 985                 990

Ser Asp Tyr Ile Asn Lys Trp Thr Phe Val Thr Ile Thr Asn Asn Arg
                995                 1000                1005

Leu Gly His Ser Lys Leu Tyr Ile Asn Gly Asn Leu Thr Asp Gln
                1010                1015                1020

Lys Ser Ile Leu Asn Leu Gly Asn Ile His Val Asp Asp Asn Ile
                1025                1030                1035

Leu Phe Lys Ile Val Gly Cys Asn Asp Thr Arg Tyr Val Gly Ile
                1040                1045                1050

Arg Tyr Phe Lys Ile Phe Asn Met Glu Leu Asp Lys Thr Glu Ile
                1055                1060                1065

Glu Thr Leu Tyr His Ser Glu Pro Asp Ser Thr Ile Leu Lys Asp
                1070                1075                1080

Phe Trp Gly Asn Tyr Leu Leu Tyr Asn Lys Lys Tyr Tyr Leu Leu
                1085                1090                1095

Asn Leu Leu Lys Pro Asn Met Ser Val Thr Lys Asn Ser Asp Ile
                1100                1105                1110

Leu Asn Ile Asn Arg Gln Arg Gly Ile Tyr Ser Lys Thr Asn Ile
                1115                1120                1125

Phe Ser Asn Ala Arg Leu Tyr Thr Gly Val Glu Val Ile Ile Arg
                1130                1135                1140

Lys Val Gly Ser Thr Asp Thr Ser Asn Thr Asp Asn Phe Val Arg
                1145                1150                1155

Lys Asn Asp Thr Val Tyr Ile Asn Val Val Asp Gly Asn Ser Glu
                1160                1165                1170

Tyr Gln Leu Tyr Ala Asp Val Ser Thr Ser Ala Val Glu Lys Thr
                1175                1180                1185
```

```
Ile Lys Leu Arg Arg Ile Ser Asn Ser Asn Tyr Asn Ser Asn Gln
    1190                1195                1200

Met Ile Ile Met Asp Ser Ile Gly Asp Asn Cys Thr Met Asn Phe
    1205                1210                1215

Lys Thr Asn Asn Gly Asn Asp Ile Gly Leu Leu Gly Phe His Leu
    1220                1225                1230

Asn Asn Leu Val Ala Ser Ser Trp Tyr Tyr Lys Asn Ile Arg Asn
    1235                1240                1245

Asn Thr Arg Asn Asn Gly Cys Phe Trp Ser Phe Ile Ser Lys Glu
    1250                1255                1260

His Gly Trp Gln Glu
    1265

<210> SEQ ID NO 14
<211> LENGTH: 1268
<212> TYPE: PRT
<213> ORGANISM: Clostridium botulinum

<400> SEQUENCE: 14

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Asp Asn Leu Leu Ser Asn Tyr Thr Ala
```

```
            275                 280                 285
Ile Ala Ser Arg Leu Ser Gln Val Asn Ile Asn Asn Ser Ala Leu Asn
290                 295                 300
Thr Thr Tyr Tyr Lys Asn Phe Phe Gln Trp Lys Tyr Gly Leu Asp Gln
305                 310                 315                 320
Asp Ser Asn Gly Asn Tyr Thr Val Asn Ile Ser Lys Phe Asn Ala Ile
                325                 330                 335
Tyr Lys Lys Leu Phe Ser Phe Thr Glu Cys Asp Leu Ala Gln Lys Phe
                340                 345                 350
Gln Val Lys Asn Arg Ser Asn Tyr Leu Phe His Phe Lys Pro Phe Arg
                355                 360                 365
Leu Leu Asp Leu Leu Asp Asp Asn Ile Tyr Ser Ile Ser Glu Gly Phe
370                 375                 380
Asn Ile Gly Ser Leu Arg Val Asn Asn Asn Gly Gln Asn Ile Asn Leu
385                 390                 395                 400
Asn Ser Arg Ile Val Gly Pro Ile Pro Asp Asn Gly Leu Val Glu Arg
                405                 410                 415
Phe Val Gly Leu Cys Lys Ser Ile Val Ser Lys Lys Gly Thr Lys Asn
                420                 425                 430
Ser Leu Cys Ile Lys Val Asn Asn Arg Asp Leu Phe Phe Val Ala Ser
                435                 440                 445
Glu Ser Ser Tyr Asn Glu Asn Gly Ile Asn Ser Pro Lys Glu Ile Asp
450                 455                 460
Asp Thr Thr Ile Thr Asn Asn Asn Tyr Lys Lys Asn Leu Asp Glu Val
465                 470                 475                 480
Ile Leu Asp Tyr Asn Ser Asp Ala Ile Pro Asn Leu Ser Ser Arg Leu
                485                 490                 495
Leu Asn Thr Thr Ala Gln Asn Asp Ser Tyr Val Pro Lys Tyr Asp Ser
                500                 505                 510
Asn Gly Thr Ser Glu Ile Lys Glu Tyr Thr Val Asp Lys Leu Asn Val
                515                 520                 525
Phe Phe Tyr Leu Tyr Ala Gln Lys Ala Pro Glu Gly Glu Ser Ala Ile
                530                 535                 540
Ser Leu Thr Ser Ser Val Asn Thr Ala Leu Leu Asp Ala Ser Lys Val
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Gln Val Ile Asn Asp Phe
                580                 585                 590
Thr Thr Glu Ala Thr Gln Lys Ser Thr Ile Asp Lys Ile Ala Asp Ile
                595                 600                 605
Ser Leu Val Val Pro Tyr Val Gly Leu Ala Leu Asn Ile Gly Asn Glu
                610                 615                 620
Val Gln Lys Gly Asn Phe Lys Glu Ala Ile Glu Leu Leu Gly Ala Gly
625                 630                 635                 640
Ile Leu Leu Glu Phe Val Pro Glu Leu Leu Ile Pro Thr Ile Leu Val
                645                 650                 655
Phe Thr Ile Lys Ser Phe Ile Asn Ser Asp Asp Ser Lys Asn Lys Ile
                660                 665                 670
Ile Lys Ala Ile Asn Asn Ala Leu Arg Glu Arg Glu Leu Lys Trp Lys
                675                 680                 685
Glu Val Tyr Ser Trp Ile Val Ser Asn Trp Leu Thr Arg Ile Asn Thr
                690                 695                 700
```

```
Gln Phe Asn Lys Arg Lys Glu Gln Met Tyr Gln Ala Leu Gln Asn Gln
705                 710                 715                 720

Val Asp Gly Ile Lys Lys Ile Ile Glu Tyr Lys Tyr Asn Asn Tyr Thr
            725                 730                 735

Leu Asp Glu Lys Asn Arg Leu Lys Ala Glu Tyr Asn Ile Tyr Ser Ile
            740                 745                 750

Lys Glu Glu Leu Asn Lys Val Ser Leu Ala Met Gln Asn Ile Asp
            755                 760                 765

Arg Phe Leu Thr Glu Ser Ser Ile Ser Tyr Leu Met Lys Leu Ile Asn
            770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Gln Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile Ser
            835                 840                 845

Tyr Phe Asn Arg Phe Tyr Lys Arg Ile Ile Asp Ser Ser Ile Leu Asn
            850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
                900                 905                 910

Asn Asn Thr Ile Ile Tyr Asn Ser Arg Tyr Gln Asn Phe Ser Val Ser
            915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
            995                1000                1005

Leu Gly His Ser Lys Leu Tyr Ile Asn Gly Asn Leu Thr Asp Gln
            1010                1015                1020

Lys Ser Ile Leu Asn Leu Gly Asn Ile His Val Asp Asp Asn Ile
1025                1030                1035

Leu Phe Lys Ile Val Gly Cys Asn Asp Thr Arg Tyr Val Gly Ile
1040                1045                1050

Arg Tyr Phe Lys Ile Phe Asn Met Glu Leu Asp Lys Thr Glu Ile
1055                1060                1065

Glu Thr Leu Tyr His Ser Glu Pro Asp Ser Thr Ile Leu Lys Asp
1070                1075                1080

Phe Trp Gly Asn Tyr Leu Leu Tyr Asn Lys Lys Tyr Tyr Leu Leu
1085                1090                1095

Asn Leu Leu Lys Pro Asn Met Ser Val Thr Lys Asn Ser Asp Ile
1100                1105                1110
```

```
Leu Asn Ile Asn Arg Gln Arg Gly Ile Tyr Ser Lys Thr Asn Ile
    1115                1120                1125

Phe Ser Asn Ala Arg Leu Tyr Thr Gly Val Glu Val Ile Ile Arg
    1130                1135                1140

Lys Val Gly Ser Thr Asp Thr Ser Asn Thr Asp Asn Phe Val Arg
    1145                1150                1155

Lys Asn Asp Thr Val Tyr Ile Asn Val Val Asp Gly Asn Ser Glu
    1160                1165                1170

Tyr Gln Leu Tyr Ala Asp Val Ser Thr Ser Ala Val Glu Lys Thr
    1175                1180                1185

Ile Lys Leu Arg Arg Ile Ser Asn Ser Asn Tyr Asn Ser Asn Gln
    1190                1195                1200

Met Ile Ile Met Asp Ser Ile Gly Asp Asn Cys Thr Met Asn Phe
    1205                1210                1215

Lys Thr Asn Asn Gly Asn Asp Ile Gly Leu Leu Gly Phe His Leu
    1220                1225                1230

Asn Asn Leu Val Ala Ser Ser Trp Tyr Tyr Lys Asn Ile Arg Asn
    1235                1240                1245

Asn Thr Arg Asn Asn Gly Cys Phe Trp Ser Phe Ile Ser Lys Glu
    1250                1255                1260

His Gly Trp Gln Glu
    1265

<210> SEQ ID NO 15
<211> LENGTH: 1268
<212> TYPE: PRT
<213> ORGANISM: Clostridium botulinum

<400> SEQUENCE: 15

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205
```

```
Phe Ile Ala Asp Pro Ala Ile Ser Leu Ala His Glu Leu Ile His Val
    210                 215                 220
Leu His Gly Leu Tyr Gly Ala Lys Gly Val Thr Asn Lys Lys Val Ile
225                 230                 235                 240
Glu Val Asp Gln Gly Ala Leu Met Ala Ala Glu Lys Asp Ile Lys Ile
                245                 250                 255
Glu Glu Phe Ile Thr Phe Gly Gly Gln Asp Leu Asn Ile Ile Thr Asn
            260                 265                 270
Ser Thr Asn Gln Lys Ile Tyr Val Ile Leu Leu Ser Asn Tyr Thr Ala
        275                 280                 285
Ile Ala Ser Arg Leu Ser Gln Val Asn Arg Asn Ser Ala Leu Asn
290                 295                 300
Thr Thr Tyr Tyr Lys Asn Phe Phe Gln Trp Lys Tyr Gly Leu Asp Gln
305                 310                 315                 320
Asp Ser Asn Gly Asn Tyr Thr Val Asn Ile Ser Lys Phe Asn Ala Ile
                325                 330                 335
Tyr Lys Lys Leu Phe Ser Phe Thr Glu Cys Asp Leu Ala Gln Lys Phe
            340                 345                 350
Gln Val Lys Asn Arg Ser Asn Tyr Leu Phe His Phe Lys Pro Phe Arg
        355                 360                 365
Leu Leu Asp Leu Leu Asp Asp Asn Ile Tyr Ser Ile Ser Glu Gly Phe
370                 375                 380
Asn Ile Gly Ser Leu Arg Val Asn Asn Asn Gly Gln Asn Ile Asn Leu
385                 390                 395                 400
Asn Ser Arg Ile Val Gly Pro Ile Pro Asp Asn Gly Leu Val Glu Arg
                405                 410                 415
Phe Val Gly Leu Cys Lys Ser Ile Val Ser Lys Lys Gly Thr Lys Asn
            420                 425                 430
Ser Leu Cys Ile Lys Val Asn Asn Arg Asp Leu Phe Phe Val Ala Ser
        435                 440                 445
Glu Ser Ser Tyr Asn Glu Asn Gly Ile Asn Ser Pro Lys Glu Ile Asp
450                 455                 460
Asp Thr Thr Ile Thr Asn Asn Tyr Lys Lys Asn Leu Asp Glu Val
465                 470                 475                 480
Ile Leu Asp Tyr Asn Ser Asp Ala Ile Pro Asn Leu Ser Ser Arg Leu
                485                 490                 495
Leu Asn Thr Thr Ala Gln Asn Asp Ser Tyr Val Pro Lys Tyr Asp Ser
            500                 505                 510
Asn Gly Thr Ser Glu Ile Lys Glu Tyr Thr Val Asp Lys Leu Asn Val
        515                 520                 525
Phe Phe Tyr Leu Tyr Ala Gln Lys Ala Pro Gly Gly Glu Ser Ala Ile
530                 535                 540
Ser Leu Thr Ser Ser Val Asn Thr Ala Leu Leu Asp Ala Ser Lys Val
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Gln Val Ile Asn Asp Phe
            580                 585                 590
Thr Thr Glu Ala Thr Gln Lys Ser Thr Ile Asp Lys Ile Ala Asp Ile
        595                 600                 605
Ser Leu Ile Val Pro Tyr Val Gly Leu Ala Leu Asn Ile Gly Asn Glu
610                 615                 620
```

```
Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
            645                 650                 655

Phe Thr Ile Lys Ser Phe Ile Asn Ser Asp Ser Lys Asn Lys Ile
                660                 665                 670

Ile Lys Ala Ile Asn Asn Ala Leu Arg Glu Arg Glu Leu Lys Trp Lys
        675                 680                 685

Glu Val Tyr Ser Trp Ile Val Ser Asn Trp Leu Thr Arg Ile Asn Thr
    690                 695                 700

Gln Phe Asn Lys Arg Lys Glu Gln Met Tyr Gln Ala Leu Gln Asn Gln
705                 710                 715                 720

Val Asp Gly Ile Lys Lys Ile Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
                740                 745                 750

Lys Glu Glu Leu Asn Lys Lys Val Ser Leu Ala Met Gln Asn Ile Asp
            755                 760                 765

Arg Phe Leu Thr Glu Ser Ser Ile Ser Tyr Leu Met Lys Leu Ile Asn
770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Thr Leu Gly Thr Ser
                805                 810                 815

Ser Val Pro Glu Leu Asn Asn Leu Val Ser Asn Thr Leu Asn Asn Ser
                820                 825                 830

Ile Pro Phe Glu Leu Ser Glu Tyr Thr Asn Asp Lys Ile Leu Ile His
        835                 840                 845

Ile Leu Ile Arg Phe Tyr Lys Arg Ile Ile Asp Ser Ser Ile Leu Asn
850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
            900                 905                 910

Asn Asn Thr Ile Ile Tyr Asn Ser Arg Tyr Gln Asn Phe Ser Val Ser
            915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
                980                 985                 990

Ser Asp Tyr Ile Asn Lys Trp Thr Phe Val Thr Ile Thr Asn Asn Arg
                995                 1000                1005

Leu Gly His Ser Lys Leu Tyr Ile Asn Gly Asn Leu Thr Asp Gln
    1010                1015                1020

Lys Ser Ile Leu Asn Leu Gly Asn Ile His Val Asp Asp Asn Ile
    1025                1030                1035

Leu Phe Lys Ile Val Gly Cys Asn Asp Thr Arg Tyr Val Gly Ile
```

```
            1040                1045                1050

Arg Tyr Phe Lys Ile Phe Asn Met Glu Leu Asp Lys Thr Glu Ile
    1055                1060                1065

Glu Thr Leu Tyr His Ser Glu Pro Asp Ser Thr Ile Leu Lys Asp
    1070                1075                1080

Phe Trp Gly Asn Tyr Leu Leu Tyr Asn Lys Lys Tyr Tyr Leu Leu
    1085                1090                1095

Asn Leu Leu Lys Pro Asn Met Ser Val Thr Lys Asn Ser Asp Ile
    1100                1105                1110

Leu Asn Ile Asn Arg Gln Arg Gly Ile Tyr Ser Lys Thr Asn Ile
    1115                1120                1125

Phe Ser Asn Ala Arg Leu Tyr Thr Gly Val Glu Val Ile Ile Arg
    1130                1135                1140

Lys Val Gly Ser Thr Asp Thr Ser Asn Thr Asp Asn Phe Val Arg
    1145                1150                1155

Lys Asn Asp Thr Val Tyr Ile Asn Val Val Asp Gly Asn Ser Glu
    1160                1165                1170

Tyr Gln Leu Tyr Ala Asp Val Ser Thr Ser Ala Val Glu Lys Thr
    1175                1180                1185

Ile Lys Leu Arg Arg Ile Ser Asn Ser Asn Tyr Asn Ser Asn Gln
    1190                1195                1200

Met Ile Ile Met Asp Ser Ile Gly Asp Asn Cys Thr Met Asn Phe
    1205                1210                1215

Lys Thr Asn Asn Gly Asn Asp Ile Gly Leu Leu Gly Phe His Leu
    1220                1225                1230

Asn Asn Leu Val Ala Ser Ser Trp Tyr Tyr Lys Asn Ile Arg Asn
    1235                1240                1245

Asn Thr Arg Asn Asn Gly Cys Phe Trp Ser Phe Ile Ser Lys Glu
    1250                1255                1260

His Gly Trp Gln Glu
    1265

<210> SEQ ID NO 16
<211> LENGTH: 1268
<212> TYPE: PRT
<213> ORGANISM: Clostridium botulinum

<400> SEQUENCE: 16

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
                20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
                100                 105                 110

Asn Gly Lys Pro Tyr Leu Gly Asn Asp His Thr Ala Val Asn Glu Phe
        115                 120                 125
```

```
Cys Ala Asn Asn Arg Ser Thr Ser Val Glu Ile Lys Glu Ser Asn Gly
130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Val Thr Asn
            260                 265                 270

Ser Thr Asn Gln Lys Ile Tyr Asp Asn Leu Leu Ser Asn Tyr Thr Ala
        275                 280                 285

Ile Ala Ser Arg Leu Ser Gln Val Asn Ile Asn Asn Ser Ala Leu Asn
290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Lys
        355                 360                 365

Leu Leu Asp Leu Leu Asp Asp Asn Ile Tyr Ser Ile Ser Glu Gly Phe
370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
450                 455                 460

Asp Thr Thr Ile Thr Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Ala Thr Ala Gln Asn Asp Ser Tyr Val Pro Lys Tyr Asp Ser
            500                 505                 510

Asn Gly Thr Ser Glu Ile Asn Glu Tyr Thr Val Asp Lys Leu Asn Val
        515                 520                 525

Phe Phe Tyr Leu Tyr Ala Gln Lys Ala Pro Glu Gly Glu Ser Ala Ile
530                 535                 540

Ser Leu Thr Ser Ser Val Asp Thr Ala Leu Leu Asp Ala Ser Lys Val
```

```
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Val Ile Asn Asp Phe
                580                 585                 590
Thr Thr Glu Ala Thr Gln Lys Ser Thr Ile Asp Lys Ile Ala Asp Ile
                595                 600                 605
Ser Leu Val Val Pro Tyr Val Gly Leu Ala Leu Asn Ile Gly Asn Glu
        610                 615                 620
Val Gln Lys Gly Asn Phe Lys Glu Ala Ile Glu Leu Leu Gly Ala Gly
625                 630                 635                 640
Ile Leu Leu Glu Phe Val Pro Glu Leu Leu Ile Pro Thr Ile Leu Val
                645                 650                 655
Phe Thr Ile Lys Ser Phe Ile Asn Ser Asp Asp Ser Lys Asn Lys Ile
                660                 665                 670
Ile Lys Ala Ile Asn Asn Ala Leu Arg Glu Arg Glu Leu Lys Trp Lys
                675                 680                 685
Glu Val Tyr Ser Trp Ile Val Ser Asn Trp Leu Thr Arg Ile Asn Thr
        690                 695                 700
Gln Phe Asn Lys Arg Lys Glu Gln Met Tyr Gln Ala Leu Gln Asn Gln
705                 710                 715                 720
Val Asp Gly Ile Lys Lys Ile Glu Tyr Lys Tyr Asn Asn Tyr Thr
                725                 730                 735
Leu Asp Glu Lys Asn Arg Leu Lys Ala Glu Tyr Asn Ile Tyr Asn Ile
                740                 745                 750
Lys Glu Glu Leu Asn Lys Lys Val Ser Leu Ala Met Gln Asn Ile Asp
        755                 760                 765
Arg Phe Leu Thr Glu Ser Ser Ile Ser Tyr Leu Met Lys Leu Ile Asn
        770                 775                 780
Glu Ala Lys Ile Asn Lys Leu Ser Glu Tyr Asp Lys Arg Val Asn Gln
785                 790                 795                 800
Tyr Leu Leu Asn Tyr Ile Leu Glu Asn Ser Ser Thr Leu Gly Thr Ser
                805                 810                 815
Ser Val Gln Glu Leu Asn Asn Leu Val Ser Asn Thr Leu Asn Asn Ser
        820                 825                 830
Ile Pro Phe Glu Leu Ser Glu Tyr Thr Asn Asp Lys Ile Leu Ile Ser
        835                 840                 845
Tyr Phe Asn Arg Phe Tyr Lys Arg Ile Ile Asp Ser Ser Ile Leu Asn
        850                 855                 860
Met Lys Tyr Glu Asn Asn Arg Phe Ile Asp Ser Ser Gly Tyr Gly Ser
865                 870                 875                 880
Asn Ile Ser Ile Asn Gly Asp Ile Tyr Ile Tyr Ser Thr Asn Arg Asn
                885                 890                 895
Gln Phe Gly Ile Tyr Ser Ser Arg Leu Ser Glu Val Asn Ile Thr Gln
                900                 905                 910
Asn Asn Thr Ile Ile Tyr Asn Ser Arg Tyr Gln Asn Phe Ser Val Ser
        915                 920                 925
Phe Trp Val Arg Ile Pro Lys Tyr Asn Asn Leu Lys Asn Leu Asn Asn
        930                 935                 940
Glu Tyr Thr Ile Ile Asn Cys Met Arg Asn Asn Asn Ser Gly Trp Lys
945                 950                 955                 960
Ile Ser Leu Asn Tyr Asn Asn Ile Ile Trp Thr Leu Gln Asp Thr Thr
                965                 970                 975
```

```
Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr  Asn Asn Arg
        995                 1000                1005

Leu Gly His Ser Lys Leu Tyr Ile Asn Gly Asn Leu  Thr Asp Gln
       1010                1015                1020

Lys Ser Ile Ser Asn Leu Gly Asn Ile His Val Asp  Asp Asn Ile
       1025                1030                1035

Leu Phe Lys Ile Val Gly Cys Asn Asp Thr Arg Tyr  Val Gly Ile
       1040                1045                1050

Arg Tyr Phe Lys Ile Phe Asn Met Glu Leu Asp Lys  Thr Glu Ile
       1055                1060                1065

Glu Thr Leu Tyr His Ser Glu Pro Asp Ser Thr Ile  Leu Lys Asp
       1070                1075                1080

Phe Trp Gly Asn Tyr Leu Leu Tyr Asn Lys Lys Tyr  Tyr Leu Leu
       1085                1090                1095

Asn Leu Leu Lys Pro Asn Met Ser Val Thr Lys Asn  Ser Asp Ile
       1100                1105                1110

Leu Asn Ile Asn Arg Gln Arg Gly Ile Tyr Ser Lys  Thr Asn Ile
       1115                1120                1125

Phe Ser Asn Ala Arg Leu Tyr Thr Gly Val Glu Val  Ile Ile Arg
       1130                1135                1140

Lys Phe Gly Ser Thr Asp Thr Ser Asn Thr Asp Asn  Phe Val Arg
       1145                1150                1155

Lys Asn Asp Thr Val Tyr Ile Ser Val Val Asp Gly  Asn Ser Glu
       1160                1165                1170

Tyr Gln Leu Tyr Ala Asp Val Ser Thr Ser Ala Val  Glu Lys Thr
       1175                1180                1185

Ile Lys Leu Arg Arg Ile Ser Asn Ser Asn Tyr Asn  Ser Asn Gln
       1190                1195                1200

Met Ile Ile Met Asp Ser Ile Gly Asp Asn Cys Thr  Met Asn Phe
       1205                1210                1215

Lys Thr Asn Asn Gly Asn Asp Ile Gly Leu Leu Gly  Phe His Leu
       1220                1225                1230

Asn Asn Leu Val Ala Ser Ser Trp Tyr Tyr Lys Asn  Ile Arg Asn
       1235                1240                1245

Asn Thr Arg Asn Asn Gly Cys Phe Trp Ser Phe Ile  Ser Lys Glu
       1250                1255                1260

His Gly Trp Gln Glu
       1265

<210> SEQ ID NO 17
<211> LENGTH: 834
<212> TYPE: PRT
<213> ORGANISM: Clostridium botulinum
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
```

```
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (646)..(646)
<223> OTHER INFORMATION: Xaa can be any naturally occurring amino acid
<220> FEATURE:
<221> NAME/KEY: misc_feature
<222> LOCATION: (797)..(797)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (813)..(813)
<223> OTHER INFORMATION: Xaa can be any naturally occurring amino acid

<400> SEQUENCE: 17

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
            20                  25                  30

Pro Glu Arg Asn Thr Ile Gly Thr Lys Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Ile Lys Leu
65                  70                  75                  80

Phe Lys Arg Ile Asn Ser Asn Pro Ala Gly Lys Val Leu Leu Xaa Glu
                85                  90                  95

Ile Ser Xaa Ala Lys Pro Tyr Leu Gly Asn Asp His Thr Pro Ile Asn
            100                 105                 110

Glu Phe Xaa Pro Val Asn Arg Thr Thr Ser Val Asn Ile Lys Leu Ser
        115                 120                 125

Thr Asn Val Glu Ser Ser Met Leu Leu Asn Leu Val Leu Gly Ala
    130                 135                 140

Gly Pro Asp Ile Phe Glu Xaa Ser Cys Tyr Pro Val Arg Lys Xaa Pro
145                 150                 155                 160

Asn Ser Asp Xaa Val Tyr Asp Pro Ser Asn Xaa Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
```

```
              195                 200                 205
Ile Ser Leu Ala His Glu Leu Ile His Ala Leu His Gly Leu Tyr Gly
210                 215                 220

Ala Xaa Gly Val Thr Tyr Lys Glu Thr Ile Glu Val Lys Gln Xaa Pro
225                 230                 235                 240

Leu Met Ile Ala Glu Lys Pro Ile Arg Leu Glu Phe Leu Thr Phe
                245                 250                 255

Gly Gly Gln Asp Leu Asn Ile Ile Thr Ser Ala Met Lys Glu Lys Ile
                260                 265                 270

Tyr Asn Asn Leu Leu Ala Asn Tyr Glu Lys Ile Ala Thr Arg Leu Ser
                275                 280                 285

Glu Val Asn Ser Ala Pro Pro Glu Tyr Asp Ile Asn Glu Tyr Lys Asp
                290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
                355                 360                 365

Asp Asp Ile Tyr Thr Val Ser Glu Gly Phe Asn Ile Gly Asn Leu Ala
370                 375                 380

Val Asn Asn Arg Gly Gln Asn Ile Asn Leu Asn Pro Lys Ile Ile Asp
385                 390                 395                 400

Ser Ile Pro Asp Lys Gly Leu Val Glu Lys Ile Val Lys Phe Cys Lys
                405                 410                 415

Ser Ile Ile Pro Arg Lys Gly Thr Lys Ala Pro Pro Arg Leu Cys Ile
                420                 425                 430

Arg Val Asn Asn Arg Glu Leu Phe Phe Val Ala Ser Glu Ser Ser Tyr
                435                 440                 445

Asn Glu Asn Asp Ile Asn Thr Pro Lys Glu Ile Asp Asp Thr Thr Asn
450                 455                 460

Leu Asn Asn Asn Tyr Arg Asn Asn Leu Asp Glu Val Ile Leu Asp Tyr
465                 470                 475                 480

Asn Ser Glu Thr Ile Pro Gln Ile Ser Asn Arg Thr Leu Asn Thr Leu
                485                 490                 495

Val Gln Asp Asp Ser Tyr Val Pro Arg Tyr Asp Ser Asn Gly Thr Ser
                500                 505                 510

Glu Ile Glu Glu Tyr Asp Val Val Asp Leu Asn Val Phe Phe Tyr Leu
                515                 520                 525

His Ala Gln Lys Val Pro Glu Gly Glu Thr Asn Ile Ser Leu Thr Ser
                530                 535                 540

Ser Ile Asp Thr Ala Leu Leu Glu Glu Ser Lys Val Tyr Thr Phe Phe
545                 550                 555                 560

Ser Ser Glu Phe Ile Asp Thr Ile Asn Lys Pro Val Asn Ala Ala Leu
                565                 570                 575

Phe Ile Asp Trp Ile Ser Lys Val Ile Arg Asp Phe Thr Glu Ala
                580                 585                 590

Thr Gln Lys Ser Thr Val Asp Lys Ile Ala Asp Ile Ser Leu Ile Val
                595                 600                 605

Pro Tyr Val Gly Leu Ala Leu Asn Ile Gly Asn Glu Ala Glu Lys Gly
610                 615                 620
```

```
Asn Phe Lys Glu Ala Phe Glu Leu Leu Gly Ala Gly Ile Leu Leu Glu
625                 630                 635                 640

Phe Val Pro Glu Leu Xaa Ile Pro Val Ile Leu Val Phe Thr Ile Lys
                645                 650                 655

Ser Tyr Ile Asp Ser Tyr Glu Asn Lys Asn Lys Ile Ile Lys Ala Ile
            660                 665                 670

Asn Asn Ser Leu Ile Glu Arg Glu Ala Lys Trp Lys Glu Ile Tyr Ser
            675                 680                 685

Trp Ile Val Ser Asn Trp Leu Thr Arg Ile Asn Thr Gln Phe Asn Lys
690                 695                 700

Arg Lys Glu Gln Met Tyr Gln Ala Leu Gln Asn Val Asp Ala Ile
705                 710                 715                 720

Lys Thr Ala Ile Glu Tyr Lys Tyr Asn Asn Tyr Thr Ser Asp Glu Lys
                725                 730                 735

Asn Arg Leu Glu Ser Glu Tyr Asn Ile Asn Asn Ile Glu Glu Glu Leu
            740                 745                 750

Asn Lys Lys Val Ser Leu Ala Met Lys Asn Ile Glu Arg Phe Met Thr
            755                 760                 765

Glu Ser Ser Ile Ser Tyr Leu Met Lys Leu Ile Asn Glu Ala Lys Val
770                 775                 780

Gly Lys Leu Lys Glu Tyr Asp Lys His Val Lys Ser Xaa Leu Leu Asn
785                 790                 795                 800

Tyr Ile Leu Xaa His Arg Ser Ile Leu Gly Glu Gln Xaa Gln Glu Leu
                805                 810                 815

Asn Asp Leu Val Thr Ser Thr Leu Asn Ser Ser Ile Pro Phe Glu Leu
            820                 825                 830

Ser Ser

<210> SEQ ID NO 18
<211> LENGTH: 834
<212> TYPE: PRT
<213> ORGANISM: Clostridium botulinum

<400> SEQUENCE: 18

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
                20                  25                  30

Pro Glu Arg Asn Thr Ile Gly Thr Asp Pro Ser Asp Phe Asp Pro Pro
            35                  40                  45

Ala Ser Leu Glu Asn Gly Ser Ser Ala Tyr Tyr Asp Pro Asn Tyr Leu
50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Glu Val Leu Leu Gln Glu
                85                  90                  95

Ile Ser Tyr Ala Lys Pro Tyr Leu Gly Asn Glu His Thr Pro Ile Asn
            100                 105                 110

Glu Phe His Pro Val Thr Arg Thr Thr Ser Val Asn Ile Lys Ser Ser
            115                 120                 125

Thr Asn Val Lys Ser Ser Ile Ile Leu Asn Leu Leu Val Leu Gly Ala
            130                 135                 140

Gly Pro Asp Ile Phe Glu Asn Ser Ser Tyr Pro Val Arg Lys Leu Met
145                 150                 155                 160
```

```
Asp Ser Gly Gly Val Tyr Asp Pro Ser Asn Asp Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly Tyr Asn Ser Ser Thr Glu Ser Phe Ile Ala Asp Pro Ala
            195                 200                 205

Ile Ser Leu Ala His Glu Leu Ile His Ala Leu His Gly Leu Tyr Gly
            210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
            245                 250                 255

Gly Gly Gln Asp Leu Asn Ile Ile Thr Ser Ala Met Lys Glu Lys Ile
            260                 265                 270

Tyr Asn Asn Leu Leu Ala Asn Tyr Glu Lys Ile Ala Thr Arg Leu Ser
            275                 280                 285

Arg Val Asn Ser Ala Pro Pro Glu Tyr Asp Ile Asn Glu Tyr Lys Asp
            290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
            325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
            355                 360                 365

Asp Asp Ile Tyr Thr Val Ser Glu Gly Phe Asn Ile Gly Asn Leu Ala
            370                 375                 380

Val Asn Asn Arg Gly Gln Asn Ile Lys Leu Asn Pro Lys Ile Ile Asp
385                 390                 395                 400

Ser Ile Pro Asp Lys Gly Leu Val Glu Lys Ile Val Lys Phe Cys Lys
            405                 410                 415

Ser Val Ile Pro Arg Lys Gly Thr Lys Ala Pro Pro Arg Leu Cys Ile
            420                 425                 430

Arg Val Asn Asn Arg Glu Leu Phe Phe Val Ala Ser Glu Ser Ser Tyr
            435                 440                 445

Asn Glu Asn Asp Ile Asn Thr Pro Lys Glu Ile Asp Asp Thr Thr Asn
450                 455                 460

Leu Asn Asn Asn Tyr Arg Asn Asn Leu Asp Glu Val Ile Leu Asp Tyr
465                 470                 475                 480

Asn Ser Glu Thr Ile Pro Gln Ile Ser Asn Gln Thr Leu Asn Thr Leu
            485                 490                 495

Val Gln Asp Asp Ser Tyr Val Pro Arg Tyr Asp Ser Asn Gly Thr Ser
            500                 505                 510

Glu Ile Glu Glu His Asn Val Val Asp Leu Asn Val Phe Phe Tyr Leu
            515                 520                 525

His Ala Gln Lys Val Pro Glu Gly Glu Thr Asn Ile Ser Leu Thr Ser
            530                 535                 540

Ser Ile Asp Thr Ala Leu Ser Glu Glu Ser Gln Val Tyr Thr Phe Phe
545                 550                 555                 560

Ser Ser Glu Phe Ile Asn Thr Ile Asn Lys Pro Val His Ala Ala Leu
            565                 570                 575
```

```
Phe Ile Ser Trp Ile Asn Gln Val Ile Arg Asp Phe Thr Thr Glu Ala
            580                 585                 590

Thr Gln Lys Ser Thr Phe Asp Lys Ile Ala Asp Ile Ser Leu Val Val
        595                 600                 605

Pro Tyr Val Gly Leu Ala Leu Asn Ile Gly Asn Glu Val Gln Lys Glu
    610                 615                 620

Asn Phe Lys Glu Ala Phe Glu Leu Leu Gly Ala Gly Ile Leu Leu Glu
625                 630                 635                 640

Phe Val Pro Glu Leu Leu Ile Pro Thr Ile Leu Val Phe Thr Ile Lys
                645                 650                 655

Ser Phe Ile Gly Ser Ser Glu Asn Lys Asn Lys Ile Ile Lys Ala Ile
            660                 665                 670

Asn Asn Ser Leu Met Glu Arg Glu Thr Lys Trp Lys Glu Ile Tyr Ser
        675                 680                 685

Trp Ile Val Ser Asn Trp Leu Thr Arg Ile Asn Thr Gln Phe Asn Lys
    690                 695                 700

Arg Lys Glu Gln Met Tyr Gln Ala Leu Gln Asn Gln Val Asp Ala Ile
705                 710                 715                 720

Lys Thr Val Ile Glu Tyr Lys Tyr Asn Asn Tyr Thr Ser Asp Glu Arg
                725                 730                 735

Asn Arg Leu Glu Ser Glu Tyr Asn Ile Asn Asn Ile Arg Glu Glu Leu
            740                 745                 750

Asn Lys Lys Val Ser Leu Ala Met Glu Asn Ile Glu Arg Phe Ile Thr
        755                 760                 765

Glu Ser Ser Ile Phe Tyr Leu Met Lys Leu Ile Asn Glu Ala Lys Val
770                 775                 780

Ser Lys Leu Arg Glu Tyr Asp Glu Gly Val Lys Glu Tyr Leu Leu Asp
785                 790                 795                 800

Tyr Ile Ser Glu His Arg Ser Ile Leu Gly Asn Ser Val Gln Glu Leu
                805                 810                 815

Asn Asp Leu Val Thr Ser Thr Leu Asn Asn Ser Ile Pro Phe Glu Leu
            820                 825                 830

Ser Ser

<210> SEQ ID NO 19
<211> LENGTH: 834
<212> TYPE: PRT
<213> ORGANISM: Clostridium botulinum

<400> SEQUENCE: 19

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
            20                  25                  30

Pro Glu Arg Asp Thr Ile Gly Thr Lys Pro Asp Glu Phe Gln Val Pro
        35                  40                  45

Asp Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Met Ile Lys Leu
65                  70                  75                  80

Phe Asn Arg Ile Asn Ser Asn Pro Thr Gly Lys Val Leu Leu Glu Glu
                85                  90                  95

Val Ser Asn Ala Arg Pro Tyr Leu Gly Asp Asp Thr Leu Ile Asn
            100                 105                 110
```

```
Glu Phe Phe Pro Val Asn Val Thr Thr Ser Val Asn Ile Lys Phe Ser
            115                 120                 125

Thr Asp Val Glu Ser Ser Ile Ile Ser Asn Leu Leu Val Leu Gly Ala
130                 135                 140

Gly Pro Asp Ile Phe Lys Ala Tyr Cys Thr Pro Leu Val Arg Phe Asn
145                 150                 155                 160

Lys Ser Asp Lys Leu Ile Glu Pro Ser Asn His Gly Phe Gly Ser Ile
                165                 170                 175

Asn Ile Leu Thr Phe Ser Pro Glu Tyr Glu His Ile Phe Asn Asp Ile
            180                 185                 190

Ser Gly Gly Asn His Asn Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Lys Ala Val Thr His Lys Glu Ser Leu Val Ala Glu Arg Gly Pro
225                 230                 235                 240

Leu Met Ile Ala Glu Lys Pro Ile Arg Leu Glu Glu Phe Leu Thr Phe
                245                 250                 255

Gly Gly Glu Asp Leu Asn Ile Ile Pro Ser Ala Met Lys Glu Lys Ile
            260                 265                 270

Tyr Asn Asp Leu Leu Ala Asn Tyr Glu Lys Ile Ala Thr Arg Leu Arg
        275                 280                 285

Glu Val Asn Thr Ala Pro Pro Gly Tyr Asp Ile Asn Glu Tyr Lys Asp
    290                 295                 300

Tyr Phe Gln Trp Lys Tyr Gly Leu Asp Arg Asn Ala Asp Gly Ser Tyr
305                 310                 315                 320

Thr Val Asn Arg Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Val Lys Val Pro Asp Leu Leu Asp
        355                 360                 365

Asp Asp Ile Tyr Thr Val Ser Glu Gly Phe Asn Ile Gly Asn Leu Ala
370                 375                 380

Val Asn Asn Arg Gly Gln Asn Ile Asn Leu Asn Pro Lys Ile Ile Asp
385                 390                 395                 400

Ser Ile Pro Asp Lys Gly Leu Val Glu Lys Ile Lys Phe Cys Lys
                405                 410                 415

Ser Ile Ile Pro Arg Lys Gly Thr Lys Gln Ser Pro Ser Leu Cys Ile
                420                 425                 430

Arg Val Asn Asn Arg Glu Leu Phe Phe Val Ala Ser Glu Ser Ser Tyr
            435                 440                 445

Asn Glu Ser Asp Ile Asn Thr Pro Lys Glu Ile Asp Asp Thr Thr Asn
    450                 455                 460

Leu Asn Asn Asn Tyr Arg Asn Asn Leu Asp Glu Val Ile Leu Asp Tyr
465                 470                 475                 480

Asn Ser Glu Thr Ile Pro Gln Ile Ser Asn Arg Thr Leu Asn Thr Leu
                485                 490                 495

Val Gln Asp Asn Ser Tyr Val Pro Arg Tyr Asp Ser Asn Gly Thr Ser
            500                 505                 510

Glu Ile Glu Glu Tyr Asp Val Val Asp Phe Asn Val Phe Phe Tyr Leu
    515                 520                 525

His Ala Gln Lys Val Pro Glu Gly Glu Thr Asn Ile Ser Leu Thr Ser
```

```
                    530                 535                 540
Ser Ile Asp Thr Ala Leu Leu Glu Glu Ser Lys Val Tyr Thr Phe Phe
545                 550                 555                 560

Ser Ser Glu Phe Ile Asp Thr Ile Asn Lys Pro Val Asn Ala Ala Leu
                    565                 570                 575

Phe Ile Asp Trp Ile Ser Lys Val Ile Arg Asp Phe Thr Thr Glu Ala
                580                 585                 590

Thr Gln Lys Ser Thr Val Asp Lys Ile Ala Asp Ile Ser Leu Ile Val
                595                 600                 605

Pro Tyr Val Gly Leu Ala Leu Asn Ile Val Ile Glu Ala Glu Lys Gly
                610                 615                 620

Asn Phe Glu Glu Ala Phe Glu Leu Leu Gly Ala Gly Ile Leu Leu Glu
625                 630                 635                 640

Phe Val Pro Glu Leu Thr Ile Pro Val Ile Leu Val Phe Thr Ile Lys
                645                 650                 655

Ser Tyr Ile Asp Ser Tyr Glu Asn Lys Asn Lys Ala Ile Lys Ala Ile
                660                 665                 670

Asn Asn Ser Leu Ile Glu Arg Glu Ala Lys Trp Lys Glu Ile Tyr Ser
                675                 680                 685

Trp Ile Val Ser Asn Trp Leu Thr Arg Ile Asn Thr Gln Phe Asn Lys
                690                 695                 700

Arg Lys Glu Gln Met Tyr Gln Ala Leu Gln Asn Gln Val Asp Ala Ile
705                 710                 715                 720

Lys Thr Ala Ile Glu Tyr Lys Tyr Asn Asn Tyr Thr Ser Asp Glu Lys
                725                 730                 735

Asn Arg Leu Glu Ser Lys Tyr Asn Ile Asn Asn Ile Glu Glu Glu Leu
                740                 745                 750

Asn Lys Lys Val Ser Leu Ala Met Lys Asn Ile Glu Arg Phe Met Thr
                755                 760                 765

Glu Ser Ser Ile Ser Tyr Leu Met Lys Leu Ile Asn Glu Ala Glu Val
                770                 775                 780

Gly Lys Leu Lys Glu Tyr Asp Lys His Val Lys Ser Asp Leu Leu Asp
785                 790                 795                 800

Tyr Ile Leu Tyr His Lys Leu Ile Leu Gly Glu Gln Thr Lys Glu Leu
                805                 810                 815

Ile Asp Leu Val Thr Ser Thr Leu Asn Ser Ser Ile Pro Phe Glu Leu
                820                 825                 830

Ser Ser

<210> SEQ ID NO 20
<211> LENGTH: 834
<212> TYPE: PRT
<213> ORGANISM: Clostridium botulinum

<400> SEQUENCE: 20

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
                20                  25                  30

Pro Glu Arg Asp Thr Ile Gly Thr Lys Pro Asp Glu Phe Gln Val Pro
                35                  40                  45

Asp Ser Leu Lys Asn Gly Ser Ser Ala Tyr Tyr Asp Pro Asn Tyr Leu
                50                  55                  60

Thr Thr Asp Ala Glu Lys Asp Arg Tyr Leu Lys Thr Met Ile Lys Leu
```

-continued

```
                65                  70                  75                  80
        Phe Asn Arg Ile Asn Ser Asn Pro Thr Gly Lys Val Leu Leu Glu Glu
                            85                  90                  95

Val Ser Asn Ala Arg Pro Tyr Leu Gly Asp Asp Thr Leu Ile Asn
                        100                 105                 110

Glu Phe Leu Pro Val Asn Val Thr Thr Ser Val Asn Ile Lys Phe Ser
                        115                 120                 125

Thr Asp Val Glu Ser Ser Ile Ile Ser Asn Leu Leu Val Leu Gly Ala
                    130                 135                 140

Gly Pro Asp Ile Phe Lys Ala Tyr Cys Thr Pro Leu Val Arg Phe Asn
        145                 150                 155                 160

Lys Ser Asp Lys Leu Ile Glu Pro Ser Asn His Gly Phe Gly Ser Ile
                            165                 170                 175

Asn Ile Leu Thr Phe Ser Pro Glu Tyr Glu His Ile Phe Asn Asp Ile
                        180                 185                 190

Ser Gly Gly Asn His Asn Ser Thr Glu Ser Phe Ile Ala Asp Pro Ala
                        195                 200                 205

Ile Ser Leu Ala His Glu Leu Ile His Ala Leu His Gly Leu Tyr Gly
                    210                 215                 220

Ala Lys Ala Val Thr His Lys Glu Ser Leu Val Ala Glu Arg Gly Pro
        225                 230                 235                 240

Leu Met Ile Ala Glu Lys Pro Ile Arg Leu Glu Glu Phe Leu Thr Phe
                            245                 250                 255

Gly Gly Glu Asp Leu Asn Ile Ile Pro Ser Ala Met Lys Glu Lys Ile
                        260                 265                 270

Tyr Asn Asp Leu Leu Ala Asn Tyr Glu Lys Ile Ala Thr Arg Leu Arg
                        275                 280                 285

Glu Val Asn Thr Ala Pro Pro Gly Tyr Asp Ile Asn Glu Tyr Lys Asp
                    290                 295                 300

Tyr Phe Gln Trp Lys Tyr Gly Leu Asp Arg Asn Ala Asp Gly Ser Tyr
        305                 310                 315                 320

Thr Val Asn Arg Asn Lys Phe Asn Glu Ile Tyr Lys Lys Leu Tyr Ser
                            325                 330                 335

Phe Thr Glu Ile Asp Leu Ala Asn Lys Phe Lys Val Lys Cys Arg Asn
                        340                 345                 350

Thr Tyr Phe Ile Lys Tyr Gly Phe Val Lys Val Pro Asn Leu Leu Asp
                        355                 360                 365

Asp Asp Ile Tyr Thr Val Ser Glu Gly Phe Asn Ile Gly Asn Leu Ala
                    370                 375                 380

Val Asn Asn Arg Gly Gln Asn Ile Asn Leu Asn Pro Lys Ile Ile Asp
        385                 390                 395                 400

Ser Ile Pro Asp Lys Gly Leu Val Glu Lys Ile Lys Phe Cys Lys
                            405                 410                 415

Ser Ile Ile Pro Arg Lys Gly Thr Lys Gln Ser Pro Ser Leu Cys Ile
                        420                 425                 430

Arg Val Asn Asn Arg Glu Leu Phe Phe Val Ala Ser Glu Ser Ser Tyr
                        435                 440                 445

Asn Glu Ser Asp Ile Asn Thr Pro Lys Glu Ile Asp Asp Thr Thr Asn
                    450                 455                 460

Leu Asn Asn Asn Tyr Arg Asn Asn Leu Asp Glu Val Ile Leu Asp Tyr
        465                 470                 475                 480

Asn Ser Glu Thr Ile Pro Gln Ile Ser Asn Arg Thr Leu Asn Thr Leu
                            485                 490                 495
```

```
Val Gln Asp Asn Ser Tyr Val Pro Arg Tyr Asp Ser Asn Gly Thr Ser
            500                 505                 510

Glu Ile Glu Glu Tyr Asp Val Asp Phe Asn Val Phe Tyr Leu
            515                 520                 525

His Ala Gln Lys Val Pro Glu Gly Thr Asn Ile Ser Leu Thr Ser
            530                 535                 540

Ser Ile Asp Thr Ala Leu Leu Glu Glu Ser Lys Val Tyr Thr Phe Phe
545                 550                 555                 560

Ser Ser Glu Phe Ile Asp Thr Ile Asn Lys Pro Val Asn Ala Ala Leu
                565                 570                 575

Phe Ile Asp Trp Ile Ser Lys Val Ile Arg Asp Phe Thr Thr Glu Ala
            580                 585                 590

Thr Gln Lys Ser Thr Val Asp Lys Ile Ala Asp Ile Ser Leu Ile Val
            595                 600                 605

Pro Tyr Val Gly Leu Ala Leu Asn Ile Val Ile Glu Ala Glu Lys Gly
            610                 615                 620

Asn Phe Glu Glu Ala Phe Glu Leu Leu Gly Ala Gly Ile Leu Leu Glu
625                 630                 635                 640

Phe Val Pro Glu Leu Thr Ile Pro Val Ile Leu Val Phe Thr Ile Lys
                645                 650                 655

Ser Tyr Ile Asp Ser Tyr Glu Asn Lys Asn Lys Ala Ile Lys Ala Ile
            660                 665                 670

Asn Asn Ser Leu Ile Glu Arg Glu Ala Lys Trp Lys Glu Ile Tyr Ser
            675                 680                 685

Trp Ile Val Ser Asn Trp Leu Thr Arg Ile Asn Thr Gln Phe Asn Lys
            690                 695                 700

Arg Lys Glu Gln Met Tyr Gln Ala Leu Gln Asn Gln Val Asp Ala Ile
705                 710                 715                 720

Lys Thr Ala Ile Glu Tyr Lys Tyr Asn Asn Tyr Thr Ser Asp Glu Lys
                725                 730                 735

Asn Arg Leu Glu Ser Lys Tyr Asn Ile Asn Asn Ile Glu Glu Glu Leu
            740                 745                 750

Asn Lys Lys Val Ser Leu Ala Met Lys Asn Ile Glu Arg Phe Met Thr
            755                 760                 765

Glu Ser Ser Ile Ser Tyr Leu Met Lys Leu Ile Asn Glu Ala Glu Val
            770                 775                 780

Gly Lys Leu Lys Glu Tyr Asp Lys His Val Lys Ser Asp Leu Leu Asp
785                 790                 795                 800

Tyr Ile Leu Tyr His Lys Leu Ile Leu Gly Glu Gln Thr Lys Glu Leu
                805                 810                 815

Ile Asp Leu Val Thr Ser Thr Leu Asn Ser Ser Ile Pro Phe Glu Leu
            820                 825                 830

Ser Ser

<210> SEQ ID NO 21
<211> LENGTH: 834
<212> TYPE: PRT
<213> ORGANISM: Clostridium botulinum

<400> SEQUENCE: 21

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
                20                  25                  30
```

```
Pro Glu Arg Asp Thr Ile Gly Thr Lys Pro Asp Asp Phe Gln Val Pro
            35                  40                  45

Asp Ser Leu Lys Asn Gly Ser Ser Ala Tyr Tyr Asp Pro Asn Tyr Leu
            50                  55                  60

Thr Thr Asp Ala Glu Lys Asp Arg Tyr Leu Lys Thr Met Ile Lys Leu
 65              70                  75                      80

Phe Asn Arg Ile Asn Ser Asn Pro Thr Gly Lys Val Leu Leu Glu Glu
                    85                  90                  95

Val Ser Asn Ala Arg Pro Tyr Leu Gly Asp Asp Thr Leu Ile Asn
                100                 105                 110

Glu Phe Phe Pro Val Asn Val Thr Thr Ser Val Asn Ile Lys Phe Ser
            115                 120                 125

Thr Asp Val Glu Ser Ser Ile Ile Ser Asn Leu Leu Val Leu Gly Ala
            130                 135                 140

Gly Pro Asp Ile Phe Lys Ala Tyr Cys Thr Pro Leu Val Arg Phe Asn
145                 150                 155                 160

Lys Ser Asp Lys Leu Ile Glu Pro Ser Asn His Gly Phe Gly Ser Ile
                165                 170                 175

Asn Ile Leu Thr Phe Ser Pro Glu Tyr Glu His Ile Phe Asn Asp Ile
                180                 185                 190

Ser Gly Gly Asp His Asn Ser Thr Glu Ser Phe Ile Ala Asp Pro Ala
            195                 200                 205

Ile Ser Leu Ala His Glu Leu Ile His Ala Leu His Gly Leu Tyr Gly
            210                 215                 220

Ala Lys Ala Val Thr His Lys Glu Thr Ile Glu Val Lys Arg Gly Pro
225                 230                 235                 240

Leu Met Ile Ala Glu Lys Pro Ile Arg Leu Glu Glu Phe Leu Thr Phe
                245                 250                 255

Gly Gly Glu Asp Leu Asn Ile Ile Pro Ser Ala Met Lys Glu Lys Ile
                260                 265                 270

Tyr Asn Asp Leu Leu Ala Asn Tyr Glu Lys Ile Ala Thr Arg Leu Arg
            275                 280                 285

Glu Val Asn Thr Ala Pro Pro Glu Tyr Asp Ile Asn Glu Tyr Lys Asp
            290                 295                 300

Tyr Phe Gln Trp Lys Tyr Gly Leu Asp Arg Asn Ala Asp Gly Ser Tyr
305                 310                 315                 320

Thr Val Asn Arg Asn Lys Phe Asn Gly Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Val Lys Val Pro Asp Leu Leu Asp
            355                 360                 365

Asp Asp Ile Tyr Thr Val Ser Glu Gly Phe Asn Ile Gly Asn Leu Ala
370                 375                 380

Val Asn Asn Arg Gly Gln Asn Ile Asn Leu Asn Pro Lys Ile Ile Asp
385                 390                 395                 400

Ser Ile Pro Asp Lys Gly Leu Val Glu Lys Ile Ile Lys Phe Cys Lys
                405                 410                 415

Ser Ile Ile Pro Arg Lys Gly Thr Lys Gln Ser Pro Ser Leu Cys Ile
                420                 425                 430

Arg Val Asn Asn Arg Glu Leu Phe Phe Val Ala Ser Glu Ser Ser Tyr
            435                 440                 445
```

```
Asn Glu Ser Asp Ile Asn Thr Pro Lys Glu Ile Asp Thr Thr Asn
    450                 455                 460

Leu Asn Asn Asn Tyr Arg Asn Asn Leu Asp Glu Val Ile Leu Asp Tyr
465                 470                 475                 480

Asn Ser Glu Thr Ile Pro Gln Ile Ser Asn Arg Thr Leu Asn Thr Leu
                485                 490                 495

Val Gln Asp Asn Ser Tyr Val Pro Arg Tyr Asp Ser Asn Gly Thr Ser
            500                 505                 510

Glu Ile Glu Glu Tyr Asp Val Asp Phe Asn Val Phe Phe Tyr Leu
        515                 520                 525

His Ala Gln Lys Val Pro Glu Gly Thr Asn Ile Ser Leu Thr Ser
    530                 535                 540

Ser Ile Asp Thr Ala Leu Leu Glu Lys Ser Lys Val Tyr Thr Phe Phe
545                 550                 555                 560

Ser Ser Glu Phe Ile Asp Thr Ile Asn Glu Ser Val Asn Ala Ala Leu
                565                 570                 575

Phe Ile Asp Trp Ile Asn Lys Val Ile Arg Asp Phe Thr Glu Ala
            580                 585                 590

Thr Gln Lys Ser Thr Val Asp Lys Ile Ala Asp Ile Ser Leu Ile Val
            595                 600                 605

Pro Tyr Val Gly Leu Ala Leu Asn Ile Val Ile Asp Ala Glu Lys Gly
    610                 615                 620

Asn Phe Gln Glu Ala Phe Glu Leu Leu Gly Ala Gly Ile Leu Leu Glu
625                 630                 635                 640

Phe Val Pro Glu Leu Thr Ile Pro Val Ile Leu Val Phe Thr Ile Lys
                645                 650                 655

Ser Tyr Ile Asp Ser Tyr Glu Asn Lys Asn Lys Ala Ile Lys Ala Ile
            660                 665                 670

Asn Asn Ala Leu Ile Glu Arg Glu Ala Lys Trp Lys Glu Ile Tyr Ser
            675                 680                 685

Trp Ile Val Ser Asn Trp Leu Thr Lys Ile Asn Thr Gln Phe Asn Lys
    690                 695                 700

Arg Lys Glu Gln Met Tyr Gln Ala Leu Gln Asn Gln Val Asp Ala Ile
705                 710                 715                 720

Lys Thr Ala Ile Glu Tyr Lys Tyr Asn Asn Tyr Thr Ser Asp Glu Lys
                725                 730                 735

Asn Arg Leu Glu Ser Glu Tyr Asn Ile Asn Asn Ile Glu Glu Leu
            740                 745                 750

Asn Lys Lys Val Ser Leu Ala Met Lys Asn Ile Glu Arg Phe Met Thr
755                 760                 765

Glu Ser Ser Ile Ser Tyr Leu Met Lys Leu Ile Asn Glu Ala Glu Val
770                 775                 780

Gly Lys Leu Lys Lys Tyr Asp Arg His Val Lys Ser Asp Leu Leu Asp
785                 790                 795                 800

Tyr Ile Leu Tyr His Lys Leu Ile Leu Gly Asp Gln Thr Lys Glu Leu
                805                 810                 815

Ile Asp Leu Val Thr Ser Thr Leu Asn Ser Ser Ile Pro Phe Glu Leu
            820                 825                 830

Ser Ser

<210> SEQ ID NO 22
<211> LENGTH: 834
<212> TYPE: PRT
<213> ORGANISM: Clostridium botulinum
```

<400> SEQUENCE: 22

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Met
            20                  25                  30

Pro Glu Arg Asn Thr Ile Gly Thr Asn Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Glu Val Leu Leu Gln Glu
                85                  90                  95

Ile Ser Tyr Ala Lys Pro Tyr Leu Gly Asn Asp His Thr Pro Ile Asn
            100                 105                 110

Glu Phe His Pro Val Thr Arg Thr Ser Val Asn Ile Lys Ser Ser
        115                 120                 125

Thr Asn Val Glu Ser Ser Ile Ile Leu Asn Leu Leu Val Leu Gly Ala
130                 135                 140

Gly Pro Asn Ile Phe Glu Asn Ser Ser Tyr Pro Val Arg Lys Leu Met
145                 150                 155                 160

Asn Ser Gly Glu Val Tyr Asp Pro Ser Asn Asp Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
            260                 265                 270

Tyr Asn Asp Leu Leu Ala Asn Tyr Glu Lys Ile Ala Thr Arg Leu Ser
        275                 280                 285

Glu Val Asn Ser Ala Pro Pro Glu Tyr Asp Ile Asn Glu Tyr Lys Asn
    290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
        355                 360                 365

Asp Asp Ile Tyr Thr Val Ser Glu Gly Phe Asn Ile Gly Asn Leu Ala
    370                 375                 380

Val Asn Asn Arg Gly Gln Asn Ile Asn Leu Asn Pro Lys Ile Ile Asp
385                 390                 395                 400

Ser Ile Pro Asp Lys Gly Leu Val Glu Lys Ile Val Lys Leu Cys Lys

```
            405                 410                 415
Ser Ile Ile Pro Arg Lys Gly Thr Lys Ala Pro Pro Arg Leu Cys Ile
        420                 425                 430

Arg Val Asn Asn Arg Glu Leu Phe Phe Val Ala Ser Glu Ser Ser Tyr
            435                 440                 445

Asn Glu Asn Asp Ile Asn Thr Pro Lys Glu Ile Asp Asp Thr Thr Asn
        450                 455                 460

Leu Asn Asn Asn Tyr Arg Asn Asn Leu Asp Glu Val Ile Leu Asp Tyr
465                 470                 475                 480

Asn Ser Glu Thr Ile Pro Gln Ile Ser Ser Gln Thr Leu Asn Thr Leu
            485                 490                 495

Val Gln Asp Asp Ser Tyr Val Pro Arg Tyr Asp Ser Asn Gly Thr Ser
        500                 505                 510

Glu Ile Glu Glu His Asn Val Val Asp Leu Asn Ala Phe Phe Tyr Leu
        515                 520                 525

His Ala Gln Lys Val Pro Glu Gly Glu Thr Asn Ile Ser Leu Thr Ser
        530                 535                 540

Ser Ile Asp Thr Ala Leu Ser Glu Glu Ser Lys Val Tyr Thr Phe Phe
545                 550                 555                 560

Ser Ser Glu Phe Ile Asn Asn Ile Asn Lys Pro Val His Ala Ala Leu
                565                 570                 575

Phe Ile Gly Trp Ile Ser Gln Val Ile Arg Asp Phe Thr Thr Glu Ser
            580                 585                 590

Thr Gln Lys Ser Thr Val Asp Lys Ile Ala Asp Ile Ser Leu Ile Val
        595                 600                 605

Pro Tyr Val Gly Leu Ala Leu Asn Ile Gly Asn Asp Ala Arg Lys Gly
    610                 615                 620

Asn Phe Lys Glu Ala Phe Glu Leu Leu Gly Ala Ala Ile Leu Leu Glu
625                 630                 635                 640

Val Val Pro Glu Leu Leu Ile Pro Val Ile Leu Val Phe Thr Ile Lys
            645                 650                 655

Ser Phe Ile Asp Ser Ser Lys Asn Glu Asp Lys Ile Ile Lys Ala Ile
        660                 665                 670

Asn Asn Ser Leu Ile Glu Arg Glu Ala Lys Trp Lys Glu Val Tyr Ser
        675                 680                 685

Trp Ile Val Ser Asn Trp Leu Thr Arg Ile Asn Thr Gln Phe Asn Lys
    690                 695                 700

Arg Lys Glu Gln Met Tyr Gln Ala Leu Gln Asn Gln Val Asp Ala Ile
705                 710                 715                 720

Lys Thr Val Ile Glu Tyr Lys Tyr Asn Ser Tyr Thr Ser Asp Glu Lys
            725                 730                 735

Asn Arg Leu Glu Ser Glu Tyr Asn Ile Asn Asn Ile Glu Glu Glu Leu
        740                 745                 750

Asn Lys Lys Val Ser Leu Ala Met Lys Asn Ile Glu Arg Phe Ile Ala
        755                 760                 765

Glu Ser Ser Ile Ser Tyr Leu Met Lys Leu Ile Asn Glu Ala Lys Val
    770                 775                 780

Ser Glu Leu Arg Glu Tyr Asp Glu Gly Val Lys Glu Tyr Leu Leu Asp
785                 790                 795                 800

Tyr Ile Leu Lys Asn Gly Ser Ile Leu Gly Asp His Val Gln Glu Leu
            805                 810                 815

Asn Asp Leu Val Thr Ser Thr Leu Asn Ser Ser Ile Pro Phe Glu Leu
        820                 825                 830
```

Ser Ser

<210> SEQ ID NO 23
<211> LENGTH: 834
<212> TYPE: PRT
<213> ORGANISM: Clostridium botulinum

<400> SEQUENCE: 23

```
Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Met
            20                  25                  30

Pro Glu Arg Asn Thr Ile Gly Thr Asn Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Glu Val Leu Leu Gln Glu
                85                  90                  95

Ile Ser Tyr Ala Lys Pro Tyr Leu Gly Asn Asp His Thr Pro Ile Asn
            100                 105                 110

Glu Phe His Pro Val Thr Arg Thr Thr Ser Val Asn Ile Lys Ser Ser
        115                 120                 125

Thr Asn Val Glu Ser Ser Ile Ile Leu Asn Leu Leu Val Leu Gly Ala
    130                 135                 140

Gly Pro Asn Ile Phe Glu Asn Ser Ser Tyr Pro Val Arg Lys Leu Met
145                 150                 155                 160

Asn Ser Gly Glu Val Tyr Asp Pro Ser Asn Asp Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
            260                 265                 270

Tyr Asn Asp Leu Leu Ala Asn Tyr Glu Lys Ile Ala Thr Arg Leu Ser
        275                 280                 285

Glu Val Asn Ser Ala Pro Pro Glu Tyr Asp Ile Asn Glu Tyr Lys Asn
    290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
        355                 360                 365
```

```
Asp Asp Ile Tyr Thr Val Ser Glu Gly Phe Asn Ile Gly Asn Leu Ala
    370             375                 380
Val Asn Asn Arg Gly Gln Asn Ile Asn Leu Asn Pro Lys Ile Ile Asp
385             390                 395                 400
Ser Ile Pro Asp Lys Gly Leu Val Glu Lys Ile Val Lys Leu Cys Lys
            405                 410                 415
Ser Ile Ile Pro Arg Lys Gly Thr Lys Ala Pro Pro Arg Leu Cys Ile
            420                 425                 430
Arg Val Asn Asn Arg Glu Leu Phe Phe Val Ala Ser Glu Ser Ser Tyr
        435                 440                 445
Asn Glu Asn Asp Ile Asn Thr Pro Lys Glu Ile Asp Asp Thr Thr Asn
    450                 455                 460
Leu Asn Asn Asn Tyr Arg Asn Asn Leu Asp Glu Val Ile Leu Asp Tyr
465                 470                 475                 480
Asn Ser Glu Thr Ile Pro Gln Ile Ser Ser Gln Thr Leu Asn Thr Leu
                485                 490                 495
Val Gln Asp Asp Ser Tyr Val Pro Arg Tyr Asp Ser Asn Gly Thr Ser
            500                 505                 510
Glu Ile Glu Glu His Asn Val Val Asp Leu Asn Ala Phe Phe Tyr Leu
            515                 520                 525
His Ala Gln Lys Val Pro Glu Gly Gly Thr Asn Ile Ser Leu Thr Ser
    530                 535                 540
Ser Ile Asp Thr Ala Leu Ser Glu Glu Ser Lys Val Tyr Thr Phe Phe
545                 550                 555                 560
Ser Ser Glu Phe Ile Asn Asn Ile Asn Lys Pro Val His Ala Ala Leu
                565                 570                 575
Phe Ile Gly Trp Ile Ser Gln Val Ile Arg Asp Phe Thr Thr Glu Ser
            580                 585                 590
Thr Gln Lys Ser Thr Val Asp Lys Ile Ala Asp Ile Ser Leu Ile Val
        595                 600                 605
Pro Tyr Val Gly Leu Ala Leu Asn Ile Gly Asn Asp Ala Arg Lys Gly
    610                 615                 620
Asn Phe Lys Glu Ala Phe Glu Leu Leu Gly Ala Ala Ile Leu Leu Glu
625                 630                 635                 640
Val Val Pro Glu Leu Leu Ile Pro Val Ile Leu Val Phe Thr Ile Lys
                645                 650                 655
Ser Phe Ile Asp Ser Ser Lys Asn Glu Asp Lys Ile Ile Lys Ala Ile
            660                 665                 670
Asn Asn Ser Leu Ile Glu Arg Glu Ala Lys Trp Lys Glu Val Tyr Ser
        675                 680                 685
Trp Ile Val Ser Asn Trp Leu Thr Arg Ile Asn Thr Gln Phe Asn Lys
    690                 695                 700
Arg Lys Glu Gln Met Tyr Gln Ala Leu Gln Asn Gln Val Asp Ala Ile
705                 710                 715                 720
Lys Thr Val Ile Glu Tyr Lys Tyr Asn Ser Tyr Thr Ser Asp Glu Lys
                725                 730                 735
Asn Arg Leu Glu Ser Glu Tyr Asn Ile Asn Asn Ile Glu Glu Glu Leu
            740                 745                 750
Asn Lys Lys Val Ser Leu Ala Met Lys Asn Ile Glu Arg Phe Ile Ala
        755                 760                 765
Glu Ser Ser Ile Ser Tyr Leu Met Lys Leu Ile Asn Glu Ala Lys Val
    770                 775                 780
```

Ser Glu Leu Arg Glu Tyr Asp Glu Gly Val Lys Glu Tyr Leu Leu Asp
785                 790                 795                 800

Tyr Ile Leu Lys Asn Gly Ser Ile Leu Gly Asp His Val Gln Glu Leu
            805                 810                 815

Asn Asp Leu Val Thr Ser Thr Leu Asn Ser Ser Ile Pro Phe Glu Leu
            820                 825                 830

Ser Ser

<210> SEQ ID NO 24
<211> LENGTH: 831
<212> TYPE: PRT
<213> ORGANISM: Clostridium botulinum

<400> SEQUENCE: 24

Asn Asp Asn Thr Ile Leu Tyr Ile Arg Pro Pro Tyr Tyr Glu Arg Ser
1               5                   10                  15

Asn Thr Tyr Phe Lys Ala Phe Asn Ile Met Glu Asn Val Trp Ile Ile
            20                  25                  30

Pro Glu Arg Tyr Arg Leu Gly Ile Glu Ala Ser Lys Phe Asp Pro Pro
        35                  40                  45

Asp Ser Leu Lys Ala Gly Ser Asp Gly Tyr Phe Asp Pro Asn Tyr Leu
    50                  55                  60

Ser Thr Asn Thr Glu Lys Asn Arg Tyr Leu Gln Ile Met Ile Lys Leu
65                  70                  75                  80

Phe Lys Arg Ile Asn Ser Asn Glu Ala Gly Lys Ile Leu Leu Asn Gln
                85                  90                  95

Ile Lys Asp Ala Ile Pro Tyr Leu Gly Asn Ser Tyr Thr Ala Glu Asp
            100                 105                 110

Gln Phe Thr Thr Asn Asn Arg Thr Ile Ser Phe Asn Val Arg Leu Ala
        115                 120                 125

Asn Gly Thr Ile Glu Gln Glu Met Ala Asn Leu Ile Ile Trp Gly Pro
130                 135                 140

Gly Pro Asp Leu Thr Thr Asn Arg Thr Gly Gly Thr Thr Tyr Thr Pro
145                 150                 155                 160

Ala Gln Ser Leu Glu Ala Ile Pro Tyr Lys Glu Gly Phe Gly Ser Ile
                165                 170                 175

Met Thr Ile Glu Phe Ser Pro Glu Tyr Ala Thr Ala Phe Asn Asp Ile
            180                 185                 190

Ser Leu Thr Ser His Ala Pro Ser Leu Phe Ile Lys Asp Pro Ala Leu
        195                 200                 205

Ile Leu Met His Glu Leu Ile His Val Leu His Gly Leu Tyr Gly Thr
210                 215                 220

Tyr Thr Thr Gly Phe Lys Ile Lys Pro Asn Ile Thr Glu Pro Tyr Met
225                 230                 235                 240

Glu Val Thr Lys Pro Ile Thr Ser Gly Glu Phe Leu Thr Phe Gly Gly
                245                 250                 255

Asn Asp Val Asn Lys Ile Pro Gln Leu Ile Gln Ser Gln Leu Arg Ser
            260                 265                 270

Lys Val Leu Asp Asp Tyr Glu Lys Ile Ala Ser Arg Leu Asn Lys Val
        275                 280                 285

Asn Arg Ala Thr Ala Glu Ile Asn Ile Asp Lys Phe Lys Tyr Ser Tyr
    290                 295                 300

Gln Leu Lys Tyr Gln Phe Val Leu Asp Ser Asn Gly Tyr Ser Val
305                 310                 315                 320

```
Asp Leu Asp Lys Phe Asn Lys Leu Tyr Asp Lys Ile Tyr Ser Phe Thr
            325                 330                 335

Glu Phe Asn Leu Ala His Glu Phe Lys Ile Lys Thr Arg Asn Ser Tyr
        340                 345                 350

Leu Ala Lys Asn Phe Gly Pro Phe Tyr Leu Pro Asn Leu Leu Asp Asn
            355                 360                 365

Ser Ile Tyr Asn Glu Ala Asp Gly Phe Asn Ile Gly Asp Leu Ser Val
        370                 375                 380

Asn Tyr Lys Gly Gln Val Ile Gly Ser Asp Ile Asp Ser Ile Lys Lys
385                 390                 395                 400

Leu Glu Gly Gln Gly Val Val Ser Arg Val Arg Leu Cys Leu Asn
                405                 410                 415

Ser Ser Phe Lys Lys Asn Thr Lys Lys Pro Leu Cys Ile Thr Val Asn
            420                 425                 430

Asn Gly Asp Leu Phe Phe Ile Ala Ser Glu Asp Ser Tyr Gly Glu Asp
            435                 440                 445

Thr Ile Asn Thr Pro Lys Glu Ile Asp Asp Thr Thr Leu Val Pro
        450                 455                 460

Ser Phe Lys Asn Ile Leu Asp Lys Val Ile Leu Asp Phe Asn Lys Gln
465                 470                 475                 480

Val Thr Pro Gln Ile Pro Asn Arg Arg Ile Arg Thr Asp Ile Gln Glu
                485                 490                 495

Asp Asn Tyr Ile Pro Glu Tyr Asp Ser Asn Gly Thr Ser Glu Ile Glu
                500                 505                 510

Glu Tyr Asn Val Val Asp Leu Asn Ala Phe Phe Tyr Leu His Ala Gln
        515                 520                 525

Lys Val Pro Glu Gly Glu Thr Asn Ile Ser Leu Thr Ser Ser Ile Asp
        530                 535                 540

Thr Ala Leu Ser Glu Glu Ser Lys Val Tyr Thr Phe Phe Ser Ser Glu
545                 550                 555                 560

Phe Ile Asp Thr Ile Asn Glu Pro Val Asn Ala Ala Leu Phe Ile Asp
                565                 570                 575

Trp Ile Ser Lys Val Ile Arg Asp Phe Thr Thr Glu Ala Thr Gln Lys
            580                 585                 590

Ser Thr Val Asp Lys Ile Ala Asp Ile Ser Leu Ile Val Pro Tyr Val
        595                 600                 605

Gly Leu Ala Leu Asn Ile Val Asn Glu Thr Glu Lys Gly Asn Phe Lys
        610                 615                 620

Glu Ala Phe Glu Leu Leu Gly Ala Gly Ile Leu Leu Glu Phe Val Pro
625                 630                 635                 640

Glu Leu Ala Ile Pro Val Ile Leu Val Phe Thr Ile Lys Ser Tyr Ile
                645                 650                 655

Asp Ser Tyr Glu Asn Lys Asn Lys Ile Ile Lys Ala Ile Asn Asn Ser
            660                 665                 670

Leu Ile Glu Arg Glu Ala Lys Trp Lys Glu Ile Tyr Ser Trp Ile Val
        675                 680                 685

Ser Asn Trp Leu Thr Arg Ile Asn Thr Gln Phe Asn Lys Arg Lys Glu
        690                 695                 700

Gln Met Tyr Gln Ala Leu Gln Asn Gln Val Asp Ala Ile Lys Thr Ala
705                 710                 715                 720

Ile Glu Tyr Lys Tyr Asn Asn Tyr Thr Ser Asp Glu Lys Asn Arg Leu
                725                 730                 735

Glu Ser Glu Tyr Asn Ile Asn Asn Ile Glu Glu Glu Leu Asn Lys Lys
```

-continued

```
                740                 745                 750
Val Ser Leu Ala Met Lys Asn Ile Glu Arg Phe Ile Thr Glu Ser Ser
            755                 760                 765

Ile Ser Tyr Leu Met Lys Leu Ile Asn Glu Ala Glu Val Gly Lys Leu
        770                 775                 780

Lys Glu Tyr Asp Lys Arg Val Lys Arg His Leu Glu Tyr Ile Phe
785                 790                 795                 800

Asp Tyr Arg Leu Ile Leu Gly Glu Gln Gly Gly Glu Leu Ile Asp Leu
                805                 810                 815

Val Thr Ser Thr Leu Asn Thr Ser Ile Pro Phe Glu Leu Ser Ser
            820                 825                 830

<210> SEQ ID NO 25
<211> LENGTH: 834
<212> TYPE: PRT
<213> ORGANISM: Clostridium botulinum

<400> SEQUENCE: 25

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
            20                  25                  30

Pro Glu Arg Asn Thr Ile Gly Thr Asn Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Lys Val Leu Leu Gln Glu
                85                  90                  95

Ile Ser Tyr Ala Lys Pro Tyr Leu Gly Asn Asp His Thr Pro Ile Asp
            100                 105                 110

Glu Phe Ser Pro Val Thr Arg Thr Thr Ser Val Asn Ile Lys Leu Ser
        115                 120                 125

Thr Asn Val Glu Ser Ser Met Leu Leu Asn Leu Leu Val Leu Gly Ala
    130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
            260                 265                 270

Tyr Asn Asn Leu Leu Ala Asn Tyr Glu Lys Ile Ala Thr Arg Leu Ser
        275                 280                 285
```

-continued

```
Glu Val Asn Ser Ala Pro Pro Glu Tyr Asp Ile Asn Glu Tyr Lys Asp
    290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
            325                 330                 335

Phe Thr Glu Ser Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
            355                 360                 365

Asp Asp Ile Tyr Thr Val Ser Glu Gly Phe Asn Ile Gly Asn Leu Ala
370                 375                 380

Val Asn Asn Arg Gly Gln Ser Ile Lys Leu Asn Pro Lys Ile Ile Asp
385                 390                 395                 400

Ser Ile Pro Asp Lys Gly Leu Val Glu Lys Ile Val Lys Phe Cys Lys
                405                 410                 415

Ser Val Ile Pro Arg Lys Gly Thr Lys Ala Pro Pro Arg Leu Cys Ile
            420                 425                 430

Arg Val Asn Asn Ser Glu Leu Phe Phe Val Ala Ser Glu Ser Ser Tyr
            435                 440                 445

Asn Glu Asn Asp Ile Asn Thr Pro Lys Glu Ile Asp Asp Thr Thr Asn
450                 455                 460

Leu Asn Asn Asn Tyr Arg Asn Asn Leu Asp Glu Val Ile Leu Asp Tyr
465                 470                 475                 480

Asn Ser Gln Thr Ile Pro Gln Ile Ser Asn Arg Thr Leu Asn Thr Leu
                485                 490                 495

Val Gln Asp Asn Ser Tyr Val Pro Arg Tyr Asp Ser Asn Gly Thr Ser
            500                 505                 510

Glu Ile Glu Glu Tyr Asp Val Asp Phe Asn Val Phe Phe Tyr Leu
            515                 520                 525

His Ala Gln Lys Val Pro Glu Gly Glu Thr Asn Ile Ser Leu Thr Ser
            530                 535                 540

Ser Ile Asp Thr Ala Leu Leu Glu Glu Ser Lys Val Tyr Thr Phe Phe
545                 550                 555                 560

Ser Ser Glu Phe Ile Asp Thr Ile Asn Lys Pro Val Asn Ala Ala Leu
                565                 570                 575

Phe Ile Asp Trp Ile Ser Lys Val Ile Arg Asp Phe Thr Thr Glu Ala
            580                 585                 590

Thr Gln Lys Ser Thr Val Asp Lys Ile Ala Asp Ile Ser Leu Ile Val
            595                 600                 605

Pro Tyr Val Gly Leu Ala Leu Asn Ile Ile Glu Ala Glu Lys Gly
610                 615                 620

Asn Phe Glu Glu Ala Phe Glu Leu Leu Gly Val Gly Ile Leu Leu Glu
625                 630                 635                 640

Phe Val Pro Glu Leu Thr Ile Pro Val Ile Leu Val Phe Thr Ile Lys
                645                 650                 655

Ser Tyr Ile Asp Ser Tyr Glu Asn Lys Asn Lys Ala Ile Lys Ala Ile
            660                 665                 670

Asn Asn Ser Leu Ile Glu Arg Glu Ala Lys Trp Lys Glu Ile Tyr Ser
            675                 680                 685

Trp Ile Val Ser Asn Trp Leu Thr Arg Ile Asn Thr Gln Phe Asn Lys
690                 695                 700

Arg Lys Glu Gln Met Tyr Gln Ala Leu Gln Asn Gln Val Asp Ala Ile
```

```
            705                 710                 715                 720
Lys Thr Ala Ile Glu Tyr Lys Tyr Asn Asn Tyr Thr Ser Asp Glu Lys
                    725                 730                 735

Asn Arg Leu Glu Ser Glu Tyr Asn Ile Asn Ile Glu Glu Glu Leu
                740                 745                 750

Asn Lys Lys Val Ser Leu Ala Met Lys Asn Ile Glu Arg Phe Met Thr
                755                 760                 765

Glu Ser Ser Ile Ser Tyr Leu Met Lys Leu Ile Asn Glu Ala Lys Val
                770                 775                 780

Gly Lys Leu Lys Lys Tyr Asp Asn His Val Lys Ser Asp Leu Leu Asn
785                 790                 795                 800

Tyr Ile Leu Asp His Arg Ser Ile Leu Gly Glu Gln Thr Asn Glu Leu
                805                 810                 815

Ser Asp Leu Val Thr Ser Thr Leu Asn Ser Ser Ile Pro Phe Glu Leu
                820                 825                 830

Ser Ser
```

```
<210> SEQ ID NO 26
<211> LENGTH: 833
<212> TYPE: PRT
<213> ORGANISM: Clostridium botulinum

<400> SEQUENCE: 26

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
                20                  25                  30

Pro Glu Arg Asn Thr Ile Gly Thr Asn Pro Ser Asp Phe Asp Pro Pro
                35                  40                  45

Ala Ser Leu Lys Asn Gly Ser Ser Ala Tyr Tyr Asp Pro Asn Tyr Leu
50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Lys Val Leu Leu Gln Glu
                85                  90                  95

Ile Ser Tyr Ala Lys Pro Tyr Leu Gly Asn Asp His Thr Pro Ile Asp
                100                 105                 110

Glu Phe Ser Pro Val Thr Arg Thr Thr Ser Val Asn Ile Lys Leu Ser
                115                 120                 125

Thr Asn Val Glu Ser Ser Met Leu Leu Asn Leu Leu Val Leu Gly Ala
                130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                165                 170                 175

Asn Ile Val Thr Phe Ser Pro Glu Tyr Glu Tyr Thr Phe Asn Asp Ile
                180                 185                 190

Ser Gly Gly His Asn Ser Ser Thr Glu Ser Phe Ile Ala Asp Pro Ala
                195                 200                 205

Ile Ser Leu Ala His Glu Leu Ile His Ala Leu His Gly Leu Tyr Gly
                210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
```

-continued

```
            245                 250                 255
Gly Gly Gln Asp Leu Asn Ile Ile Thr Ser Ala Met Lys Glu Lys Ile
            260                 265                 270

Tyr Asn Asn Leu Leu Ala Asn Tyr Glu Lys Ile Ala Thr Arg Leu Ser
            275                 280                 285

Glu Val Asn Ser Ala Pro Pro Glu Tyr Asp Ile Asn Glu Tyr Lys Asp
            290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ser Asp Leu Ala Asn Lys Phe Lys Val Lys Cys Arg Asn
                340                 345                 350

Thr Tyr Phe Ile Lys Tyr Glu Phe Leu Lys Val Pro Asn Leu Leu Asp
                355                 360                 365

Asp Asp Ile Tyr Thr Val Ser Glu Gly Phe Asn Ile Gly Asn Leu Ala
            370                 375                 380

Val Asn Asn Arg Gly Gln Ser Ile Lys Leu Asn Pro Lys Ile Ile Asp
385                 390                 395                 400

Ser Ile Pro Asp Lys Gly Leu Val Glu Lys Ile Val Lys Phe Cys Lys
                405                 410                 415

Ser Val Ile Pro Arg Lys Gly Thr Lys Ala Pro Pro Arg Leu Cys Ile
                420                 425                 430

Arg Val Asn Asn Ser Glu Leu Phe Phe Val Ala Ser Glu Ser Ser Tyr
                435                 440                 445

Asn Glu Asn Asp Ile Asn Thr Pro Lys Glu Ile Asp Asp Thr Thr Asn
            450                 455                 460

Leu Asn Asn Asn Tyr Arg Asn Asn Leu Asp Glu Val Ile Leu Asp Tyr
465                 470                 475                 480

Asn Ser Gln Thr Ile Pro Gln Ile Ser Asn Arg Thr Leu Asn Thr Leu
                485                 490                 495

Val Gln Asp Asn Ser Tyr Val Pro Arg Tyr Asp Ser Asn Gly Thr Ser
                500                 505                 510

Glu Ile Glu Glu Tyr Asp Val Asp Phe Asn Val Phe Phe Tyr Leu
                515                 520                 525

His Ala Gln Lys Val Pro Glu Gly Glu Thr Asn Ile Ser Leu Thr Ser
            530                 535                 540

Ser Ile Asp Thr Ala Leu Leu Glu Glu Ser Lys Asp Ile Phe Phe Ser
545                 550                 555                 560

Ser Glu Phe Ile Asp Thr Ile Asn Lys Pro Val Asn Ala Ala Leu Phe
                565                 570                 575

Ile Asp Trp Ile Ser Lys Val Ile Arg Asp Phe Thr Thr Glu Ala Thr
                580                 585                 590

Gln Lys Ser Thr Val Asp Lys Ile Ala Asp Ile Ser Leu Ile Val Pro
                595                 600                 605

Tyr Val Gly Leu Ala Leu Asn Ile Ile Ile Glu Ala Glu Lys Gly Asn
            610                 615                 620

Phe Glu Glu Ala Phe Glu Leu Leu Gly Val Gly Ile Leu Leu Glu Phe
625                 630                 635                 640

Val Pro Glu Leu Thr Ile Pro Val Ile Leu Val Phe Thr Ile Lys Ser
                645                 650                 655

Tyr Ile Asp Ser Tyr Glu Asn Lys Asn Lys Ala Ile Lys Ala Ile Asn
            660                 665                 670
```

```
Asn Ser Leu Ile Glu Arg Glu Ala Lys Trp Lys Glu Ile Tyr Ser Trp
            675                 680                 685

Ile Val Ser Asn Trp Leu Thr Arg Ile Asn Thr Gln Phe Asn Lys Arg
        690                 695                 700

Lys Glu Gln Met Tyr Gln Ala Leu Gln Asn Gln Val Asp Ala Ile Lys
705                 710                 715                 720

Thr Ala Ile Glu Tyr Lys Tyr Asn Asn Tyr Thr Ser Asp Lys Asn
                725                 730                 735

Arg Leu Glu Ser Glu Tyr Asn Ile Asn Asn Ile Glu Glu Leu Asn
            740                 745                 750

Lys Lys Val Ser Leu Ala Met Lys Asn Ile Glu Arg Phe Met Thr Glu
755                 760                 765

Ser Ser Ile Ser Tyr Leu Met Lys Leu Ile Asn Glu Ala Lys Val Gly
        770                 775                 780

Lys Leu Lys Lys Tyr Asp Asn His Val Lys Ser Asp Leu Leu Asn Tyr
785                 790                 795                 800

Ile Leu Asp His Arg Ser Ile Leu Gly Glu Gln Thr Asn Glu Leu Ser
                805                 810                 815

Asp Leu Val Thr Ser Thr Leu Asn Ser Ser Ile Pro Phe Glu Leu Ser
            820                 825                 830

Ser

<210> SEQ ID NO 27
<211> LENGTH: 834
<212> TYPE: PRT
<213> ORGANISM: Clostridium botulinum

<400> SEQUENCE: 27

Asn Asp Asp Thr Ile Leu Tyr Met Gln Ile Pro Tyr Lys Glu Lys Ser
1               5                   10                  15

Lys Lys Tyr Tyr Lys Ala Phe Glu Ile Met Arg Asn Val Trp Ile Ile
            20                  25                  30

Pro Glu Arg Asn Thr Ile Gly Thr Asn Pro Ser Asp Phe Asp Pro Pro
        35                  40                  45

Ala Ser Leu Lys Asn Gly Ser Ser Ala Tyr Tyr Asp Pro Asn Tyr Leu
50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Lys Val Leu Leu Gln Glu
                85                  90                  95

Ile Ser Tyr Ala Lys Pro Tyr Leu Gly Asn Asp His Thr Pro Ile Asp
            100                 105                 110

Glu Phe Ser Pro Val Thr Arg Thr Thr Ser Val Asn Ile Lys Leu Ser
        115                 120                 125

Thr Asn Val Glu Ser Ser Met Leu Leu Asn Leu Leu Val Leu Gly Ala
130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205
```

```
Ile Ser Leu Ala His Glu Leu Ile His Ala Leu His Gly Leu Tyr Gly
    210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
                260                 265                 270

Tyr Asn Asn Leu Leu Ala Asn Tyr Glu Lys Ile Ala Thr Arg Leu Ser
            275                 280                 285

Glu Val Asn Ser Ala Pro Pro Glu Tyr Asp Ile Asn Glu Tyr Lys Asp
290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ser Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
            355                 360                 365

Asp Asp Ile Tyr Thr Val Ser Glu Gly Phe Asn Ile Gly Asn Leu Ala
370                 375                 380

Val Asn Asn Arg Gly Gln Ser Ile Lys Leu Asn Pro Lys Ile Ile Asp
385                 390                 395                 400

Ser Ile Pro Asp Lys Gly Leu Val Glu Lys Ile Val Lys Phe Cys Lys
                405                 410                 415

Ser Val Ile Pro Arg Lys Gly Thr Lys Ala Pro Pro Arg Leu Cys Ile
                420                 425                 430

Arg Val Asn Asn Ser Glu Leu Phe Phe Val Ala Ser Glu Ser Ser Tyr
            435                 440                 445

Asn Glu Asn Asp Ile Asn Thr Pro Lys Glu Ile Asp Asp Thr Thr Asn
450                 455                 460

Leu Asn Asn Asn Tyr Arg Asn Asn Leu Asp Glu Val Ile Leu Asp Tyr
465                 470                 475                 480

Asn Ser Gln Thr Ile Pro Gln Ile Ser Asn Arg Thr Leu Asn Thr Leu
                485                 490                 495

Val Gln Asp Asn Ser Tyr Val Pro Arg Tyr Asp Ser Asn Gly Thr Ser
                500                 505                 510

Glu Ile Glu Glu Tyr Asp Val Asp Phe Asn Val Phe Phe Tyr Leu
            515                 520                 525

His Ala Gln Lys Val Pro Glu Gly Glu Thr Asn Ile Ser Leu Thr Ser
530                 535                 540

Ser Ile Asp Thr Ala Leu Leu Glu Glu Ser Lys Val Tyr Thr Phe Phe
545                 550                 555                 560

Ser Ser Glu Phe Ile Asp Thr Ile Asn Lys Pro Val Asn Ala Ala Leu
                565                 570                 575

Phe Ile Asp Trp Ile Ser Lys Val Ile Arg Asp Phe Thr Thr Glu Ala
                580                 585                 590

Thr Gln Lys Ser Thr Val Asp Lys Ile Ala Asp Ile Ser Leu Ile Val
            595                 600                 605

Pro Tyr Val Gly Leu Ala Leu Asn Ile Ile Ile Glu Ala Glu Lys Gly
610                 615                 620
```

-continued

Asn Phe Glu Glu Ala Phe Glu Leu Leu Gly Val Gly Ile Leu Leu Glu
625                 630                 635                 640

Phe Val Pro Glu Leu Thr Ile Pro Val Ile Leu Val Phe Thr Ile Lys
            645                 650                 655

Ser Tyr Ile Asp Ser Tyr Glu Asn Lys Asn Lys Ala Ile Lys Ala Ile
            660                 665                 670

Asn Asn Ser Leu Ile Glu Arg Glu Ala Lys Trp Lys Glu Ile Tyr Ser
            675                 680                 685

Trp Ile Val Ser Asn Trp Leu Thr Arg Ile Asn Thr Gln Phe Asn Lys
690                 695                 700

Arg Lys Glu Gln Met Tyr Gln Ala Leu Gln Asn Gln Val Asp Ala Ile
705                 710                 715                 720

Lys Thr Ala Ile Glu Tyr Lys Tyr Asn Asn Tyr Thr Ser Asp Glu Lys
            725                 730                 735

Asn Arg Leu Glu Ser Glu Tyr Asn Ile Asn Asn Ile Glu Glu Glu Leu
            740                 745                 750

Asn Lys Lys Val Ser Leu Ala Met Lys Asn Ile Glu Arg Phe Met Thr
            755                 760                 765

Glu Ser Ser Ile Ser Tyr Leu Met Lys Leu Ile Asn Glu Ala Lys Val
770                 775                 780

Gly Lys Leu Lys Lys Tyr Asp Asn His Val Lys Ser Asp Leu Leu Asn
785                 790                 795                 800

Tyr Ile Leu Asp His Arg Ser Ile Leu Gly Glu Gln Thr Asn Glu Leu
            805                 810                 815

Ser Asp Leu Val Thr Ser Thr Leu Asn Ser Ser Ile Pro Phe Glu Leu
            820                 825                 830

Ser Ser

<210> SEQ ID NO 28
<211> LENGTH: 834
<212> TYPE: PRT
<213> ORGANISM: Clostridium botulinum

<400> SEQUENCE: 28

Asn Asp Asp Thr Ile Leu Tyr Met Gln Ile Pro Tyr Lys Glu Lys Ser
1               5                   10                  15

Lys Lys Tyr Tyr Lys Ala Phe Glu Ile Met Arg Asn Val Trp Ile Ile
            20                  25                  30

Pro Glu Arg Asn Thr Ile Gly Thr Asn Pro Ser Asp Phe Asp Pro Pro
            35                  40                  45

Ala Ser Leu Lys Asn Gly Ser Ser Ala Tyr Tyr Asp Pro Asn Tyr Leu
50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Lys Val Leu Leu Gln Glu
            85                  90                  95

Ile Ser Tyr Ala Lys Pro Tyr Leu Gly Asn Asp His Thr Pro Ile Asp
            100                 105                 110

Glu Phe Ser Pro Val Thr Arg Thr Thr Ser Val Asn Ile Lys Leu Ser
            115                 120                 125

Thr Asn Val Glu Ser Ser Met Leu Leu Asn Leu Leu Val Leu Gly Ala
            130                 135                 140

Gly Pro Asp Ile Phe Glu Ser Cys Cys Tyr Pro Val Arg Lys Leu Ile
145                 150                 155                 160

```
Asp Pro Asp Val Val Tyr Asp Pro Ser Asn Tyr Gly Phe Gly Ser Ile
            165                 170                 175
Asn Ile Val Thr Phe Ser Pro Glu Tyr Glu Tyr Thr Phe Asn Asp Ile
            180                 185                 190
Ser Gly Gly His Asn Ser Ser Thr Glu Ser Phe Ile Ala Asp Pro Ala
            195                 200                 205
Ile Ser Leu Ala His Glu Leu Ile His Ala Leu His Gly Leu Tyr Gly
            210                 215                 220
Ala Arg Gly Val Thr Tyr Glu Glu Thr Ile Glu Val Lys Gln Ala Pro
225                 230                 235                 240
Leu Met Ile Ala Glu Lys Pro Ile Arg Leu Glu Glu Phe Leu Thr Phe
            245                 250                 255
Gly Gly Gln Asp Leu Asn Ile Ile Thr Ser Ala Met Lys Glu Lys Ile
            260                 265                 270
Tyr Asn Asn Leu Leu Ala Asn Tyr Glu Lys Ile Ala Thr Arg Leu Ser
            275                 280                 285
Glu Val Asn Ser Ala Pro Pro Glu Tyr Asp Ile Asn Glu Tyr Lys Asp
            290                 295                 300
Tyr Phe Gln Trp Lys Tyr Gly Leu Asp Lys Asn Ala Asp Gly Ser Tyr
305                 310                 315                 320
Thr Val Asn Glu Asn Lys Phe Asn Glu Ile Tyr Lys Lys Leu Tyr Ser
            325                 330                 335
Phe Thr Glu Ser Asp Leu Ala Asn Lys Phe Lys Val Lys Cys Arg Asn
            340                 345                 350
Thr Tyr Phe Ile Lys Tyr Gly Phe Leu Lys Val Pro Asn Leu Leu Asp
            355                 360                 365
Asp Asp Ile Tyr Thr Val Ser Glu Gly Phe Asn Ile Gly Asn Leu Ala
370                 375                 380
Val Asn Asn Arg Gly Gln Ser Ile Lys Leu Asn Pro Lys Ile Ile Asp
385                 390                 395                 400
Ser Ile Pro Asp Lys Gly Leu Val Glu Lys Ile Val Lys Phe Cys Lys
            405                 410                 415
Ser Val Ile Pro Arg Lys Gly Thr Lys Ala Pro Pro Arg Leu Cys Ile
            420                 425                 430
Arg Val Asn Asn Ser Glu Leu Phe Phe Val Ala Ser Glu Ser Ser Tyr
            435                 440                 445
Asn Glu Asn Asp Ile Asn Thr Pro Lys Glu Ile Asp Asp Thr Thr Asn
            450                 455                 460
Leu Asn Asn Asn Tyr Arg Asn Asn Leu Asp Glu Val Ile Leu Asp Tyr
465                 470                 475                 480
Asn Ser Gln Thr Ile Pro Gln Ile Ser Asn Arg Thr Leu Asn Thr Leu
            485                 490                 495
Val Gln Asp Asn Ser Tyr Val Pro Arg Tyr Asp Ser Asn Gly Thr Ser
            500                 505                 510
Glu Ile Glu Glu Tyr Asp Val Val Asp Phe Asn Val Phe Phe Tyr Leu
            515                 520                 525
His Ala Gln Lys Val Pro Glu Gly Glu Thr Asn Ile Ser Leu Thr Ser
            530                 535                 540
Ser Ile Asp Thr Ala Leu Leu Glu Glu Ser Lys Val Tyr Thr Phe Phe
545                 550                 555                 560
Ser Ser Glu Phe Ile Asp Thr Ile Asn Lys Pro Val Asn Ala Ala Leu
            565                 570                 575
Phe Ile Asp Trp Ile Ser Lys Val Ile Arg Asp Phe Thr Thr Glu Ala
```

```
                    580                 585                 590
Thr Gln Lys Ser Thr Val Asp Lys Ile Ala Asp Ile Ser Leu Ile Val
            595                 600                 605

Pro Tyr Val Gly Leu Ala Leu Asn Ile Ile Glu Ala Glu Lys Gly
        610                 615                 620

Asn Phe Glu Glu Ala Phe Glu Leu Leu Gly Val Gly Ile Leu Leu Glu
625                 630                 635                 640

Phe Val Pro Glu Leu Thr Ile Pro Val Ile Leu Val Phe Thr Ile Lys
                    645                 650                 655

Ser Tyr Ile Asp Ser Tyr Glu Asn Lys Asn Lys Ala Ile Lys Ala Ile
            660                 665                 670

Asn Asn Ser Leu Ile Glu Arg Glu Ala Lys Trp Lys Glu Ile Tyr Ser
        675                 680                 685

Trp Ile Val Ser Asn Trp Leu Thr Arg Ile Asn Thr Gln Phe Asn Lys
        690                 695                 700

Arg Lys Glu Gln Met Tyr Gln Ala Leu Gln Asn Gln Val Asp Ala Ile
705                 710                 715                 720

Lys Thr Ala Ile Glu Tyr Lys Tyr Asn Asn Tyr Thr Ser Asp Glu Lys
                    725                 730                 735

Asn Arg Leu Glu Ser Glu Tyr Asn Ile Asn Asn Ile Glu Glu Leu
            740                 745                 750

Asn Lys Lys Val Ser Leu Ala Met Lys Asn Ile Glu Arg Phe Met Thr
        755                 760                 765

Glu Ser Ser Ile Ser Tyr Leu Met Lys Leu Ile Asn Glu Ala Lys Val
770                 775                 780

Gly Lys Leu Lys Lys Tyr Asp Asn His Val Lys Ser Asp Leu Leu Asn
785                 790                 795                 800

Tyr Ile Leu Asp His Arg Ser Ile Leu Gly Glu Gln Thr Asn Glu Leu
                    805                 810                 815

Ser Asp Leu Val Thr Ser Thr Leu Asn Ser Ser Ile Pro Phe Glu Leu
            820                 825                 830

Ser Ser

<210> SEQ ID NO 29
<211> LENGTH: 825
<212> TYPE: PRT
<213> ORGANISM: Clostridium botulinum

<400> SEQUENCE: 29

Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
            20                  25                  30

Pro Glu Arg Asn Ile Ile Gly Lys Lys Pro Ser Asp Phe Tyr Pro Pro
        35                  40                  45

Ile Ser Leu Asp Ser Gly Ser Ser Ala Tyr Tyr Asp Pro Asn Tyr Leu
    50                  55                  60

Thr Thr Asp Ala Glu Lys Asp Arg Phe Leu Lys Thr Val Ile Lys Leu
65                  70                  75                  80

Phe Asn Arg Ile Asn Ser Asn Pro Ala Gly Gln Val Leu Leu Glu Glu
                85                  90                  95

Ile Lys Asn Gly Lys Pro Tyr Leu Gly Asn Asp His Thr Ala Val Asn
            100                 105                 110

Glu Phe Cys Ala Asn Asn Arg Ser Thr Ser Val Glu Ile Lys Glu Ser
```

-continued

```
            115                 120                 125
Lys Gly Thr Thr Asp Ser Met Leu Leu Asn Leu Val Ile Leu Gly Pro
        130                 135                 140

Gly Pro Asn Ile Leu Glu Cys Ser Thr Phe Pro Val Arg Ile Phe Pro
145                 150                 155                 160

Asn Asn Ile Ala Tyr Asp Pro Ser Glu Lys Gly Phe Gly Ser Ile Gln
                165                 170                 175

Leu Met Ser Phe Ser Thr Glu Tyr Glu Tyr Ala Phe Asn Asp Asn Thr
            180                 185                 190

Asp Leu Phe Ile Ala Asp Pro Ala Ile Ser Leu Ala His Glu Leu Ile
        195                 200                 205

His Val Leu His Gly Leu Tyr Gly Ala Lys Gly Val Thr Asn Lys Lys
    210                 215                 220

Val Ile Glu Val Asp Gln Gly Ala Leu Met Ala Ala Glu Lys Asp Ile
225                 230                 235                 240

Lys Ile Glu Glu Phe Ile Thr Phe Gly Gly Gln Asp Leu Asn Ile Ile
                245                 250                 255

Thr Asn Ser Thr Asn Gln Lys Ile Tyr Asp Asn Leu Leu Ser Asn Tyr
            260                 265                 270

Thr Ala Ile Ala Ser Arg Leu Ser Gln Val Asn Ile Asn Asn Ser Ala
        275                 280                 285

Leu Asn Thr Thr Tyr Tyr Lys Asn Phe Phe Gln Trp Lys Tyr Gly Leu
    290                 295                 300

Asp Gln Asp Ser Asn Gly Asn Tyr Thr Val Asn Ile Ser Lys Phe Asn
305                 310                 315                 320

Ala Ile Tyr Lys Lys Leu Phe Ser Phe Thr Glu Cys Asp Leu Ala Gln
                325                 330                 335

Lys Phe Gln Val Lys Asn Arg Ser Asn Tyr Leu Phe His Phe Lys Pro
            340                 345                 350

Phe Arg Leu Leu Asp Leu Leu Asp Asp Asn Ile Tyr Ser Ile Ser Glu
        355                 360                 365

Gly Phe Asn Ile Gly Ser Leu Arg Val Asn Asn Asn Gly Gln Asn Ile
    370                 375                 380

Asn Leu Asn Ser Arg Ile Val Gly Pro Ile Pro Asp Asn Gly Leu Val
385                 390                 395                 400

Glu Arg Phe Val Gly Leu Cys Lys Ser Ile Val Ser Lys Lys Gly Thr
                405                 410                 415

Lys Asn Ser Leu Cys Ile Lys Val Asn Asn Arg Asp Leu Phe Phe Val
            420                 425                 430

Ala Ser Glu Ser Ser Tyr Asn Glu Asn Gly Ile Asn Ser Pro Lys Glu
        435                 440                 445

Ile Asp Asp Thr Thr Ile Thr Asn Asn Tyr Lys Lys Asn Leu Asp
    450                 455                 460

Glu Val Ile Leu Asp Tyr Asn Ser Asp Ala Ile Pro Asn Leu Ser Ser
465                 470                 475                 480

Arg Leu Leu Asn Thr Thr Ala Gln Asn Asp Ser Tyr Val Pro Lys Tyr
                485                 490                 495

Asp Ser Asn Gly Thr Ser Glu Ile Lys Glu Tyr Thr Val Asp Lys Leu
            500                 505                 510

Asn Val Phe Phe Tyr Leu Tyr Ala Gln Lys Ala Pro Glu Gly Glu Ser
        515                 520                 525

Ala Ile Ser Leu Thr Ser Ser Val Asn Thr Ala Leu Leu Asp Ala Ser
    530                 535                 540
```

```
Lys Val Tyr Thr Phe Phe Ser Ser Asp Phe Ile Asn Thr Val Asn Lys
545                 550                 555                 560

Pro Val Gln Ala Ala Leu Phe Ile Ser Trp Ile Gln Gln Val Ile Asn
                565                 570                 575

Asp Phe Thr Thr Glu Ala Thr Gln Lys Ser Thr Ile Asp Lys Ile Ala
            580                 585                 590

Asp Ile Ser Leu Val Val Pro Tyr Val Gly Leu Ala Leu Asn Ile Gly
        595                 600                 605

Asn Glu Val Gln Lys Gly Asn Phe Lys Glu Ala Ile Glu Leu Leu Gly
    610                 615                 620

Ala Gly Ile Leu Leu Glu Phe Val Pro Glu Leu Leu Ile Pro Thr Ile
625                 630                 635                 640

Leu Val Phe Thr Ile Lys Ser Phe Ile Asn Ser Asp Asp Ser Lys Asn
                645                 650                 655

Lys Ile Ile Lys Ala Ile Asn Asn Ala Leu Arg Glu Arg Glu Leu Lys
            660                 665                 670

Trp Lys Glu Val Tyr Ser Trp Ile Val Ser Asn Trp Leu Thr Arg Ile
        675                 680                 685

Asn Thr Gln Phe Asn Lys Arg Lys Glu Gln Met Tyr Gln Ala Leu Gln
    690                 695                 700

Asn Gln Val Asp Gly Ile Lys Lys Ile Glu Tyr Lys Tyr Asn Asn
705                 710                 715                 720

Tyr Thr Leu Asp Glu Lys Asn Arg Leu Lys Ala Glu Tyr Asn Ile Tyr
                725                 730                 735

Ser Ile Lys Glu Glu Leu Asn Lys Lys Val Ser Leu Ala Met Gln Asn
            740                 745                 750

Ile Asp Arg Phe Leu Thr Glu Ser Ser Ile Ser Tyr Leu Met Lys Leu
        755                 760                 765

Ile Asn Glu Ala Lys Ile Asn Lys Leu Ser Gly Tyr Asp Lys Arg Val
    770                 775                 780

Asn Gln Tyr Leu Leu Asn Tyr Ile Leu Glu Asn Ser Ser Thr Leu Gly
785                 790                 795                 800

Thr Ser Ser Val Gln Glu Leu Asn Asn Leu Val Ser Asn Thr Leu Asn
                805                 810                 815

Asn Ser Ile Pro Phe Glu Leu Ser Glu
            820                 825

<210> SEQ ID NO 30
<211> LENGTH: 825
<212> TYPE: PRT
<213> ORGANISM: Clostridium botulinum

<400> SEQUENCE: 30

Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
                20                  25                  30

Pro Glu Arg Asn Ile Ile Gly Lys Lys Pro Ser Asp Phe Tyr Pro Pro
            35                  40                  45

Ile Ser Leu Asp Ser Gly Ser Ser Ala Tyr Tyr Asp Pro Asn Tyr Leu
        50                  55                  60

Thr Thr Asp Ala Glu Lys Asp Arg Phe Leu Lys Thr Val Ile Lys Leu
65                  70                  75                  80

Phe Asn Arg Ile Asn Ser Asn Pro Ala Gly Gln Val Leu Leu Glu Glu
```

```
                    85                    90                    95
Ile Lys Asn Gly Lys Pro Tyr Leu Gly Asn Asp His Thr Ala Val Asn
                100                   105                   110

Glu Phe Cys Ala Asn Asn Arg Ser Thr Ser Val Glu Ile Lys Glu Ser
                115                   120                   125

Asn Gly Thr Thr Asp Ser Met Leu Leu Asn Leu Val Ile Leu Gly Pro
            130                   135                   140

Gly Pro Asn Ile Leu Glu Cys Ser Thr Phe Pro Val Arg Ile Phe Pro
145                   150                   155                   160

Asn Asn Ile Ala Tyr Asp Pro Ser Glu Lys Gly Phe Gly Ser Ile Gln
                165                   170                   175

Leu Met Ser Phe Ser Thr Glu Tyr Glu Tyr Ala Phe Asn Asp Asn Thr
            180                   185                   190

Asp Leu Phe Ile Ala Asp Pro Ala Ile Ser Leu Ala His Glu Leu Ile
            195                   200                   205

His Val Leu His Gly Leu Tyr Gly Ala Lys Gly Val Thr Asn Lys Lys
        210                   215                   220

Val Ile Glu Val Asp Gln Gly Ala Leu Met Ala Ala Glu Lys Asp Ile
225                   230                   235                   240

Lys Ile Glu Glu Phe Ile Thr Phe Gly Gly Gln Asp Leu Asn Ile Ile
                245                   250                   255

Thr Asn Ser Thr Asn Gln Lys Ile Tyr Asp Asn Leu Leu Ser Asn Tyr
            260                   265                   270

Thr Ala Ile Ala Ser Arg Leu Ser Gln Val Asn Ile Asn Asn Ser Ala
        275                   280                   285

Leu Asn Thr Thr Tyr Tyr Lys Asn Phe Phe Gln Trp Lys Tyr Gly Leu
        290                   295                   300

Asp Gln Asp Ser Asn Gly Asn Tyr Thr Val Asn Ile Ser Lys Phe Asn
305                   310                   315                   320

Ala Ile Tyr Lys Lys Leu Phe Ser Phe Thr Glu Cys Asp Leu Ala Gln
                325                   330                   335

Lys Phe Gln Val Lys Asn Arg Ser Asn Tyr Leu Phe His Phe Lys Pro
                340                   345                   350

Phe Arg Leu Leu Asp Leu Leu Asp Asp Asn Ile Tyr Ser Ile Ser Glu
            355                   360                   365

Gly Phe Asn Ile Gly Ser Leu Arg Val Asn Asn Gly Gln Asn Ile
        370                   375                   380

Asn Leu Asn Ser Arg Ile Val Gly Pro Ile Pro Asp Asn Gly Leu Val
385                   390                   395                   400

Glu Arg Phe Val Gly Leu Cys Lys Ser Ile Val Ser Lys Lys Gly Thr
                405                   410                   415

Lys Asn Ser Leu Cys Ile Lys Val Asn Asn Arg Asp Leu Phe Phe Val
                420                   425                   430

Ala Ser Glu Ser Ser Tyr Asn Glu Asn Gly Ile Asn Ser Pro Lys Glu
            435                   440                   445

Ile Asp Asp Thr Thr Ile Thr Asn Asn Asn Tyr Lys Lys Asn Leu Asp
            450                   455                   460

Glu Val Ile Leu Asp Tyr Asn Ser Asp Ala Ile Pro Asn Leu Ser Ser
465                   470                   475                   480

Arg Leu Leu Asn Thr Thr Ala Gln Asn Asp Ser Tyr Val Pro Lys Tyr
                485                   490                   495

Asp Ser Asn Gly Thr Ser Glu Ile Lys Glu Tyr Thr Val Asp Lys Leu
            500                   505                   510
```

Asn Val Phe Phe Tyr Leu Tyr Ala Gln Lys Ala Pro Glu Gly Glu Ser
            515                 520                 525
Ala Ile Ser Leu Thr Ser Ser Val Asn Thr Ala Leu Leu Asp Ala Ser
            530                 535                 540
Lys Val Tyr Thr Phe Phe Ser Ser Asp Phe Ile Asn Thr Val Asn Lys
545                 550                 555                 560
Pro Val Gln Ala Ala Leu Phe Ile Ser Trp Ile Gln Gln Val Ile Asn
            565                 570                 575
Asp Phe Thr Thr Glu Ala Thr Gln Lys Ser Thr Ile Asp Lys Ile Ala
            580                 585                 590
Asp Ile Ser Leu Val Val Pro Tyr Val Gly Leu Ala Leu Asn Ile Gly
            595                 600                 605
Asn Glu Val Gln Lys Gly Asn Phe Lys Glu Ala Ile Glu Leu Leu Gly
            610                 615                 620
Ala Gly Ile Leu Leu Glu Phe Val Pro Glu Leu Leu Ile Pro Thr Ile
625                 630                 635                 640
Leu Val Phe Thr Ile Lys Ser Phe Ile Asn Ser Asp Asp Ser Lys Asn
            645                 650                 655
Lys Ile Ile Lys Ala Ile Asn Asn Ala Leu Arg Glu Arg Glu Leu Lys
            660                 665                 670
Trp Lys Glu Val Tyr Ser Trp Ile Val Ser Asn Trp Leu Thr Arg Ile
            675                 680                 685
Asn Thr Gln Phe Asn Lys Arg Lys Glu Gln Met Tyr Gln Ala Leu Gln
            690                 695                 700
Asn Gln Val Asp Gly Ile Lys Lys Ile Ile Glu Tyr Lys Tyr Asn Asn
705                 710                 715                 720
Tyr Thr Leu Asp Glu Lys Asn Arg Leu Lys Ala Glu Tyr Asn Ile Tyr
            725                 730                 735
Ser Ile Lys Glu Glu Leu Asn Lys Lys Val Ser Leu Ala Met Gln Asn
            740                 745                 750
Ile Asp Arg Phe Leu Thr Glu Ser Ser Ile Ser Tyr Leu Met Lys Leu
            755                 760                 765
Ile Asn Glu Ala Lys Ile Asn Lys Leu Ser Glu Tyr Asp Lys Arg Val
            770                 775                 780
Asn Gln Tyr Leu Leu Asn Tyr Ile Leu Glu Asn Ser Ser Thr Leu Gly
785                 790                 795                 800
Thr Ser Ser Val Gln Glu Leu Asn Asn Leu Val Ser Asn Thr Leu Asn
            805                 810                 815
Asn Ser Ile Pro Phe Glu Leu Ser Glu
            820                 825

<210> SEQ ID NO 31
<211> LENGTH: 825
<212> TYPE: PRT
<213> ORGANISM: Clostridium botulinum

<400> SEQUENCE: 31

Asn Asn Thr Thr Ile Leu Tyr Met Lys Met Pro Tyr Tyr Glu Asp Ser
1               5                   10                  15
Asn Lys Tyr Tyr Lys Ala Phe Glu Ile Met Asp Asn Val Trp Ile Ile
            20                  25                  30
Pro Glu Arg Asn Ile Ile Gly Lys Lys Pro Ser Asp Phe Tyr Pro Pro
            35                  40                  45
Ile Ser Leu Asp Ser Gly Ser Ser Ala Tyr Tyr Asp Pro Asn Tyr Leu

```
            50                  55                  60
Thr Thr Asp Ala Glu Lys Asp Arg Phe Leu Lys Thr Val Ile Lys Leu
 65                  70                  75                  80

Phe Asn Arg Ile Asn Ser Asn Pro Ala Gly Gln Val Leu Leu Glu Glu
                     85                  90                  95

Ile Lys Asn Gly Lys Pro Tyr Leu Gly Asn Asp His Thr Ala Val Asn
                100                 105                 110

Glu Phe Cys Ala Asn Asn Arg Ser Thr Ser Val Glu Ile Lys Glu Ser
            115                 120                 125

Asn Gly Thr Thr Asp Ser Met Leu Leu Asn Leu Val Ile Leu Gly Pro
        130                 135                 140

Gly Pro Asn Ile Leu Glu Cys Ser Thr Phe Pro Val Arg Ile Phe Pro
145                 150                 155                 160

Asn Asn Ile Ala Tyr Asp Pro Ser Glu Lys Gly Phe Gly Ser Ile Gln
                165                 170                 175

Leu Met Ser Phe Ser Thr Glu Tyr Glu Tyr Ala Phe Asn Asp Asn Thr
                180                 185                 190

Asp Leu Phe Ile Ala Asp Pro Ala Ile Ser Leu Ala His Glu Leu Ile
            195                 200                 205

His Val Leu His Gly Leu Tyr Gly Ala Lys Gly Val Thr Asn Lys Lys
        210                 215                 220

Val Ile Glu Val Asp Gln Gly Ala Leu Met Ala Glu Lys Asp Ile
225                 230                 235                 240

Lys Ile Glu Glu Phe Ile Thr Phe Gly Gly Gln Asp Leu Asn Ile Ile
                245                 250                 255

Thr Asn Ser Thr Asn Gln Lys Ile Tyr Val Ile Leu Leu Ser Asn Tyr
                260                 265                 270

Thr Ala Ile Ala Ser Arg Leu Ser Gln Val Asn Arg Asn Asn Ser Ala
            275                 280                 285

Leu Asn Thr Thr Tyr Tyr Lys Asn Phe Phe Gln Trp Lys Tyr Gly Leu
        290                 295                 300

Asp Gln Asp Ser Asn Gly Asn Tyr Thr Val Asn Ile Ser Lys Phe Asn
305                 310                 315                 320

Ala Ile Tyr Lys Lys Leu Phe Ser Phe Thr Glu Cys Asp Leu Ala Gln
                325                 330                 335

Lys Phe Gln Val Lys Asn Arg Ser Asn Tyr Leu Phe His Phe Lys Pro
                340                 345                 350

Phe Arg Leu Leu Asp Leu Leu Asp Asp Asn Ile Tyr Ser Ile Ser Glu
            355                 360                 365

Gly Phe Asn Ile Gly Ser Leu Arg Val Asn Asn Gly Gln Asn Ile
        370                 375                 380

Asn Leu Asn Ser Arg Ile Val Gly Pro Ile Pro Asp Asn Gly Leu Val
385                 390                 395                 400

Glu Arg Phe Val Gly Leu Cys Lys Ser Ile Val Ser Lys Lys Gly Thr
                405                 410                 415

Lys Asn Ser Leu Cys Ile Lys Val Asn Asn Arg Asp Leu Phe Phe Val
            420                 425                 430

Ala Ser Glu Ser Ser Tyr Asn Glu Asn Gly Ile Asn Ser Pro Lys Glu
        435                 440                 445

Ile Asp Asp Thr Thr Ile Thr Asn Asn Tyr Lys Lys Asn Leu Asp
        450                 455                 460

Glu Val Ile Leu Asp Tyr Asn Ser Asp Ala Ile Pro Asn Leu Ser Ser
465                 470                 475                 480
```

```
Arg Leu Leu Asn Thr Thr Ala Gln Asn Asp Ser Tyr Val Pro Lys Tyr
            485                 490                 495

Asp Ser Asn Gly Thr Ser Glu Ile Lys Glu Tyr Thr Val Asp Lys Leu
        500                 505                 510

Asn Val Phe Phe Tyr Leu Tyr Ala Gln Lys Ala Pro Glu Gly Glu Ser
        515                 520                 525

Ala Ile Ser Leu Thr Ser Ser Val Asn Thr Ala Leu Leu Asp Ala Ser
    530                 535                 540

Lys Val Tyr Thr Phe Phe Ser Ser Asp Phe Ile Asn Thr Val Asn Lys
545                 550                 555                 560

Pro Val Gln Ala Ala Leu Phe Ile Ser Trp Ile Gln Gln Val Ile Asn
            565                 570                 575

Asp Phe Thr Thr Glu Ala Thr Gln Lys Ser Thr Ile Asp Lys Ile Ala
        580                 585                 590

Asp Ile Ser Leu Ile Val Pro Tyr Val Gly Leu Ala Leu Asn Ile Gly
        595                 600                 605

Asn Glu Val Gln Lys Gly Asn Phe Lys Glu Ala Ile Glu Leu Leu Gly
        610                 615                 620

Ala Gly Ile Leu Leu Glu Phe Val Pro Glu Leu Leu Ile Pro Thr Ile
625                 630                 635                 640

Leu Val Phe Thr Ile Lys Ser Phe Ile Asn Ser Asp Asp Ser Lys Asn
            645                 650                 655

Lys Ile Ile Lys Ala Ile Asn Asn Ala Leu Arg Glu Arg Glu Leu Lys
        660                 665                 670

Trp Lys Glu Val Tyr Ser Trp Ile Val Ser Asn Trp Leu Thr Arg Ile
        675                 680                 685

Asn Thr Gln Phe Asn Lys Arg Lys Glu Gln Met Tyr Gln Ala Leu Gln
        690                 695                 700

Asn Gln Val Asp Gly Ile Lys Lys Ile Glu Tyr Lys Tyr Asn Asn
705                 710                 715                 720

Tyr Thr Leu Asp Glu Lys Asn Arg Leu Arg Ala Glu Tyr Asn Ile Tyr
            725                 730                 735

Ser Ile Lys Glu Glu Leu Asn Lys Lys Val Ser Leu Ala Met Gln Asn
        740                 745                 750

Ile Asp Arg Phe Leu Thr Glu Ser Ser Ile Ser Tyr Leu Met Lys Leu
        755                 760                 765

Ile Asn Glu Ala Lys Ile Asn Lys Leu Ser Glu Tyr Asp Lys Arg Val
    770                 775                 780

Asn Gln Tyr Leu Leu Asn Tyr Ile Leu Glu Asn Ser Ser Thr Leu Gly
785                 790                 795                 800

Thr Ser Ser Val Pro Glu Leu Asn Asn Leu Val Ser Asn Thr Leu Asn
            805                 810                 815

Asn Ser Ile Pro Phe Glu Leu Ser Glu
        820                 825

<210> SEQ ID NO 32
<211> LENGTH: 825
<212> TYPE: PRT
<213> ORGANISM: Clostridium botulinum

<400> SEQUENCE: 32

Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
```

```
            20                  25                  30
Pro Glu Arg Asn Ile Ile Gly Lys Lys Pro Ser Asp Phe Tyr Pro Pro
            35                  40                  45
Ile Ser Leu Asp Ser Gly Ser Ser Ala Tyr Tyr Asp Pro Asn Tyr Leu
 50                  55                  60
Thr Thr Asp Ala Glu Lys Asp Arg Phe Leu Lys Thr Val Ile Lys Leu
 65                  70                  75                  80
Phe Asn Arg Ile Asn Ser Asn Pro Ala Gly Gln Val Leu Leu Glu Glu
                85                  90                  95
Ile Lys Asn Gly Lys Pro Tyr Leu Gly Asn Asp His Thr Ala Val Asn
            100                 105                 110
Glu Phe Cys Ala Asn Asn Arg Ser Thr Ser Val Glu Ile Lys Glu Ser
            115                 120                 125
Asn Gly Thr Thr Asp Ser Met Leu Leu Asn Leu Val Ile Leu Gly Pro
            130                 135                 140
Gly Pro Asn Ile Leu Glu Cys Ser Thr Phe Pro Val Arg Ile Phe Pro
145                 150                 155                 160
Asn Asn Ile Ala Tyr Asp Pro Ser Glu Lys Gly Phe Gly Ser Ile Gln
                165                 170                 175
Leu Met Ser Phe Ser Thr Glu Tyr Glu Tyr Ala Phe Asn Asp Asn Thr
            180                 185                 190
Asp Leu Phe Ile Ala Asp Pro Ala Ile Ser Leu Ala His Glu Leu Ile
            195                 200                 205
His Val Leu His Gly Leu Tyr Gly Ala Lys Gly Val Thr Asn Lys Lys
            210                 215                 220
Val Ile Glu Val Asp Gln Gly Ala Leu Met Ala Ala Glu Lys Asp Ile
225                 230                 235                 240
Lys Ile Glu Glu Phe Ile Thr Phe Gly Gly Gln Asp Leu Asn Ile Val
                245                 250                 255
Thr Asn Ser Thr Asn Gln Lys Ile Tyr Asp Asn Leu Leu Ser Asn Tyr
            260                 265                 270
Thr Ala Ile Ala Ser Arg Leu Ser Gln Val Asn Ile Asn Asn Ser Ala
            275                 280                 285
Leu Asn Thr Thr Tyr Tyr Lys Asn Phe Phe Gln Trp Lys Tyr Gly Leu
            290                 295                 300
Asp Gln Asp Ser Asn Gly Asn Tyr Thr Val Asn Ile Ser Lys Phe Asn
305                 310                 315                 320
Ala Ile Tyr Lys Lys Leu Phe Ser Phe Thr Glu Cys Asp Leu Ala Gln
                325                 330                 335
Lys Phe Gln Val Lys Asn Arg Ser Asn Tyr Leu Phe His Phe Lys Pro
            340                 345                 350
Phe Lys Leu Leu Asp Leu Leu Asp Asp Asn Ile Tyr Ser Ile Ser Glu
            355                 360                 365
Gly Phe Asn Ile Gly Ser Leu Arg Val Asn Asn Gly Gln Asn Ile
            370                 375                 380
Asn Leu Asn Ser Arg Ile Val Gly Pro Ile Pro Asp Asn Gly Leu Val
385                 390                 395                 400
Glu Arg Phe Val Gly Leu Cys Lys Ser Ile Val Ser Lys Lys Gly Thr
                405                 410                 415
Lys Asn Ser Leu Cys Ile Lys Val Asn Asn Arg Asp Leu Phe Phe Val
            420                 425                 430
Ala Ser Glu Ser Ser Tyr Asn Glu Asn Gly Ile Asn Ser Pro Lys Glu
            435                 440                 445
```

```
Ile Asp Asp Thr Thr Ile Thr Asn Asn Asn Tyr Lys Lys Asn Leu Asp
        450                 455                 460

Glu Val Ile Leu Asp Tyr Asn Ser Asp Ala Ile Pro Asn Leu Ser Ser
465                 470                 475                 480

Arg Leu Leu Asn Ala Thr Ala Gln Asn Asp Ser Tyr Val Pro Lys Tyr
                485                 490                 495

Asp Ser Asn Gly Thr Ser Glu Ile Asn Glu Tyr Thr Val Asp Lys Leu
            500                 505                 510

Asn Val Phe Phe Tyr Leu Tyr Ala Gln Lys Ala Pro Glu Gly Glu Ser
        515                 520                 525

Ala Ile Ser Leu Thr Ser Ser Val Asp Thr Ala Leu Leu Asp Ala Ser
    530                 535                 540

Lys Val Tyr Thr Phe Phe Ser Ser Asp Phe Ile Asn Thr Val Asn Lys
545                 550                 555                 560

Pro Val Gln Ala Ala Leu Phe Ile Ser Trp Ile Gln Gln Val Ile Asn
                565                 570                 575

Asp Phe Thr Thr Glu Ala Thr Gln Lys Ser Thr Ile Asp Lys Ile Ala
            580                 585                 590

Asp Ile Ser Leu Val Val Pro Tyr Val Gly Leu Ala Leu Asn Ile Gly
        595                 600                 605

Asn Glu Val Gln Lys Gly Asn Phe Lys Glu Ala Ile Glu Leu Leu Gly
    610                 615                 620

Ala Gly Ile Leu Leu Glu Phe Val Pro Glu Leu Leu Ile Pro Thr Ile
625                 630                 635                 640

Leu Val Phe Thr Ile Lys Ser Phe Ile Asn Ser Asp Asp Ser Lys Asn
                645                 650                 655

Lys Ile Ile Lys Ala Ile Asn Asn Ala Leu Arg Glu Arg Glu Leu Lys
            660                 665                 670

Trp Lys Glu Val Tyr Ser Trp Ile Val Ser Asn Trp Leu Thr Arg Ile
        675                 680                 685

Asn Thr Gln Phe Asn Lys Arg Lys Glu Gln Met Tyr Gln Ala Leu Gln
    690                 695                 700

Asn Gln Val Asp Gly Ile Lys Lys Ile Glu Tyr Lys Tyr Asn Asn
705                 710                 715                 720

Tyr Thr Leu Asp Glu Lys Asn Arg Leu Lys Ala Glu Tyr Asn Ile Tyr
                725                 730                 735

Asn Ile Lys Glu Glu Leu Asn Lys Lys Val Ser Leu Ala Met Gln Asn
            740                 745                 750

Ile Asp Arg Phe Leu Thr Glu Ser Ile Ser Tyr Leu Met Lys Leu
        755                 760                 765

Ile Asn Glu Ala Lys Ile Asn Lys Leu Glu Tyr Asp Lys Arg Val
    770                 775                 780

Asn Gln Tyr Leu Leu Asn Tyr Ile Leu Glu Asn Ser Ser Thr Leu Gly
785                 790                 795                 800

Thr Ser Ser Val Gln Glu Leu Asn Asn Leu Val Ser Asn Thr Leu Asn
                805                 810                 815

Asn Ser Ile Pro Phe Glu Leu Ser Glu
            820                 825

<210> SEQ ID NO 33
<211> LENGTH: 397
<212> TYPE: PRT
<213> ORGANISM: Clostridium botulinum
<220> FEATURE:
```

```
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid

<400> SEQUENCE: 33

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
            20                  25                  30

Pro Glu Arg Asn Thr Ile Gly Thr Lys Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Lys Val Leu Leu Xaa Glu
                85                  90                  95

Ile Ser Xaa Ala Lys Pro Tyr Leu Gly Asn Asp His Thr Pro Ile Asn
            100                 105                 110

Glu Phe Xaa Pro Val Asn Arg Thr Thr Ser Val Asn Ile Lys Leu Ser
        115                 120                 125

Thr Asn Val Glu Ser Ser Met Leu Leu Asn Leu Val Leu Gly Ala
    130                 135                 140

Gly Pro Asp Ile Phe Glu Xaa Ser Cys Tyr Pro Val Arg Lys Xaa Pro
145                 150                 155                 160

Asn Ser Asp Xaa Val Tyr Asp Pro Ser Asn Xaa Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220
```

```
Ala Xaa Gly Val Thr Tyr Lys Glu Thr Ile Glu Val Lys Gln Xaa Pro
225                 230                 235                 240

Leu Met Ile Ala Glu Lys Pro Ile Arg Leu Glu Phe Leu Thr Phe
            245                 250                 255

Gly Gly Gln Asp Leu Asn Ile Ile Thr Ser Ala Met Lys Glu Lys Ile
                260                 265                 270

Tyr Asn Asn Leu Leu Ala Asn Tyr Glu Lys Ile Ala Thr Arg Leu Ser
            275                 280                 285

Glu Val Asn Ser Ala Pro Pro Glu Tyr Asp Ile Asn Glu Tyr Lys Asp
        290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
            355                 360                 365

Asp Asp Ile Tyr Thr Val Ser Glu Gly Phe Asn Ile Gly Asn Leu Ala
370                 375                 380

Val Asn Asn Arg Gly Gln Asn Ile Asn Leu Asn Pro Lys
385                 390                 395
```

<210> SEQ ID NO 34
<211> LENGTH: 397
<212> TYPE: PRT
<213> ORGANISM: Clostridium botulinum

<400> SEQUENCE: 34

```
Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
                20                  25                  30

Pro Glu Arg Asn Thr Ile Gly Thr Asp Pro Ser Asp Phe Asp Pro Pro
            35                  40                  45

Ala Ser Leu Glu Asn Gly Ser Ser Ala Tyr Tyr Asp Pro Asn Tyr Leu
        50                  55                  60

Thr Thr Asp Ala Glu Lys Asp Arg Tyr Leu Lys Thr Ile Lys Leu
65                  70                  75                  80

Phe Lys Arg Ile Asn Ser Asn Pro Ala Gly Glu Val Leu Leu Gln Glu
                85                  90                  95

Ile Ser Tyr Ala Lys Pro Tyr Leu Gly Asn Glu His Thr Pro Ile Asn
            100                 105                 110

Glu Phe His Pro Val Thr Arg Thr Thr Ser Val Asn Ile Lys Ser Ser
        115                 120                 125

Thr Asn Val Lys Ser Ser Ile Ile Leu Asn Leu Leu Val Leu Gly Ala
    130                 135                 140

Gly Pro Asp Ile Phe Glu Asn Ser Ser Tyr Pro Val Arg Lys Leu Met
145                 150                 155                 160

Asp Ser Gly Gly Val Tyr Asp Pro Ser Asn Asp Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly Tyr Asn Ser Ser Thr Glu Ser Phe Ile Ala Asp Pro Ala
```

```
                195                 200                 205
Ile Ser Leu Ala His Glu Leu Ile His Ala Leu His Gly Leu Tyr Gly
210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
                260                 265                 270

Tyr Asn Asn Leu Leu Ala Asn Tyr Glu Lys Ile Ala Thr Arg Leu Ser
                275                 280                 285

Arg Val Asn Ser Ala Pro Pro Glu Tyr Asp Ile Asn Glu Tyr Lys Asp
290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
                355                 360                 365

Asp Asp Ile Tyr Thr Val Ser Glu Gly Phe Asn Ile Gly Asn Leu Ala
370                 375                 380

Val Asn Asn Arg Gly Gln Asn Ile Lys Leu Asn Pro Lys
385                 390                 395

<210> SEQ ID NO 35
<211> LENGTH: 397
<212> TYPE: PRT
<213> ORGANISM: Clostridium botulinum

<400> SEQUENCE: 35

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
                20                  25                  30

Pro Glu Arg Asp Thr Ile Gly Thr Lys Pro Asp Glu Phe Gln Val Pro
            35                  40                  45

Asp Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Met Ile Lys Leu
65                  70                  75                  80

Phe Asn Arg Ile Asn Ser Asn Pro Thr Gly Lys Val Leu Leu Glu Glu
                85                  90                  95

Val Ser Asn Ala Arg Pro Tyr Leu Gly Asp Asp Thr Leu Ile Asn
            100                 105                 110

Glu Phe Phe Pro Val Asn Val Thr Thr Ser Val Asn Ile Lys Phe Ser
            115                 120                 125

Thr Asp Val Glu Ser Ser Ile Ile Ser Asn Leu Leu Val Leu Gly Ala
        130                 135                 140

Gly Pro Asp Ile Phe Lys Ala Tyr Cys Thr Pro Leu Val Arg Phe Asn
145                 150                 155                 160

Lys Ser Asp Lys Leu Ile Glu Pro Ser Asn His Gly Phe Gly Ser Ile
                165                 170                 175
```

```
Asn Ile Leu Thr Phe Ser Pro Glu Tyr Glu His Ile Phe Asn Asp Ile
            180                 185                 190

Ser Gly Gly Asn His Asn Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Lys Ala Val Thr His Lys Glu Ser Leu Val Ala Glu Arg Gly Pro
225                 230                 235                 240

Leu Met Ile Ala Glu Lys Pro Ile Arg Leu Glu Glu Phe Leu Thr Phe
                245                 250                 255

Gly Gly Glu Asp Leu Asn Ile Ile Pro Ser Ala Met Lys Glu Lys Ile
            260                 265                 270

Tyr Asn Asp Leu Leu Ala Asn Tyr Glu Lys Ile Ala Thr Arg Leu Arg
        275                 280                 285

Glu Val Asn Thr Ala Pro Pro Gly Tyr Asp Ile Asn Glu Tyr Lys Asp
    290                 295                 300

Tyr Phe Gln Trp Lys Tyr Gly Leu Asp Arg Asn Ala Asp Gly Ser Tyr
305                 310                 315                 320

Thr Val Asn Arg Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Val Lys Val Pro Asp Leu Leu Asp
        355                 360                 365

Asp Asp Ile Tyr Thr Val Ser Glu Gly Phe Asn Ile Gly Asn Leu Ala
    370                 375                 380

Val Asn Asn Arg Gly Gln Asn Ile Asn Leu Asn Pro Lys
385                 390                 395

<210> SEQ ID NO 36
<211> LENGTH: 397
<212> TYPE: PRT
<213> ORGANISM: Clostridium botulinum

<400> SEQUENCE: 36

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
            20                  25                  30

Pro Glu Arg Asp Thr Ile Gly Thr Lys Pro Asp Glu Phe Gln Val Pro
        35                  40                  45

Asp Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Met Ile Lys Leu
65                  70                  75                  80

Phe Asn Arg Ile Asn Ser Asn Pro Thr Gly Lys Val Leu Leu Glu Glu
                85                  90                  95

Val Ser Asn Ala Arg Pro Tyr Leu Gly Asp Asp Thr Leu Ile Asn
            100                 105                 110

Glu Phe Leu Pro Val Asn Val Thr Thr Ser Val Asn Ile Lys Phe Ser
        115                 120                 125

Thr Asp Val Glu Ser Ser Ile Ile Ser Asn Leu Leu Val Leu Gly Ala
    130                 135                 140

Gly Pro Asp Ile Phe Lys Ala Tyr Cys Thr Pro Leu Val Arg Phe Asn
145                 150                 155                 160
```

Lys Ser Asp Lys Leu Ile Glu Pro Ser Asn His Gly Phe Gly Ser Ile
                165                 170                 175

Asn Ile Leu Thr Phe Ser Pro Glu Tyr Glu His Ile Phe Asn Asp Ile
            180                 185                 190

Ser Gly Gly Asn His Asn Ser Thr Glu Ser Phe Ile Ala Asp Pro Ala
        195                 200                 205

Ile Ser Leu Ala His Glu Leu Ile His Ala Leu His Gly Leu Tyr Gly
    210                 215                 220

Ala Lys Ala Val Thr His Lys Glu Ser Leu Val Ala Glu Arg Gly Pro
225                 230                 235                 240

Leu Met Ile Ala Glu Lys Pro Ile Arg Leu Glu Glu Phe Leu Thr Phe
                245                 250                 255

Gly Gly Glu Asp Leu Asn Ile Ile Pro Ser Ala Met Lys Glu Lys Ile
            260                 265                 270

Tyr Asn Asp Leu Leu Ala Asn Tyr Glu Lys Ile Ala Thr Arg Leu Arg
        275                 280                 285

Glu Val Asn Thr Ala Pro Pro Gly Tyr Asp Ile Asn Glu Tyr Lys Asp
    290                 295                 300

Tyr Phe Gln Trp Lys Tyr Gly Leu Asp Arg Asn Ala Asp Gly Ser Tyr
305                 310                 315                 320

Thr Val Asn Arg Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
        355                 360                 365

Asp Asp Ile Tyr Thr Val Ser Glu Gly Phe Asn Ile Gly Asn Leu Ala
    370                 375                 380

Val Asn Asn Arg Gly Gln Asn Ile Asn Leu Asn Pro Lys
385                 390                 395

<210> SEQ ID NO 37
<211> LENGTH: 397
<212> TYPE: PRT
<213> ORGANISM: Clostridium botulinum

<400> SEQUENCE: 37

Asn Asp Glu Thr Ile Leu Tyr Met Gln Lys Pro Tyr Glu Glu Arg Ser
1               5                   10                  15

Arg Lys Tyr Tyr Lys Ala Phe Glu Ile Met Pro Asn Val Trp Ile Met
            20                  25                  30

Pro Glu Arg Asp Thr Ile Gly Thr Lys Pro Asp Asp Phe Gln Val Pro
        35                  40                  45

Asp Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Met Ile Lys Leu
65                  70                  75                  80

Phe Asn Arg Ile Asn Ser Asn Pro Thr Gly Lys Val Leu Leu Glu Glu
                85                  90                  95

Val Ser Asn Ala Arg Pro Tyr Leu Gly Asp Asp Thr Leu Ile Asn
            100                 105                 110

Glu Phe Phe Pro Val Asn Val Thr Thr Ser Val Asn Ile Lys Phe Ser
        115                 120                 125

Thr Asp Val Glu Ser Ser Ile Ile Ser Asn Leu Leu Val Leu Gly Ala

Gly Pro Asp Ile Phe Lys Ala Tyr Cys Thr Pro Leu Val Arg Phe Asn
145                 150                 155                 160

Lys Ser Asp Lys Leu Ile Glu Pro Ser Asn His Gly Phe Gly Ser Ile
            165                 170                 175

Asn Ile Leu Thr Phe Ser Pro Glu Tyr Glu His Ile Phe Asn Asp Ile
        180                 185                 190

Ser Gly Gly Asp His Asn Ser Thr Glu Ser Phe Ile Ala Asp Pro Ala
    195                 200                 205

Ile Ser Leu Ala His Glu Leu Ile His Ala Leu His Gly Leu Tyr Gly
210                 215                 220

Ala Lys Ala Val Thr His Lys Glu Thr Ile Glu Val Lys Arg Gly Pro
225                 230                 235                 240

Leu Met Ile Ala Glu Lys Pro Ile Arg Leu Glu Phe Leu Thr Phe
                245                 250                 255

Gly Gly Glu Asp Leu Asn Ile Ile Pro Ser Ala Met Lys Glu Lys Ile
            260                 265                 270

Tyr Asn Asp Leu Leu Ala Asn Tyr Glu Lys Ile Ala Thr Arg Leu Arg
        275                 280                 285

Glu Val Asn Thr Ala Pro Pro Glu Tyr Asp Ile Asn Glu Tyr Lys Asp
    290                 295                 300

Tyr Phe Gln Trp Lys Tyr Gly Leu Asp Arg Asn Ala Asp Gly Ser Tyr
305                 310                 315                 320

Thr Val Asn Arg Asn Lys Phe Asn Gly Ile Tyr Lys Lys Leu Tyr Ser
                325                 330                 335

Phe Thr Glu Ile Asp Leu Ala Asn Lys Phe Lys Val Lys Cys Arg Asn
            340                 345                 350

Thr Tyr Phe Ile Lys Tyr Gly Phe Val Lys Val Pro Asp Leu Leu Asp
        355                 360                 365

Asp Asp Ile Tyr Thr Val Ser Glu Gly Phe Asn Ile Gly Asn Leu Ala
    370                 375                 380

Val Asn Asn Arg Gly Gln Asn Ile Asn Leu Asn Pro Lys
385                 390                 395

<210> SEQ ID NO 38
<211> LENGTH: 397
<212> TYPE: PRT
<213> ORGANISM: Clostridium botulinum

<400> SEQUENCE: 38

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Met
            20                  25                  30

Pro Glu Arg Asn Thr Ile Gly Thr Asn Pro Ser Asp Phe Asp Pro Pro
        35                  40                  45

Ala Ser Leu Lys Asn Gly Ser Ser Ala Tyr Tyr Asp Pro Asn Tyr Leu
    50                  55                  60

Thr Thr Asp Ala Glu Lys Asp Arg Tyr Leu Lys Thr Thr Ile Lys Leu
65                  70                  75                  80

Phe Lys Arg Ile Asn Ser Asn Pro Ala Gly Glu Val Leu Leu Gln Glu
                85                  90                  95

Ile Ser Tyr Ala Lys Pro Tyr Leu Gly Asn Asp His Thr Pro Ile Asn
            100                 105                 110

```
Glu Phe His Pro Val Thr Arg Thr Ser Val Asn Ile Lys Ser Ser
            115                 120                 125

Thr Asn Val Glu Ser Ser Ile Ile Leu Asn Leu Leu Val Leu Gly Ala
    130                 135                 140

Gly Pro Asn Ile Phe Glu Asn Ser Ser Tyr Pro Val Arg Lys Leu Met
145                 150                 155                 160

Asn Ser Gly Glu Val Tyr Asp Pro Ser Asn Asp Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
195                 200                 205

Ile Ser Leu Ala His Glu Leu Ile His Ala Leu His Gly Leu Tyr Gly
    210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
                260                 265                 270

Tyr Asn Asp Leu Leu Ala Asn Tyr Glu Lys Ile Ala Thr Arg Leu Ser
            275                 280                 285

Glu Val Asn Ser Ala Pro Pro Glu Tyr Asp Ile Asn Glu Tyr Lys Asn
290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
            355                 360                 365

Asp Asp Ile Tyr Thr Val Ser Glu Gly Phe Asn Ile Gly Asn Leu Ala
370                 375                 380

Val Asn Asn Arg Gly Gln Asn Ile Asn Leu Asn Pro Lys
385                 390                 395

<210> SEQ ID NO 39
<211> LENGTH: 397
<212> TYPE: PRT
<213> ORGANISM: Clostridium botulinum

<400> SEQUENCE: 39

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Met
            20                  25                  30

Pro Glu Arg Asn Thr Ile Gly Thr Asn Pro Ser Asp Phe Asp Pro Pro
                35                  40                  45

Ala Ser Leu Lys Asn Gly Ser Ser Ala Tyr Tyr Asp Pro Asn Tyr Leu
            50                  55                  60

Thr Thr Asp Ala Glu Lys Asp Arg Tyr Leu Thr Thr Ile Lys Leu
65                  70                  75                  80

Phe Lys Arg Ile Asn Ser Asn Pro Ala Gly Glu Val Leu Leu Gln Glu
                85                  90                  95
```

Ile Ser Tyr Ala Lys Pro Tyr Leu Gly Asn Asp His Thr Pro Ile Asn
                100                 105                 110

Glu Phe His Pro Val Thr Arg Thr Ser Val Asn Ile Lys Ser Ser
                115                 120                 125

Thr Asn Val Glu Ser Ser Ile Ile Leu Asn Leu Leu Val Leu Gly Ala
    130                 135                 140

Gly Pro Asn Ile Phe Glu Asn Ser Ser Tyr Pro Val Arg Lys Leu Met
145                 150                 155                 160

Asn Ser Gly Glu Val Tyr Asp Pro Ser Asn Asp Gly Phe Gly Ser Ile
                165                 170                 175

Asn Ile Val Thr Phe Ser Pro Glu Tyr Glu Tyr Thr Phe Asn Asp Ile
                180                 185                 190

Ser Gly Gly His Asn Ser Ser Thr Glu Ser Phe Ile Ala Asp Pro Ala
                195                 200                 205

Ile Ser Leu Ala His Glu Leu Ile His Ala Leu His Gly Leu Tyr Gly
                210                 215                 220

Ala Arg Gly Val Thr Tyr Lys Glu Thr Ile Lys Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
                260                 265                 270

Tyr Asn Asp Leu Leu Ala Asn Tyr Glu Lys Ile Ala Thr Arg Leu Ser
                275                 280                 285

Glu Val Asn Ser Ala Pro Pro Glu Tyr Asp Ile Asn Glu Tyr Lys Asn
                290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ile Asp Leu Ala Asn Lys Phe Lys Val Lys Cys Arg Asn
                340                 345                 350

Thr Tyr Phe Ile Lys Tyr Gly Phe Leu Lys Val Pro Asn Leu Leu Asp
                355                 360                 365

Asp Asp Ile Tyr Thr Val Ser Glu Gly Phe Asn Ile Gly Asn Leu Ala
                370                 375                 380

Val Asn Asn Arg Gly Gln Asn Ile Asn Leu Asn Pro Lys
385                 390                 395

<210> SEQ ID NO 40
<211> LENGTH: 396
<212> TYPE: PRT
<213> ORGANISM: Clostridium botulinum

<400> SEQUENCE: 40

Asn Asp Asn Thr Ile Leu Tyr Ile Arg Pro Tyr Tyr Glu Arg Ser
1               5                   10                  15

Asn Thr Tyr Phe Lys Ala Phe Asn Ile Met Glu Asn Val Trp Ile Ile
                20                  25                  30

Pro Glu Arg Tyr Arg Leu Gly Ile Glu Ala Ser Lys Phe Asp Pro Pro
                35                  40                  45

Asp Ser Leu Lys Ala Gly Ser Asp Gly Tyr Phe Asp Pro Asn Tyr Leu
                50                  55                  60

Ser Thr Asn Thr Glu Lys Asn Arg Tyr Leu Gln Ile Met Ile Lys Leu

```
                65                  70                  75                  80
        Phe Lys Arg Ile Asn Ser Asn Glu Ala Gly Lys Ile Leu Leu Asn Gln
                        85                  90                  95

Ile Lys Asp Ala Ile Pro Tyr Leu Gly Asn Ser Tyr Thr Ala Glu Asp
                        100                 105                 110

Gln Phe Thr Thr Asn Asn Arg Thr Ile Ser Phe Asn Val Arg Leu Ala
                        115                 120                 125

Asn Gly Thr Ile Glu Gln Glu Met Ala Asn Leu Ile Ile Trp Gly Pro
                        130                 135                 140

Gly Pro Asp Leu Thr Thr Asn Arg Thr Gly Gly Thr Thr Tyr Thr Pro
        145                 150                 155                 160

Ala Gln Ser Leu Glu Ala Ile Pro Tyr Lys Glu Gly Phe Gly Ser Ile
                        165                 170                 175

Met Thr Ile Glu Phe Ser Pro Glu Tyr Ala Thr Ala Phe Asn Asp Ile
                        180                 185                 190

Ser Leu Thr Ser His Ala Pro Ser Leu Phe Ile Lys Asp Pro Ala Leu
                        195                 200                 205

Ile Leu Met His Glu Leu Ile His Val Leu His Gly Leu Tyr Gly Thr
                        210                 215                 220

Tyr Thr Thr Gly Phe Lys Ile Lys Pro Asn Ile Thr Glu Pro Tyr Met
        225                 230                 235                 240

Glu Val Thr Lys Pro Ile Thr Ser Gly Glu Phe Leu Thr Phe Gly Gly
                        245                 250                 255

Asn Asp Val Asn Lys Ile Pro Gln Leu Ile Gln Ser Gln Leu Arg Ser
                        260                 265                 270

Lys Val Leu Asp Asp Tyr Glu Lys Ile Ala Ser Arg Leu Asn Lys Val
                        275                 280                 285

Asn Arg Ala Thr Ala Glu Ile Asn Ile Asp Lys Phe Lys Tyr Ser Tyr
                        290                 295                 300

Gln Leu Lys Tyr Gln Phe Val Lys Asp Ser Asn Gly Val Tyr Ser Val
        305                 310                 315                 320

Asp Leu Asp Lys Phe Asn Lys Leu Tyr Asp Lys Ile Tyr Ser Phe Thr
                        325                 330                 335

Glu Phe Asn Leu Ala His Glu Phe Lys Ile Lys Thr Arg Asn Ser Tyr
                        340                 345                 350

Leu Ala Lys Asn Phe Gly Pro Phe Tyr Leu Pro Asn Leu Leu Asp Asn
                        355                 360                 365

Ser Ile Tyr Asn Glu Ala Asp Gly Phe Asn Ile Gly Asp Leu Ser Val
                        370                 375                 380

Asn Tyr Lys Gly Gln Val Ile Gly Ser Asp Ile Asp
        385                 390                 395

<210> SEQ ID NO 41
<211> LENGTH: 397
<212> TYPE: PRT
<213> ORGANISM: Clostridium botulinum

<400> SEQUENCE: 41

Asn Asp Asp Thr Ile Leu Tyr Met Gln Ile Pro Tyr Glu Glu Lys Ser
        1               5                   10                  15

Lys Lys Tyr Tyr Lys Ala Phe Glu Ile Met Arg Asn Val Trp Ile Ile
                        20                  25                  30

Pro Glu Arg Asn Thr Ile Gly Thr Asn Pro Ser Asp Phe Asp Pro Pro
                        35                  40                  45
```

```
Ala Ser Leu Lys Asn Gly Ser Ser Ala Tyr Tyr Asp Pro Asn Tyr Leu
 50                  55                  60

Thr Thr Asp Ala Glu Lys Asp Arg Tyr Leu Lys Thr Thr Ile Lys Leu
 65                  70                  75                  80

Phe Lys Arg Ile Asn Ser Asn Pro Ala Gly Lys Val Leu Leu Gln Glu
                 85                  90                  95

Ile Ser Tyr Ala Lys Pro Tyr Leu Gly Asn Asp His Thr Pro Ile Asp
                100                 105                 110

Glu Phe Ser Pro Val Thr Arg Thr Thr Ser Val Asn Ile Lys Leu Ser
            115                 120                 125

Thr Asn Val Glu Ser Ser Met Leu Leu Asn Leu Leu Val Leu Gly Ala
130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
            260                 265                 270

Tyr Asn Asn Leu Leu Ala Asn Tyr Glu Lys Ile Ala Thr Arg Leu Ser
        275                 280                 285

Glu Val Asn Ser Ala Pro Pro Glu Tyr Asp Ile Asn Glu Tyr Lys Asp
290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ser Asp Leu Ala Asn Lys Phe Lys Val Lys Cys Arg Asn
            340                 345                 350

Thr Tyr Phe Ile Lys Tyr Gly Phe Leu Lys Val Pro Asn Leu Leu Asp
        355                 360                 365

Asp Asp Ile Tyr Thr Val Ser Glu Gly Phe Asn Ile Gly Asn Leu Ala
370                 375                 380

Val Asn Asn Arg Gly Gln Ser Ile Lys Leu Asn Pro Lys
385                 390                 395

<210> SEQ ID NO 42
<211> LENGTH: 397
<212> TYPE: PRT
<213> ORGANISM: Clostridium botulinum

<400> SEQUENCE: 42

Asn Asp Asp Thr Ile Leu Tyr Met Gln Ile Pro Tyr Glu Glu Lys Ser
1               5                   10                  15

Lys Lys Tyr Tyr Lys Ala Phe Glu Ile Met Arg Asn Val Trp Ile Ile
                20                  25                  30
```

Pro Glu Arg Asn Thr Ile Gly Thr Asn Pro Ser Asp Phe Asp Pro Pro
          35                  40                  45

Ala Ser Leu Lys Asn Gly Ser Ser Ala Tyr Tyr Asp Pro Asn Tyr Leu
 50                  55                  60

Thr Thr Asp Ala Glu Lys Asp Arg Tyr Leu Lys Thr Thr Ile Lys Leu
 65                  70                  75                  80

Phe Lys Arg Ile Asn Ser Asn Pro Ala Gly Lys Val Leu Leu Gln Glu
                 85                  90                  95

Ile Ser Tyr Ala Lys Pro Tyr Leu Gly Asn Asp His Thr Pro Ile Asp
                100                 105                 110

Glu Phe Ser Pro Val Thr Arg Thr Thr Ser Val Asn Ile Lys Leu Ser
            115                 120                 125

Thr Asn Val Glu Ser Ser Met Leu Leu Asn Leu Leu Val Leu Gly Ala
        130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                165                 170                 175

Asn Ile Val Thr Phe Ser Pro Glu Tyr Glu Tyr Thr Phe Asn Asp Ile
            180                 185                 190

Ser Gly Gly His Asn Ser Ser Thr Glu Ser Phe Ile Ala Asp Pro Ala
        195                 200                 205

Ile Ser Leu Ala His Glu Leu Ile His Ala Leu His Gly Leu Tyr Gly
        210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
                245                 250                 255

Gly Gly Gln Asp Leu Asn Ile Ile Thr Ser Ala Met Lys Glu Lys Ile
            260                 265                 270

Tyr Asn Asn Leu Leu Ala Asn Tyr Glu Lys Ile Ala Thr Arg Leu Ser
        275                 280                 285

Glu Val Asn Ser Ala Pro Pro Glu Tyr Asp Ile Asn Glu Tyr Lys Asp
        290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                325                 330                 335

Phe Thr Glu Ser Asp Leu Ala Asn Lys Phe Lys Val Lys Cys Arg Asn
            340                 345                 350

Thr Tyr Phe Ile Lys Tyr Glu Phe Leu Lys Val Pro Asn Leu Leu Asp
        355                 360                 365

Asp Asp Ile Tyr Thr Val Ser Glu Gly Phe Asn Ile Gly Asn Leu Ala
        370                 375                 380

Val Asn Asn Arg Gly Gln Ser Ile Lys Leu Asn Pro Lys
385                 390                 395

<210> SEQ ID NO 43
<211> LENGTH: 397
<212> TYPE: PRT
<213> ORGANISM: Clostridium botulinum

<400> SEQUENCE: 43

Asn Asp Asp Thr Ile Leu Tyr Met Gln Ile Pro Tyr Lys Glu Lys Ser

```
  1               5                   10                  15
Lys Lys Tyr Tyr Lys Ala Phe Glu Ile Met Arg Asn Val Trp Ile Ile
                 20                  25                  30

Pro Glu Arg Asn Thr Ile Gly Thr Asn Pro Ser Asp Phe Asp Pro Pro
                 35                  40                  45

Ala Ser Leu Lys Asn Gly Ser Ser Ala Tyr Tyr Asp Pro Asn Tyr Leu
 50                  55                  60

Thr Thr Asp Ala Glu Lys Asp Arg Tyr Leu Lys Thr Thr Ile Lys Leu
 65                  70                  75                  80

Phe Lys Arg Ile Asn Ser Asn Pro Ala Gly Lys Val Leu Leu Gln Glu
                 85                  90                  95

Ile Ser Tyr Ala Lys Pro Tyr Leu Gly Asn Asp His Thr Pro Ile Asp
                 100                 105                 110

Glu Phe Ser Pro Val Thr Arg Thr Ser Val Asn Ile Lys Leu Ser
                 115                 120                 125

Thr Asn Val Glu Ser Ser Met Leu Leu Asn Leu Leu Val Leu Gly Ala
 130                 135                 140

Gly Pro Asp Ile Phe Glu Ser Cys Cys Tyr Pro Val Arg Lys Leu Ile
145                 150                 155                 160

Asp Pro Asp Val Val Tyr Asp Pro Ser Asn Tyr Gly Phe Gly Ser Ile
                 165                 170                 175

Asn Ile Val Thr Phe Ser Pro Glu Tyr Glu Tyr Thr Phe Asn Asp Ile
                 180                 185                 190

Ser Gly Gly His Asn Ser Ser Thr Glu Ser Phe Ile Ala Asp Pro Ala
                 195                 200                 205

Ile Ser Leu Ala His Glu Leu Ile His Ala Leu His Gly Leu Tyr Gly
                 210                 215                 220

Ala Arg Gly Val Thr Tyr Glu Glu Thr Ile Glu Val Lys Gln Ala Pro
225                 230                 235                 240

Leu Met Ile Ala Glu Lys Pro Ile Arg Leu Glu Glu Phe Leu Thr Phe
                 245                 250                 255

Gly Gly Gln Asp Leu Asn Ile Ile Thr Ser Ala Met Lys Glu Lys Ile
                 260                 265                 270

Tyr Asn Asn Leu Leu Ala Asn Tyr Glu Lys Ile Ala Thr Arg Leu Ser
                 275                 280                 285

Glu Val Asn Ser Ala Pro Pro Glu Tyr Asp Ile Asn Glu Tyr Lys Asp
                 290                 295                 300

Tyr Phe Gln Trp Lys Tyr Gly Leu Asp Lys Asn Ala Asp Gly Ser Tyr
305                 310                 315                 320

Thr Val Asn Glu Asn Lys Phe Asn Glu Ile Tyr Lys Lys Leu Tyr Ser
                 325                 330                 335

Phe Thr Glu Ser Asp Leu Ala Asn Lys Phe Lys Val Lys Cys Arg Asn
                 340                 345                 350

Thr Tyr Phe Ile Lys Tyr Gly Phe Leu Lys Val Pro Asn Leu Leu Asp
                 355                 360                 365

Asp Asp Ile Tyr Thr Val Ser Glu Gly Phe Asn Ile Gly Asn Leu Ala
                 370                 375                 380

Val Asn Asn Arg Gly Gln Ser Ile Lys Leu Asn Pro Lys
385                 390                 395

<210> SEQ ID NO 44
<211> LENGTH: 397
<212> TYPE: PRT
<213> ORGANISM: Clostridium botulinum
```

<400> SEQUENCE: 44

```
Asn Asp Asp Thr Ile Leu Tyr Met Gln Ile Pro Tyr Lys Glu Lys Ser
1               5                   10                  15
Lys Lys Tyr Tyr Lys Ala Phe Glu Ile Met Arg Asn Val Trp Ile Ile
            20                  25                  30
Pro Glu Arg Asn Thr Ile Gly Thr Asn Pro Ser Asp Phe Asp Pro Pro
        35                  40                  45
Ala Ser Leu Lys Asn Gly Ser Ser Ala Tyr Tyr Asp Pro Asn Tyr Leu
    50                  55                  60
Thr Thr Asp Ala Glu Lys Asp Arg Tyr Leu Lys Thr Thr Ile Lys Leu
65                  70                  75                  80
Phe Lys Arg Ile Asn Ser Asn Pro Ala Gly Lys Val Leu Leu Gln Glu
                85                  90                  95
Ile Ser Tyr Ala Lys Pro Tyr Leu Gly Asn Asp His Thr Pro Ile Asp
            100                 105                 110
Glu Phe Ser Pro Val Thr Arg Thr Thr Ser Val Asn Ile Lys Leu Ser
        115                 120                 125
Thr Asn Val Glu Ser Ser Met Leu Leu Asn Leu Leu Val Leu Gly Ala
    130                 135                 140
Gly Pro Asp Ile Phe Glu Ser Cys Cys Tyr Pro Val Arg Lys Leu Ile
145                 150                 155                 160
Asp Pro Asp Val Val Tyr Asp Pro Ser Asn Tyr Gly Phe Gly Ser Ile
                165                 170                 175
Asn Ile Val Thr Phe Ser Pro Glu Tyr Glu Tyr Thr Phe Asn Asp Ile
            180                 185                 190
Ser Gly Gly His Asn Ser Ser Thr Glu Ser Phe Ile Ala Asp Pro Ala
        195                 200                 205
Ile Ser Leu Ala His Glu Leu Ile His Ala Leu His Gly Leu Tyr Gly
    210                 215                 220
Ala Arg Gly Val Thr Tyr Glu Glu Thr Ile Glu Val Lys Gln Ala Pro
225                 230                 235                 240
Leu Met Ile Ala Glu Lys Pro Ile Arg Leu Glu Glu Phe Leu Thr Phe
                245                 250                 255
Gly Gly Gln Asp Leu Asn Ile Ile Thr Ser Ala Met Lys Glu Lys Ile
            260                 265                 270
Tyr Asn Asn Leu Leu Ala Asn Tyr Glu Lys Ile Ala Thr Arg Leu Ser
        275                 280                 285
Glu Val Asn Ser Ala Pro Pro Glu Tyr Asp Ile Asn Glu Tyr Lys Asp
    290                 295                 300
Tyr Phe Gln Trp Lys Tyr Gly Leu Asp Lys Asn Ala Asp Gly Ser Tyr
305                 310                 315                 320
Thr Val Asn Glu Asn Lys Phe Asn Glu Ile Tyr Lys Lys Leu Tyr Ser
                325                 330                 335
Phe Thr Glu Ser Asp Leu Ala Asn Lys Phe Lys Val Lys Cys Arg Asn
            340                 345                 350
Thr Tyr Phe Ile Lys Tyr Gly Phe Leu Lys Val Pro Asn Leu Leu Asp
        355                 360                 365
Asp Asp Ile Tyr Thr Val Ser Glu Gly Phe Asn Ile Gly Asn Leu Ala
    370                 375                 380
Val Asn Asn Arg Gly Gln Ser Ile Lys Leu Asn Pro Lys
385                 390                 395
```

<210> SEQ ID NO 45
<211> LENGTH: 389
<212> TYPE: PRT
<213> ORGANISM: Clostridium botulinum

<400> SEQUENCE: 45

Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
            20                  25                  30

Pro Glu Arg Asn Ile Ile Gly Lys Lys Pro Ser Asp Phe Tyr Pro Pro
        35                  40                  45

Ile Ser Leu Asp Ser Gly Ser Ser Ala Tyr Tyr Asp Pro Asn Tyr Leu
    50                  55                  60

Thr Thr Asp Ala Glu Lys Asp Arg Phe Leu Lys Thr Val Ile Lys Leu
65                  70                  75                  80

Phe Asn Arg Ile Asn Ser Asn Pro Ala Gly Gln Val Leu Leu Glu Glu
                85                  90                  95

Ile Lys Asn Gly Lys Pro Tyr Leu Gly Asn Asp His Thr Ala Val Asn
            100                 105                 110

Glu Phe Cys Ala Asn Asn Arg Ser Thr Ser Val Glu Ile Lys Glu Ser
        115                 120                 125

Lys Gly Thr Thr Asp Ser Met Leu Leu Asn Leu Val Ile Leu Gly Pro
    130                 135                 140

Gly Pro Asn Ile Leu Glu Cys Ser Thr Phe Pro Val Arg Ile Phe Pro
145                 150                 155                 160

Asn Asn Ile Ala Tyr Asp Pro Ser Glu Lys Gly Phe Gly Ser Ile Gln
                165                 170                 175

Leu Met Ser Phe Ser Thr Glu Tyr Glu Tyr Ala Phe Asn Asp Asn Thr
            180                 185                 190

Asp Leu Phe Ile Ala Asp Pro Ala Ile Ser Leu Ala His Glu Leu Ile
        195                 200                 205

His Val Leu His Gly Leu Tyr Gly Ala Lys Gly Val Thr Asn Lys Lys
    210                 215                 220

Val Ile Glu Val Asp Gln Gly Ala Leu Met Ala Ala Glu Lys Asp Ile
225                 230                 235                 240

Lys Ile Glu Glu Phe Ile Thr Phe Gly Gly Gln Asp Leu Asn Ile Ile
                245                 250                 255

Thr Asn Ser Thr Asn Gln Lys Ile Tyr Asp Asn Leu Leu Ser Asn Tyr
            260                 265                 270

Thr Ala Ile Ala Ser Arg Leu Ser Gln Val Asn Ile Asn Asn Ser Ala
        275                 280                 285

Leu Asn Thr Thr Tyr Tyr Lys Asn Phe Phe Gln Trp Lys Tyr Gly Leu
    290                 295                 300

Asp Gln Asp Ser Asn Gly Asn Tyr Thr Val Asn Ile Ser Lys Phe Asn
305                 310                 315                 320

Ala Ile Tyr Lys Lys Leu Phe Ser Phe Thr Glu Cys Asp Leu Ala Gln
                325                 330                 335

Lys Phe Gln Val Lys Asn Arg Ser Asn Tyr Leu Phe His Phe Lys Pro
            340                 345                 350

Phe Arg Leu Leu Asp Leu Leu Asp Asp Asn Ile Tyr Ser Ile Ser Glu
        355                 360                 365

Gly Phe Asn Ile Gly Ser Leu Arg Val Asn Asn Asn Gly Gln Asn Ile
    370                 375                 380

Asn Leu Asn Ser Arg
385

<210> SEQ ID NO 46
<211> LENGTH: 389
<212> TYPE: PRT
<213> ORGANISM: Clostridium botulinum

<400> SEQUENCE: 46

```
Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
            20                  25                  30

Pro Glu Arg Asn Ile Ile Gly Lys Lys Pro Ser Asp Phe Tyr Pro Pro
        35                  40                  45

Ile Ser Leu Asp Ser Gly Ser Ser Ala Tyr Tyr Asp Pro Asn Tyr Leu
    50                  55                  60

Thr Thr Asp Ala Glu Lys Asp Arg Phe Leu Lys Thr Val Ile Lys Leu
65                  70                  75                  80

Phe Asn Arg Ile Asn Ser Asn Pro Ala Gly Gln Val Leu Leu Glu Glu
                85                  90                  95

Ile Lys Asn Gly Lys Pro Tyr Leu Gly Asn Asp His Thr Ala Val Asn
            100                 105                 110

Glu Phe Cys Ala Asn Asn Arg Ser Thr Ser Val Glu Ile Lys Glu Ser
        115                 120                 125

Asn Gly Thr Thr Asp Ser Met Leu Leu Asn Leu Val Ile Leu Gly Pro
    130                 135                 140

Gly Pro Asn Ile Leu Glu Cys Ser Thr Phe Pro Val Arg Ile Phe Pro
145                 150                 155                 160

Asn Asn Ile Ala Tyr Asp Pro Ser Glu Lys Gly Phe Gly Ser Ile Gln
                165                 170                 175

Leu Met Ser Phe Ser Thr Glu Tyr Glu Tyr Ala Phe Asn Asp Asn Thr
            180                 185                 190

Asp Leu Phe Ile Ala Asp Pro Ala Ile Ser Leu Ala His Glu Leu Ile
        195                 200                 205

His Val Leu His Gly Leu Tyr Gly Ala Lys Gly Val Thr Asn Lys Lys
    210                 215                 220

Val Ile Glu Val Asp Gln Gly Ala Leu Met Ala Ala Glu Lys Asp Ile
225                 230                 235                 240

Lys Ile Glu Glu Phe Ile Thr Phe Gly Gly Gln Asp Leu Asn Ile Ile
                245                 250                 255

Thr Asn Ser Thr Asn Gln Lys Ile Tyr Asp Asn Leu Leu Ser Asn Tyr
            260                 265                 270

Thr Ala Ile Ala Ser Arg Leu Ser Gln Val Asn Ile Asn Asn Ser Ala
        275                 280                 285

Leu Asn Thr Thr Tyr Tyr Lys Asn Phe Phe Gln Trp Lys Tyr Gly Leu
    290                 295                 300

Asp Gln Asp Ser Asn Gly Asn Tyr Thr Val Asn Ile Ser Lys Phe Asn
305                 310                 315                 320

Ala Ile Tyr Lys Lys Leu Phe Ser Phe Thr Glu Cys Asp Leu Ala Gln
                325                 330                 335

Lys Phe Gln Val Lys Asn Arg Ser Asn Tyr Leu Phe His Phe Lys Pro
            340                 345                 350

Phe Arg Leu Leu Asp Leu Leu Asp Asp Asn Ile Tyr Ser Ile Ser Glu
        355                 360                 365
```

Gly Phe Asn Ile Gly Ser Leu Arg Val Asn Asn Gly Gln Asn Ile
    370                 375                 380

Asn Leu Asn Ser Arg
385

<210> SEQ ID NO 47
<211> LENGTH: 389
<212> TYPE: PRT
<213> ORGANISM: Clostridium botulinum

<400> SEQUENCE: 47

Asn Asn Thr Thr Ile Leu Tyr Met Lys Met Pro Tyr Tyr Glu Asp Ser
1               5                   10                  15

Asn Lys Tyr Tyr Lys Ala Phe Glu Ile Met Asp Asn Val Trp Ile Ile
            20                  25                  30

Pro Glu Arg Asn Ile Ile Gly Lys Lys Pro Ser Asp Phe Tyr Pro Pro
        35                  40                  45

Ile Ser Leu Asp Ser Gly Ser Ser Ala Tyr Tyr Asp Pro Asn Tyr Leu
    50                  55                  60

Thr Thr Asp Ala Glu Lys Asp Arg Phe Leu Lys Thr Val Ile Lys Leu
65                  70                  75                  80

Phe Asn Arg Ile Asn Ser Asn Pro Ala Gly Gln Val Leu Leu Glu Glu
                85                  90                  95

Ile Lys Asn Gly Lys Pro Tyr Leu Gly Asn Asp His Thr Ala Val Asn
            100                 105                 110

Glu Phe Cys Ala Asn Asn Arg Ser Thr Ser Val Glu Ile Lys Glu Ser
        115                 120                 125

Asn Gly Thr Thr Asp Ser Met Leu Leu Asn Leu Val Ile Leu Gly Pro
    130                 135                 140

Gly Pro Asn Ile Leu Glu Cys Ser Thr Phe Pro Val Arg Ile Phe Pro
145                 150                 155                 160

Asn Asn Ile Ala Tyr Asp Pro Ser Glu Lys Gly Phe Gly Ser Ile Gln
                165                 170                 175

Leu Met Ser Phe Ser Thr Glu Tyr Glu Tyr Ala Phe Asn Asp Asn Thr
            180                 185                 190

Asp Leu Phe Ile Ala Asp Pro Ala Ile Ser Leu Ala His Glu Leu Ile
        195                 200                 205

His Val Leu His Gly Leu Tyr Gly Ala Lys Gly Val Thr Asn Lys Lys
    210                 215                 220

Val Ile Glu Val Asp Gln Gly Ala Leu Met Ala Ala Glu Lys Asp Ile
225                 230                 235                 240

Lys Ile Glu Glu Phe Ile Thr Phe Gly Gly Gln Asp Leu Asn Ile Ile
                245                 250                 255

Thr Asn Ser Thr Asn Gln Lys Ile Tyr Val Ile Leu Leu Ser Asn Tyr
            260                 265                 270

Thr Ala Ile Ala Ser Arg Leu Ser Gln Val Asn Arg Asn Asn Ser Ala
        275                 280                 285

Leu Asn Thr Thr Tyr Tyr Lys Asn Phe Phe Gln Trp Lys Tyr Gly Leu
    290                 295                 300

Asp Gln Asp Ser Asn Gly Asn Tyr Thr Val Asn Ile Ser Lys Phe Asn
305                 310                 315                 320

Ala Ile Tyr Lys Lys Leu Phe Ser Phe Thr Glu Cys Asp Leu Ala Gln
                325                 330                 335

Lys Phe Gln Val Lys Asn Arg Ser Asn Tyr Leu Phe His Phe Lys Pro

```
                    340               345               350
Phe Arg Leu Leu Asp Leu Leu Asp Asp Asn Ile Tyr Ser Ile Ser Glu
            355               360               365
Gly Phe Asn Ile Gly Ser Leu Arg Val Asn Asn Gly Gln Asn Ile
        370               375               380
Asn Leu Asn Ser Arg
385
```

<210> SEQ ID NO 48
<211> LENGTH: 389
<212> TYPE: PRT
<213> ORGANISM: Clostridium botulinum

<400> SEQUENCE: 48

```
Asn Asn Thr Thr Ile Leu Tyr Met Lys Met Pro Tyr Tyr Glu Asp Ser
1               5                  10                  15
Asn Lys Tyr Tyr Lys Ala Phe Glu Ile Met Asp Asn Val Trp Ile Ile
                20                  25                  30
Pro Glu Arg Asn Ile Ile Gly Lys Lys Pro Ser Asp Phe Tyr Pro Pro
            35                  40                  45
Ile Ser Leu Asp Ser Gly Ser Ser Ala Tyr Tyr Asp Pro Asn Tyr Leu
        50                  55                  60
Thr Thr Asp Ala Glu Lys Asp Arg Phe Leu Lys Thr Val Ile Lys Leu
65                  70                  75                  80
Phe Asn Arg Ile Asn Ser Asn Pro Ala Gly Gln Val Leu Leu Glu Glu
                85                  90                  95
Ile Lys Asn Gly Lys Pro Tyr Leu Gly Asn Asp His Thr Ala Val Asn
            100                 105                 110
Glu Phe Cys Ala Asn Asn Arg Ser Thr Ser Val Glu Ile Lys Glu Ser
        115                 120                 125
Asn Gly Thr Thr Asp Ser Met Leu Leu Asn Leu Val Ile Leu Gly Pro
130                 135                 140
Gly Pro Asn Ile Leu Glu Cys Ser Thr Phe Pro Val Arg Ile Phe Pro
145                 150                 155                 160
Asn Asn Ile Ala Tyr Asp Pro Ser Glu Lys Gly Phe Gly Ser Ile Gln
                165                 170                 175
Leu Met Ser Phe Ser Thr Glu Tyr Glu Tyr Ala Phe Asn Asp Asn Thr
            180                 185                 190
Asp Leu Phe Ile Ala Asp Pro Ala Ile Ser Leu Ala His Glu Leu Ile
        195                 200                 205
His Val Leu His Gly Leu Tyr Gly Ala Lys Gly Val Thr Asn Lys Lys
210                 215                 220
Val Ile Glu Val Asp Gln Gly Ala Leu Met Ala Ala Glu Lys Asp Ile
225                 230                 235                 240
Lys Ile Glu Glu Phe Ile Thr Phe Gly Gly Gln Asp Leu Asn Ile Val
                245                 250                 255
Thr Asn Ser Thr Asn Gln Lys Ile Tyr Asp Asn Leu Leu Ser Asn Tyr
            260                 265                 270
Thr Ala Ile Ala Ser Arg Leu Ser Gln Val Asn Ile Asn Asn Ser Ala
        275                 280                 285
Leu Asn Thr Thr Tyr Tyr Lys Asn Phe Phe Gln Trp Lys Tyr Gly Leu
290                 295                 300
Asp Gln Asp Ser Asn Gly Asn Tyr Thr Val Asn Ile Ser Lys Phe Asn
305                 310                 315                 320
```

```
Ala Ile Tyr Lys Lys Leu Phe Ser Phe Thr Glu Cys Asp Leu Ala Gln
            325                 330                 335

Lys Phe Gln Val Lys Asn Arg Ser Asn Tyr Leu Phe His Phe Lys Pro
        340                 345                 350

Phe Lys Leu Leu Asp Leu Leu Asp Asp Asn Ile Tyr Ser Ile Ser Glu
        355                 360                 365

Gly Phe Asn Ile Gly Ser Leu Arg Val Asn Asn Asn Gly Gln Asn Ile
        370                 375                 380

Asn Leu Asn Ser Arg
385

<210> SEQ ID NO 49
<211> LENGTH: 312
<212> TYPE: PRT
<213> ORGANISM: Clostridium botulinum
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid

<400> SEQUENCE: 49

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
                20                  25                  30

Lys Val Tyr Thr Phe Phe Ser Ser Glu Phe Ile Asp Thr Ile Asn Lys
            35                  40                  45

Pro Val Asn Ala Ala Leu Phe Ile Asp Trp Ile Ser Lys Val Ile Arg
50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Gly
                85                  90                  95

Asn Glu Ala Glu Lys Gly Asn Phe Lys Glu Ala Phe Glu Leu Leu Gly
            100                 105                 110

Ala Gly Ile Leu Leu Glu Phe Val Pro Glu Leu Xaa Ile Pro Val Ile
        115                 120                 125

Leu Val Phe Thr Ile Lys Ser Tyr Ile Asp Ser Tyr Glu Asn Lys Asn
        130                 135                 140

Lys Ile Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205

Tyr Thr Ser Asp Glu Lys Asn Arg Leu Glu Ser Glu Tyr Asn Ile Asn
```

```
                210                 215                 220
Asn Ile Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Lys Val Gly Lys Leu Lys Glu Tyr Asp Lys His Val
                260                 265                 270

Lys Ser Xaa Leu Leu Asn Tyr Ile Leu Xaa His Arg Ser Ile Leu Gly
        275                 280                 285

Glu Gln Xaa Gln Glu Leu Asn Asp Leu Val Thr Ser Thr Leu Asn Ser
        290                 295                 300

Ser Ile Pro Phe Glu Leu Ser Ser
305                 310

<210> SEQ ID NO 50
<211> LENGTH: 312
<212> TYPE: PRT
<213> ORGANISM: Clostridium botulinum

<400> SEQUENCE: 50

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Ser Glu Glu Ser
                20                  25                  30

Gln Val Tyr Thr Phe Phe Ser Ser Glu Phe Ile Asn Thr Ile Asn Lys
            35                  40                  45

Pro Val His Ala Ala Leu Phe Ile Ser Trp Ile Asn Gln Val Ile Arg
50                  55                  60

Asp Phe Thr Thr Glu Ala Thr Gln Lys Ser Thr Phe Asp Lys Ile Ala
65                  70                  75                  80

Asp Ile Ser Leu Val Val Pro Tyr Val Gly Leu Ala Leu Asn Ile Gly
                85                  90                  95

Asn Glu Val Gln Lys Glu Asn Phe Lys Glu Ala Phe Glu Leu Leu Gly
            100                 105                 110

Ala Gly Ile Leu Leu Glu Phe Val Pro Glu Leu Leu Ile Pro Thr Ile
        115                 120                 125

Leu Val Phe Thr Ile Lys Ser Phe Ile Gly Ser Ser Glu Asn Lys Asn
130                 135                 140

Lys Ile Ile Lys Ala Ile Asn Asn Ser Leu Met Glu Arg Glu Thr Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Val Ile Glu Tyr Lys Tyr Asn Asn
        195                 200                 205

Tyr Thr Ser Asp Glu Arg Asn Arg Leu Glu Ser Glu Tyr Asn Ile Asn
    210                 215                 220

Asn Ile Arg Glu Glu Leu Asn Lys Lys Val Ser Leu Ala Met Glu Asn
225                 230                 235                 240

Ile Glu Arg Phe Ile Thr Glu Ser Ser Ile Phe Tyr Leu Met Lys Leu
                245                 250                 255

Ile Asn Glu Ala Lys Val Ser Lys Leu Arg Glu Tyr Asp Glu Gly Val
                260                 265                 270
```

Lys Glu Tyr Leu Leu Asp Tyr Ile Ser Glu His Arg Ser Ile Leu Gly
                275                 280                 285

Asn Ser Val Gln Glu Leu Asn Asp Leu Val Thr Ser Thr Leu Asn Asn
        290                 295                 300

Ser Ile Pro Phe Glu Leu Ser Ser
305                 310

<210> SEQ ID NO 51
<211> LENGTH: 312
<212> TYPE: PRT
<213> ORGANISM: Clostridium botulinum

<400> SEQUENCE: 51

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
            20                  25                  30

Lys Val Tyr Thr Phe Phe Ser Ser Glu Phe Ile Asp Thr Ile Asn Lys
        35                  40                  45

Pro Val Asn Ala Ala Leu Phe Ile Asp Trp Ile Ser Lys Val Ile Arg
    50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Val
                85                  90                  95

Ile Glu Ala Glu Lys Gly Asn Phe Glu Glu Ala Phe Glu Leu Leu Gly
            100                 105                 110

Ala Gly Ile Leu Leu Glu Phe Val Pro Glu Leu Thr Ile Pro Val Ile
        115                 120                 125

Leu Val Phe Thr Ile Lys Ser Tyr Ile Asp Ser Tyr Glu Asn Lys Asn
    130                 135                 140

Lys Ala Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205

Tyr Thr Ser Asp Glu Lys Asn Arg Leu Glu Ser Lys Tyr Asn Ile Asn
    210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Glu Val Gly Lys Leu Lys Glu Tyr Asp Lys His Val
            260                 265                 270

Lys Ser Asp Leu Leu Asp Tyr Ile Leu Tyr His Lys Leu Ile Leu Gly
        275                 280                 285

Glu Gln Thr Lys Glu Leu Ile Asp Leu Val Thr Ser Thr Leu Asn Ser
    290                 295                 300

Ser Ile Pro Phe Glu Leu Ser Ser
305                 310

<210> SEQ ID NO 52

<211> LENGTH: 312
<212> TYPE: PRT
<213> ORGANISM: Clostridium botulinum

<400> SEQUENCE: 52

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
            20                  25                  30

Lys Val Tyr Thr Phe Phe Ser Ser Glu Phe Ile Asp Thr Ile Asn Lys
        35                  40                  45

Pro Val Asn Ala Ala Leu Phe Ile Asp Trp Ile Ser Lys Val Ile Arg
    50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Val
                85                  90                  95

Ile Glu Ala Glu Lys Gly Asn Phe Glu Glu Ala Phe Glu Leu Leu Gly
            100                 105                 110

Ala Gly Ile Leu Leu Glu Phe Val Pro Glu Leu Thr Ile Pro Val Ile
        115                 120                 125

Leu Val Phe Thr Ile Lys Ser Tyr Ile Asp Ser Tyr Glu Asn Lys Asn
    130                 135                 140

Lys Ala Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205

Tyr Thr Ser Asp Glu Lys Asn Arg Leu Glu Ser Lys Tyr Asn Ile Asn
    210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Glu Val Gly Lys Leu Lys Glu Tyr Asp Lys His Val
            260                 265                 270

Lys Ser Asp Leu Leu Asp Tyr Ile Leu Tyr His Lys Leu Ile Leu Gly
        275                 280                 285

Glu Gln Thr Lys Glu Leu Ile Asp Leu Val Thr Ser Thr Leu Asn Ser
    290                 295                 300

Ser Ile Pro Phe Glu Leu Ser Ser
305                 310

<210> SEQ ID NO 53
<211> LENGTH: 312
<212> TYPE: PRT
<213> ORGANISM: Clostridium botulinum

<400> SEQUENCE: 53

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Lys Ser
            20                  25                  30

Lys Val Tyr Thr Phe Phe Ser Ser Glu Phe Ile Asp Thr Ile Asn Glu
            35                  40                  45

Ser Val Asn Ala Ala Leu Phe Ile Asp Trp Ile Asn Lys Val Ile Arg
    50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Val
                85                  90                  95

Ile Asp Ala Glu Lys Gly Asn Phe Gln Glu Ala Phe Glu Leu Leu Gly
                100                 105                 110

Ala Gly Ile Leu Leu Glu Phe Val Pro Glu Leu Thr Ile Pro Val Ile
            115                 120                 125

Leu Val Phe Thr Ile Lys Ser Tyr Ile Asp Ser Tyr Glu Asn Lys Asn
130                 135                 140

Lys Ala Ile Lys Ala Ile Asn Asn Ala Leu Ile Glu Arg Glu Ala Lys
145                 150                 155                 160

Trp Lys Glu Ile Tyr Ser Trp Ile Val Ser Asn Trp Leu Thr Lys Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205

Tyr Thr Ser Asp Glu Lys Asn Arg Leu Glu Ser Glu Tyr Asn Ile Asn
    210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Glu Val Gly Lys Leu Lys Lys Tyr Asp Arg His Val
            260                 265                 270

Lys Ser Asp Leu Leu Asp Tyr Ile Leu Tyr His Lys Leu Ile Leu Gly
        275                 280                 285

Asp Gln Thr Lys Glu Leu Ile Asp Leu Val Thr Ser Thr Leu Asn Ser
    290                 295                 300

Ser Ile Pro Phe Glu Leu Ser Ser
305                 310

<210> SEQ ID NO 54
<211> LENGTH: 312
<212> TYPE: PRT
<213> ORGANISM: Clostridium botulinum

<400> SEQUENCE: 54

Asn Ala Phe Phe Tyr Leu His Ala Gln Lys Val Pro Glu Gly Glu Thr
1               5                   10                  15

Asn Ile Ser Leu Thr Ser Ser Ile Asp Thr Ala Leu Ser Glu Glu Ser
            20                  25                  30

Lys Val Tyr Thr Phe Phe Ser Ser Glu Phe Ile Asn Asn Ile Asn Lys
            35                  40                  45

Pro Val His Ala Ala Leu Phe Ile Gly Trp Ile Ser Gln Val Ile Arg
    50                  55                  60

Asp Phe Thr Thr Glu Ser Thr Gln Lys Ser Thr Val Asp Lys Ile Ala
65                  70                  75                  80

Asp Ile Ser Leu Ile Val Pro Tyr Val Gly Leu Ala Leu Asn Ile Gly

```
                    85                  90                  95
Asn Asp Ala Arg Lys Gly Asn Phe Lys Glu Ala Phe Glu Leu Leu Gly
                100                 105                 110

Ala Ala Ile Leu Leu Glu Val Val Pro Glu Leu Leu Ile Pro Val Ile
            115                 120                 125

Leu Val Phe Thr Ile Lys Ser Phe Ile Asp Ser Ser Lys Asn Glu Asp
        130                 135                 140

Lys Ile Ile Lys Ala Ile Asn Asn Ser Leu Ile Glu Arg Glu Ala Lys
145                 150                 155                 160

Trp Lys Glu Val Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
                180                 185                 190

Asn Gln Val Asp Ala Ile Lys Thr Val Ile Glu Tyr Lys Tyr Asn Ser
                195                 200                 205

Tyr Thr Ser Asp Glu Lys Asn Arg Leu Glu Ser Glu Tyr Asn Ile Asn
            210                 215                 220

Asn Ile Glu Glu Glu Leu Asn Lys Lys Val Ser Leu Ala Met Lys Asn
225                 230                 235                 240

Ile Glu Arg Phe Ile Ala Glu Ser Ser Ile Ser Tyr Leu Met Lys Leu
                245                 250                 255

Ile Asn Glu Ala Lys Val Ser Glu Leu Arg Gly Tyr Asp Glu Gly Val
                260                 265                 270

Lys Glu Tyr Leu Leu Asp Tyr Ile Leu Lys Asn Gly Ser Ile Leu Gly
            275                 280                 285

Asp His Val Gln Glu Leu Asn Asp Leu Val Thr Ser Thr Leu Asn Ser
        290                 295                 300

Ser Ile Pro Phe Glu Leu Ser Ser
305                 310

<210> SEQ ID NO 55
<211> LENGTH: 312
<212> TYPE: PRT
<213> ORGANISM: Clostridium botulinum

<400> SEQUENCE: 55

Asn Ala Phe Phe Tyr Leu His Ala Gln Lys Val Pro Glu Gly Glu Thr
1               5                   10                  15

Asn Ile Ser Leu Thr Ser Ser Ile Asp Thr Ala Leu Ser Glu Glu Ser
            20                  25                  30

Lys Val Tyr Thr Phe Phe Ser Ser Glu Phe Ile Asn Asn Ile Asn Lys
        35                  40                  45

Pro Val His Ala Ala Leu Phe Ile Gly Trp Ile Ser Gln Val Ile Arg
    50                  55                  60

Asp Phe Thr Thr Glu Ser Thr Gln Lys Ser Thr Val Asp Lys Ile Ala
65                  70                  75                  80

Asp Ile Ser Leu Ile Val Pro Tyr Val Gly Leu Ala Leu Asn Ile Gly
                85                  90                  95

Asn Asp Ala Arg Lys Gly Asn Phe Lys Glu Ala Phe Glu Leu Leu Gly
                100                 105                 110

Ala Ala Ile Leu Leu Glu Val Val Pro Glu Leu Leu Ile Pro Val Ile
            115                 120                 125

Leu Val Phe Thr Ile Lys Ser Phe Ile Asp Ser Ser Lys Asn Glu Asp
        130                 135                 140
```

```
Lys Ile Ile Lys Ala Ile Asn Asn Ser Leu Ile Glu Arg Glu Ala Lys
145                 150                 155                 160

Trp Lys Glu Val Tyr Ser Trp Ile Val Ser Asn Trp Leu Thr Arg Ile
            165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Val Ile Glu Tyr Lys Tyr Asn Ser
            195                 200                 205

Tyr Thr Ser Asp Glu Lys Asn Arg Leu Glu Ser Glu Tyr Asn Ile Asn
        210                 215                 220

Asn Ile Glu Glu Glu Leu Asn Lys Lys Val Ser Leu Ala Met Lys Asn
225                 230                 235                 240

Ile Glu Arg Phe Ile Ala Glu Ser Ser Ile Ser Tyr Leu Met Lys Leu
                245                 250                 255

Ile Asn Glu Ala Lys Val Ser Glu Leu Arg Glu Tyr Asp Glu Gly Val
            260                 265                 270

Lys Glu Tyr Leu Leu Asp Tyr Ile Leu Lys Asn Gly Ser Ile Leu Gly
        275                 280                 285

Asp His Val Gln Glu Leu Asn Asp Leu Val Thr Ser Thr Leu Asn Ser
    290                 295                 300

Ser Ile Pro Phe Glu Leu Ser Ser
305                 310
```

<210> SEQ ID NO 56
<211> LENGTH: 312
<212> TYPE: PRT
<213> ORGANISM: Clostridium botulinum

<400> SEQUENCE: 56

```
Asn Ala Phe Phe Tyr Leu His Ala Gln Lys Val Pro Glu Gly Glu Thr
1               5                   10                  15

Asn Ile Ser Leu Thr Ser Ser Ile Asp Thr Ala Leu Ser Glu Glu Ser
            20                  25                  30

Lys Val Tyr Thr Phe Phe Ser Ser Glu Phe Ile Asp Thr Ile Asn Glu
        35                  40                  45

Pro Val Asn Ala Ala Leu Phe Ile Asp Trp Ile Ser Lys Val Ile Arg
    50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Val
                85                  90                  95

Asn Glu Thr Glu Lys Gly Asn Phe Lys Glu Ala Phe Glu Leu Leu Gly
            100                 105                 110

Ala Gly Ile Leu Leu Glu Phe Val Pro Glu Leu Ala Ile Pro Val Ile
        115                 120                 125

Leu Val Phe Thr Ile Lys Ser Tyr Ile Asp Ser Tyr Glu Asn Lys Asn
    130                 135                 140

Lys Ile Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205
```

Tyr Thr Ser Asp Glu Lys Asn Arg Leu Glu Ser Glu Tyr Asn Ile Asn
210                 215                 220

Asn Ile Glu Glu Glu Leu Asn Lys Lys Val Ser Leu Ala Met Lys Asn
225                 230                 235                 240

Ile Glu Arg Phe Ile Thr Glu Ser Ser Ile Ser Tyr Leu Met Lys Leu
                245                 250                 255

Ile Asn Glu Ala Glu Val Gly Lys Leu Lys Glu Tyr Asp Lys Arg Val
                260                 265                 270

Lys Arg His Leu Leu Glu Tyr Ile Phe Asp Tyr Arg Leu Ile Leu Gly
275                 280                 285

Glu Gln Gly Gly Glu Leu Ile Asp Leu Val Thr Ser Thr Leu Asn Thr
290                 295                 300

Ser Ile Pro Phe Glu Leu Ser Ser
305                 310

<210> SEQ ID NO 57
<211> LENGTH: 312
<212> TYPE: PRT
<213> ORGANISM: Clostridium botulinum

<400> SEQUENCE: 57

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
                20                  25                  30

Lys Val Tyr Thr Phe Phe Ser Ser Glu Phe Ile Asp Thr Ile Asn Lys
                35                  40                  45

Pro Val Asn Ala Ala Leu Phe Ile Asp Trp Ile Ser Lys Val Ile Arg
50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Ile
                85                  90                  95

Ile Glu Ala Glu Lys Gly Asn Phe Glu Glu Ala Phe Glu Leu Leu Gly
                100                 105                 110

Val Gly Ile Leu Leu Glu Phe Val Pro Glu Leu Thr Ile Pro Val Ile
                115                 120                 125

Leu Val Phe Thr Ile Lys Ser Tyr Ile Asp Ser Tyr Glu Asn Lys Asn
130                 135                 140

Lys Ala Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
                180                 185                 190

Asn Gln Val Asp Ala Ile Lys Thr Ala Ile Glu Tyr Lys Tyr Asn Asn
                195                 200                 205

Tyr Thr Ser Asp Glu Lys Asn Arg Leu Glu Ser Glu Tyr Asn Ile Asn
210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Lys Val Gly Lys Leu Lys Lys Tyr Asp Asn His Val

```
                        260                  265                  270
Lys Ser Asp Leu Leu Asn Tyr Ile Leu Asp His Arg Ser Ile Leu Gly
            275                  280                  285

Glu Gln Thr Asn Glu Leu Ser Asp Leu Val Thr Ser Thr Leu Asn Ser
            290                  295                  300

Ser Ile Pro Phe Glu Leu Ser Ser
305                 310

<210> SEQ ID NO 58
<211> LENGTH: 311
<212> TYPE: PRT
<213> ORGANISM: Clostridium botulinum

<400> SEQUENCE: 58

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
            20                  25                  30

Lys Asp Ile Phe Phe Ser Ser Glu Phe Ile Asp Thr Ile Asn Lys Pro
        35                  40                  45

Val Asn Ala Ala Leu Phe Ile Asp Trp Ile Ser Lys Val Ile Arg Asp
    50                  55                  60

Phe Thr Thr Glu Ala Thr Gln Lys Ser Thr Val Asp Lys Ile Ala Asp
65                  70                  75                  80

Ile Ser Leu Ile Val Pro Tyr Val Gly Leu Ala Leu Asn Ile Ile Ile
                85                  90                  95

Glu Ala Glu Lys Gly Asn Phe Glu Glu Ala Phe Glu Leu Leu Gly Val
            100                 105                 110

Gly Ile Leu Leu Glu Phe Val Pro Glu Leu Thr Ile Pro Val Ile Leu
        115                 120                 125

Val Phe Thr Ile Lys Ser Tyr Ile Asp Ser Tyr Glu Asn Lys Asn Lys
130                 135                 140

Ala Ile Lys Ala Ile Asn Asn Ser Leu Ile Glu Arg Glu Ala Lys Trp
145                 150                 155                 160

Lys Glu Ile Tyr Ser Trp Ile Val Ser Asn Trp Leu Thr Arg Ile Asn
                165                 170                 175

Thr Gln Phe Asn Lys Arg Lys Glu Gln Met Tyr Gln Ala Leu Gln Asn
            180                 185                 190

Gln Val Asp Ala Ile Lys Thr Ala Ile Glu Tyr Lys Tyr Asn Asn Tyr
        195                 200                 205

Thr Ser Asp Glu Lys Asn Arg Leu Glu Ser Glu Tyr Asn Ile Asn Asn
    210                 215                 220

Ile Glu Glu Glu Leu Asn Lys Lys Val Ser Leu Ala Met Lys Asn Ile
225                 230                 235                 240

Glu Arg Phe Met Thr Glu Ser Ser Ile Ser Tyr Leu Met Lys Leu Ile
                245                 250                 255

Asn Glu Ala Lys Val Gly Lys Leu Lys Lys Tyr Asp Asn His Val Lys
            260                 265                 270

Ser Asp Leu Leu Asn Tyr Ile Leu Asp His Arg Ser Ile Leu Gly Glu
        275                 280                 285

Gln Thr Asn Glu Leu Ser Asp Leu Val Thr Ser Thr Leu Asn Ser Ser
    290                 295                 300

Ile Pro Phe Glu Leu Ser Ser
305                 310
```

<210> SEQ ID NO 59
<211> LENGTH: 312
<212> TYPE: PRT
<213> ORGANISM: Clostridium botulinum

<400> SEQUENCE: 59

Asn Val Phe Phe Tyr Leu His Ala Gln Lys Val Pro Glu Gly Glu Thr
1               5                   10                  15

Asn Ile Ser Leu Thr Ser Ser Ile Asp Thr Ala Leu Leu Glu Glu Ser
            20                  25                  30

Lys Val Tyr Thr Phe Phe Ser Ser Glu Phe Ile Asp Thr Ile Asn Lys
        35                  40                  45

Pro Val Asn Ala Ala Leu Phe Ile Asp Trp Ile Ser Lys Val Ile Arg
    50                  55                  60

Asp Phe Thr Thr Glu Ala Thr Gln Lys Ser Thr Val Asp Lys Ile Ala
65                  70                  75                  80

Asp Ile Ser Leu Ile Val Pro Tyr Val Gly Leu Ala Leu Asn Ile Ile
                85                  90                  95

Ile Glu Ala Glu Lys Gly Asn Phe Glu Glu Ala Phe Glu Leu Leu Gly
            100                 105                 110

Val Gly Ile Leu Leu Glu Phe Val Pro Glu Leu Thr Ile Pro Val Ile
        115                 120                 125

Leu Val Phe Thr Ile Lys Ser Tyr Ile Asp Ser Tyr Glu Asn Lys Asn
130                 135                 140

Lys Ala Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Ala Ile Lys Thr Ala Ile Glu Tyr Lys Tyr Asn Asn
        195                 200                 205

Tyr Thr Ser Asp Glu Lys Asn Arg Leu Glu Ser Glu Tyr Asn Ile Asn
    210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Lys Val Gly Lys Leu Lys Lys Tyr Asp Asn His Val
            260                 265                 270

Lys Ser Asp Leu Leu Asn Tyr Ile Leu Asp His Arg Ser Ile Leu Gly
        275                 280                 285

Glu Gln Thr Asn Glu Leu Ser Asp Leu Val Thr Ser Thr Leu Asn Ser
    290                 295                 300

Ser Ile Pro Phe Glu Leu Ser Ser
305                 310

<210> SEQ ID NO 60
<211> LENGTH: 312
<212> TYPE: PRT
<213> ORGANISM: Clostridium botulinum

<400> SEQUENCE: 60

Asn Val Phe Phe Tyr Leu His Ala Gln Lys Val Pro Glu Gly Glu Thr
1               5                   10                  15

```
Asn Ile Ser Leu Thr Ser Ser Ile Asp Thr Ala Leu Leu Glu Glu Ser
             20                  25                  30

Lys Val Tyr Thr Phe Phe Ser Ser Glu Phe Ile Asp Thr Ile Asn Lys
         35                  40                  45

Pro Val Asn Ala Ala Leu Phe Ile Asp Trp Ile Ser Lys Val Ile Arg
 50                  55                  60

Asp Phe Thr Thr Glu Ala Thr Gln Lys Ser Thr Val Asp Lys Ile Ala
 65                  70                  75                  80

Asp Ile Ser Leu Ile Val Pro Tyr Val Gly Leu Ala Leu Asn Ile Ile
                 85                  90                  95

Ile Glu Ala Glu Lys Gly Asn Phe Glu Glu Ala Phe Glu Leu Leu Gly
                100                 105                 110

Val Gly Ile Leu Leu Glu Phe Val Pro Glu Leu Thr Ile Pro Val Ile
                115                 120                 125

Leu Val Phe Thr Ile Lys Ser Tyr Ile Asp Ser Tyr Glu Asn Lys Asn
                130                 135                 140

Lys Ala Ile Lys Ala Ile Asn Asn Ser Leu Ile Glu Arg Glu Ala Lys
145                 150                 155                 160

Trp Lys Glu Ile Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
                180                 185                 190

Asn Gln Val Asp Ala Ile Lys Thr Ala Ile Glu Tyr Lys Tyr Asn Asn
                195                 200                 205

Tyr Thr Ser Asp Glu Lys Asn Arg Leu Glu Ser Glu Tyr Asn Ile Asn
                210                 215                 220

Asn Ile Glu Glu Glu Leu Asn Lys Lys Val Ser Leu Ala Met Lys Asn
225                 230                 235                 240

Ile Glu Arg Phe Met Thr Glu Ser Ser Ile Ser Tyr Leu Met Lys Leu
                245                 250                 255

Ile Asn Glu Ala Lys Val Gly Lys Leu Lys Lys Tyr Asp Asn His Val
                260                 265                 270

Lys Ser Asp Leu Leu Asn Tyr Ile Leu Asp His Arg Ser Ile Leu Gly
                275                 280                 285

Glu Gln Thr Asn Glu Leu Ser Asp Leu Val Thr Ser Thr Leu Asn Ser
                290                 295                 300

Ser Ile Pro Phe Glu Leu Ser Ser
305                 310

<210> SEQ ID NO 61
<211> LENGTH: 313
<212> TYPE: PRT
<213> ORGANISM: Clostridium botulinum

<400> SEQUENCE: 61

Asn Val Phe Phe Tyr Leu Tyr Ala Gln Lys Ala Pro Glu Gly Glu Ser
 1               5                  10                  15

Ala Ile Ser Leu Thr Ser Ser Val Asn Thr Ala Leu Leu Asp Ala Ser
                 20                  25                  30

Lys Val Tyr Thr Phe Phe Ser Ser Asp Phe Ile Asn Thr Val Asn Lys
                 35                  40                  45

Pro Val Gln Ala Ala Leu Phe Ile Ser Trp Ile Gln Gln Val Ile Asn
 50                  55                  60

Asp Phe Thr Thr Glu Ala Thr Gln Lys Ser Thr Ile Asp Lys Ile Ala
 65                  70                  75                  80
```

```
Asp Ile Ser Leu Val Val Pro Tyr Val Gly Leu Ala Leu Asn Ile Gly
                85                  90                  95

Asn Glu Val Gln Lys Gly Asn Phe Lys Glu Ala Ile Glu Leu Leu Gly
            100                 105                 110

Ala Gly Ile Leu Leu Glu Phe Val Pro Glu Leu Leu Ile Pro Thr Ile
        115                 120                 125

Leu Val Phe Thr Ile Lys Ser Phe Ile Asn Ser Asp Asp Ser Lys Asn
130                 135                 140

Lys Ile Ile Lys Ala Ile Asn Asn Ala Leu Arg Glu Arg Glu Leu Lys
145                 150                 155                 160

Trp Lys Glu Val Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Gly Ile Lys Lys Ile Ile Glu Tyr Lys Tyr Asn Asn
        195                 200                 205

Tyr Thr Leu Asp Glu Lys Asn Arg Leu Lys Ala Glu Tyr Asn Ile Tyr
210                 215                 220

Ser Ile Lys Glu Glu Leu Asn Lys Lys Val Ser Leu Ala Met Gln Asn
225                 230                 235                 240

Ile Asp Arg Phe Leu Thr Glu Ser Ser Ile Ser Tyr Leu Met Lys Leu
                245                 250                 255

Ile Asn Glu Ala Lys Ile Asn Lys Leu Ser Glu Tyr Asp Lys Arg Val
            260                 265                 270

Asn Gln Tyr Leu Leu Asn Tyr Ile Leu Glu Asn Ser Ser Thr Leu Gly
        275                 280                 285

Thr Ser Ser Val Gln Glu Leu Asn Asn Leu Val Ser Asn Thr Leu Asn
290                 295                 300

Asn Ser Ile Pro Phe Glu Leu Ser Glu
305                 310

<210> SEQ ID NO 62
<211> LENGTH: 313
<212> TYPE: PRT
<213> ORGANISM: Clostridium botulinum

<400> SEQUENCE: 62

Asn Val Phe Phe Tyr Leu Tyr Ala Gln Lys Ala Pro Glu Gly Glu Ser
1               5                   10                  15

Ala Ile Ser Leu Thr Ser Ser Val Asn Thr Ala Leu Leu Asp Ala Ser
            20                  25                  30

Lys Val Tyr Thr Phe Phe Ser Ser Asp Phe Ile Asn Thr Val Asn Lys
        35                  40                  45

Pro Val Gln Ala Ala Leu Phe Ile Ser Trp Ile Gln Gln Val Ile Asn
50                  55                  60

Asp Phe Thr Thr Glu Ala Thr Gln Lys Ser Thr Ile Asp Lys Ile Ala
65                  70                  75                  80

Asp Ile Ser Leu Val Val Pro Tyr Val Gly Leu Ala Leu Asn Ile Gly
                85                  90                  95

Asn Glu Val Gln Lys Gly Asn Phe Lys Glu Ala Ile Glu Leu Leu Gly
            100                 105                 110

Ala Gly Ile Leu Leu Glu Phe Val Pro Glu Leu Leu Ile Pro Thr Ile
        115                 120                 125

Leu Val Phe Thr Ile Lys Ser Phe Ile Asn Ser Asp Asp Ser Lys Asn
```

130                 135                 140
Lys Ile Ile Lys Ala Ile Asn Asn Ala Leu Arg Glu Arg Glu Leu Lys
145                 150                 155                 160

Trp Lys Glu Val Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Gly Ile Lys Lys Ile Glu Tyr Lys Tyr Asn Asn
        195                 200                 205

Tyr Thr Leu Asp Glu Lys Asn Arg Leu Lys Ala Glu Tyr Asn Ile Tyr
    210                 215                 220

Ser Ile Lys Glu Glu Leu Asn Lys Lys Val Ser Leu Ala Met Gln Asn
225                 230                 235                 240

Ile Asp Arg Phe Leu Thr Glu Ser Ser Ile Ser Tyr Leu Met Lys Leu
                245                 250                 255

Ile Asn Glu Ala Lys Ile Asn Lys Leu Ser Glu Tyr Asp Lys Arg Val
            260                 265                 270

Asn Gln Tyr Leu Leu Asn Tyr Ile Leu Glu Asn Ser Ser Thr Leu Gly
        275                 280                 285

Thr Ser Ser Val Gln Glu Leu Asn Asn Leu Val Ser Asn Thr Leu Asn
    290                 295                 300

Asn Ser Ile Pro Phe Glu Leu Ser Glu
305                 310

<210> SEQ ID NO 63
<211> LENGTH: 313
<212> TYPE: PRT
<213> ORGANISM: Clostridium botulinum

<400> SEQUENCE: 63

Asn Val Phe Phe Tyr Leu Tyr Ala Gln Lys Ala Pro Glu Gly Glu Ser
1                5                  10                  15

Ala Ile Ser Leu Thr Ser Ser Val Asn Thr Ala Leu Leu Asp Ala Ser
            20                  25                  30

Lys Val Tyr Thr Phe Phe Ser Ser Asp Phe Ile Asn Thr Val Asn Lys
        35                  40                  45

Pro Val Gln Ala Ala Leu Phe Ile Ser Trp Ile Gln Gln Val Ile Asn
    50                  55                  60

Asp Phe Thr Thr Glu Ala Thr Gln Lys Ser Thr Ile Asp Lys Ile Ala
65                  70                  75                  80

Asp Ile Ser Leu Ile Val Pro Tyr Val Gly Leu Ala Leu Asn Ile Gly
                85                  90                  95

Asn Glu Val Gln Lys Gly Asn Phe Lys Glu Ala Ile Glu Leu Leu Gly
            100                 105                 110

Ala Gly Ile Leu Leu Glu Phe Val Pro Glu Leu Leu Ile Pro Thr Ile
        115                 120                 125

Leu Val Phe Thr Ile Lys Ser Phe Ile Asn Ser Asp Asp Ser Lys Asn
    130                 135                 140

Lys Ile Ile Lys Ala Ile Asn Asn Ala Leu Arg Glu Arg Glu Leu Lys
145                 150                 155                 160

Trp Lys Glu Val Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

-continued

Asn Gln Val Asp Gly Ile Lys Lys Ile Ile Glu Tyr Lys Tyr Asn Asn
            195                 200                 205

Tyr Thr Leu Asp Glu Lys Asn Arg Leu Arg Ala Glu Tyr Asn Ile Tyr
210                 215                 220

Ser Ile Lys Glu Glu Leu Asn Lys Lys Val Ser Leu Ala Met Gln Asn
225                 230                 235                 240

Ile Asp Arg Phe Leu Thr Glu Ser Ser Ile Ser Tyr Leu Met Lys Leu
                245                 250                 255

Ile Asn Glu Ala Lys Ile Asn Lys Leu Ser Glu Tyr Asp Lys Arg Val
            260                 265                 270

Asn Gln Tyr Leu Leu Asn Tyr Ile Leu Glu Asn Ser Ser Thr Leu Gly
        275                 280                 285

Thr Ser Ser Val Pro Glu Leu Asn Asn Leu Val Ser Asn Thr Leu Asn
    290                 295                 300

Asn Ser Ile Pro Phe Glu Leu Ser Glu
305                 310

<210> SEQ ID NO 64
<211> LENGTH: 313
<212> TYPE: PRT
<213> ORGANISM: Clostridium botulinum

<400> SEQUENCE: 64

Asn Val Phe Phe Tyr Leu Tyr Ala Gln Lys Pro Glu Gly Glu Ser
1               5                   10                  15

Ala Ile Ser Leu Thr Ser Ser Val Asp Thr Ala Leu Leu Asp Ala Ser
            20                  25                  30

Lys Val Tyr Thr Phe Phe Ser Ser Asp Phe Ile Asn Thr Val Asn Lys
        35                  40                  45

Pro Val Gln Ala Ala Leu Phe Ile Ser Trp Ile Gln Val Ile Asn
    50                  55                  60

Asp Phe Thr Thr Glu Ala Thr Gln Lys Ser Thr Ile Asp Lys Ile Ala
65                  70                  75                  80

Asp Ile Ser Leu Val Val Pro Tyr Val Gly Leu Ala Leu Asn Ile Gly
                85                  90                  95

Asn Glu Val Gln Lys Gly Asn Phe Lys Glu Ala Ile Glu Leu Leu Gly
            100                 105                 110

Ala Gly Ile Leu Leu Glu Phe Val Pro Glu Leu Leu Ile Pro Thr Ile
        115                 120                 125

Leu Val Phe Thr Ile Lys Ser Phe Ile Asn Ser Asp Asp Ser Lys Asn
    130                 135                 140

Lys Ile Ile Lys Ala Ile Asn Asn Ala Leu Arg Glu Arg Glu Leu Lys
145                 150                 155                 160

Trp Lys Glu Val Tyr Ser Trp Ile Val Ser Asn Trp Leu Thr Arg Ile
                165                 170                 175

Asn Thr Gln Phe Asn Lys Arg Lys Glu Gln Met Tyr Gln Ala Leu Gln
            180                 185                 190

Asn Gln Val Asp Gly Ile Lys Lys Ile Ile Glu Tyr Lys Tyr Asn Asn
        195                 200                 205

Tyr Thr Leu Asp Glu Lys Asn Arg Leu Lys Ala Glu Tyr Asn Ile Tyr
    210                 215                 220

Asn Ile Lys Glu Glu Leu Asn Lys Lys Val Ser Leu Ala Met Gln Asn
225                 230                 235                 240

Ile Asp Arg Phe Leu Thr Glu Ser Ser Ile Ser Tyr Leu Met Lys Leu
                245                 250                 255

```
Ile Asn Glu Ala Lys Ile Asn Lys Leu Ser Glu Tyr Asp Lys Arg Val
            260                 265                 270

Asn Gln Tyr Leu Leu Asn Tyr Ile Leu Glu Asn Ser Ser Thr Leu Gly
        275                 280                 285

Thr Ser Ser Val Gln Glu Leu Asn Asn Leu Val Ser Asn Thr Leu Asn
    290                 295                 300

Asn Ser Ile Pro Phe Glu Leu Ser Glu
305                 310

<210> SEQ ID NO 65
<211> LENGTH: 15
<212> TYPE: PRT
<213> ORGANISM: Clostridium botulinum

<400> SEQUENCE: 65

Lys Ser Ile Ile Pro Arg Lys Gly Thr Lys Ala Pro Pro Arg Leu
1               5                   10                  15

<210> SEQ ID NO 66
<211> LENGTH: 15
<212> TYPE: PRT
<213> ORGANISM: Clostridium botulinum

<400> SEQUENCE: 66

Lys Ser Val Ile Pro Arg Lys Gly Thr Lys Ala Pro Pro Arg Leu
1               5                   10                  15

<210> SEQ ID NO 67
<211> LENGTH: 15
<212> TYPE: PRT
<213> ORGANISM: Clostridium botulinum

<400> SEQUENCE: 67

Lys Ser Ile Ile Pro Arg Lys Gly Thr Lys Gln Ser Pro Ser Leu
1               5                   10                  15

<210> SEQ ID NO 68
<211> LENGTH: 13
<212> TYPE: PRT
<213> ORGANISM: Clostridium botulinum

<400> SEQUENCE: 68

Leu Asn Ser Ser Phe Lys Lys Asn Thr Lys Lys Pro Leu
1               5                   10

<210> SEQ ID NO 69
<211> LENGTH: 13
<212> TYPE: PRT
<213> ORGANISM: Clostridium botulinum

<400> SEQUENCE: 69

Lys Ser Ile Val Ser Lys Lys Gly Thr Lys Asn Ser Leu
1               5                   10

<210> SEQ ID NO 70
<211> LENGTH: 8
<212> TYPE: PRT
<213> ORGANISM: Artificial Sequence
<220> FEATURE:
<223> OTHER INFORMATION: F1/4/6 activation loop sequence (after cleavage
      site) + start of F7 heavy chain sequence

<400> SEQUENCE: 70
```

Ala Pro Pro Arg Leu Cys Ile Lys
1               5

<210> SEQ ID NO 71
<211> LENGTH: 8
<212> TYPE: PRT
<213> ORGANISM: Artificial Sequence
<220> FEATURE:
<223> OTHER INFORMATION: F1/4/6 activation loop sequence (after cleavage
      site) + start of F5 heavy chain sequence

<400> SEQUENCE: 71

Ala Pro Pro Arg Leu Cys Ile Thr
1               5

<210> SEQ ID NO 72
<211> LENGTH: 8
<212> TYPE: PRT
<213> ORGANISM: Artificial Sequence
<220> FEATURE:
<223> OTHER INFORMATION: F2/3 activation loop sequence (after cleavage
      site) + start of F7 heavy chain sequence

<400> SEQUENCE: 72

Gln Ser Pro Ser Leu Cys Ile Lys
1               5

<210> SEQ ID NO 73
<211> LENGTH: 8
<212> TYPE: PRT
<213> ORGANISM: Artificial Sequence
<220> FEATURE:
<223> OTHER INFORMATION: F2/3 activation loop sequence (after cleavage
      site) + start of F5 heavy chain sequence

<400> SEQUENCE: 73

Gln Ser Pro Ser Leu Cys Ile Thr
1               5

<210> SEQ ID NO 74
<211> LENGTH: 9
<212> TYPE: PRT
<213> ORGANISM: Artificial Sequence
<220> FEATURE:
<223> OTHER INFORMATION: F1/4/6 activation loop sequence (after cleavage
      site) + start of F7 heavy chain sequence

<400> SEQUENCE: 74

Ala Pro Pro Arg Leu Cys Ile Lys Val
1               5

<210> SEQ ID NO 75
<211> LENGTH: 1270
<212> TYPE: PRT
<213> ORGANISM: Artificial Sequence
<220> FEATURE:
<223> OTHER INFORMATION: full-length recombinant BoNT/F7-1
      (SXN102875_rBoNT-F7-1)

<400> SEQUENCE: 75

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

```
Arg Asn Ile Ile Gly Lys Lys Pro Ser Asp Phe Tyr Pro Pro Ile Ser
 50                  55                  60

Leu Asp Ser Gly Ser Ser Ala Tyr Tyr Asp Pro Asn Tyr Leu Thr Thr
 65                  70                  75                  80

Asp Ala Glu Lys Asp Arg Phe Leu Lys Thr Val Ile Lys Leu Phe Asn
                 85                  90                  95

Arg Ile Asn Ser Asn Pro Ala Gly Gln Val Leu Leu Glu Glu Ile Lys
                100                 105                 110

Asn Gly Lys Pro Tyr Leu Gly Asn Asp His Thr Ala Val Asn Glu Phe
            115                 120                 125

Cys Ala Asn Asn Arg Ser Thr Ser Val Glu Ile Lys Glu Ser Lys Gly
130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
    195                 200                 205

Phe Ile Ala Asp Pro Ala Ile Ser Leu Ala His Glu Leu Ile His Val
210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
                260                 265                 270

Ser Thr Asn Gln Lys Ile Tyr Asp Asn Leu Leu Ser Asn Tyr Thr Ala
    275                 280                 285

Ile Ala Ser Arg Leu Ser Gln Val Asn Ile Asn Asn Ser Ala Leu Asn
    290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
    355                 360                 365

Leu Leu Asp Leu Leu Asp Asp Asn Ile Tyr Ser Ile Ser Glu Gly Phe
370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Val Ile Pro Arg Lys Gly Thr Lys Ala
                420                 425                 430

Pro Pro Arg Leu Cys Ile Lys Val Asn Asn Arg Asp Leu Phe Phe Val
            435                 440                 445

Ala Ser Glu Ser Ser Tyr Asn Glu Asn Gly Ile Asn Ser Pro Lys Glu
450                 455                 460

Ile Asp Asp Thr Thr Ile Thr Asn Asn Asn Tyr Lys Lys Asn Leu Asp
```

-continued

```
            465                 470                 475                 480
        Glu Val Ile Leu Asp Tyr Asn Ser Asp Ala Ile Pro Asn Leu Ser Ser
                            485                 490                 495
        Arg Leu Leu Asn Thr Thr Ala Gln Asn Asp Ser Tyr Val Pro Lys Tyr
                            500                 505                 510
        Asp Ser Asn Gly Thr Ser Glu Ile Lys Glu Tyr Thr Val Asp Lys Leu
                            515                 520                 525
        Asn Val Phe Phe Tyr Leu Tyr Ala Gln Lys Ala Pro Glu Gly Glu Ser
                            530                 535                 540
        Ala Ile Ser Leu Thr Ser Ser Val Asn Thr Ala Leu Leu Asp Ala Ser
        545                 550                 555                 560
        Lys Val Tyr Thr Phe Phe Ser Ser Asp Phe Ile Asn Thr Val Asn Lys
                            565                 570                 575
        Pro Val Gln Ala Ala Leu Phe Ile Ser Trp Ile Gln Asn Val Ile Asn
                            580                 585                 590
        Asp Phe Thr Thr Glu Ala Thr Gln Lys Ser Thr Ile Asp Lys Ile Ala
                            595                 600                 605
        Asp Ile Ser Leu Val Val Pro Tyr Val Gly Leu Ala Leu Asn Ile Gly
            610                 615                 620
        Asn Glu Val Gln Lys Gly Asn Phe Lys Glu Ala Ile Glu Leu Leu Gly
        625                 630                 635                 640
        Ala Gly Ile Leu Leu Glu Phe Val Pro Glu Leu Leu Ile Pro Thr Ile
                            645                 650                 655
        Leu Val Phe Thr Ile Lys Ser Phe Ile Asn Ser Asp Asp Ser Lys Asn
                            660                 665                 670
        Lys Ile Ile Lys Ala Ile Asn Asn Ala Leu Arg Glu Arg Glu Leu Lys
                            675                 680                 685
        Trp Lys Glu Val Tyr Ser Trp Ile Val Ser Asn Trp Leu Thr Arg Ile
                            690                 695                 700
        Asn Thr Gln Phe Asn Lys Arg Lys Glu Gln Met Tyr Gln Ala Leu Gln
        705                 710                 715                 720
        Asn Gln Val Asp Gly Ile Lys Lys Ile Glu Tyr Lys Tyr Asn Asn
                            725                 730                 735
        Tyr Thr Leu Asp Glu Lys Asn Arg Leu Lys Ala Glu Tyr Asn Ile Tyr
                            740                 745                 750
        Ser Ile Lys Glu Glu Leu Asn Lys Lys Val Ser Leu Ala Met Gln Asn
                            755                 760                 765
        Ile Asp Arg Phe Leu Thr Glu Ser Ser Ile Ser Tyr Leu Met Lys Leu
                            770                 775                 780
        Ile Asn Glu Ala Lys Ile Asn Lys Leu Ser Glu Tyr Asp Lys Arg Val
        785                 790                 795                 800
        Asn Gln Tyr Leu Leu Asn Tyr Ile Leu Glu Asn Ser Ser Thr Leu Gly
                            805                 810                 815
        Thr Ser Ser Val Gln Glu Leu Asn Asn Leu Val Ser Asn Thr Leu Asn
                            820                 825                 830
        Asn Ser Ile Pro Phe Glu Leu Ser Glu Tyr Thr Asn Asp Lys Ile Leu
                            835                 840                 845
        Ile Ser Tyr Phe Asn Arg Phe Tyr Lys Arg Ile Asp Ser Ser Ile
                            850                 855                 860
        Leu Asn Met Lys Tyr Glu Asn Asn Arg Phe Ile Asp Ser Ser Gly Tyr
        865                 870                 875                 880
        Gly Ser Asn Ile Ser Ile Asn Gly Asp Ile Tyr Ile Tyr Ser Thr Asn
                            885                 890                 895
```

Arg Asn Gln Phe Gly Ile Tyr Ser Ser Arg Leu Ser Glu Val Asn Ile
                900                 905                 910

Thr Gln Asn Asn Thr Ile Ile Tyr Asn Ser Arg Tyr Gln Asn Phe Ser
        915                 920                 925

Val Ser Phe Trp Val Arg Ile Pro Lys Tyr Asn Leu Lys Asn Leu
930                 935                 940

Asn Asn Glu Tyr Thr Ile Ile Asn Cys Met Arg Asn Asn Ser Gly
945                 950                 955                 960

Trp Lys Ile Ser Leu Asn Tyr Asn Asn Ile Ile Trp Thr Leu Gln Asp
                965                 970                 975

Thr Thr Gly Asn Asn Gln Lys Leu Val Phe Asn Tyr Thr Gln Met Ile
        980                 985                 990

Asp Ile Ser Asp Tyr Ile Asn Lys Trp Thr Phe Val Thr Ile Thr Asn
                995                 1000                1005

Asn Arg Leu Gly His Ser Lys Leu Tyr Ile Asn Gly Asn Leu Thr
        1010                1015                1020

Asp Gln Lys Ser Ile Leu Asn Leu Gly Asn Ile His Val Asp Asp
        1025                1030                1035

Asn Ile Leu Phe Lys Ile Val Gly Cys Asn Asp Thr Arg Tyr Val
        1040                1045                1050

Gly Ile Arg Tyr Phe Lys Ile Phe Asn Met Glu Leu Asp Lys Thr
        1055                1060                1065

Glu Ile Glu Thr Leu Tyr His Ser Glu Pro Asp Ser Thr Ile Leu
        1070                1075                1080

Lys Asp Phe Trp Gly Asn Tyr Leu Leu Tyr Asn Lys Lys Tyr Tyr
        1085                1090                1095

Leu Leu Asn Leu Leu Lys Pro Asn Met Ser Val Thr Lys Asn Ser
        1100                1105                1110

Asp Ile Leu Asn Ile Asn Arg Gln Arg Gly Ile Tyr Ser Lys Thr
        1115                1120                1125

Asn Ile Phe Ser Asn Ala Arg Leu Tyr Thr Gly Val Glu Val Ile
        1130                1135                1140

Ile Arg Lys Val Gly Ser Thr Asp Thr Ser Asn Thr Asp Asn Phe
        1145                1150                1155

Val Arg Lys Asn Asp Thr Val Tyr Ile Asn Val Val Asp Gly Asn
        1160                1165                1170

Ser Glu Tyr Gln Leu Tyr Ala Asp Val Ser Thr Ser Ala Val Glu
        1175                1180                1185

Lys Thr Ile Lys Leu Arg Arg Ile Ser Asn Ser Asn Tyr Asn Ser
        1190                1195                1200

Asn Gln Met Ile Ile Met Asp Ser Ile Gly Asp Asn Cys Thr Met
        1205                1210                1215

Asn Phe Lys Thr Asn Asn Gly Asn Asp Ile Gly Leu Leu Gly Phe
        1220                1225                1230

His Leu Asn Asn Leu Val Ala Ser Ser Trp Tyr Tyr Lys Asn Ile
        1235                1240                1245

Arg Asn Asn Thr Arg Asn Asn Gly Cys Phe Trp Ser Phe Ile Ser
        1250                1255                1260

Lys Glu His Gly Trp Gln Glu
        1265                1270

<210> SEQ ID NO 76
<211> LENGTH: 56

<212> TYPE: PRT
<213> ORGANISM: Clostridium botulinum

<400> SEQUENCE: 76

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 77
<211> LENGTH: 56
<212> TYPE: PRT
<213> ORGANISM: Clostridium botulinum

<400> SEQUENCE: 77

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 78
<211> LENGTH: 56
<212> TYPE: PRT
<213> ORGANISM: Clostridium botulinum

<400> SEQUENCE: 78

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 79
<211> LENGTH: 56
<212> TYPE: PRT
<213> ORGANISM: Clostridium botulinum

<400> SEQUENCE: 79

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 80

```
<211> LENGTH: 56
<212> TYPE: PRT
<213> ORGANISM: Clostridium botulinum

<400> SEQUENCE: 80

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 81
<211> LENGTH: 56
<212> TYPE: PRT
<213> ORGANISM: Clostridium botulinum

<400> SEQUENCE: 81

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 82
<211> LENGTH: 56
<212> TYPE: PRT
<213> ORGANISM: Clostridium botulinum

<400> SEQUENCE: 82

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 83
<211> LENGTH: 56
<212> TYPE: PRT
<213> ORGANISM: Clostridium botulinum

<400> SEQUENCE: 83

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55
```

```
<210> SEQ ID NO 84
<211> LENGTH: 56
<212> TYPE: PRT
<213> ORGANISM: Clostridium botulinum

<400> SEQUENCE: 84

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 85
<211> LENGTH: 56
<212> TYPE: PRT
<213> ORGANISM: Clostridium botulinum

<400> SEQUENCE: 85

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 86
<211> LENGTH: 56
<212> TYPE: PRT
<213> ORGANISM: Clostridium botulinum

<400> SEQUENCE: 86

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 87
<211> LENGTH: 56
<212> TYPE: PRT
<213> ORGANISM: Clostridium botulinum

<400> SEQUENCE: 87

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55
```

```
<210> SEQ ID NO 88
<211> LENGTH: 56
<212> TYPE: PRT
<213> ORGANISM: Clostridium botulinum

<400> SEQUENCE: 88

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 89
<211> LENGTH: 56
<212> TYPE: PRT
<213> ORGANISM: Clostridium botulinum

<400> SEQUENCE: 89

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 90
<211> LENGTH: 56
<212> TYPE: PRT
<213> ORGANISM: Clostridium botulinum

<400> SEQUENCE: 90

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55

<210> SEQ ID NO 91
<211> LENGTH: 56
<212> TYPE: PRT
<213> ORGANISM: Clostridium botulinum

<400> SEQUENCE: 91

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
                20                  25                  30

Asp Leu Cys Ile Lys Val Asn Asn Trp Asp Leu Phe Phe Ser Pro Ser
            35                  40                  45

Glu Asp Asn Phe Thr Asn Asp Leu
    50                  55
```

<210> SEQ ID NO 92
<211> LENGTH: 56
<212> TYPE: PRT
<213> ORGANISM: Clostridium botulinum

<400> SEQUENCE: 92

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 93
<211> LENGTH: 56
<212> TYPE: PRT
<213> ORGANISM: Clostridium botulinum

<400> SEQUENCE: 93

Thr Gly Leu Phe Glu Phe Tyr Lys Leu Leu Cys Val Arg Gly Ile Ile
1               5                   10                  15

Thr Ser Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 94
<211> LENGTH: 56
<212> TYPE: PRT
<213> ORGANISM: Clostridium botulinum

<400> SEQUENCE: 94

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Tyr Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 95
<211> LENGTH: 56
<212> TYPE: PRT
<213> ORGANISM: Clostridium botulinum

<400> SEQUENCE: 95

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu

-continued

```
        50                  55

<210> SEQ ID NO 96
<211> LENGTH: 56
<212> TYPE: PRT
<213> ORGANISM: Clostridium botulinum

<400> SEQUENCE: 96

Thr Gly Leu Phe Glu Phe Tyr Lys Leu Leu Cys Val Arg Gly Ile Ile
1               5                   10                  15

Pro Phe Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 97
<211> LENGTH: 56
<212> TYPE: PRT
<213> ORGANISM: Clostridium botulinum

<400> SEQUENCE: 97

Thr Gly Leu Phe Glu Phe Tyr Lys Leu Leu Cys Val Arg Gly Ile Ile
1               5                   10                  15

Thr Ser Lys Thr Lys Ser Leu Asp Glu Gly Tyr Asn Lys Ala Leu Asn
            20                  25                  30

Glu Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 98
<211> LENGTH: 56
<212> TYPE: PRT
<213> ORGANISM: Clostridium botulinum

<400> SEQUENCE: 98

Thr Gly Leu Phe Glu Phe Tyr Lys Leu Leu Cys Val Arg Gly Ile Ile
1               5                   10                  15

Thr Ser Lys Thr Lys Ser Leu Asp Glu Gly Tyr Asn Lys Ala Leu Asn
            20                  25                  30

Glu Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 99
<211> LENGTH: 56
<212> TYPE: PRT
<213> ORGANISM: Clostridium botulinum

<400> SEQUENCE: 99

Thr Gly Leu Phe Glu Phe Tyr Lys Leu Leu Cys Val Arg Gly Ile Ile
1               5                   10                  15

Thr Ser Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45
```

Glu Asp Asn Phe Thr Asn Asp Leu
    50                  55

<210> SEQ ID NO 100
<211> LENGTH: 56
<212> TYPE: PRT
<213> ORGANISM: Clostridium botulinum

<400> SEQUENCE: 100

Thr Gly Leu Phe Glu Phe Tyr Lys Leu Leu Cys Val Arg Gly Ile Ile
1               5                   10                  15

Thr Ser Lys Thr Lys Ser Leu Asp Glu Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 101
<211> LENGTH: 56
<212> TYPE: PRT
<213> ORGANISM: Clostridium botulinum

<400> SEQUENCE: 101

Thr Gly Leu Phe Glu Phe Tyr Lys Leu Leu Cys Val Arg Gly Ile Ile
1               5                   10                  15

Thr Ser Lys Thr Lys Ser Leu Asp Lys Gly Tyr Asn Lys Ala Leu Asn
            20                  25                  30

Asp Leu Cys Ile Lys Val Asn Asn Trp Asp Leu Phe Phe Ser Pro Ser
        35                  40                  45

Glu Asp Asn Phe Thr Asn Asp Leu
    50                  55

<210> SEQ ID NO 102
<211> LENGTH: 48
<212> TYPE: PRT
<213> ORGANISM: Clostridium botulinum

<400> SEQUENCE: 102

Lys Gly Leu Val Glu Lys Ile Val Lys Phe Cys Lys Ser Val Ile Pro
1               5                   10                  15

Arg Lys Gly Thr Lys Ala Pro Pro Arg Leu Cys Ile Arg Val Asn Asn
            20                  25                  30

Arg Glu Leu Phe Phe Val Ala Ser Glu Ser Ser Tyr Asn Glu Asn Asp
        35                  40                  45

<210> SEQ ID NO 103
<211> LENGTH: 48
<212> TYPE: PRT
<213> ORGANISM: Clostridium botulinum

<400> SEQUENCE: 103

Lys Gly Leu Val Glu Lys Ile Ile Lys Phe Cys Lys Ser Ile Ile Pro
1               5                   10                  15

Arg Lys Gly Thr Lys Gln Ser Pro Ser Leu Cys Ile Arg Val Asn Asn
            20                  25                  30

Arg Glu Leu Phe Phe Val Ala Ser Glu Ser Ser Tyr Asn Glu Ser Asp
        35                  40                  45

<210> SEQ ID NO 104

```
<211> LENGTH: 48
<212> TYPE: PRT
<213> ORGANISM: Clostridium botulinum

<400> SEQUENCE: 104

Lys Gly Leu Val Glu Lys Ile Ile Lys Phe Cys Lys Ser Ile Ile Pro
1               5                   10                  15

Arg Lys Gly Thr Lys Gln Ser Pro Ser Leu Cys Ile Arg Val Asn Asn
            20                  25                  30

Arg Glu Leu Phe Phe Val Ala Ser Glu Ser Ser Tyr Asn Glu Ser Asp
        35                  40                  45

<210> SEQ ID NO 105
<211> LENGTH: 48
<212> TYPE: PRT
<213> ORGANISM: Clostridium botulinum

<400> SEQUENCE: 105

Lys Gly Leu Val Glu Lys Ile Ile Lys Phe Cys Lys Ser Ile Ile Pro
1               5                   10                  15

Arg Lys Gly Thr Lys Gln Ser Pro Ser Leu Cys Ile Arg Val Asn Asn
            20                  25                  30

Arg Glu Leu Phe Phe Val Ala Ser Glu Ser Ser Tyr Asn Glu Ser Asp
        35                  40                  45

<210> SEQ ID NO 106
<211> LENGTH: 48
<212> TYPE: PRT
<213> ORGANISM: Clostridium botulinum

<400> SEQUENCE: 106

Lys Gly Leu Val Glu Lys Ile Val Lys Leu Cys Lys Ser Ile Ile Pro
1               5                   10                  15

Arg Lys Gly Thr Lys Ala Pro Pro Arg Leu Cys Ile Arg Val Asn Asn
            20                  25                  30

Arg Glu Leu Phe Phe Val Ala Ser Glu Ser Ser Tyr Asn Glu Asn Asp
        35                  40                  45

<210> SEQ ID NO 107
<211> LENGTH: 48
<212> TYPE: PRT
<213> ORGANISM: Clostridium botulinum

<400> SEQUENCE: 107

Lys Gly Leu Val Glu Lys Ile Val Lys Leu Cys Lys Ser Ile Ile Pro
1               5                   10                  15

Arg Lys Gly Thr Lys Ala Pro Pro Arg Leu Cys Ile Arg Val Asn Asn
            20                  25                  30

Arg Glu Leu Phe Phe Val Ala Ser Glu Ser Ser Tyr Asn Glu Asn Asp
        35                  40                  45

<210> SEQ ID NO 108
<211> LENGTH: 46
<212> TYPE: PRT
<213> ORGANISM: Clostridium botulinum

<400> SEQUENCE: 108

Gln Gly Val Val Ser Arg Val Val Arg Leu Cys Leu Asn Ser Ser Phe
1               5                   10                  15

Lys Lys Asn Thr Lys Lys Pro Leu Cys Ile Thr Val Asn Asn Gly Asp
            20                  25                  30
```

```
Leu Phe Phe Ile Ala Ser Glu Asp Ser Tyr Gly Glu Asp Thr
        35                  40                  45

<210> SEQ ID NO 109
<211> LENGTH: 48
<212> TYPE: PRT
<213> ORGANISM: Clostridium botulinum

<400> SEQUENCE: 109

Lys Gly Leu Val Glu Lys Ile Val Lys Phe Cys Lys Ser Val Ile Pro
1               5                   10                  15

Arg Lys Gly Thr Lys Ala Pro Pro Arg Leu Cys Ile Arg Val Asn Asn
            20                  25                  30

Ser Glu Leu Phe Phe Val Ala Ser Glu Ser Ser Tyr Asn Glu Asn Asp
        35                  40                  45

<210> SEQ ID NO 110
<211> LENGTH: 48
<212> TYPE: PRT
<213> ORGANISM: Clostridium botulinum

<400> SEQUENCE: 110

Lys Gly Leu Val Glu Lys Ile Val Lys Phe Cys Lys Ser Val Ile Pro
1               5                   10                  15

Arg Lys Gly Thr Lys Ala Pro Pro Arg Leu Cys Ile Arg Val Asn Asn
            20                  25                  30

Ser Glu Leu Phe Phe Val Ala Ser Glu Ser Ser Tyr Asn Glu Asn Asp
        35                  40                  45

<210> SEQ ID NO 111
<211> LENGTH: 48
<212> TYPE: PRT
<213> ORGANISM: Clostridium botulinum

<400> SEQUENCE: 111

Lys Gly Leu Val Glu Lys Ile Val Lys Phe Cys Lys Ser Val Ile Pro
1               5                   10                  15

Arg Lys Gly Thr Lys Ala Pro Pro Arg Leu Cys Ile Arg Val Asn Asn
            20                  25                  30

Ser Glu Leu Phe Phe Val Ala Ser Glu Ser Ser Tyr Asn Glu Asn Asp
        35                  40                  45

<210> SEQ ID NO 112
<211> LENGTH: 46
<212> TYPE: PRT
<213> ORGANISM: Clostridium botulinum

<400> SEQUENCE: 112

Asn Gly Leu Val Glu Arg Phe Val Gly Leu Cys Lys Ser Ile Val Ser
1               5                   10                  15

Lys Lys Gly Thr Lys Asn Ser Leu Cys Ile Lys Val Asn Asn Arg Asp
            20                  25                  30

Leu Phe Phe Val Ala Ser Glu Ser Ser Tyr Asn Glu Asn Gly
        35                  40                  45

<210> SEQ ID NO 113
<211> LENGTH: 46
<212> TYPE: PRT
<213> ORGANISM: Clostridium botulinum

<400> SEQUENCE: 113
```

```
Asn Gly Leu Val Glu Arg Phe Val Gly Leu Cys Lys Ser Ile Val Ser
1               5                   10                  15

Lys Lys Gly Thr Lys Asn Ser Leu Cys Ile Lys Val Asn Asn Arg Asp
                20                  25                  30

Leu Phe Phe Val Ala Ser Glu Ser Ser Tyr Asn Glu Asn Gly
            35                  40                  45
```

<210> SEQ ID NO 114
<211> LENGTH: 46
<212> TYPE: PRT
<213> ORGANISM: Clostridium botulinum

<400> SEQUENCE: 114

```
Asn Gly Leu Val Glu Arg Phe Val Gly Leu Cys Lys Ser Ile Val Ser
1               5                   10                  15

Lys Lys Gly Thr Lys Asn Ser Leu Cys Ile Lys Val Asn Asn Arg Asp
                20                  25                  30

Leu Phe Phe Val Ala Ser Glu Ser Ser Tyr Asn Glu Asn Gly
            35                  40                  45
```

<210> SEQ ID NO 115
<211> LENGTH: 46
<212> TYPE: PRT
<213> ORGANISM: Clostridium botulinum

<400> SEQUENCE: 115

```
Asn Gly Leu Val Glu Arg Phe Val Gly Leu Cys Lys Ser Ile Val Ser
1               5                   10                  15

Lys Lys Gly Thr Lys Asn Ser Leu Cys Ile Lys Val Asn Asn Arg Asp
                20                  25                  30

Leu Phe Phe Val Ala Ser Glu Ser Ser Tyr Asn Glu Asn Gly
            35                  40                  45
```

<210> SEQ ID NO 116
<211> LENGTH: 65
<212> TYPE: DNA
<213> ORGANISM: Artificial Sequence
<220> FEATURE:
<223> OTHER INFORMATION: BoNT/F7/1 chimeric nucleic acid sequence
      spanning activation loop

<400> SEQUENCE: 116
ggcctgtgca aaagcgttat tccgcgtaag ggtacgaaag caccgcctcg cctgtgcatt    60
aaagt                                                                65

<210> SEQ ID NO 117
<211> LENGTH: 22
<212> TYPE: PRT
<213> ORGANISM: Artificial Sequence
<220> FEATURE:
<223> OTHER INFORMATION: BoNT/F7/1 chimeric amino acid sequence
      spanning activation loop

<400> SEQUENCE: 117

```
Gly Leu Cys Lys Ser Val Ile Pro Arg Lys Gly Thr Lys Ala Pro Pro
1               5                   10                  15

Arg Leu Cys Ile Lys Val
                20
```

<210> SEQ ID NO 118
<211> LENGTH: 41

```
<212> TYPE: PRT
<213> ORGANISM: Clostridium botulinum

<400> SEQUENCE: 118

Gly Leu Val Glu Lys Ile Val Lys Phe Cys Lys Ser Ile Ile Pro Arg
1               5                   10                  15

Lys Gly Thr Lys Ala Pro Pro Arg Leu Cys Ile Arg Val Asn Asn Arg
            20                  25                  30

Glu Leu Phe Phe Val Ala Ser Glu Ser
        35                  40

<210> SEQ ID NO 119
<211> LENGTH: 41
<212> TYPE: PRT
<213> ORGANISM: Clostridium botulinum

<400> SEQUENCE: 119

Gly Leu Val Glu Lys Ile Val Lys Phe Cys Lys Ser Val Ile Pro Arg
1               5                   10                  15

Lys Gly Thr Lys Ala Pro Pro Arg Leu Cys Ile Arg Val Asn Asn Arg
            20                  25                  30

Glu Leu Phe Phe Val Ala Ser Glu Ser
        35                  40

<210> SEQ ID NO 120
<211> LENGTH: 41
<212> TYPE: PRT
<213> ORGANISM: Clostridium botulinum

<400> SEQUENCE: 120

Gly Leu Val Glu Lys Ile Ile Lys Phe Cys Lys Ser Ile Ile Pro Arg
1               5                   10                  15

Lys Gly Thr Lys Gln Ser Pro Ser Leu Cys Ile Arg Val Asn Asn Arg
            20                  25                  30

Glu Leu Phe Phe Val Ala Ser Glu Ser
        35                  40

<210> SEQ ID NO 121
<211> LENGTH: 41
<212> TYPE: PRT
<213> ORGANISM: Clostridium botulinum

<400> SEQUENCE: 121

Gly Leu Val Glu Lys Ile Ile Lys Phe Cys Lys Ser Ile Ile Pro Arg
1               5                   10                  15

Lys Gly Thr Lys Gln Ser Pro Ser Leu Cys Ile Arg Val Asn Asn Arg
            20                  25                  30

Glu Leu Phe Phe Val Ala Ser Glu Ser
        35                  40

<210> SEQ ID NO 122
<211> LENGTH: 41
<212> TYPE: PRT
<213> ORGANISM: Clostridium botulinum

<400> SEQUENCE: 122

Gly Leu Val Glu Lys Ile Val Lys Leu Cys Lys Ser Ile Ile Pro Arg
1               5                   10                  15

Lys Gly Thr Lys Ala Pro Pro Arg Leu Cys Ile Arg Val Asn Asn Arg
            20                  25                  30
```

```
Glu Leu Phe Phe Val Ala Ser Glu Ser
        35                  40

<210> SEQ ID NO 123
<211> LENGTH: 39
<212> TYPE: PRT
<213> ORGANISM: Clostridium botulinum

<400> SEQUENCE: 123

Gly Val Val Ser Arg Val Val Arg Leu Cys Leu Asn Ser Ser Phe Lys
1               5                   10                  15

Lys Asn Thr Lys Lys Pro Leu Cys Ile Thr Val Asn Asn Gly Asp Leu
            20                  25                  30

Phe Phe Ile Ala Ser Glu Asp
        35

<210> SEQ ID NO 124
<211> LENGTH: 41
<212> TYPE: PRT
<213> ORGANISM: Clostridium botulinum

<400> SEQUENCE: 124

Gly Leu Val Glu Lys Ile Val Lys Phe Cys Lys Ser Val Ile Pro Arg
1               5                   10                  15

Lys Gly Thr Lys Ala Pro Pro Arg Leu Cys Ile Arg Val Asn Asn Ser
            20                  25                  30

Glu Leu Phe Phe Val Ala Ser Glu Ser
        35                  40

<210> SEQ ID NO 125
<211> LENGTH: 39
<212> TYPE: PRT
<213> ORGANISM: Clostridium botulinum

<400> SEQUENCE: 125

Gly Leu Val Glu Arg Phe Val Gly Leu Cys Lys Ser Ile Val Ser Lys
1               5                   10                  15

Lys Gly Thr Lys Asn Ser Leu Cys Ile Lys Val Asn Asn Arg Asp Leu
            20                  25                  30

Phe Phe Val Ala Ser Glu Ser
        35

<210> SEQ ID NO 126
<211> LENGTH: 6
<212> TYPE: PRT
<213> ORGANISM: Artificial Sequence
<220> FEATURE:
<223> OTHER INFORMATION: His tag

<400> SEQUENCE: 126

His His His His His His
1               5

<210> SEQ ID NO 127
<211> LENGTH: 4
<212> TYPE: PRT
<213> ORGANISM: Artificial Sequence
<220> FEATURE:
<223> OTHER INFORMATION: F1/4/6 activation loop sequence (after cleavage
      site) + start of F7 heavy chain sequence
```

```
<400> SEQUENCE: 127

Ala Pro Pro Arg
1

<210> SEQ ID NO 128
<211> LENGTH: 4
<212> TYPE: PRT
<213> ORGANISM: Artificial Sequence
<220> FEATURE:
<223> OTHER INFORMATION: F2/3 activation loop sequence (after cleavage
      site) + start of F5 heavy chain sequence

<400> SEQUENCE: 128

Gln Ser Pro Ser
1

<210> SEQ ID NO 129
<211> LENGTH: 47
<212> TYPE: DNA
<213> ORGANISM: Artificial Sequence
<220> FEATURE:
<223> OTHER INFORMATION: F7 1 forward primer

<400> SEQUENCE: 129
ccaagaaggg tacgaaagca ccgcctcgcc tgtgcattaa agtcaac                    47

<210> SEQ ID NO 130
<211> LENGTH: 47
<212> TYPE: DNA
<213> ORGANISM: Artificial Sequence
<220> FEATURE:
<223> OTHER INFORMATION: F7 1 reverse primer

<400> SEQUENCE: 130
gttgacttta atgcacaggc gaggcggtgc tttcgtaccc ttcttgg                    47

<210> SEQ ID NO 131
<211> LENGTH: 50
<212> TYPE: DNA
<213> ORGANISM: Artificial Sequence
<220> FEATURE:
<223> OTHER INFORMATION: F7 2 forward primer

<400> SEQUENCE: 131
cttcgtgggc ctgtgcaaaa gcgttattcc gcgtaagggt acgaaagcac                 50

<210> SEQ ID NO 132
<211> LENGTH: 50
<212> TYPE: DNA
<213> ORGANISM: Artificial Sequence
<220> FEATURE:
<223> OTHER INFORMATION: F7 2 reverse primer

<400> SEQUENCE: 132
gtgctttcgt acccttacgc ggaataacgc ttttgcacag gcccacgaag                 50
```

The invention claimed is:

1. A chimeric polypeptide comprising:
   (a) an $LH_N$ backbone from a BoNT/$F_2$ subtype; and
   (b) an activation loop region from a BoNT/$F_1$ subtype;
   wherein the $LH_N$ backbone comprises both:
   (i) a light chain domain of the BoNT/$F_7$ subtype; and
   (ii) a $H_N$ domain of the BoNT/$F_7$ subtype.

2. The polypeptide of claim 1, wherein the activation loop comprises the amino acid sequence of SEQ ID NO: 66.

3. The polypeptide of claim 1, wherein a cleavage site within the activation loop is specifically recognized and capable of being cleaved by an endopeptidase.

4. The polypeptide of claim 3, wherein cleavage thereof by the endopeptidase results in the formation of an active holotoxin.

5. The polypeptide of claim 1, further comprising a targeting moiety capable of binding directly to a cell or to a ligand or ligands that bind to a cell.

6. The polypeptide of claim 5, wherein the targeting moiety is from a clostridial neurotoxin.

7. The polypeptide of claim 6, wherein the targeting moiety is a non-clostridial targeting moiety.

8. A polynucleotide encoding the polypeptide of claim 1.

9. A method of producing the polypeptide of claim 1, comprising expressing a polynucleotide encoding the polypeptide in a cell, and recovering the expressed polypeptide.

10. A method of activating the polypeptide of claim 1, comprising incubating the polypeptide with an endopeptidase.

11. A method of preventing or treating a disease or disorder for which a therapy with a botulinum neurotoxin is indicated, the method comprising administering a composition comprising the polypeptide of claim 1 to a patient in need thereof.

12. A method of preventing or alleviating a cosmetic indication for which the application of a botulinum neurotoxin is indicated, the method comprising administering the composition comprising the polypeptide of claim 1 to a subject in need thereof.

\* \* \* \* \*